US010640507B2

(12) United States Patent
Rahman et al.

(10) Patent No.: US 10,640,507 B2
(45) Date of Patent: May 5, 2020

(54) PBD ANTIBACTERIAL AGENTS

(71) Applicants: KING'S COLLEGE LONDON, London (GB); Secretary of State for Health and Social Care, London (GB)

(72) Inventors: Khondaker Mirazur Rahman, London (GB); John Mark Sutton, Salisbury (GB); Pietro Picconi, London (GB)

(73) Assignees: King's College London (GB); Secretary of State for Health and Social Care (GB)

( * ) Notice: Subject to any disclaimer, the term of this patent is extended or adjusted under 35 U.S.C. 154(b) by 0 days.

(21) Appl. No.: 16/061,295

(22) PCT Filed: Dec. 9, 2016

(86) PCT No.: PCT/GB2016/053882
§ 371 (c)(1),
(2) Date: Jun. 11, 2018

(87) PCT Pub. No.: WO2017/098257
PCT Pub. Date: Jun. 15, 2017

(65) Prior Publication Data
US 2018/0354958 A1    Dec. 13, 2018

(30) Foreign Application Priority Data
Dec. 9, 2015   (GB) .................................. 1521709.4

(51) Int. Cl.
*C07D 487/04*    (2006.01)
*A61P 31/04*    (2006.01)
(Continued)

(52) U.S. Cl.
CPC ........ *C07D 487/04* (2013.01); *A61K 31/5517* (2013.01); *A61K 45/06* (2013.01); *A61P 31/04* (2018.01)

(58) Field of Classification Search
CPC ... C07D 487/04; A61P 31/04; A61K 31/5517; A61K 45/06
See application file for complete search history.

(56) References Cited

U.S. PATENT DOCUMENTS 9,321,774 B2 *  4/2016  Howard ............... C07D 487/04
9,376,440 B2 *  6/2016  Howard ............... C07D 487/04
(Continued)

FOREIGN PATENT DOCUMENTS

WO   WO-2005085250 A1 *  9/2005  ........... C07D 487/04
WO   WO2007039752 A1     4/2007
(Continued)

OTHER PUBLICATIONS

Chemical Entities of Biological Interest (Downloaded Feb. 21, 2019); https://www.ebi.ac.uk/chebi/ (Year: 2019).*
Z. J. Witczac, Monosaccharides: Occurrence, Significance, and Properties, in Glycoscience (2008) (Year: 2008).*
A. Hinkova, Handbook of Food Chemistry, (2014) (Year: 2014).*
Damayanthi et al., "Design and synthesis of novel pyrrolo[2,1-c],[1,4]benzodiazepine-lexitropsin conjugates", Journal of Organic Chemistry, vol. 64, No. 1, pp. 290-292, 1999.
Bakboord, Joan, "PCT International Search Report", 9 pages, dated Jan. 25, 2017.
Cole, Dr. Natalie, "Patents Act 1977: Search Report under Section 17(5)", 4 pages, dated Sep. 21, 2016.

*Primary Examiner* — Alexander R Pagano
(74) *Attorney, Agent, or Firm* — Thomas G. Peterson; Maynard Cooper & Gale

(57) ABSTRACT

The invention relates to pyrrolobenzodiazepines compounds (PBDs) and to pharmaceutically acceptable salts thereof, which are useful as medicaments, in particular, to treat bacterial infections. The PBDs are compounds of formula (I): and salts and solvates thereof; wherein: dotted lines indicates the optional presence of a double bond; X, $X_1$, $X_2$, $X_3$ and $X_4$ are connecting functional groups; L is $C_{1-12}$ alkylene; $R_4$, $R_5$ and $R_6$ are independently selected from phenylene, cyclopentanylene, cyclohexanylene, 5- to 9-membered heteroarylene and 5- to 6-membered heterocyclylene groups, and these groups are optionally substituted with up to three optional substituent groups; $R_7$ is selected from $N(C_{1-6}$ alkyl)($C_{1-6}$alkyl), 5- to 6-membered nitrogen-containing hetereocyclyl groups, a monosaccharide moiety and an amino monosaccharide moiety wherein these groups are optionally substituted; and $R_8$ and $R_9$ either together form a double bond, or are selected from H and $OR_{14}$, or $R_8$ is a prodrug moiety and $R_9$ is $OR_{14}$; m is 0 or 1; with the proviso that when $X_4$ is C(O)NH then the up to three optional substituents of $R_7$ are not selected from $(CH2)_k$-$CO_2R_{12}$; with the proviso that when $X_4$ is $(CH_2)_tO$ then $R_4$ is not phenylene, m is 1 and $R_6$ is not a 5- to 9-membered heteroarylene; and with the proviso that when $X_4$ is C(O)NH or NHC(O) that $R_4$ and/or $R_6$ is not 5- to 9-membered heteroarylene.

22 Claims, 7 Drawing Sheets

(51) Int. Cl.
*A61K 31/5517* (2006.01)
*A61K 45/06* (2006.01)

(56) References Cited

U.S. PATENT DOCUMENTS

| | | | |
|---|---|---|---|
| 9,592,240 B2 * | 3/2017 | Howard | C07K 16/30 |
| 9,669,107 B2 * | 6/2017 | Kim | C12Q 1/48 |
| 9,713,647 B2 * | 7/2017 | Jeffrey | C07D 487/04 |
| 9,999,625 B2 * | 6/2018 | Thurston | C07D 487/04 |
| 10,143,695 B2 * | 12/2018 | Yin | A61K 31/55 |
| 10,183,997 B2 * | 1/2019 | Kim | A61K 47/6889 |
| 2007/0191349 A1 * | 8/2007 | Howard | C07D 487/04 514/220 |

FOREIGN PATENT DOCUMENTS

| | | |
|---|---|---|
| WO | WO2012110840 A1 | 8/2012 |
| WO | WO-2013164592 A1 * | 11/2013 |
| WO | WO2013164592 A1 | 11/2013 |

* cited by examiner

PBD ANTIBACTERIAL AGENTS

CROSS-REFERENCE TO RELATED APPLICATIONS

This application is a national stage under 35 U.S.C. 371 of International Application No. PCT/GB2016/053882 having an international filing date of Dec. 9, 2016 (currently published). International Application No. PCT/GB2016/053882 cites the priority of GB Patent Application No. 1521709.4, filed Dec. 9, 2015 (abandoned).

FIELD OF THE INVENTION

The invention relates to pyrrolobenzodiazepines (PBDs) comprising three fused 6-7-5-membered rings. In particular it relates to compounds comprising a PBD group linked via the A-ring to heterocyclic groups, and to pharmaceutically acceptable salts thereof, which are useful as medicaments, in particular, to treat bacterial infections.

BACKGROUND TO THE INVENTION

The pyrrolobenzodiazepines (PBDs) are a group of compounds some of which have been shown to be sequence-selective DNA minor-groove binding agents. The PBDs were originally discovered in *Streptomyces* species (1-5). They are tricyclic in nature, and are comprised of fused 6-7-5-membered rings that comprise an anthranilate (A ring), a diazepine (B ring) and a pyrrolidine (C ring) (3). They are characterized by an electrophilic $N_{10}=C_{11}$ imine group (as shown below) or the hydrated equivalent, a carbinolamine [NH—CH(OH)], or a carbinolamine alkyl ether ([NH—CH(OR), where R=alkyl)] which can form a covalent bond to a C2-amino group of guanine in DNA to form a DNA adduct (6).

A number of monomeric PBD structures have been isolated from *Streptomyces* species, including anthramycin (18) the first PBD, tomamycin (19), and more recently usabamycin (20) from a marine sediment *Streptomyces* species in a marine sediment. This has led to the development of a large range of synthetic analogues which have been reviewed (1, 21). More recently, a number of monomeric PBD structures that are linked through their C8 position to pyrroles and imidazoles have been reported WO 2007/039752, WO 2013/164592 (22-27).

Infectious diseases are a leading cause of mortality and morbidity worldwide. The ability to treat effectively a range of bacterial infections rose dramatically following the introduction of penicillin and other antibiotics. However, the evolution of multidrug-resistant pathogens capable of rapid and efficient horizontal transmission of genes encoding antibiotic resistance determinants has diminished the therapeutic value of many frontline antibacterial therapeutic agents (28, 29). These multidrug-resistant pathogens are a serious threat to efforts to continue to keep infectious diseases under control.

WO 2005/085260 reported PBD dimers that had an effect on Gram-positive bacterial species, such as *Staphylococcus aureus*. The bactericidal activity of such PBD dimers against a range of Gram-positive pathogens have been reported (30, 31). More recently, WO 2013/164592 disclosed that conjugates of PBD with multi-aromatic species such as phenyls, pyrroles and imidazoles can be used against some drug resistant Gram-positive bacterial strains, such as methicillin resistant *Staphylococcus aureus* strains, see also (32). These conjugates failed to show any activity against Gram-negative bacteria.

PBD compounds have not been reported to have any useful effect against any Gram-negative bacterial species. It has been speculated that PBD compounds were not effective

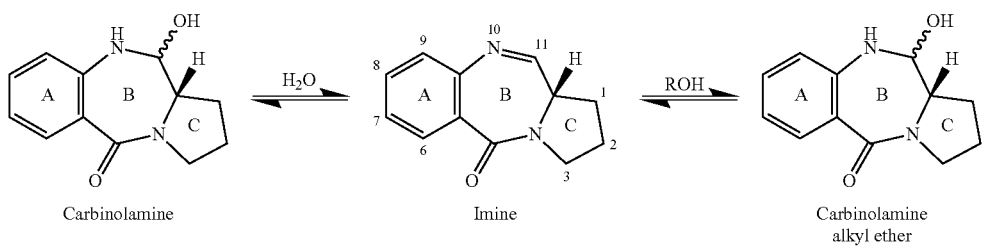

Carbinolamine        Imine        Carbinolamine alkyl ether

The natural products interact in the minor groove of the DNA helix with excellent fit (i.e., good "isohelicity") due to a right-handed longitudinal twist induced by a chiral $C_{11a}$-position which has the (S)-configuration (6). The DNA adduct has been reported to inhibit a number of biological processes including the binding of transcription factors (7-9) and the function of enzymes such as endonucleases (10, 11) and RNA polymerase (12). PBD monomers (e.g., anthramycin) have been shown by footprinting (6), NMR (13, 14), molecular modeling (15) and X-ray crystallography (16) to span three base pairs and to have a thermodynamic preference for the sequence 5'-Pu-G-Pu-3' (where Pu=purine, and G is the reacting guanine) (17) and a kinetic preference for Py-5-Py (where Py=Pyrimidine).

The ability of PBDs to form an adduct in the minor groove and crosslink DNA enables them to interfere with DNA processing and, hence, their potential for use as antiproliferative agents.

against Gram-negative bacterial species because the PBD compounds are unable to traverse the outer membrane of Gram-negative bacterial species (28). This is significant as increasing multidrug resistance has been a particular problem with Gram-negative pathogens, such as *Pseudomonas aeruginosa* and *Acinetobacter baumannii*.

In addition, many PBD compound have a high degree of cytotoxicity which has rendered them unattractive for use as antibacterial agents.

The present invention seeks to alleviate these problems associated with the prior art.

SUMMARY OF THE INVENTION

The present invention provides a compound of formula (I):

$$\text{(I)}$$

[Structure of formula (I): $R_7\text{—}X_4\text{—}[R_6\text{—}X_3\text{—}]_m R_5\text{—}X_2\text{—}R_4\text{—}X_1\text{—}L\text{—}X\text{—}$ attached to a benzodiazepine core with substituents $R_3$, $R_8$, $R_9$, H, $R_1$, $R_2$, and a carbonyl (=O)]

and salts and solvates thereof;
wherein:
the dotted lines indicates the optional presence of a double bond between $C_1$ and $C_2$, or $C_2$ and $C_3$;

X is selected from $(CR_{15}R_{16})_nO$, $O(CR_{15}R_{16})_n$, S, $NR_{15}$, $CR_{15}R_{16}$, C(O), C(O)NR$_{15}$, NR$_{15}$C(O), O—C(O) and C(O)—O;

$X_1$ is selected from $(CH_2)_pO$, $O(CH_2)_p$, C(O), NHC(O) and C(O)NH or is absent;

$X_2$ is selected from $(CH_2)_qO$, $O(CH_2)_q$, C(O), NHC(O) and C(O)NH or is absent;

$X_3$ is selected from $(CH_2)_sO$, $O(CH_2)_s$, C(O), NHC(O) and C(O)NH or is absent;

$X_4$ is selected from $(CH_2)_tO$, $O(CH_2)_v$, C(O), NHC(O) and C(O)NH;

L is $C_{1-12}$ alkylene;

$R_1$ is selected from H, $C_{1-6}$ alkyl, $OC_{1-6}$ alkyl, OH, CN, =CHR$_{17}$, halogen, CO$_2$H and CO$_2$(C$_{1-6}$ alkyl);

$R_2$ is selected from H, $C_{1-6}$ alkyl, $OC_{1-6}$ alkyl, OH, CN, =CHR$_{18}$, halogen, CO$_2$H and CO$_2$(C$_{1-6}$ alkyl);

$R_3$ is selected from H, F, OH, $OC_{1-6}$ alkyl, $OCH_2$Ph, a monosaccharide moiety and an amino monosaccharide moiety wherein the monosaccharide and amino monosaccharide moieties may be optionally acetyl substituted;

$R_4$, $R_5$ and $R_6$ are independently selected from phenylene, cyclopentanylene, cyclohexanylene, 5- to 9-membered heteroarylene and 5- to 6-membered hetereocyclylene groups, and these groups are optionally substituted with up to three optional substituent groups each independently selected from OH, $C_{1-6}$ alkyl, $OC_{1-6}$ alkyl, halogen, $(CH_2)_j$—CO$_2$R$_{10}$ and $(CH_2)_j$—NR$_{10}$R$_{11}$;

$R_7$ is selected from $N(C_{1-6}$ alkyl)$(C_{1-6}$ alkyl), 5- to 6-membered nitrogen-containing hetereocyclyl groups, a monosaccharide moiety and an amino monosaccharide moiety wherein these nitrogen-containing hetereocyclyl groups are optionally substituted with up to three optional substituent groups each independently selected from OH, $C_{1-6}$ alkyl, $OC_{1-6}$ alkyl, halogen, $(CH_2)_k$—CO$_2$R$_{12}$, $(CH_2)_k$—NR$_{12}$R$_{13}$ and a prodrug moiety, and wherein the monosaccharide and amino monosaccharide moieties may be optionally acetyl substituted;

$R_8$ and $R_9$ either together form a double bond, or are selected from H and OR$_{14}$, or $R_8$ is a prodrug moiety and $R_9$ is OR$_{14}$;

m is 0 or 1;

j, k, n, p, q, s and t are each independently selected from an integer from 0 to 6;

v is selected from an integer from 1 to 6;

each $R_{10}$, $R_{11}$, $R_{12}$, $R_{13}$, $R_{15}$, $R_{16}$, $R_{17}$ and $R_{18}$ are independently selected from H and $C_{1-6}$ alkyl; and $R_{14}$ is selected from H, $C_{1-6}$ alkyl and tetrahydro-2H-pyran-2-yl;

with the proviso that when $X_4$ is C(O)NH then the up to three optional substituents of $R_7$ are not selected from $(CH_2)_k$—CO$_2$R$_{12}$;

with the proviso that when $X_4$ is $(CH_2)_tO$ then $R_4$ is not phenylene, m is 1 and $R_6$ is not a 5- to 9-membered heteroarylene; and with the proviso that when $X_4$ is C(O)NH or NHC(O) that $R_4$ and/or $R_6$ is not 5- to 9-membered heteroarylene.

In a further aspect, the present invention provides a compound of formula (I):

$$\text{(I)}$$

[Structure of formula (I): $R_7\text{—}X_4\text{—}[R_6\text{—}X_3\text{—}]_m R_5\text{—}X_2\text{—}R_4\text{—}X_1\text{—}L\text{—}X\text{—}$ attached to a benzodiazepine core with substituents $R_3$, $R_8$, $R_9$, H, $R_1$, $R_2$, and a carbonyl (=O)]

and salts and solvates thereof;
wherein:
the dotted lines indicates the optional presence of a double bond between $C_1$ and $C_2$, or $C_2$ and $C_3$;

X is selected from $(CR_{15}R_{16})_nO$, $O(CR_{15}R_{16})_n$, S, $NR_{15}$, $CR_{15}R_{16}$, C(O), C(O)NR$_{15}$, NR$_{15}$C(O), O—C(O) and C(O)—O;

$X_1$ is selected from $(CH_2)_pO$, $O(CH_2)_p$, C(O), NHC(O) and C(O)NH or is absent;

$X_2$ is selected from $(CH_2)_qO$, $O(CH_2)_q$, C(O), NHC(O) and C(O)NH or is absent;

$X_3$ is selected from $(CH_2)_sO$, $O(CH_2)_s$, C(O), NHC(O) and C(O)NH or is absent;

$X_4$ is selected from $(CH_2)_tO$, $O(CH_2)_v$, C(O), NHC(O) and C(O)NH;

L is $C_{1-12}$ alkylene;

$R_1$ is selected from H, $C_{1-6}$ alkyl, $OC_{1-6}$ alkyl, OH, CN, =CHR$_{17}$, halogen, CO$_2$H and CO$_2$(C$_{1-6}$ alkyl);

$R_2$ is selected from H, $C_{1-6}$ alkyl, $OC_{1-6}$ alkyl, OH, CN, =CHR$_{18}$, halogen, CO$_2$H and CO$_2$(C$_{1-6}$ alkyl);

$R_3$ is selected from H, OH, $OC_{1-6}$ alkyl and $OCH_2$Ph;

$R_4$, $R_5$ and $R_6$ are independently selected from phenylene, cyclopentanylene, cyclohexanylene, 5- to 9-membered heteroarylene and 5- to 6-membered hetereocyclylene groups, and these groups are optionally substituted with up to three optional substituent groups each independently selected from OH, $C_{1-6}$ alkyl, $OC_{1-6}$ alkyl, halogen, $(CH_2)_j$—CO$_2$R$_{10}$ and $(CH_2)_j$—NR$_{10}$R$_{11}$;

$R_7$ is selected from $N(C_{1-6}$ alkyl)$(C_{1-6}$ alkyl) and 5- to 6-membered nitrogen-containing hetereocyclyl groups, and these hetereocyclyl groups are optionally substituted with up to three optional substituent groups each independently selected from OH, $C_{1-6}$ alkyl, $OC_{1-6}$ alkyl, halogen, $(CH_2)_k$—CO$_2$R$_{12}$ and $(CH_2)_k$—NR$_{12}$R$_{13}$;

$R_8$ and $R_9$ either together form a double bond, or are selected from H and OR$_{14}$;

m is 0 or 1;

j, k, n, p, q, s and t are each independently selected from an integer from 0 to 6;

v is selected from an integer from 1 to 6; and each $R_{10}$, $R_{11}$, $R_{12}$, $R_{13}$, $R_{14}$, $R_{15}$, $R_{16}$, $R_{17}$ and $R_{18}$ are independently selected from H and $C_{1-6}$ alkyl;

with the proviso that when $X_4$ is C(O)NH then the up to three optional substituents of $R_7$ are not selected from $(CH_2)_k$—CO$_2$R$_{12}$;

with the proviso that when $X_4$ is $(CH_2)_tO$ then $R_4$ is not phenylene, m is 1 and $R_6$ is not a 5- to 9-membered heteroarylene; and with the proviso that when $X_4$ is C(O)NH or NHC(O) that $R_4$ and/or $R_6$ is not 5- to 9-membered heteroarylene.

In a further aspect, the present invention provides a pharmaceutical composition comprising a compound of formula (I) and salts and solvates thereof, and a pharmaceutically acceptable carrier or diluent.

In a further aspect, the present invention provides a kit comprising:
(i) a compound of formula (I) and salts and solvates thereof;
(ii) an agent for increasing the permeability of bacterial membranes; and/or
(iii) an efflux pump inhibitor.

In a further aspect, the present invention provides a compound of formula (I) and salts and solvates thereof, or a pharmaceutical composition of the present invention, for use as a medicament.

In a further aspect, the present invention provides a compound of formula (I) and salts and solvates thereof, or a pharmaceutical composition of the present invention, for use in the treatment of a bacterial infection in a subject.

In a further aspect, the present invention provides the use of a compound of formula (I) and salts and solvates thereof, or a pharmaceutical composition of the present invention, in the manufacture of a medicament for treating a bacterial infection.

In a further aspect, the present invention provides a method for treating a subject with a bacterial infection comprising the step of administering to the subject in need thereof a therapeutically effective amount of a compound of formula (I) and salts and solvates thereof, or a pharmaceutical composition of the present invention.

In a further aspect, the present invention provides a method of inhibiting a bacterium, the method comprising the step of contacting the bacteria with a compound of formula (I) and salts and solvates thereof, or a pharmaceutical composition of the present invention.

In a further aspect, the compound of formula (I) and salts and solvates thereof, may be administered alone or in combination with other treatments, separately, simultaneously or sequentially depending upon the condition to be treated.

The pharmaceutical composition of the present invention may further comprise one or more (e.g. two, three or four) further active agents.

Definitions

The following abbreviations are used throughout the specification: Alloc allyloxy-carbonyl; BAIB bis(acetoxy) iodobenzene/(diacetoxyiodo)benzene; Bn benzyl; Boc tert-butoxycarbonyl; DCM dichloromethane; DHP dihydropyran; DIPEA N,N-Diisopropylethylamine; DMAP 4-dimethylaminopyridine; DMF dimethylformamide; EA ethyl acetate; EDCl 1-Ethyl-3-(3-dimethylaminopropyl)-carbodiimide; Et ethyl; HBTU N,N,N',N''-Tetramethyl-O-(1H-benzotriazol-1-yl)uronium hexafluorophosphate, O-(Benzotriazol-1-yl)-N,N,N',N'-tetramethyluronium hexafluorophosphate; Me methyl; MIC minimum inhibitory concentration; PBDs pyrrolo[2,1-c][1,4]benzo-diazepines; Ph phenyl; p-TSA/PTSA p-Toluenesulfonic acid; TEMPO (2,2,6,6-tetramethyl-piperidin-1-yl)oxyl; TLC thin layer chromatography; and TFA trifluoroacetic acid.

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Optionally substituted" refers to a parent group which may be unsubstituted or which may be substituted with one or more substituents. The statement that an R group is "selected from phenylene, cyclopentanylene, cyclohexanylene, 5- to 9-membered heteroarylene and 5- to 6-membered hetereocyclylene groups, and these groups are optionally substituted" indicates that any of these groups may be optionally substituted with the optional substituents, e.g. a cyclopentanylene group may be selected and it may be optionally substituted. Where the parent group contains a heteroatom and is optionally substituted, then the parent group may be optionally substituted on either a carbon atom or a heteroatom provide that the valence requirements are met. Suitably, unless otherwise specified, when optional substituents are present the optional substituted parent group comprises from one to three optional substituents, i.e. 1, 2 or 3 optional substituents. Where a group may be optionally substituted with up to with up to three groups, this means that the group may be substituted with 0, 1, 2 or 3 of the optional substituents.

"Independently selected" is used in the context of statement that, for example, "$R_4$ and $R_5$ are independently selected from H, $C_{1-12}$ alkyl, etc." and means that each instance of the functional group, e.g. $R_4$, is selected from the listed options independently of any other instance of $R_4$ or $R_5$ in the compound. Hence, for example, where "up to three optional substituent groups are independently selected from . . . $(CH_2)_k CO_2 R_{12}$" then for the first optional substituent group k may be selected as 0 and $R_{12}$ as H to give $CO_2H$, whereas for the second optional substituent group k may be selected as 1 and $R_{12}$ as $CH_3$ to give $CH_2CO_2CH_3$.

$C_{1-6}$ alkyl: refers to straight chain and branched saturated hydrocarbon groups, generally having from 1 to 6 carbon atoms; more suitably $C_{1-5}$ alkyl; more suitably $C_{1-4}$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

"Alkylene" refers to a divalent radical derived from an alkane which may be a straight chain or branched, as exemplified by —$CH_2CH_2CH_2CH_2$—.

"Amino monosaccharide moiety" refers to a substituent derived from a monosaccharide by removing a hydroxyl group or a hydrogen from the cyclic form of a monosaccharide and by replacing 1, 2, 3, 4 or 5 hydroxyl groups with amine groups. The term "amino monosaccharide moiety" includes deoxy versions of monosaccharides where 1, 2, 3, or 4 hydroxyl groups have each been replaced with a hydrogen. Suitably, one hydroxyl group is replaced with an amine group. Suitably, a hydrogen is removed from an amine group such that the amino monosaccharide moiety substituent is attached via the amine.

"5- to 9-membered ring heteroaryl": refers to unsaturated monocyclic or bicyclic aromatic groups comprising 5 to 9 ring atoms, whether carbon or heteroatoms, of which from 1 to 5 are ring heteroatoms. Suitably, any monocyclic heteroaryl ring has from 5 to 6 ring atoms including from 1 to 4 ring heteroatoms; more suitably with 1 to 3 heteroatoms. Suitably each ring heteroatom is independently selected from nitrogen, oxygen, and sulfur. The bicyclic rings include fused ring systems and, in particular, include bicyclic groups in which a monocyclic heterocycle comprising 5 ring atoms is fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:

$N_1$: pyrrole, pyridine;
$O_1$: furan;
$S_1$: thiophene isoxazole, isoxazine;
$N_1O_1$: oxazole, isoxazole;
$N_2O_1$: oxadiazole (e.g. 1-oxa-2,3-diazolyl, 1-oxa-2,4-diazolyl, 1-oxa-2,5-diazolyl, 1-oxa-3,4-diazolyl);
$N_3O_1$: oxatriazole;
$N_1S_1$: thiazole, isothiazole;
$N_2S_1$: thiadiazole (e.g. 1,3,4-thiadiazole);
$N_2$: imidazole, pyrazole, pyridazine, pyrimidine, pyrazine;
$N_3$: triazole, triazine; and,
$N_4$: tetrazole.

Examples of heteroaryl which comprise fused rings, include, but are not limited to, those derived from:

$O_1$: benzofuran, isobenzofuran;
$N_1$: indole, isoindole, indolizine, isoindoline;
$S_1$: benzothiofuran;
$N_1O_1$: benzoxazole, benzisoxazole;
$N_1S_1$: benzothiazole;
$N_2$: benzimidazole, indazole;
$O_2$: benzodioxole;
$N_2O_1$: benzofurazan;
$N_2S_1$: benzothiadiazole;
$N_3$: benzotriazole; and
$N_4$: purine (e.g., adenine, guanine).

"5- to 9-membered ring heteroarylene" refers to a divalent radical derived from an heteroaryl, as exemplified by the following benzofuranylene group:

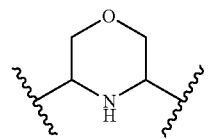

In this specification a zig-zag line indicates the point of attachment of the shown group (e.g. the benzofuranylene group above) to the rest of the compound of formula (I).

"5- to 6-membered heterocyclyl": refers to saturated or partially unsaturated monocyclic groups having from 5 to 6 ring atoms, whether carbon atoms or heteroatoms, of which from 1 to 4 are ring heteroatoms. The ring heteroatoms are independently selected from nitrogen, oxygen, and sulphur.

The heterocyclyl group may be attached to a parent group or to a substrate at any ring atom and may include one or more non-hydrogen substituents unless such attachment or substitution would violate valence requirements or result in a chemically unstable compound.

Examples of monocyclic heterocyclyl groups include, but are not limited to, those derived from:

$N_1$: pyrrolidine, pyrroline, 2H-pyrrole or 3H-pyrrole, piperidine, dihydropyridine, tetrahydropyridine;
$O_1$: dihydrofuran, tetrahydropyran, dihydropyran, pyran;
$S_1$: tetrahydrothiopyran;
$O_2$: dioxolane, dioxane;
$O_3$: trioxane;
$N_2$: pyrazolidine, imidazoline, imidazolidine, pyrazoline, piperazine;
$N_1O_1$: tetrahydrooxazole, dihydrooxazole, tetrahydroisoxazole, dihydroisoxazole, morpholine, tetrahydrooxazine, dihydrooxazine, oxazine;
$N_1S_1$: thiazoline, thiazolidine, thiomorpholine;
$N_2O_1$: oxadiazine;
$O_1S_1$: oxathiole and oxathiane (thioxane); and
$N_1O_1S_1$: oxathiazine.

"5- to 6-membered heterocyclylene" refers to a divalent radical derived from an heterocyclyl group that may be saturated or partially unsaturated, as exemplified by the following morpholinylene group:

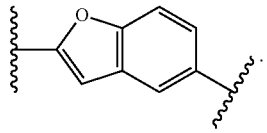 [SMILES: *c1ccc2oc(*)cc2c1]

"Bacterial infection" includes infections caused by one or more species of Gram-negative, Gram-positive, or atypical bacteria. The term "bacterial infection" pertains to the invasion of body tissues by bacteria, their multiplication and the reaction of body tissues to the bacteria and the toxins that they produce.

"Drug", "drug substance", "active pharmaceutical ingredient", and the like, refer to a compound (e.g., compounds of Formula (I) and compounds specifically named above) that may be used for treating a subject in need of treatment.

"Excipient" refers to any substance that may influence the bioavailability of a drug, but is otherwise pharmacologically inactive.

"Halogen" or "halo" refers to a halogen selected from fluoro, chloro, bromo, and iodo. Suitably the halogen may be selected from fluoro and chloro.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition.

"Monosaccharide moiety" refers to a substituent derived from a monosaccharide by removing a hydroxyl group or a hydrogen from the cyclic form of a monosaccharide. The term "monosaccharide moiety" includes deoxy versions of monosaccharides where 1, 2, 3, or 4 hydroxyl groups have each been replaced with a hydrogen.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

"phenylene, cyclopentanylene, cyclohexanylene" refers to a divalent radical derived from phenyl, cyclopentane and cyclohexane groups respectively; suitably, these groups are selected from the following:

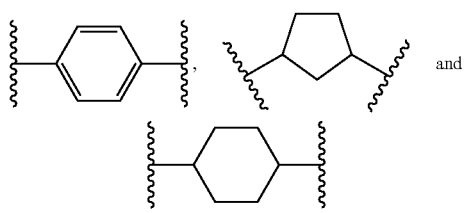

The term "prodrug moiety" is a substituent which is capable of being eliminated to produce an antibacterial agent suitable for treating a bacterial infection. Typically, the prodrug moiety is eliminated by action of an enzyme on the compound of formula (I) containing the prodrug moiety.

The term "subject" as used herein refers to a human or non-human mammal. Examples of non-human mammals include livestock animals such as sheep, horses, cows, pigs, goats, rabbits and deer; and companion animals such as cats, dogs, rodents, and horses.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things. The "effective amount" includes an amount of the compound of formula (I) that will elicit a biological or medical response of a subject, for example, the reduction or inhibition of enzyme or protein activity related to a bacterial infection, amelioration of symptoms of a bacterial infection, or the slowing or delaying of progression of a bacterial infection. In some embodiments, the language "effective amount" includes the amount of a compound of formula (I), that when administered to a subject, is effective to at least partially alleviate, inhibit, and/or ameliorate a bacterial infection and/or reduce or inhibit the bacterial growth, replication or bacterial load of a bacteria in a subject.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

As used herein the term "comprising" means "consisting at least in part of". When interpreting each statement in this specification that includes the term "comprising", features other than that or those prefaced by the term may also be present. Related terms such as "comprise" and "comprises" are to be interpreted in the same manner.

$R_1$

Suitably $R_1$ is selected from H, $CH_3$, $CH_2CH_3$, $CH_2CH_2CH_3$, $OCH_3$, $OCH_2CH_3$, $OCH_2CH_2CH_3$, OH, CN, =$CHR_{17}$, F, Cl, Br, I, $CO_2H$, $CO_2CH_3$, $CO_2CH_2CH_3$ and $CO_2CH_2CH_2CH_3$.

Suitably $R_1$ is selected from H, $CH_3$, $CH_2CH_3$, $CH_2CH_2CH_3$, $OCH_3$, $OCH_2CH_3$, OH, CN, F, Cl, Br, $CO_2H$, $CO_2CH_3$ and $CO_2CH_2CH_3$.

More suitably, $R_1$ is H.

$R_2$

Suitably $R_2$ is selected from H, $CH_3$, $CH_2CH_3$, $CH_2CH_2CH_3$, $OCH_3$, $OCH_2CH_3$, $OCH_2CH_2CH_3$, OH, CN, =$CHR_{18}$, F, Cl, Br, I, $CO_2H$, $CO_2CH_3$, $CO_2CH_2CH_3$ and $CO_2CH_2CH_2CH_3$.

Suitably $R_2$ is selected from H, $CH_3$, $CH_2CH_3$, $CH_2CH_2CH_3$, $OCH_3$, $OCH_2CH_3$, OH, CN, F, Cl, Br, $CO_2H$, $CO_2CH_3$ and $CO_2CH_2CH_3$.

More suitably, $R_2$ is H.

$R_3$

Suitably $R_3$ is selected from H, F, OH, $OCH_3$, $OCH_2CH_3$, $OCH_2CH_2CH_3$, $OCH_2Ph$, a monosaccharide moiety and an amino monosaccharide moiety wherein the monosaccharide and amino monosaccharide moieties may be optionally acetyl substituted.

Suitably $R_3$ is selected from H, F, $OCH_3$, $OCH_2CH_3$ and $OCH_2Ph$.

More suitably $R_3$ is selected from F, $OCH_3$ and $OCH_2CH_3$.

More suitably $R_3$ is $OCH_3$.

$R_4$

Suitably $R_4$ is selected from phenylene, cyclopentanylene, cyclohexanylene, pyrrolylene, N-methylpyrrolylene, furanylene, thiophenylene, N-methylimidazolylene, imidazolylene, pyrazolylene, pyridazinylene, pyrimidinylene, pyrazinylene, triazolylene, triazinylene, tetrazolylene, oxazolylene, isoxazolylene, isoxazinylene, oxatriazolylene, oxadiazolylene, thiazolylene, isothiazolylene, thiadiazolylene, pyridinylene, indolylene, isoindolylene, indolizinylene, isoindolinylene, N-methylindolylene, benzofuranylene, isobenzofuranylene, benzothiophenylene, benzimidazolylene, N-methylbenzoimidazolylene, indazolylene, benzoxazolylene, isobenzoxazolylene, benzodioxazolylene, benzothiazolylene, benzofurazanylene, benzothiadiazolylene, benzotriazolylene, purinylene, pyrrolidinylene, pyrrolinylene, tetrahydrofuranylene, dihydrofuranylene, tetrahydropyranylene, dihydropyranylene, pyranylene, tetrahydrothiophenylene, tetrahydrothiopyranylene, imidazolidinylene, pyrazolidinylene, oxazolidinylene, isoxazolidinylene, oxazinylene, thiazolinylene, thiazolidinylene, isothiazolidinylene, piperidinylene, dihydropyridinylene, tetrahydropyridinylene, oxanylene, thianylene, pipazinylene, morpholinylene and thiomorpholinylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitably $R_4$ is selected from phenylene, cyclopentanylene, cyclohexanylene, pyrrolylene, N-methylpyrrolylene, furanylene, thiophenyenel, N-methylimidazolylene, imidazolylene, triazolylene, oxazolylene, oxadiazolylene, thiazolylene, pyridinylene, indolylene, N-methylindolylene, benzofuranylene, benzothiophenylene, benzimidazolylene, N-methylbenzoimidazolylene, benzoxazolylene, benzothiazolylene, pyrrolidinylene, tetrahydrofuranylene, tetrahydrothiphenylene, imidazolidinylene, pyrazolidinylene, oxazolidinylene, isoxazolidinylene, thiazolidinylene, isothiazolidinylene, piperidinylene, oxanylene, thianylene, pipazinylene, morpholinylene and thiomorpholinylene groups, these groups are optionally substituted with up to three optional substituent groups each independently selected from OH, $C_{1-6}$ alkyl, $OC_{1-6}$ alkyl, $(CH_2)_j$—$CO_2R_{10}$ and $(CH_2)_j$—$NR_{10}R_{11}$.

In one aspect, $R_4$ is selected from phenylene, cyclopentanylene, cyclohexanylene and 5-membered heteroarylene groups optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitably $R_4$ is selected from phenylene, cyclopentanylene, cyclohexanylene, pyrrolylene, N-methylpyrrolylene, furanylene, thiophenylene, N-methylimidazolylene, imidazolylene, triazolylene, oxazolylene, oxadiazolylene and thiazolylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

$R_5$

Suitably $R_5$ is selected from phenylene, cyclopentanylene, cyclohexanylene, pyrrolylene, N-methylpyrrolylene, furanylene, thiophenylene, N-methylimidazolylene, imidazolylene, pyrazolylene, pyridazinylene, pyrimidinylene, pyrazinylene, triazolylene, triazinylene, tetrazolylene, oxazolylene, isoxazolylene, isoxazinylene, oxatriazolylene, oxadiazolylene, thiazolylene, isothiazolylene, thiadiazolylene, pyridinylene, indolylene, isoindolylene, indolizinylene, isoindolinylene, N-methylindolylene, benzofuranylene, isobenzofuranylene, benzothiophenylene, benzimidazolylene, N-methylbenzoimidazolylene, indazolylene, benzoxazolylene, isobenzoxazolylene, benzodioxazolylene, benzothiazolylene, benzofurazanylene, benzothiadiazolylene, benzotriazolylene, purinylene, pyrrolidinylene, pyrrolinylene, tetrahydrofuranylene, dihydrofuranylene, tetrahydropyranylene, dihydropyranylene, pyranylene, tetrahydrothiophenylene, tetrahydrothiopyranylene, imidazolidinylene, pyrazolidinylene, oxazolidinylene, isoxazolidinylene, oxazinylene, thiazolinylene, thiazolidinylene, isothiazolidinylene, piperidinylene, dihydropyridinylene, tetrahydropyridinylene, oxanylene, thianylene, pipazinylene, morpholinylene and thiomorpholinylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitably $R_5$ is selected from phenylene, cyclopentanylene, cyclohexanylene, pyrrolylene, N-methylpyrrolylene, furanylene, thiophenyenel, N-methylimidazolylene, imidazolylene, triazolylene, oxazolylene, oxadiazolylene, thiazolylene, pyridinylene, indolylene, N-methylindolylene, benzofuranylene, benzothiophenylene, benzimidazolylene, N-methylbenzoimidazolylene, benzoxazolylene, benzothiazolylene, pyrrolidinylene, tetrahydrofuranylene, tetrahydrothiphenylene, imidazolidinylene, pyrazolidinylene, oxazolidinylene, isoxazolidinylene, thiazolidinylene, isothiazolidinylene, piperidinylene, oxanylene, thianylene, pipazinylene, morpholinylene and thiomorpholinylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

In one aspect, $R_5$ is selected from phenylene, cyclopentanylene, cyclohexanylene and 9-membered heteroarylene groups optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitably $R_5$ is selected from phenylene, cyclopentanylene, cyclohexanylene, indolylene, N-methylindolylene, benzofuranylene, benzothiophenylene, benzimidazolylene, N-methylbenzoimidazolylene, benzoxazolylene and benzothiazolylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

$R_6$

Suitably $R_6$ is selected from phenylene, cyclopentanylene, cyclohexanylene, pyrrolylene, N-methylpyrrolylene, furanylene, thiophenylene, N-methylimidazolylene, imidazolylene, pyrazolylene, pyridazinylene, pyrimidinylene, pyrazinylene, triazolylene, triazinylene, tetrazolylene, oxazolylene, isoxazolylene, isoxazinylene, oxatriazolylene, oxadiazolylene, thiazolylene, isothiazolylene, thiadiazolylene, pyridinylene, indolylene, isoindolylene, indolizinylene, isoindolinylene, N-methylindolylene, benzofuranylene, isobenzofuranylene, benzothiophenylene, benzimidazolylene, N-methylbenzoimidazolylene, indazolylene, benzoxazolylene, isobenzoxazolylene, benzodioxazolylene, benzothiazolylene, benzofurazanylene, benzothiadiazolylene, benzotriazolylene, purinylene, pyrrolidinylene, pyrrolinylene, tetrahydrofuranylene, dihydrofuranylene, tetrahydropyranylene, dihydropyranylene, pyranylene, tetrahydrothiophenylene, tetrahydrothiopyranylene, imidazolidinylene, pyrazolidinylene, oxazolidinylene, isoxazolidinylene, oxazinylene, thiazolinylene, thiazolidinylene, isothiazolidinylene, piperidinylene, dihydropyridinylene, tetrahydropyridinylene, oxanylene, thianylene, pipazinylene, morpholinylene and thiomorpholinylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitably $R_6$ is selected from phenylene, cyclopentanylene, cyclohexanylene, pyrrolylene, N-methylpyrrolylene, furanylene, thiophenyenel, N-methylimidazolylene, imidazolylene, triazolylene, oxazolylene, oxadiazolylene, thiazolylene, pyridinylene, indolylene, N-methylindolylene, benzofuranylene, benzothiophenylene, benzimidazolylene, N-methylbenzoimidazolylene, benzoxazolylene, benzothiazolylene, pyrrolidinylene, tetrahydrofuranylene, tetrahydrothiphenylene, imidazolidinylene, pyrazolidinylene, oxazolidinylene, isoxazolidinylene, thiazolidinylene, isothiazolidinylene, piperidinylene, oxanylene, thianylene, pipazinylene, morpholinylene and thiomorpholinylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

In one aspect, $R_6$ is selected from phenylene, cyclopentanylene, cyclohexanylene and 9-membered heteroarylene groups optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitably $R_6$ is selected from phenylene, cyclopentanylene, cyclohexanylene, indolylene, N-methylindolylene, benzofuranylene, benzothiophenylene, benzimidazolylene, N-methylbenzoimidazolylene, benzoxazolylene and benzothiazolylene groups, these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

$R_7$

Suitably a nitrogen atom of $R_7$ is directly attached to $X_4$.

Suitably $R_7$ is selected from $N(C_{1-6}$ alkyl$)(C_{1-6}$ alkyl$)$, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl groups, a monosaccharide moiety and an amino monosaccharide moiety wherein these nitrogen-containing heterocyclyl groups are optionally substituted with up to three optional substituent groups each independently selected from OH, $C_{1-6}$ alkyl, $OC_{1-6}$ alkyl, halogen, $(CH_2)_k$—$CO_2R_{12}$, $(CH_2)_k$—$NR_{12}R_{13}$ and a prodrug moiety, and wherein the monosaccharide and amino monosaccharide moieties may be optionally acetyl substituted.

More suitably, when a prodrug moiety is present as a substituent group of $R_7$ there is only one prodrug moiety. More suitably, when present the prodrug moiety is attached to the nitrogen-containing heterocycle via a nitrogen of the heterocycle.

In one aspect, suitably $R_7$ is a monosaccharide moiety and an amino monosaccharide moiety wherein the monosaccharide and amino monosaccharide moieties may be optionally acetyl substituted.

Suitably $R_7$ is selected from $N(C_{1-3}$ alkyl$)(C_{1-3}$ alkyl), pyrrolidinyl, imidazolidinyl, pyrazolidinyl, oxazolidinyl, thiazolidinyl, piperidinyl, piperazinyl, morpholinyl and thiomorpholinyl groups, these groups are optionally substituted with up to three optional substituent groups each independently selected from OH, $C_{1-6}$ alkyl, $OC_{1-6}$ alkyl, halogen, $(CH_2)_k$—$CO_2R_{12}$, $(CH_2)_k$—$NR_{12}R_{13}$ and a prodrug moiety.

Suitably $R_7$ is selected from $N(C_{1-2}$ alkyl$)(C_{1-2}$ alkyl), piperidinyl, piperazinyl, morpholinyl and thiomorpholinyl groups, these groups are optionally substituted with up to three optional substituent groups each independently selected from OH, $C_{1-6}$ alkyl, $OC_{1-6}$ alkyl, halogen, $(CH_2)_k$—$CO_2R_{12}$ and $(CH_2)_k$—$NR_{12}R_{13}$.

More suitably for $R_7$ the up to three optional substituent groups are each independently selected from OH, $C_{1-6}$ alkyl, $OC_{1-6}$ alkyl, halogen and $(CH_2)_k$—$NR_{12}R_{13}$.

$R_8$ and $R_9$ $R_8$ and $R_9$ either together form a double bond, or are selected from H and $OR_{14}$, or $R_8$ is a prodrug moiety and $R_9$ is $OR_{14}$; wherein $R_{14}$ is selected from H, $C_{1-6}$ alkyl and tetrahydro-2H-pyran-2-yl. Hence, $R_8$ and $R_9$ together with the ring nitrogen and the ring carbon to which they are attached can form an imine bond, a carbinolamine (when $R_8$ is H or a prodrug moiety and $R_9$ is OH), a carbinolamine alkyl ether (when $R_8$ is H or a prodrug moiety and $R_9$ is $OC_{1-6}$ alkyl), or a carbinolamine tetrahydro-2H-pyran-2-yl ether (when $R_8$ is H or a prodrug moiety and $R_9$ is O-tetrahydro-2H-pyran-2-yl).

Suitably $R_8$ and $R_9$ either together form a double bond; or $R_8$ is H and $R_9$ is selected from OH, O—$CH_3$ and O—$CH_2CH_3$; or $R_8$ is a prodrug moiety and $R_9$ is selected from OH, O—$CH_3$, O—$CH_2CH_3$ and O-tetrahydro-2H-pyran-2-yl.

More suitably, when $R_9$ is O-tetrahydro-2H-pyran-2-yl then $R_8$ is a prodrug moiety that is eliminated by nitroreductase. Suitably, in this aspect, $R_8$ comprises a nitrobenzyl group. More suitably, in this aspect, $R_8$ is:

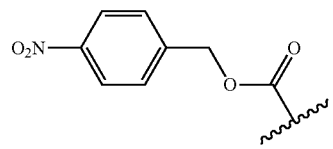 [SMILES: *C(=O)OCc1ccc([N+](=O)[O-])cc1]

More suitably, $R_8$ and $R_9$ together form a double bond.

Monosaccharide Moiety and/or Amino Monosaccharide Moiety

Suitably, the monosaccharide moiety and/or amino monosaccharide moiety is derived from arabinose, fructose, galactose, glucose, mannose, ribose, xylose and deoxy derivatives thereof, wherein the monosaccharide and/or amino monosaccharide moieties may be optionally acetyl substituted.

Suitably, where the monosaccharide moiety and/or amino monosaccharide moiety is optionally acetyl substituted it comprises 1, 2, 3 or 4 acetyl substituents, wherein each acetyl substituent replaces a hydrogen of a hydroxyl groups.

More suitably, all of the hydrogens of hydroxyl groups have been replaced with acetyl substituents.

More suitably, the monosaccharide moiety and/or amino monosaccharide moiety are selected from:

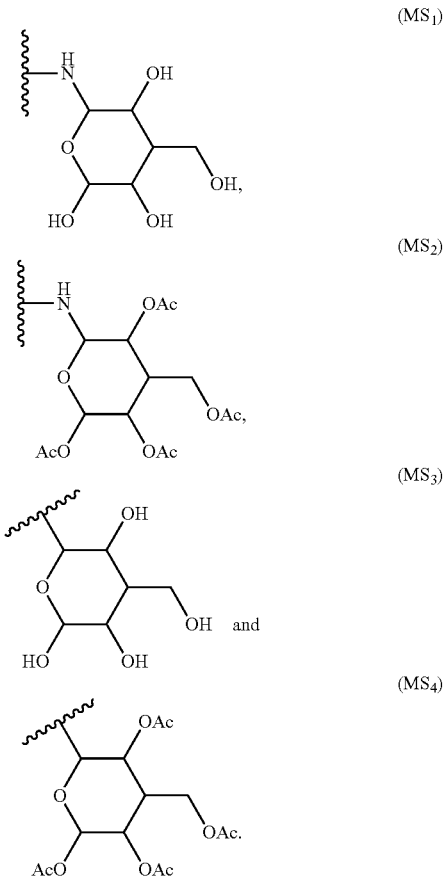

More suitably, the monosaccharide moiety and/or amino monosaccharide moiety is (MS1) or (MS2).

Prodrug Moiety

Prodrugs are well-known in the art (43, 44, 45 & 46) and are masked forms of active drugs that need to be transformed before exhibiting their pharmacological action. Typically, they are designed to be activated after an enzymatic or chemical reaction once they have been administered into the body. Activation of prodrugs typically involves the elimination of a prodrug moiety to release the drug. Prodrugs are considered to be inactive or at least significantly less active than the released drugs.

Suitably, the prodrug moiety is a moiety capable of being eliminated by an enzyme having peptidase, reductase or lactamase activity. Suitably, the prodrug moiety is a moiety capable of being eliminated by an enzyme having aminopeptidase, nitroreductase or beta-lactamase activity. Suitably, the prodrug moiety is a moiety capable of being eliminated by an enzyme having aminopeptidase, nitroreductase or beta-lactamase activity. Elimination of the prodrug moiety produces an antibacterial agent suitable for treating a bacterial infection.

In some aspects, suitably, the compound of formula (I) comprises a prodrug moiety. Suitably, in these aspects, the compound of formula (I) comprises one prodrug moiety.

More suitably, each prodrug moiety independently comprises (i) a linker; and (ii) a terminating group that comprises an optionally substituted nitrobenzyl, cephalosporin, cephalosporin sulfoxide, cephalosporin sulfone or amino acid group.

Suitably, the optional substituents for the group (ii) may comprise 1, 2 or 3 optional substituents. Suitably, each optional substituent is independently selected from, OH, O—($C_{1-6}$ alkyl), $C_{1-6}$ alkyl, $NO_2$, C(=O)—$OR_{10}$, —$CH_2$—$R_{27}$, —CH($NH_2$)—$R_{27}$, —$CH_2$S—$R_{27}$, —$CH_2$S—$CF_3$ and —$CH_2$—CN and halo.

Suitably, with regard to the optional substituents each $R_{10}$ is selected from H and $C_{1-6}$ alkyl. Suitably, each $R_{27}$ is selected from phenyl and 5- to 9-membered heteroaryl wherein the phenyl and heteroaryl groups may be optionally substituted with 1, 2 or 3 substitutents independently selected from, OH, O—($C_{1-6}$ alkyl), $C_{1-6}$ alkyl and $NO_2$.

Suitably, the prodrug moiety comprises (i) a linker wherein the linker is a self-immolative linker or spacer or a —C(O)— connecting group. Self-immolative linkers or spacers are well-known in the art and have been reviewed (47).

Suitably, the prodrug moiety is -[linker]-[terminating group]

Suitably, each linker (i) is selected from:

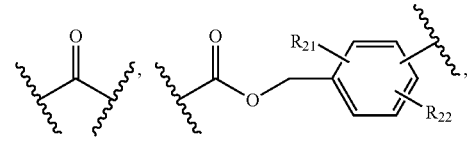

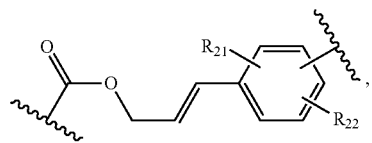

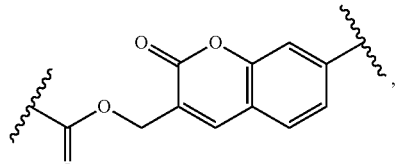

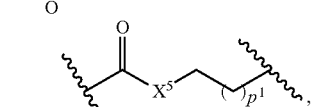

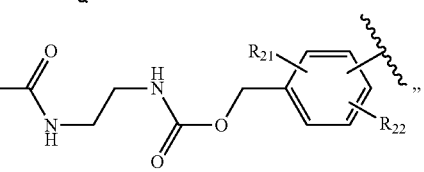

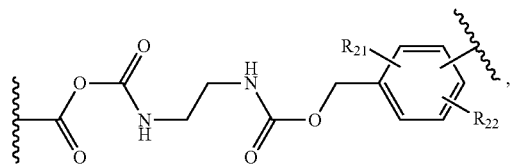

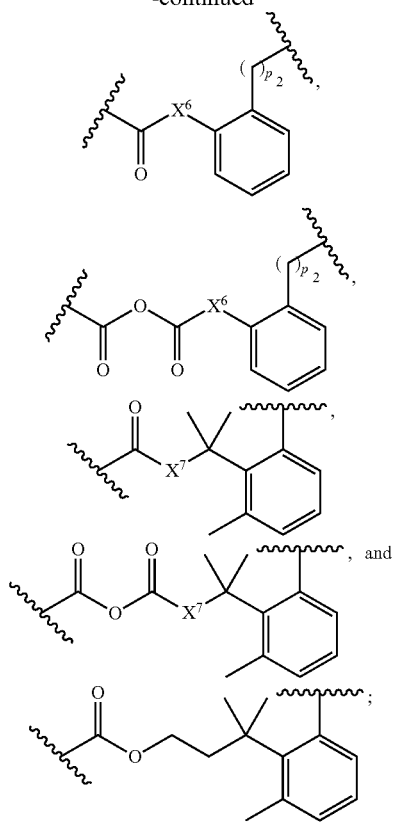

wherein each $R_{21}$ and $R_{22}$ are independently selected from H, OH, O—($C_{1-6}$ alkyl), $C_{1-6}$ alkyl and $NO_2$;

$X^5$ is $CH_2$, O or NH;

$p^1$ is an integer selected from 1 and 2;

$p^2$ is an integer selected from 0, 1 and 2;

$X^6$ is $CH_2$, O, NH or is absent; with the proviso that if $X^6$ is absent then $p^2$ is an integer selected from 1 and 2; and $X^7$ is $CH_2$, O, NH or is absent.

Suitably for each of the above linkers the terminating group of the prodrug moiety is attached on the right hand side of each of the above linker structures, to the bond ending in a zig-zag line. The rest of the PBD molecule is attached to the left hand side of each of the above linker structures.

Some of the above structure are drawn without specifying the positions on the phenyl ring of the $R_{21}$ or $R_{22}$ groups (shown by the bond going to the centre of the phenyl ring) or of the bond where the phenyl ring is attached to the rest of the molecule. Suitably, these linkers are attached to the rest of the compound of formula (I) by the carbonyl group, and is attached to the group (ii) of the prodrug moiety by the bond from the phenyl ring or the opposite end of the molecule to the carbonyl group.

Suitably, the linker:

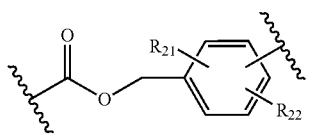

is selected from:

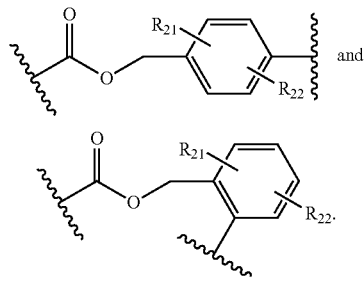 and

Suitably, the linker:

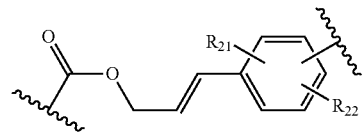

is selected from:

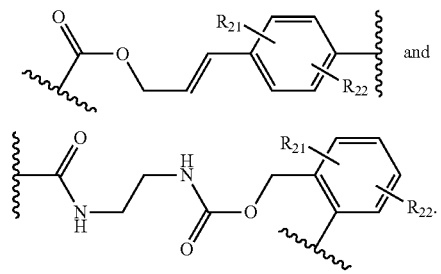 and

More suitably, each $R_{21}$ and $R_{22}$ are independently selected from H, OH, $OCH_3$, $OCH_2CH_3$, $CH_3$, $CH_2CH_3$ and $NO_2$.

More suitably, $R_{21}$ and $R_{22}$ is H.

More suitably, each linker is selected from:

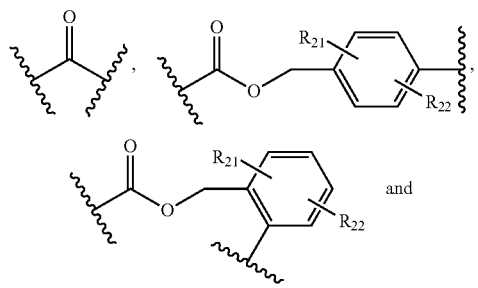 and

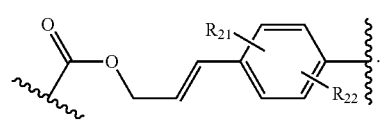

In one aspect, more suitably, each linker is:

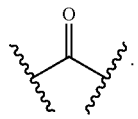

Suitably, each terminating group (ii) comprises optionally substituted nitrobenzyl, cephalosporin, cephalosporin sulfoxide, cephalosporin sulfone or amino acid groups are selected from:

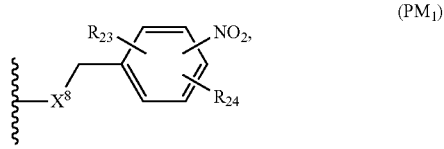 (PM$_1$)

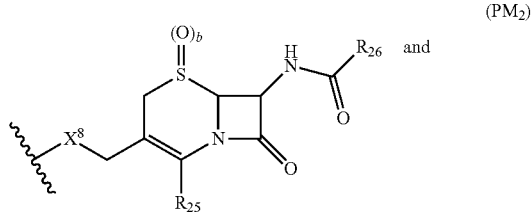 (PM$_2$)

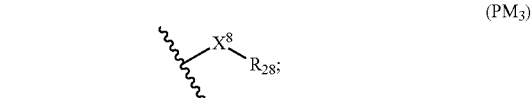 (PM$_3$)

wherein:
each $X^8$ is selected from O, NH, $NCH_3$ and S;
each $R_{23}$ and $R_{24}$ are independently selected from H, OH, O—($C_{1-6}$ alkyl), $C_{1-6}$ alkyl and $NO_2$;
each $R_{25}$ is selected from H and C(=O)—$OR_{10}$;
b is 0, 1 or 2;
each $R_{26}$ is selected from —$CH_2$—$R_{27}$, —CH($NH_2$)—$R_{27}$, —$CH_2S$—$R_{27}$, —$CH_2S$—$CF_3$ and —$CH_2$—CN;
each $R_{27}$ is selected from phenyl and 5- to 9-membered heteroaryl wherein the phenyl and heteroaryl groups may be optionally substituted with 1, 2 or 3 substitutents independently selected from halo, OH, O—($C_{1-6}$ alkyl), $C_{1-6}$ alkyl and $NO_2$; and
$R_{28}$ is an amino acid.

More suitably, each $X^8$ is selected from O and NH.

Suitably, each group (ii), or each (PM1) is:

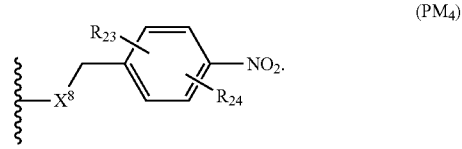 (PM$_4$)

More suitably, each group (ii), or each (PM1) is:

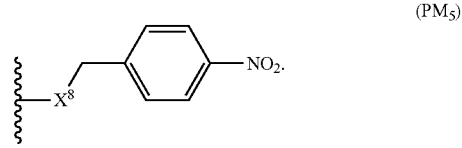 (PM$_5$)

More suitably for (PM1), (PM4) or (PM5), $X^8$ is O.

Suitably, each $R_{23}$ and $R_{24}$ are independently selected from H, OH, $OCH_3$, $OCH_2CH_3$ $CH_3$, $CH_2CH_3$ and $NO_2$. More suitably, each $R_{23}$ and $R_{24}$ are independently selected from H and $NO_2$. Most suitably, each $R_{23}$ and $R_{24}$ are H.

For (PM2) when b is 0, 1 or 2 then the structure may be represented as (PM6), (PM7) and (PM8) respectively:

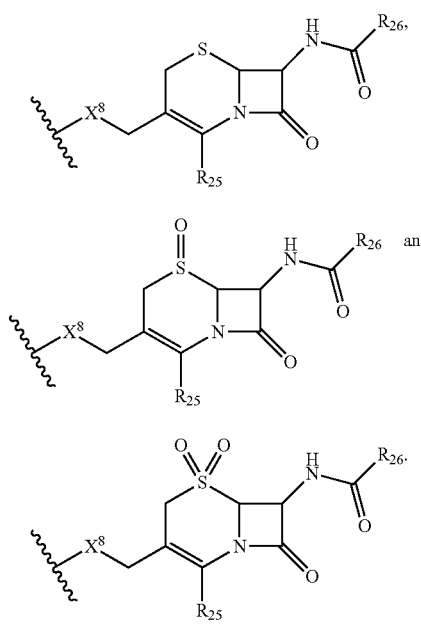

Suitably, b is 0 or 1. More suitably, b is 0.

More suitably for (PM2), (PM6), (PM7) or (PM8), $X^8$ is O.

Suitably, each terminating group (ii), or each (PM2) is (PM6) or (PM7). More suitably, each terminating group (ii), or each (PM2) is (PM6).

Suitably, each $R_{25}$ is selected from H, C(=O)—OH and C(=O)—$OCH_3$. More suitably, each $R_{25}$ is H or C(=O)—OH.

Suitably, each $R_{26}$ is selected from —$CH_2$—$R_{27}$ and —CH($NH_2$)—$R_{27}$. More suitably, each $R_{26}$ is —$CH_2$—$R_{27}$.

Suitably each $R_{27}$ is selected from phenyl, thiophenyl, furanyl, pyrrolyl, imidazolyl, tetrazolyl and pyridyl wherein the phenyl and heteroaryl groups may be optionally substituted with 1, 2 or 3 substitutents independently selected from halo, OH, O—($C_{1-6}$ alkyl), $C_{1-6}$ alkyl and $NO_2$.

More suitably, each $R_{27}$ is selected from phenyl, thiophenyl and pyridyl wherein the phenyl and heteroaryl groups may be optionally substituted with 1, 2 or 3 substitutents independently selected from Cl, OH, $OCH_3$, $OCH_2CH_3$, $CH_3$ and $CH_2CH_3$.

More suitably, each $R_{27}$ is phenyl or thiophenyl wherein the phenyl and heteroaryl groups may be optionally substituted with 1, 2 or 3 substitutents independently selected from Cl, OH, $OCH_3$, $OCH_2CH_3$, $CH_3$ and $CH_2CH_3$.

Suitably, the carboxyl group of the amino acid of $R_{28}$ connects to the N of (PM3) by the C-terminus of the amino acid or may be derived from a carboxyl group of an amino acid side chain, for example, a glutamic acid amino acid side chain.

Suitably, $R_{28}$ is an amino acid selected from alanine, argenine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

More suitably for (PM3), $X^8$ is NH.

Suitably, each group (ii), or each ($PM_3$) is:

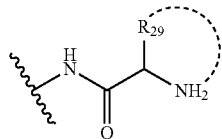

wherein $R_{29}$ represents the side chain of the amino acid. The dotted line represents the fact that the side chain may form a ring with the terminal nitrogen as is the case for proline. Hence, $R_{29}$ may be selected from $CH_3$, $(CH_2)_3$—NH—C(=$NH_2$)—$NH_2$, $CH_2$—C(=O)—$NH_2$, $CH_2$—C(=O)—OH, $CH_2$—SH, $(CH_2)_2$—C(=O)—$NH_2$, $(CH_2)_2$—C(=O)—OH, H, $CH_2$-(imidazolyl), CH($CH_3$)—$CH_2CH_3$, $CH_2CH(CH_3)_2$, $(CH_2)_4$—$NH_2$, $(CH_2)_2$—S—$CH_3$, $CH_2Ph$, $CH_2$—OH, CH(OH)$CH_3$, $CH_2$-(imidolyl), $CH_2$-p-Ph-OH and CH($CH_3$)$_2$, or $R_{29}$ the carbon to which it is attached and the adjacent terminal nitrogen form a pyrrolidinyl ring.

More suitably, each terminating group (ii) is (PM5), (PM6) or (PM9).

$R_{10}$, $R_{11}$, $R_{12}$, $R_{13}$, $R_{15}$, $R_{16}$, $R_{17}$ and $R_{18}$ Suitably each $R_{10}$, $R_{11}$, $R_{12}$, $R_{13}$, $R_{15}$, $R_{16}$, $R_{17}$ and $R_{18}$ are independently selected from H, methyl, ethyl, n-propyl, i-propyl, n-butyl, s-butyl, i-butyl and t-butyl.

Suitably each $R_{10}$, $R_{11}$, $R_{12}$, $R_{13}$, $R_{15}$, $R_{16}$, $R_{17}$ and $R_{18}$ are independently selected from H, methyl, and ethyl.

$R_{14}$

In one aspect, where $R_8$ is a prodrug moiety that is eliminated by nitroreductase, suitably, $R_{14}$ is selected from H, methyl, ethyl and tetrahydro-2H-pyran-2-yl. More suitably, in this aspect, $R_{14}$ is selected from H and tetrahydro-2H-pyran-2-yl.

Suitably, $R_{14}$ is selected from H, methyl, ethyl, n-propyl, i-propyl, n-butyl, s-butyl, i-butyl and t-butyl. More suitably $R_{14}$ is selected from H, methyl, and ethyl.

j

Each instance of j is independently selected from an integer from 0 to 6, hence, each j is independently selected from 0, 1, 2, 3, 4, 5 and 6.

Suitably each j is independently selected from 0, 1, 2 and 3.

More suitably each j is independently selected from 0 and 1.

More suitably each j is 0.

k Each instance of k is independently selected from an integer from 0 to 6, hence, each k is independently selected from 0, 1, 2, 3, 4, 5 and 6.

Suitably each k is independently selected from 0, 1, 2 and 3.

More suitably each k is 0.

m

Suitably m is 0.

n, p, q, s and t n, p, q, s and t are each independently selected from an integer from 0 to 6; hence, n, p, q, s and t are each independently selected from 0, 1, 2, 3, 4, 5 and 6.

Suitably n, p, q, s and t are each independently selected from 0, 1, 2 and 3.

More suitably n, p, q, s and t are each independently selected from 0 and 1.

v v is selected from an integer from 1 to 6; hence, v is selected from 1, 2, 3, 4, 5 and 6.

More suitably v is selected from 1, 2 and 3. More suitably v is 1.

X

X may be an ether, amide or ester bond that links L to the aromatic ring of the PBD in either direction. Thus, when X is selected from $(CR_{15}R_{16})_nO$, $C(O)NR_{15}$ and $O-C(O)$ then L is linked to the aromatic ring of the PBD as follows: L-$(CR_{15}R_{16})_nO$—Ar, L-$C(O)NR_{15}$—Ar and L-O—C(O)—Ar. Similarly, when X is selected from $O(CR_{15}R_{16})_n$, $NR_{15}C(O)$ and $C(O)$—O then X links L to the aromatic ring as follows: L-$O(CR_{15}R_{16})_n$—Ar, L-$NR_{15}C(O)$—Ar and L-C(O)—O—Ar.

Suitably X is selected from $(CH_2)_nO$, $O(CH_2)_n$, O, S, NH, $CH_2$, $C(O)$, $C(O)NR_{15}$, $NR_{15}C(O)$, O—C(O) and C(O)—O.

Suitably, X is selected from O, C(O), $C(O)NR_{15}$ and $NR_{15}C(O)$.

More suitably X is selected from O, C(O)NH and NHC(O). More suitably X is O.

$X_1$ $X_1$ may be an ether or an amide bond that links $R_4$ to L in either direction. Thus, when $X_1$ is selected from $(CH_2)_pO$ and NHC(O) then $R_4$ is linked to L as follows: $R_4$—$(CH_2)_pO$-L and $R_4$—NHC(O)-L. Similarly, when $X_1$ is selected from $O(CH_2)_p$ and C(O)NH then $R_4$ is linked to L as follows: $R_4$—$O(CH_2)_p$-L and $R_4$—C(O)NH-L.

Suitably $X_1$ is selected from NHC(O) and C(O)NH.

More suitably $X_1$ is NHC(O). That is $X_1$ links $R_4$ to L as follows: —$R_4$—NHC(O)-L-.

$X_2$ $X_2$ may be an ether or an amide bond that links $R_5$ to $R_4$ in either direction. Thus, when $X_2$ is selected from $(CH_2)_qO$ and NHC(O) then $R_5$ is linked to $R_4$ as follows: $R_5$—$(CH_2)_qO$—$R_4$ and $R_5$—NHC(O)—$R_4$. Similarly, when $X_2$ is selected from $O(CH_2)_q$ and C(O)NH then $R_5$ is linked to $R_4$ as follows: $R_5$—$O(CH_2)_q$—$R_4$ and $R_5$—C(O)NH—$R_4$.

Suitably $X_2$ is selected from NHC(O) and C(O)NH.

More suitably $X_2$ is NHC(O). That is $X_2$ links $R_5$ to $R_4$ as follows: —$R_5$—NHC(O)—$R_4$—.

$X_3$ $X_3$ may be an ether or an amide bond that links $R_6$ to $R_5$ in either direction. Thus, when $X_3$ is selected from $(CH_2)_sO$ and NHC(O) then $R_6$ is linked to $R_5$ as follows: $R_6$—$(CH_2)_sO$—$R_5$ and $R_6$—NHC(O)—$R_5$. Similarly, when $X_3$ is selected from $O(CH_2)_s$ and C(O)NH then $R_6$ is linked to $R_5$ as follows: $R_6$—$O(CH_2)_s$—$R_5$ and $R_6$—C(O)NH—$R_5$.

Suitably $X_3$ is selected from NHC(O) and C(O)NH or is absent.

More suitably $X_3$ is NHC(O). That is $X_3$ links $R_6$ to $R_5$ as follows: —$R_6$—NHC(O)—$R_5$—.

$X_4$ $X_4$ may be an ether or an amide bond that links the end group $R_7$ to the rest of the molecule in either direction. Thus, when $X_4$ is selected from $(CH_2)_tO$ and NHC(O) then $R_7$ is linked to the rest of the molecule as follows: $R_7$—$(CH_2)_tO$— and $R_7$—NHC(O)—. Similarly, when $X_4$ is selected from $O(CH_2)_v$ and C(O)NH then $R_7$ is linked to the rest of the molecule as follows: $R_7$—$O(CH_2)_v$— and $R_7$—C(O)NH—.

Suitably $X_4$ is selected from $(CH_2)_tO$, C(O), NHC(O) and C(O)NH.

More suitably, $X_4$ is $(CH_2)_tO$ or C(O). Most suitably, $X_4$ is C(O).

L

Suitably L is selected from an alkylene chain containing from 1 to 11 carbon atoms, from 1 to 10 carbon atoms, from 1 to 9 carbon atoms, from 1 to 8 carbon atoms, from 1 to 7 carbon atoms, from 1 to 6 carbon atoms, from 1 to 5 carbon atoms, from 1 to 4 carbon atoms, from 1 to 3 carbon atoms.

More suitably, L may be selected from $CH_2$, $CH_2CH_2$, $CH_2CH_2CH_2$, $CH_2CH_2CH_2CH_2$ and $CH_2CH_2CH_2CH_2CH_2$.

Optional Double Bonds in the C-Ring

The present invention provides a compound of formula (I):

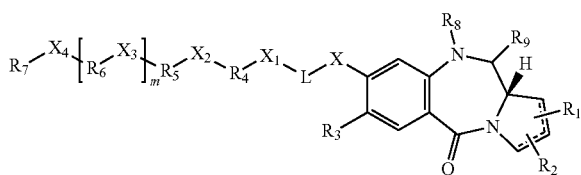

and salts and solvates thereof, wherein the dotted lines indicates the optional presence of a double bond between C1 and C2, or C2 and C3.

In one aspect, the compound of formula (I) and salts and solvates thereof, has a double bond between C1 and C2 to give a compound of formula (II):

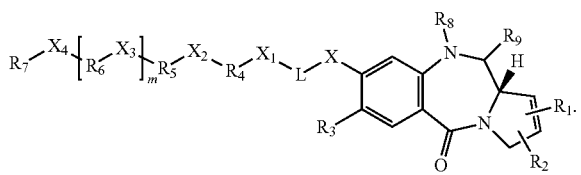

In another aspect, the compound of formula (I) and salts and solvates thereof, has a double bond between C2 and C3 to give a compound of formula (III):

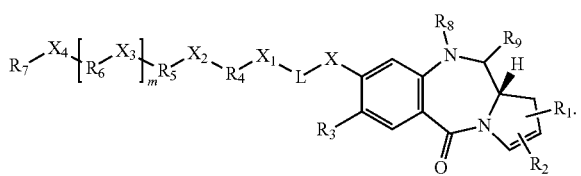

In another aspect, the compound of formula (I) and salts and solvates thereof, does not have any optional double bonds and is a compound of formula (IV):

(IV)

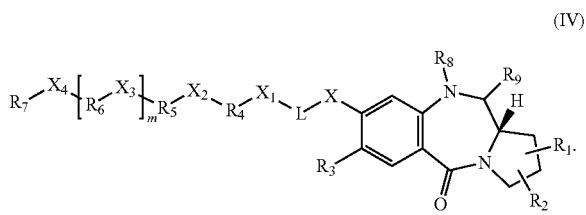

Provisos

The proviso that when $X_4$ is C(O)NH then the up to three optional substituents of $R_7$ are not selected from $(CH_2)_k$—$CO_2R_{12}$ can also be expressed as a proviso that when $X_4$ is C(O)NH then the up to three optional substituents of $R_7$ are each independently selected from OH, $C_{1-6}$ alkyl, $OC_{1-6}$ alkyl, halogen and $(CH_2)_k$—$NR_{12}R_{13}$.

The proviso that when $X_4$ is $(CH_2)_tO$ then $R_4$ is not phenylene, m is 1 and $R_6$ is not a 5- to 9-membered heteroarylene, means that $R_6$ must be present when $X_4$ is $(CH_2)_tO$. This proviso can alternatively be expressed as a proviso that when $X_4$ is $(CH_2)_tO$ then:
  $R_4$ is selected from cyclopentanylene, cyclohexanylene, 5- to 9-membered heteroarylene and 5- to 6-membered heterocyclylene groups, and these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$;
  m is 1; and
  $R_6$ is selected from phenylene, cyclopentanylene, cyclohexanylene and 5- to 6-membered heterocyclylene groups, and these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

The proviso that when with the proviso that when $X_4$ is C(O)NH or NHC(O) that $R_4$ and/or $R_6$ is not 5- to 9-membered heteroarylene may be alternatively expressed as a proviso that when $X_4$ is C(O)NH or NHC(O) then:
  $R_4$ is selected from phenylene, cyclopentanylene, cyclohexanylene and 5- to 6-membered heterocyclylene groups, and these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$; and/or
  $R_6$ is selected from phenylene, cyclopentanylene, cyclohexanylene and 5- to 6-membered heterocyclylene groups, and these groups are optionally substituted with up to three optional substituent groups each independently selected from OH, $C_{1-6}$ alkyl, $OC_{1-6}$ alkyl, halogen, $(CH_2)_j$—$CO_2R_{10}$ and $(CH_2)_j$—$NR_{10}R_{11}$.

Suitable Structures
The compound of formula (I):

(I)

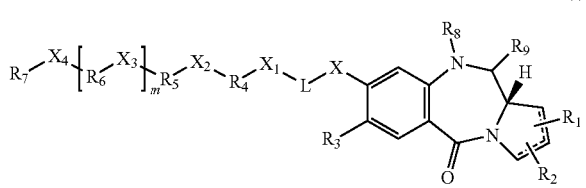

and salts and solvates thereof is drawn without specifying the position of $R_1$ and $R_2$ on the C-ring. Hence, $R_1$ and $R_2$ may be present on any position of the C-ring provided that the valence requirement are met. As the fused carbon and the nitrogen of the C-ring have all their substituents shown, this means that $R_1$ and $R_2$ may be present on any of the non-fused carbons of the C-ring [i.e. the C1, C2 or C3 positions of compounds of formula (I)]. Suitably $R_1$ and $R_2$ are present on two different non-fused carbons of the C-ring. Suitably the compound of formula (I) and salts and solvates thereof, is selected from:

(V)

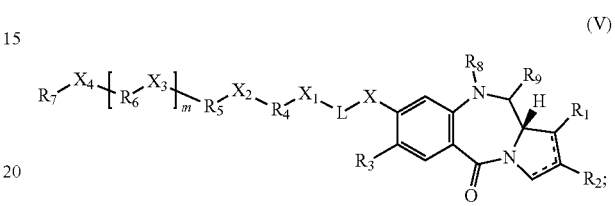

(VI)

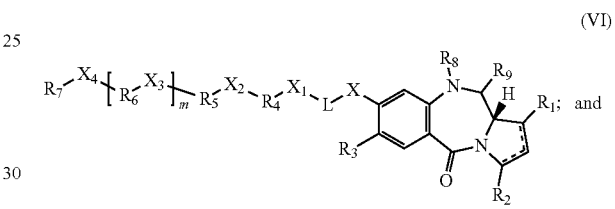

(VII)

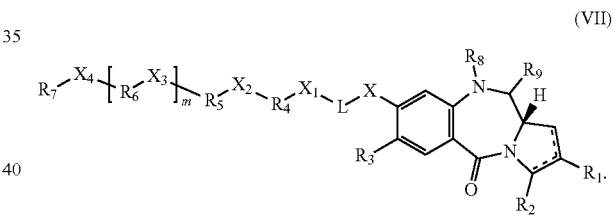

For the options where $R_1$ or $R_2$ is selected from =$CHR_{17}$ the carbon of the C-ring to which it is attached cannot have an optional double bond in order for the valence requirements of the molecule to be met. For example, for a compound of formula (I) where $R_1$ is =$CH_2$ positioned at the C1 position of the C-ring, adjacent to the fused carbon of the C-ring, and $R_2$ is H then the resulting compound of formula (I) may be represented as:

(VIII)

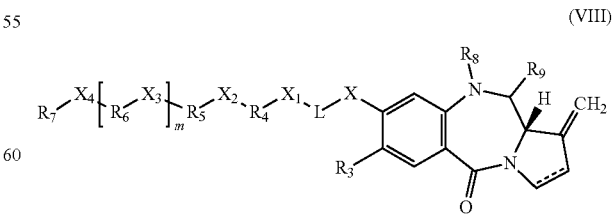

Suitably the compound of formula (I) and salts and solvates thereof, is a compound of formula (IX) or (X):

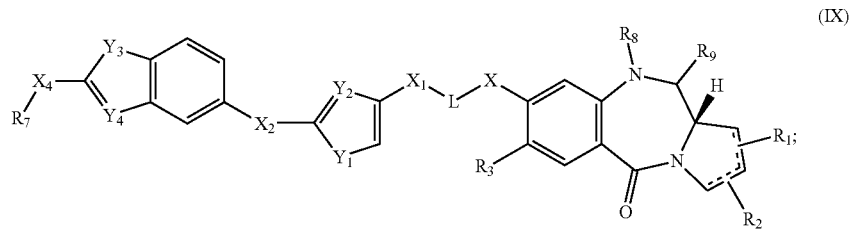

(IX)

wherein:
Y$_1$ is selected from NH, N(C$_{1-6}$ alkyl), S and O;
Y$_2$ is selected from CH, N, S and O;
Y$_3$ is selected from NH, N(C$_{1-6}$ alkyl), S and O; and
Y$_4$ is selected from CH, N, S and O.

Suitably the compound of formula (I), and salts and solvates thereof, is a compound of formula (X) or (XI):

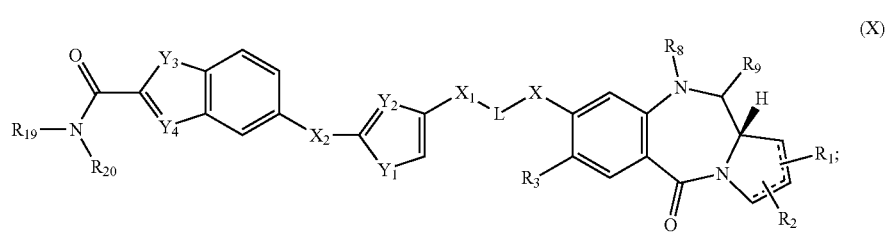

(X)

wherein:
Y$_1$ is selected from NH, N(C$_{1-6}$ alkyl), S and O;
Y$_2$ is selected from CH, N, S and O;
Y$_3$ is selected from NH, N(C$_{1-6}$ alkyl), S and O;
Y$_4$ is selected from CH, N, S and O; and
R$_{19}$ and R$_{20}$ are independently selected from C$_{1-6}$ alkyl, or are attached to each other and together form a group selected from —(CH$_2$)$_4$—; —(CH$_2$)$_5$—; —(CH$_2$)—O—(CH$_2$)$_2$—, —(CH$_2$)$_2$—O—(CH$_2$)$_2$—, —(CH$_2$)—NH—(CH$_2$)$_2$—, —(CH$_2$)$_2$—NH—(CH$_2$)$_2$—, —(CH$_2$)—N(C$_{1-6}$ alkyl)-(CH$_2$)$_2$—, —(CH$_2$)$_2$—N(C$_{1-6}$ alkyl)-(CH$_2$)$_2$—, —(CH$_2$)—S—(CH$_2$)$_2$— and —(CH$_2$)$_2$—S—(CH$_2$)$_2$—.

More suitably, R$_{19}$ and R$_{20}$ are independently selected from C$_{1-6}$ alkyl, or are attached to each other and together form a group selected from —(CH$_2$)$_4$—; —(CH$_2$)$_5$—; —(CH$_2$)—O—(CH$_2$)$_2$—, —(CH$_2$)$_2$—O—(CH$_2$)$_2$—, —(CH$_2$)—S—(CH$_2$)$_2$— and —(CH$_2$)$_2$—S—(CH$_2$)$_2$—.

For structures (IX) and/or (X):
Suitably Y$_1$ is selected from NH, N—CH$_3$ and N—CH$_2$CH$_3$.
More suitably Y$_1$ is N—CH$_3$.
Suitably Y$_2$ is selected from CH and N. More suitably, Y$_2$ is CH.
Suitably Y$_3$ is selected from NH, N—CH$_3$, N—CH$_2$CH$_3$, S and O.
More suitably, Y$_3$ is O.
Suitably Y$_4$ is selected from CH and N. More suitably, Y$_4$ is CH.

More suitably, the compound of formula (I), and salts and solvates thereof, is selected from:

(aa) (S)—N-(2-(dimethylcarbamoyl)benzo[b]thiophen-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

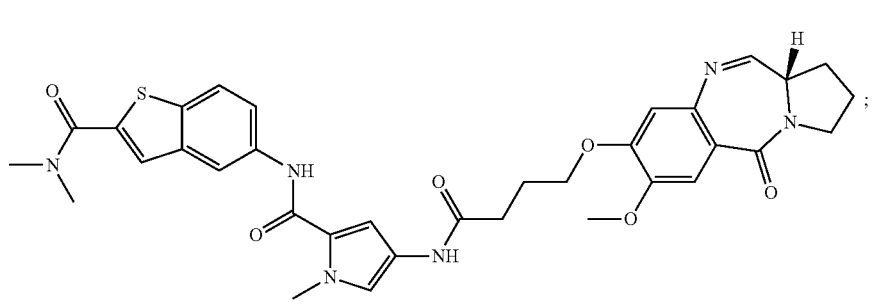

(KMR-14-33)

(ab) (S)-4-(4-((7-methoxy-5-oxo-2,3,5,11a-tetrahydro-1H-benzo-[e]pyrrolo[1,2-a][1,4]-diazepin-8-yl)oxy)butana-mido)-1-methyl-N-(2-(thiomorpholine-4-carbonyl)benzo-furan-5-yl)-1H-pyrrole-2-carboxamide

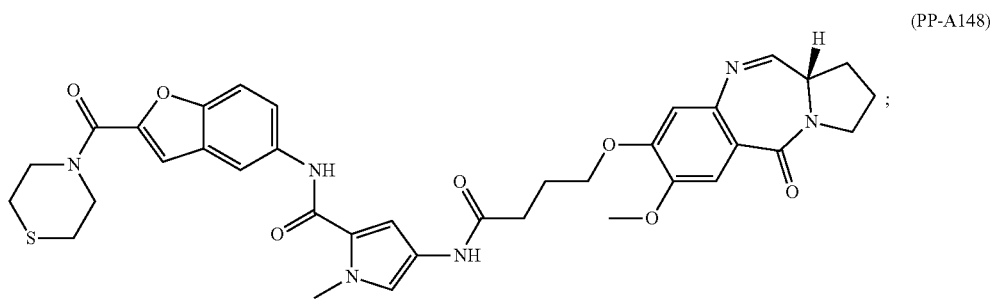

(PP-A148)

(ac) (S)-4-(4-((7-methoxy-5-oxo-2,3,5,11a-tetrahydro-1H-benzo[e]pyrrolo[1,2-a][1,4]-diazepin-8-yl)oxy)butana-mido)-1-methyl-N-(2-(morpholine-4-carbonyl)benzo-furan-5-yl)-1H-pyrrole-2-carboxamide

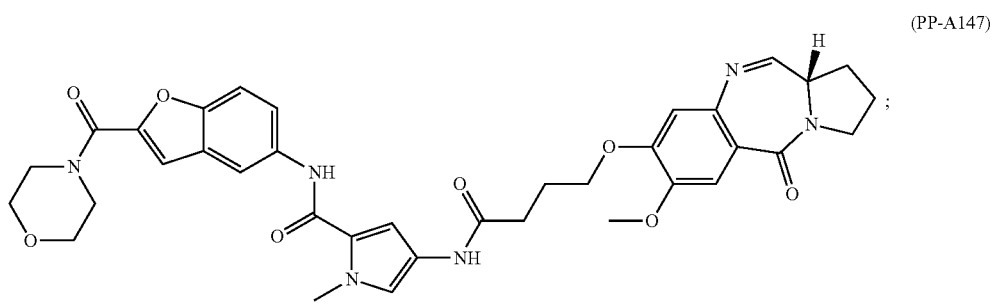 [SMILES: COc1cc2c(cc1OCCCC(=O)Nc1cc(C(=O)Nc3ccc4oc(C(=O)N5CCOCC5)cc4c3)n(C)c1)N=C[C@@H]1CCCN1C2=O]

(PP-A147)

(ad) (S)—N-(2-(dimethylcarbamoyl)benzofuran-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

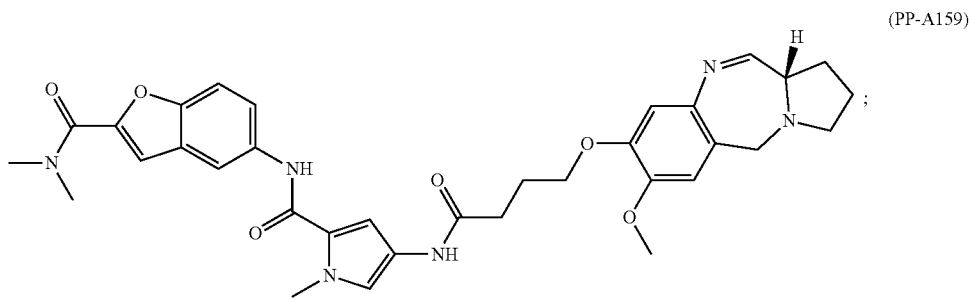 [SMILES: COc1cc2c(cc1OCCCC(=O)Nc1cc(C(=O)Nc3ccc4oc(C(=O)N(C)C)cc4c3)n(C)c1)N=C[C@@H]1CCCN1C2]

(PP-A159)

(ae) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(thiomorpholine-4-carbonyl)benzo-[b]thiophen-5-yl)-1H-pyrrole-2-carboxamide

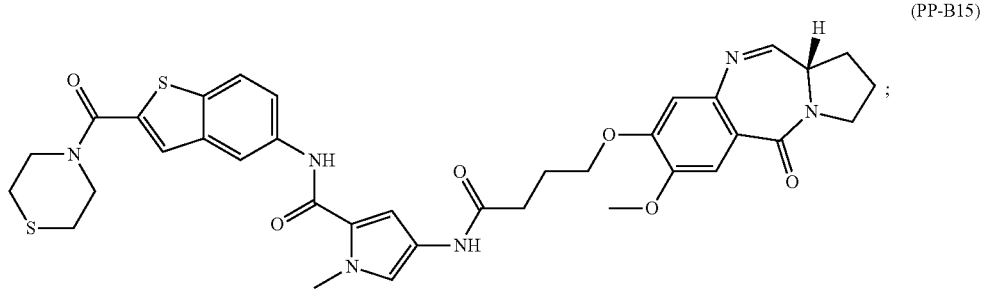 [SMILES: CCN(CC)C(=O)c1cc2cc(NC(=O)c3cc(NC(=O)CCCOc4cc5c(cc4OC)C(=O)N4CCC[C@H]4C=N5)cn3C)ccc2o1]

(PP-B15)

(af) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(2-(morpholine-4-carbonyl)benzo[b]-thiophen-5-yl)-1H-pyrrole-2-carboxamide

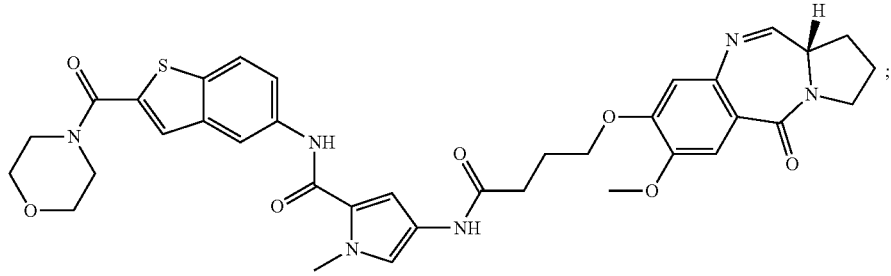

(PP-B16)

(ag) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(piperidine-1-carbonyl)benzo[b]-thiophen-5-yl)-1H-pyrrole-2-carboxamide

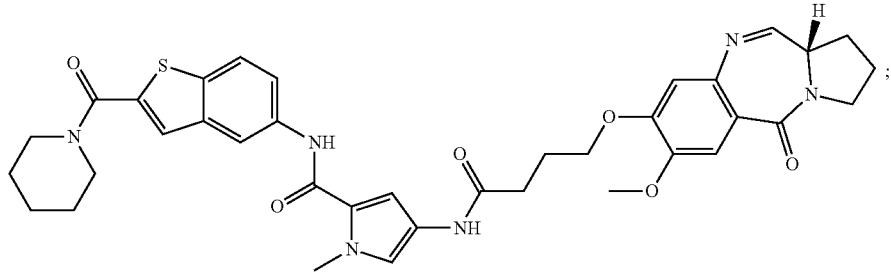

(PP-B22)

(ah) (S)-4-(4-((7-methoxy-5-oxo-2,3,5,11a-tetrahydro-1H-benzo-[e]pyrrolo[1,2-a][1,4]-diazepin-8-yl)oxy)butana-mido)-1-methyl-N-(2-(piperidine-1-carbonyl)benzo-furan-5-yl)-1H-pyrrole-2-carboxamide

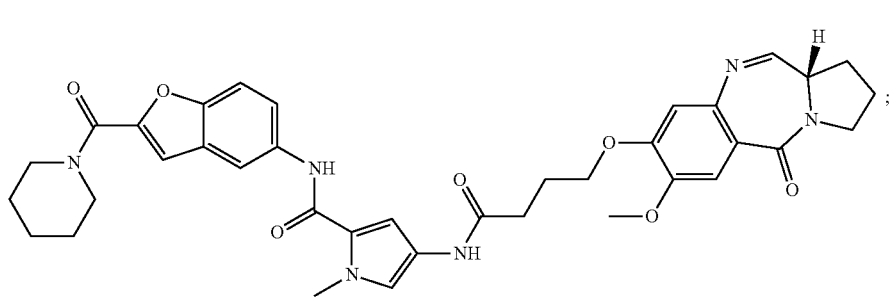

(PP-B26)

(ai) (S)—N-(2-(diethylcarbamoyl)benzofuran-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

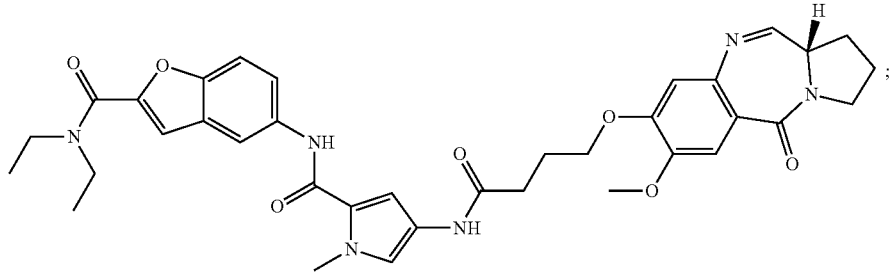

(PP-B27)

(aj) (S)—N-(2-(diethylcarbamoyl)benzo[b]thiophen-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

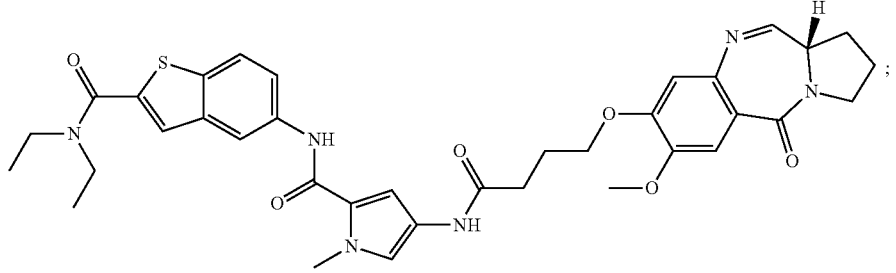

(PP-B28)

(ak) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(thio-morpholine-4-carbonyl)benzo-furan-5-yl)-1H-imidazole-2-carboxamide (PP-B52)

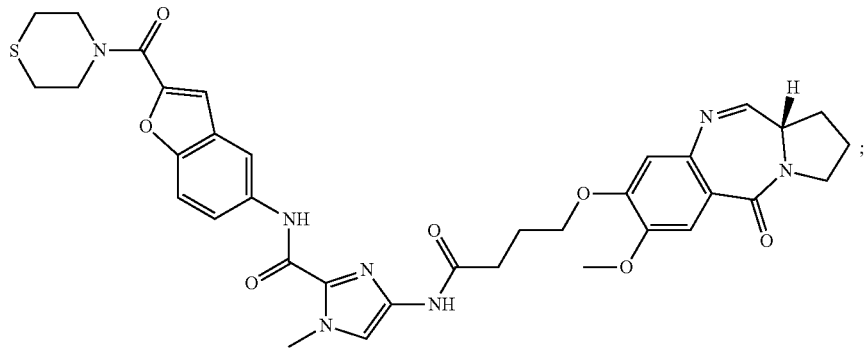

(al) (1S,4R)-4-(4-(((S)-7-methoxy-5-oxo-2,3,5,11a-tetrahydro-1H-benzo[e]pyrrolo[1,2-a][1,4]diazepin-8-yl)oxy)butanamido)-N-(2-(thio-morpholine-4-carbonyl)benzofuran-6-yl)cyclohexane-1-carboxamide (PP-B53)

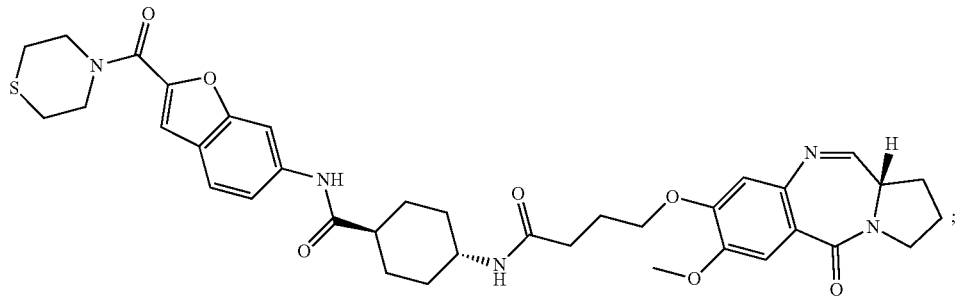

(am) (1R,4S)-4-(4-(((S)-7-methoxy-5-oxo-2,3,5,11a-tetrahydro-1H-benzo[e]pyrrolo[1,2-a][1,4]diazepin-8-yl)oxy)butanamido)-N-(2-(thio-morpholine-4-carbonyl)benzofuran-6-yl)cyclohexane-1-carboxamide (PP-B54)

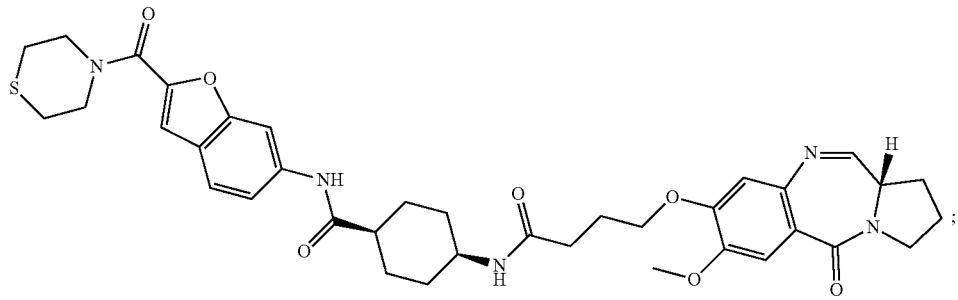

(an) (S)-4-(4-((7-methoxy-5-oxo-2,3,5,11a-tetrahydro-1H-benzo[e]pyrrolo[1,2-a][1,4]-diazepin-8-yl)oxy)butanamido)-N-(2-(thiomorpholine-4-carbonyl)benzofuran-6-yl)-benzamide (PP-B57)

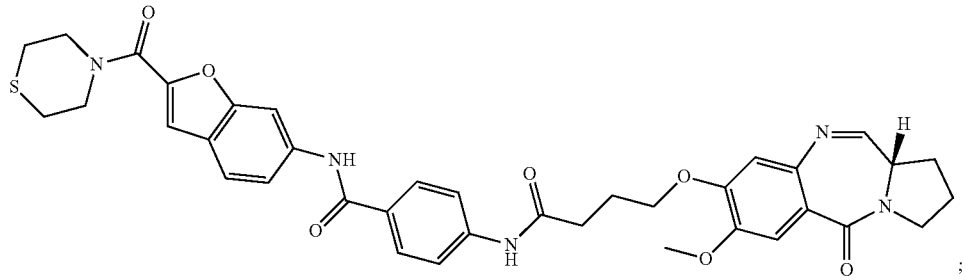

(ao) (S)—N-(2-(dimethylcarbamoyl)benzo[b]-thiophen-5-yl)-4-(4-((7-methoxy-5-oxo-2,3,5,11a-tetrahydro-1H-benzo[e]-imidazole[1,2-a][1,4]diazepin-8-yl)oxy)butanamido)-1-methyl-1H-pyrrole-2-carboxamide (PP-B73)

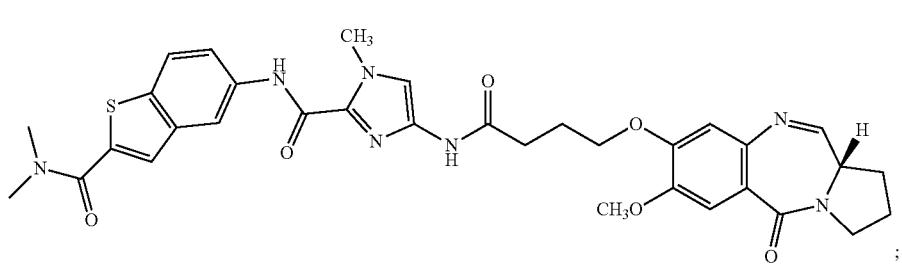

(ap) (S)-4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)-N,N,1-trimethyl-1H-pyrrole-2-carboxamide (LDM-46)

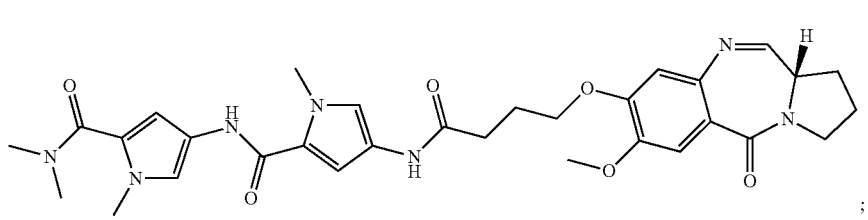

(aq) (S)—N,N-diethyl-4-(4-(4-((7-methoxy-5-oxo-2,3,5,11a-tetrahydro-1H-benzo[e]-pyrrolo[1,2-a][1,4]diazepin-8-yl)oxy)butanamido)-1-methyl-1H-pyrrole-2-carboxamido)-1-methyl-1H-pyrrole-2-carboxamide (LDM-25)

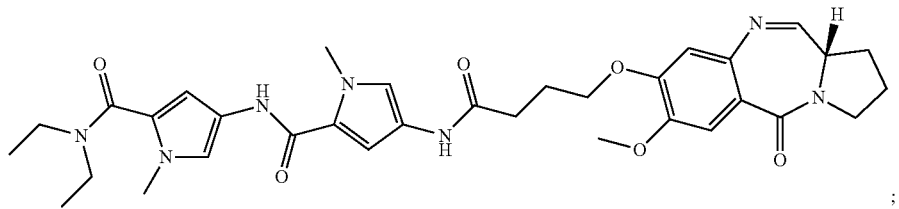

(ar) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(pyrrolidine-1-carbonyl)-1H-pyrrol-3-yl)-1H-pyrrole-2-carboxamide

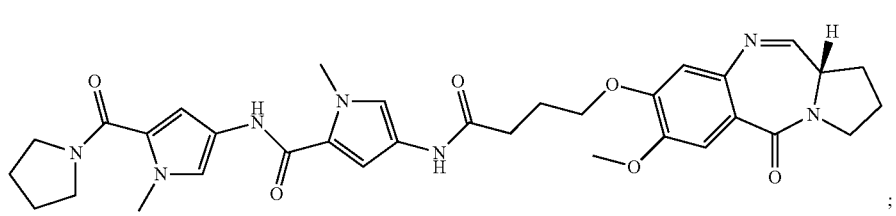

(LDM-24)

(as) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(piperidine-1-carbonyl)-1H-pyrrol-3-yl)-1H-pyrrole-2-carboxamide

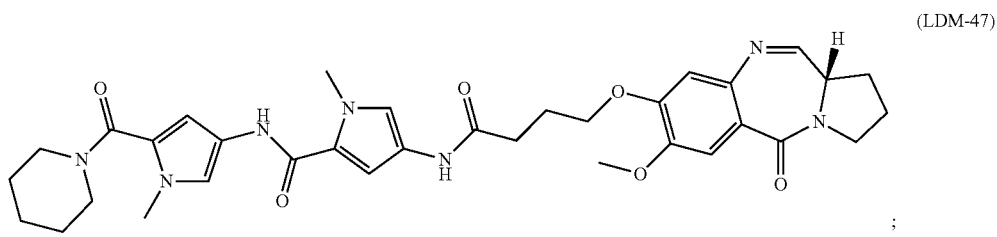 [SMILES: COc1cc2c(cc1OCCCC(=O)Nc1cc(C(=O)Nc3cc(C(=O)N4CCCCC4)n(C)c3)n(C)c1)N=C[C@@H]1CCCN1C2=O]

(LDM-47)

(at) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(morpholine-4-carbonyl)-1H-pyrrol-3-yl)-1H-pyrrole-2-carboxamide

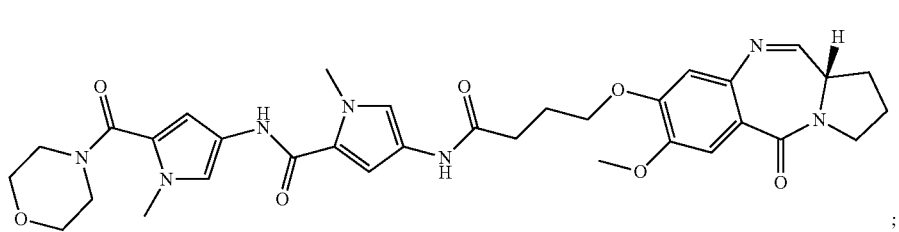

(LDM-16)

(au) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(thiomorpholine-4-carbonyl)-1H-pyrrol-3-yl)-1H-pyrrole-2-carboxamide

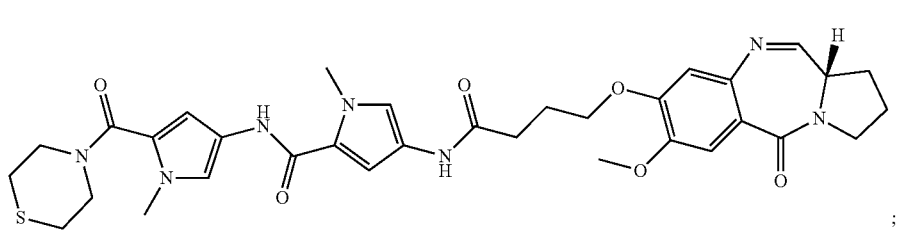

(LDM-23)

(av) (S)-4-(4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)phenyl)-N,N,1-trimethyl-1H-pyrrole-2-carboxamide

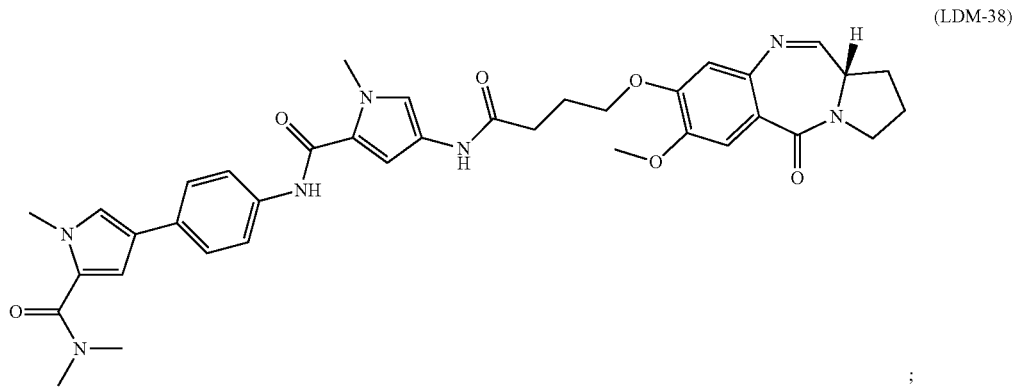 [SMILES: COc1cc2c(cc1OCCCC(=O)Nc1cc(C(=O)Nc3ccc(-c4cc(C(=O)N(C)C)n(C)c4)cc3)n(C)c1)N=C[C@@H]1CCCN1C2=O]

(LDM-38)

;

(aw) (S)—N,N-diethyl-4-(4-(4-(4-((7-methoxy-5-oxo-2,3,5,11a-tetrahydro-1H-benzo[e]-pyrrolo[1,2-a][1,4]diazepin-8-yl)oxy)butanamido)-1-methyl-1H-pyrrole-2-carboxamido)phenyl)-1-methyl-1H-pyrrole-2-carboxamide

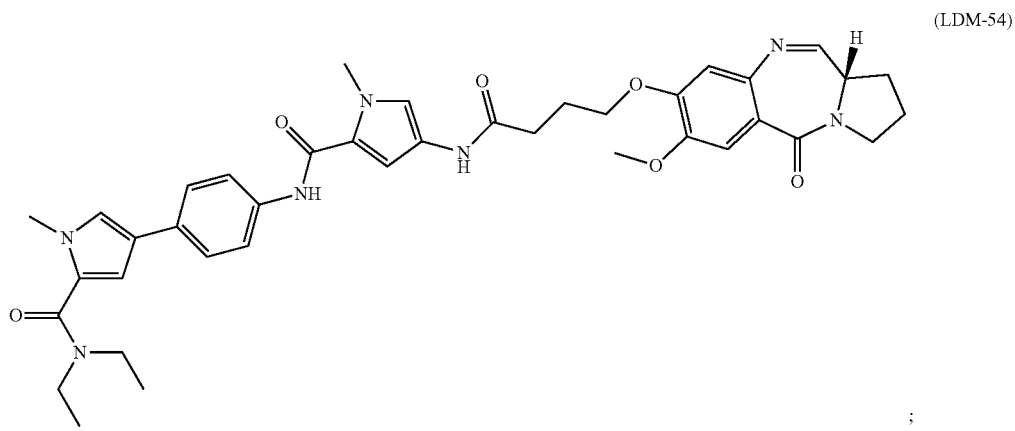 [SMILES: CCN(CC)C(=O)c1cc(-c2ccc(NC(=O)c3cc(NC(=O)CCCOc4cc5c(cc4OC)C(=O)N4CCC[C@H]4C=N5)cn3C)cc2)cn1C]

(LDM-54)

;

(ax) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(4-(1-methyl-5-(pyrrolidine-1-carbonyl)-1H-pyrrol-3-yl)phenyl)-1H-pyrrole-2-carboxamide

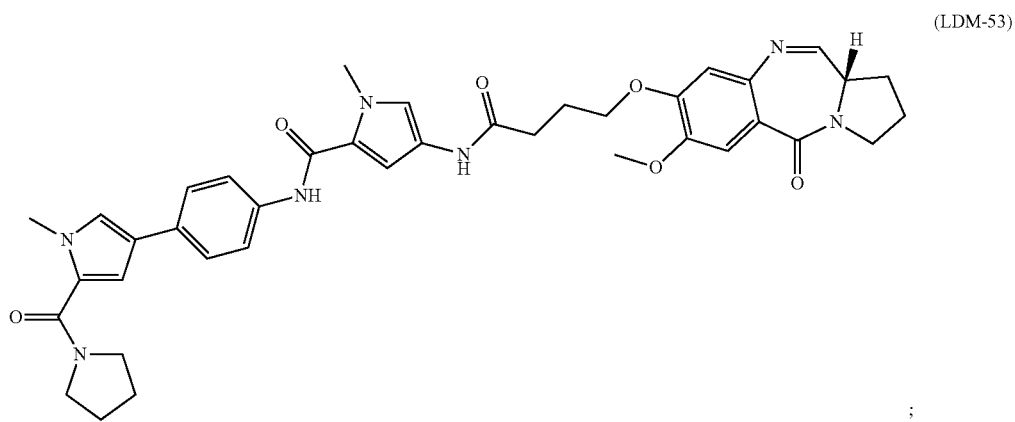 [SMILES: COc1cc2c(cc1OCCCC(=O)Nc1cc(C(=O)Nc3ccc(-c4cc(C(=O)N5CCCC5)n(C)c4)cc3)n(C)c1)N=C[C@@H]1CCCN1C2=O]

(LDM-53)

;

(ay) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(4-(1-methyl-5-(piperidine-1-carbonyl)-1H-pyrrol-3-yl)phenyl)-1H-pyrrole-2-carboxamide
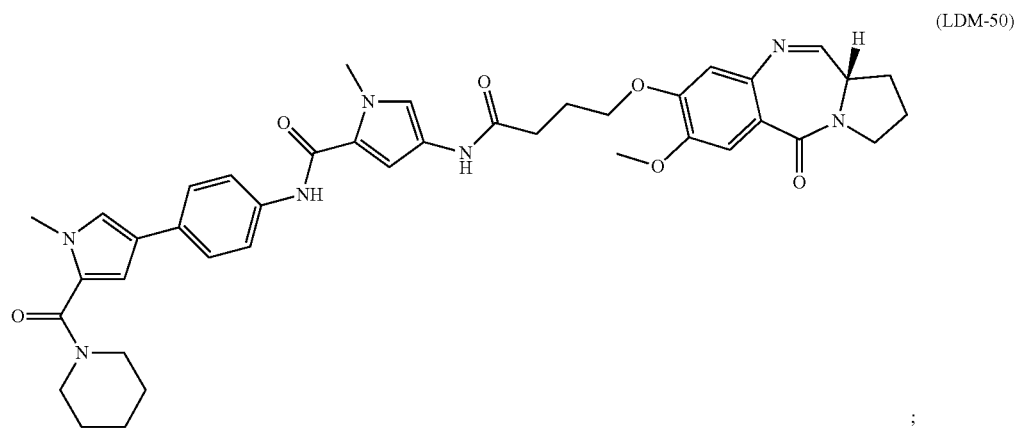 [SMILES: COc1cc2c(cc1OCCCC(=O)Nc1cc(C(=O)Nc3ccc(-c4cc(C(=O)N5CCCCC5)n(C)c4)cc3)n(C)c1)N=C[C@@H]1CCCN1C2=O]
(LDM-50)
;
(az) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(4-(1-methyl-5-(morpholine-4-carbonyl)-1H-pyrrol-3-yl)phenyl)-1H-pyrrole-2-carboxamide
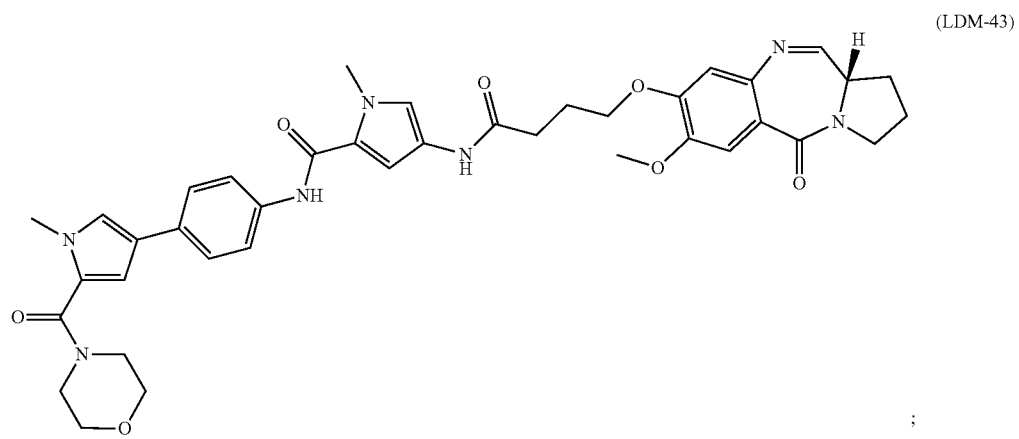 [SMILES: COc1cc2c(cc1OCCCC(=O)Nc1cc(C(=O)Nc3ccc(-c4cc(C(=O)N5CCOCC5)n(C)c4)cc3)n(C)c1)N=C[C@@H]1CCCN1C2=O]
(LDM-43)
;

(ba) (S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(4-(1-methyl-5-(thiomorpholine-4-carbonyl)-1H-pyrrol-3-yl)phenyl)-1H-pyrrole-2-carboxamide

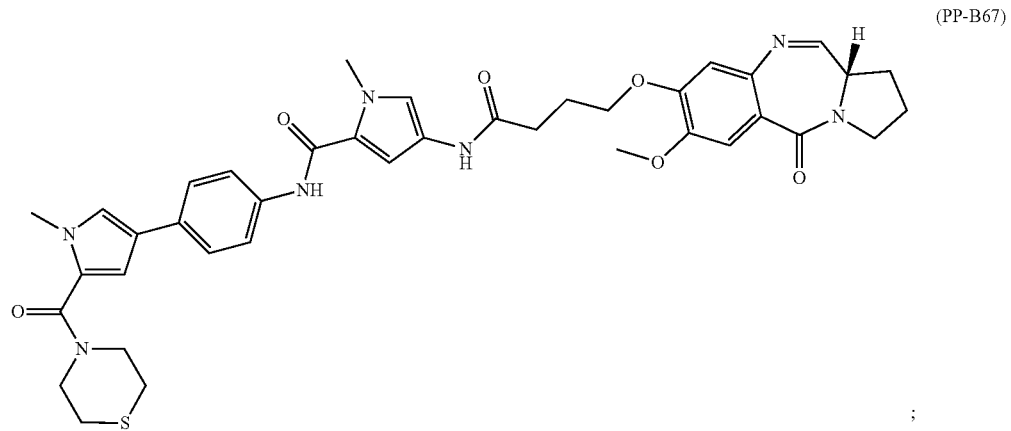 [SMILES: COc1cc2c(cc1OCCCC(=O)Nc1cc(C(=O)Nc3ccc(-c4cc(C(=O)N5CCSCC5)n(C)c4)cc3)n(C)c1)N=C[C@@H]1CCCN1C2=O]

(PP-B67)

(bb) (S)—N-(2-(dimethylcarbamoyl)benzo[b]thiophen-5-yl)-4-(4-((7-fluoro-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

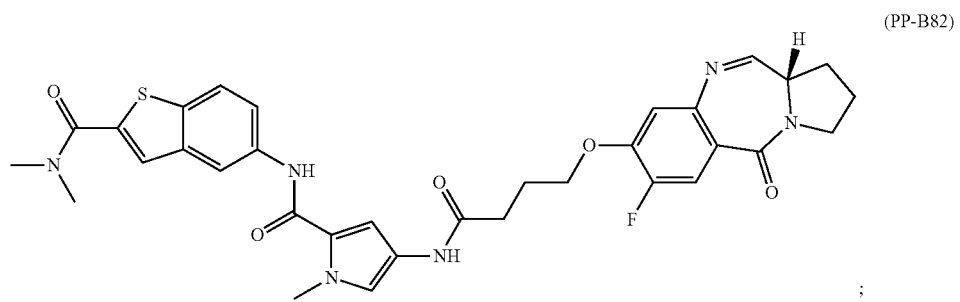 [SMILES: CN(C)C(=O)c1cc2cc(NC(=O)c3cc(NC(=O)CCCOc4cc5c(cc4F)C(=O)N4CCC[C@H]4C=N5)cn3C)ccc2s1]

(PP-B82)

(bc) (S)-4-(4-((7-fluoro-5-oxo-2,3,5,11a-tetrahydro-1H-benzo[e]pyrrolo[1,2-a][1,4]-diazepin-8-yl)oxy)butanamido)-1-methyl-N-(2-(thiomorpholine-4-carbonyl)-benzofuran-5-yl)-1H-pyrrole-2-carboxamide

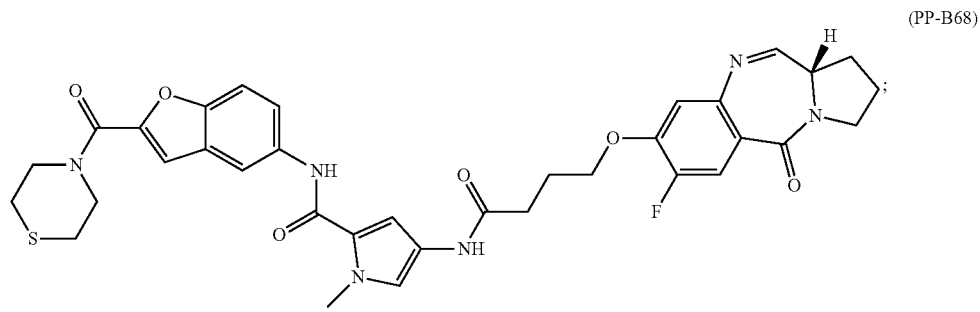 [SMILES: Cn1cc(NC(=O)CCCOc2cc3c(cc2F)C(=O)N2CCC[C@H]2C=N3)cc1C(=O)Nc1ccc2oc(C(=O)N3CCSCC3)cc2c1]

(PP-B68)

(bd) 4-(4-(((S)-7-methoxy-5-oxo-2,3,5,11a-tetrahydro-1H-benzo[e]pyrrolo[1,2-a][1,4]-diazepin-8-yl)oxy)butanamido)-1-methyl-N-(2-((2,4,5-trihydroxy-6-(hydroxymethyl)-tetrahydro-2H-pyran-3-yl)carbamoyl)benzofuran-5-yl)-1H-pyrrole-2-carboxamide PP-B102 deprotected

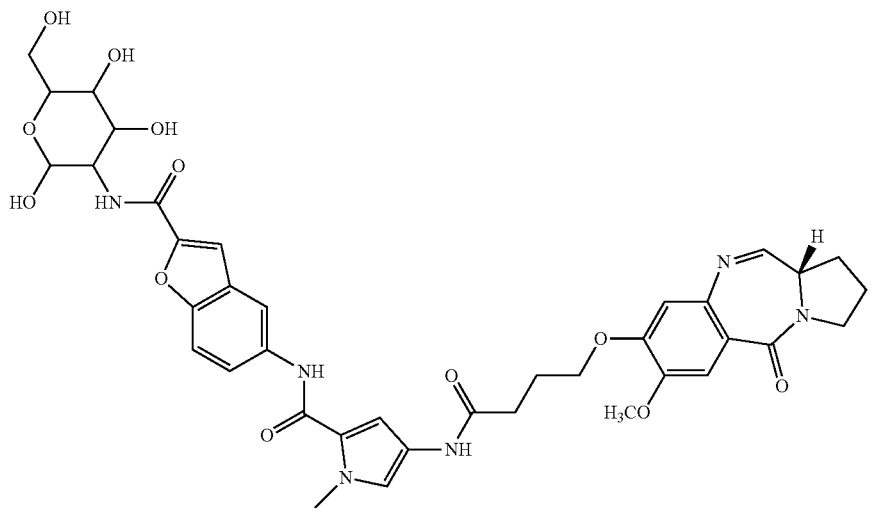

(be) 4-(2-aminopropanamido)benzyl 8-(4-((4-((2-(dimethylcarbamoyl)benzo[b]-thiophen-5-yl)carbamoyl)-1-methyl-1H-pyrrol-2-yl)amino)-4-oxobutoxy)-11-hydroxy-7-methoxy-5-oxo-2,3,11,11a-tetrahydro-1H-benzo[e]pyrrolo[1,2-a][1,4]diazepine-10(5H)-carboxylate (71)

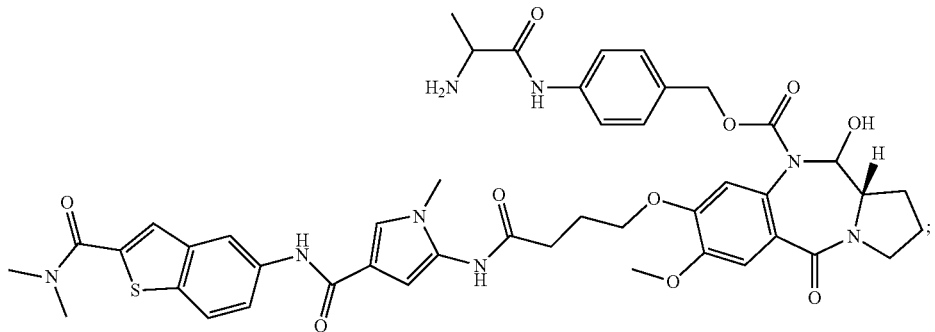

and (bf) 4-nitrobenzyl 8-(4-((4-((2-(dimethylcarbamoyl)benzo[b]thiophen-5-yl)-carbamoyl)-1-methyl-1H-pyrrol-2-yl)amino)-4-oxobutoxy)-11-hydroxy-7-methoxy-5-oxo-2,3,11,11a-tetrahydro-1H-benzo[e]pyrrolo[1,2-a][1,4]diazepine-10(5H)-carboxylate

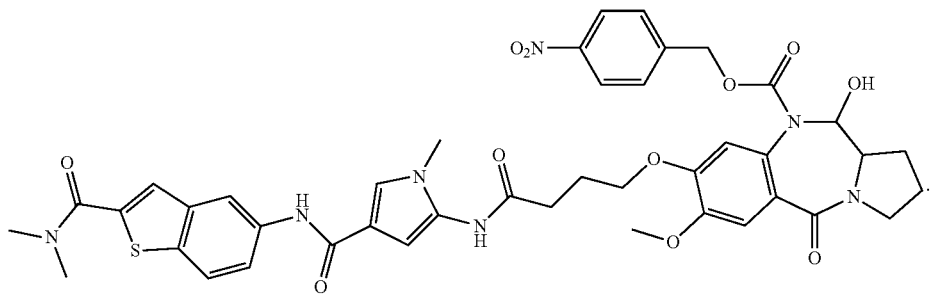 [SMILES: COc1cc2c(cc1OCCCC(=O)Nc1cc(C(=O)Nc3ccc4sc(C(=O)N(C)C)cc4c3)cn1C)N(C(=O)OCc1ccc([N+](=O)[O-])cc1)C(O)C1CCCN1C2=O]

In one embodiment, suitably the compounds of formula (I) or (II) have a c Log P value of less than 3.0; suitably, a c Log P value of less than 2.6; suitably, less than 2.5; suitably, less than 2.2; suitably, less than 2.1; suitably, less than 2.0; suitably, less than 1.9; suitably, less than 1.8; suitably, less than 1.7; suitably, less than 1.6; suitably, less than 1.5; suitably, less than 1.4; suitably, less than 1.3; suitably, less than 1.2; suitably, less than 1.1; suitably, less than 1.0.

Suitably, the values of c Log P are calculated using Chembiodraw Ultra 14.0, CambridgeSoft.

Applications

The invention finds application in the treatment of a bacterial infection in a subject.

In some aspects, the compounds of formula (I) and salts and solvates thereof, are broad spectrum agents capable of treating a bacterial infection caused by Gram-positive bacteria and/or Gram-negative bacteria and/or atypical bacteria.

Suitably the bacterial infection is caused by at least one bacterium selected from the genera *Enterococcus, Staphylococcus, Streptococcus, Bacillus, Acinetobacter, Burkholderia, Coxiella, Francisella, Yersina, Klebsiella, Escherichia, Enterobacter* and *Pseudomonas*.

Suitably the bacterial infection is caused by at least one bacterium selected from the genera *Enterococcus, Staphylococcus, Acinetobacter, Burkholderia, Klebsiella, Escherichia, Enterobacter* and *Pseudomonas*.

Suitably the bacterial infection is caused by at least one bacterium selected from *Enterococcus faeculis, Enterococcus faecium, Staphylococcus aureus, Streptococcus pyogenes, Streptococcus pneumoniae, Streptococcus agalactiae, Bacillus anthracis, Bacillus cereus, Bacillus subtilis, Haemophilus influenzae, Acinetobacter baumannii, Burkholderia multivorans, Burkholderia cenocepacia, Burkholderia cepacia, Burkholderia mallei, Burkholderia pseudomallei, Coxiella burnetii, Citrobacter freundii, Escherichia coli, Enterobacter cloacae, Enterobacter aerogenes, Francisella tularensis, Yersina pestis, Klebsiella pneumoniae, Serratia marcesens, Salmonella typhi, Salmonella typhimurum, Stenotrophomonas maltophilia, Pseudomonas aeruginosa* and *Neisseria gonorrhoeae*.

More suitably the bacterial infection is caused by at least one bacterium selected from *Enterococcus faeculis, Enterococcus faecium, Staphylococcus aureus, Acinetobacter baumannii, Burkholderia multivorans, Burkholderia cenocepacia, Burkholderia cepacia, Klebsiella pneumonia* and *Pseudomonas aeruginosa*.

In some embodiments, the bacterial infection is caused by Gram-positive bacteria selected from *Enterococcus faeculis, Enterococcus faecium, Staphylococcus aureus, Streptococcus pyogenes, Streptococcus pneumoniae, Streptococcus agalactiae, Bacillus anthracis, Bacillus cereus* and *Bacillus subtilis*.

In some embodiments, the infection is caused by Gram-negative bacteria, such as *Haemophilus influenzae, Acinetobacter baumannii, Burkholderia multivorans, Burkholderia cenocepacia, Burkholderia cepacia, Burkholderia mallei, Burkholderia pseudomallei, Coxiella burnetii, Citrobacter freundii, Escherichia coli, Enterobacter cloacae, Enterobacter aerogenes, Francisella tularensis, Yersina pestis, Klebsiella pneumoniae, Pseudomonas aeruginosa* and *Neisseria gonorrhoeae*.

In some embodiments, the bacterial infection is caused by drug-resistant bacteria. Such drug-resistant bacteria are bacteria that are resistant to one or more antibacterials other than the compounds of formula (I) described herein. The language "resistance" and "antibacterial resistance" "drug-resistant" refers to bacteria that are able to survive exposure to one or more antibacterial drugs. In some embodiments, the drug-resistant bacteria include *Streptococcus pyogenes, Streptococcus agalactiae, Streptococcus pneumoniae* (including penicillin-resistant *Streptococcus pneumoniae*), *Staphylococcus aureus* (including vancomycin-resistant *Staphylococcus aureus* (VRSA)), methicillin-resistant *Staphylococcus aureus* (MRSA) (including hospital-acquired MRSA, community acquired MRSA and coagulase negative staphylocci), *Acinetobacter baumannii, Burkholderia multivorans, Burkholderia cenocepacia, Burkholderia cepacia, Klebsiella pneumoniae Pseudomonas aeruginosa* and *Neisseria gonorrhoeae* (including penicillin-resistant *Neisseria gonorrhoeae*).

In some embodiments, the drug-resistant bacteria is a multiple drug resistant bacteria. The language "multiple drug resistant bacteria" includes bacteria that is resistant to two or more of antibiotics typically used for the treatment of such bacterial infections, for example, tetracycline, penicillin, cephalosporins (e.g., ceftriazone or cefixime), glycopeptides (e.g. vancomycin), quinolones (e.g., norfloxacin, ciprofloxacin or ofloxacin), co-trimoxazole, sulfonamides, aminoglycosides (e.g., kanamycin or gentamicin) and macrolides (e.g., azithromycin).

In one aspect, the invention provides a method for treating complicated skin and skin structure infections in a subject in need thereof comprising administering an effective amount of a compound of formula (I) and salts and solvates thereof.

In one aspect, the invention provides a compound of formula (I) and salts and solvates thereof, for use in treating a complicated skin and skin structure infections.

In one aspect, the invention provides the use of a compound of formula (I) and salts and solvates thereof, in the manufacture of a medicament for treating complicated skin and skin structure infections.

In one aspect, the invention provides a pharmaceutical composition comprising a compound of formula (I) and salts and solvates thereof, for the use in treating complicated skin and skin structure infections.

The language "complicated skin and skin structure infections" includes infections of the skin and the surrounding soft tissues that may require significant surgical intervention, including, for example, infected ulcers, burns or major abscesses. In some embodiments, the complicated skin and skin structure infections are caused by *Streptococcus pyogenes*, *Streptococcus agalactiae*, or *Staphylococcus aureus*, including MRSA and/or VRSA.

In one aspect, the invention provides a method for treating pneumonia in a subject in need thereof comprising administering an effective amount of a compound of formula (I) and salts and solvates thereof.

In one aspect, the invention provides a compound of formula (I) and salts and solvates thereof, for use in treating pneumonia.

In one aspect, the invention provides the use of a compound of formula (I) and salts and solvates thereof, in the manufacture of a medicament for treating pneumonia.

In one aspect, the invention provides a pharmaceutical composition comprising a compound of formula (I) and salts and solvates thereof, for use in treating pneumonia.

The term "pneumonia" refers to an inflammatory condition of the lungs caused by a bacterial infection. In some embodiments, the pneumonia is caused by a *Klebsiella pneumoniae*, *Streptococcus pneumoniae* or *Staphylococcus aureus* infection. In some embodiments, the pneumonia is nocosomial pneumonia (e.g., hospital-acquired pneumonia) or community-acquired pneumonia. In some embodiments, the pneumonia is caused by penicillin-resistant *Klebsiella pneumoniae*.

In another aspect, the invention provides a method for treating a condition selected from skin infections, pneumonia, urinary tract infections, soft tissue injury [including acute wounds (such as burns) and chronic wounds (such as diabetic foot ulcers)], sepsis and bacteremia in a subject in need thereof comprising administering an effective amount of a compound of formula (I) and salts and solvates thereof.

In one aspect, the invention provides a compound of formula (I) and salts and solvates thereof, for use in treating a condition selected from skin infections, pneumonia, urinary tract infections, soft tissue injury, sepsis and bacteremia.

In one aspect, the invention provides the use of a compound of formula (I) and salts and solvates thereof, in the manufacture of a medicament for treating a condition selected from skin infections, pneumonia, urinary tract infections, soft tissue injury, sepsis and bacteremia.

In one aspect, the invention provides a pharmaceutical composition comprising a compound of formula (I) and salts and solvates thereof, for use in treating a condition selected from skin infections, pneumonia, urinary tract infections, soft tissue injury, sepsis and bacteremia.

One of ordinary skill in the art is readily able to determine whether or not a candidate compound treats a bacterial infection by, for example, assays (such as those described in the examples) which may be used to determine the activity of a particular compound.

Suitably subjects are human.

Administration & Dose

Compounds of formula I may be administered alone or in combination with one or another or with one or more pharmacologically active compounds which are different from the compounds of formula I.

Compounds of the invention may suitably be combined with various components to produce compositions of the invention. Suitably the compositions are combined with a pharmaceutically acceptable carrier or diluent to produce a pharmaceutical composition (which may be for human or animal use). Suitable carriers and diluents include isotonic saline solutions, for example phosphate-buffered saline. Useful pharmaceutical compositions and methods for their preparation may be found in standard pharmaceutical texts. See, for example, *Handbook for Pharmaceutical Additives*, 3rd Edition (eds. M. Ash and I. Ash), 2007 (Synapse Information Resources, Inc., Endicott, N.Y., USA) and *Remington: The Science and Practice of Pharmacy*, 21st Edition (ed. D. B. Troy) 2006 (Lippincott, Williams and Wilkins, Philadelphia, USA) which are incorporated herein by reference.

The compounds of the invention may be administered by any suitable route. Suitably the compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form.

The compounds of the invention, their pharmaceutically acceptable salts, and pharmaceutically acceptable solvates can be administered alone but will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intravenously, intra-arterially, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Suitably formulation of the invention is optimised for the route of administration e.g. oral, intravenously, etc.

Administration may be in one dose, continuously or intermittently (e.g. in divided doses at appropriate intervals) during the course of treatment. Methods of determining the most effective means and dosage are well known to a skilled person and will vary with the formulation used for therapy, the purpose of the therapy, the target cell(s) being treated, and the subject being treated. Single or multiple administrations can be carried out with the dose level and the dose regimen being selected by the treating physician, veterinarian, or clinician.

Depending upon the disorder and patient to be treated, as well as the route of administration, the compositions may be administered at varying doses. For example, a typical dosage for an adult human may be 100 ng to 25 mg (suitably about 1 micro g to about 10 mg) per kg body weight of the subject per day.

Suitably guidance may be taken from studies in test animals when estimating an initial dose for human subjects. For example when a particular dose is identified for mice, suitably an initial test dose for humans may be approx. 0.5× to 2× the mg/Kg value given to mice.

The compound of formula (I) may be administered once, twice, three times a day or as many times in a 24 hour period as medically necessary. One of skill in the art would readily be able to determine the amount of each individual dose based on the subject. In some embodiments, the compound of formula (I) is administered in one dosage form. In some embodiments, the compound of formula (I) is administered in multiple dosage forms.

Doses are mg/Kg/day for humans unless otherwise stated.

The amount of active ingredient that is combined with one or more excipients to produce a single dosage form will necessarily vary depending upon the host treated and the particular route of administration. Further information on formulation, on routes of administration and on dosage regimes may be found in Chapter 25.2 and 25.3 in Volume 5 of Comprehensive Medicinal Chemistry (Corwin Hansch; Chairman of Editorial Board), Pergamon Press 1990.

Formulation and Compositions

In some aspects, the present invention provides a pharmaceutical composition comprising a compound of formula (I) and a pharmaceutically acceptable carrier or diluent.

Suitably the pharmaceutical composition further comprises an efflux pump inhibitor that reduces the ability of bacterial cells to pump the therapeutic compounds of the invention out of the cell. In some aspects, the pharmaceutical composition further comprise an efflux pump inhibitor and an agent for increasing the permeability of bacterial membranes.

In one aspect, suitably the pharmaceutical composition further comprises an agent for increasing the permeability of bacterial membranes.

In one aspect, the present invention provides a kit comprising: (i) a compound of formula (I) and salts and solvates thereof; (ii) an agent for increasing the permeability of bacterial membranes; and/or (iii) an efflux pump inhibitor. Thus, this kit may comprise components (i) and (ii); components (i) and (iii); or components (i), (ii) and (iii). The components of the kit may be administered separately, simultaneously or sequentially in any order.

Suitably the efflux pump inhibitor in the pharmaceutical composition or in the kit is selected from a group of compounds which inhibits the action of one or more type of efflux pump, namely the major facilitator superfamily (MFS), small multidrug resistance (SMR), resistance nodulation cell division (RND), multidrug and toxic agents extrusion (MATE) and the ATP-binding cassette (ABC) families. More suitably the efflux pump inhibitor is selected from 3-chlorophenylhydrazone, chlorpromazine, 1-(1-Naphthylmethyl)-Piperazine, Pyridopyrimidinone Analogs, Pyranopyridines, phenylalanine-arginine 3-naphthylamide and combinations thereof.

Suitably, the agent for increasing the permeability of bacterial membranes in the pharmaceutical composition or in the kit is selected from polymyxins, lipopeptides (e.g. daptomycin), antimicrobial peptides (e.g. morian and melittin), polycationic compounds (e.g. bis-guanidines [e.g. chlorhexidine digluconate]); quaternary ammonium compounds [e.g. benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide]; and polyhexanide), zeamines (38) (e.g. zeamine, zeamine I and zeamine II) and phage endolysins (39-42).

More suitably, the agent for increasing the permeability of bacterial membranes in the pharmaceutical composition or in the kit is a polymyxin. More suitably, the polymyxin is selected from a polymixin B, polymyxin C and bacitracin. More suitably the polymyxin is polymyxin B nonapeptide.

Further particular and preferred aspects are set out in the accompanying independent and dependent claims. Features of the dependent claims may be combined with features of the independent claims as appropriate, and in combinations other than those explicitly set out in the claims. Where an apparatus feature is described as being operable to provide a function, it will be appreciated that this includes an apparatus feature which provides that function or which is adapted or configured to provide that function.

Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

A reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

Compounds of Formula (I), which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —NH$_2$ may be —NH$_3^+$), then an acid addition salt may be formed with a suitable anion. Examples of suitable inorganic anions include, but are not limited to, those derived from the following inorganic acids: hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO$^-$), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium (Na$^+$) potassium (K$^+$), magnesium (Mg$^{2+}$), calcium (Ca$^{2+}$), zinc (Zn$^{2+}$), and aluminum (Al$^{3+}$). Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$. Examples of suitable amines include arginine, N,N'-dibenzylethylene-diamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react a compound of Formula (I) with an appropriate acid or base to give the desired salt. One may also react a precursor of the compound of Formula (I) with an acid or base to remove an acid- or base-labile protecting group or to open a lactone or lactam group of the precursor. Additionally, one may convert a salt of the compound of Formula (I) to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of formula I include imine, carbinolamine and carbinolamine ether forms of the PBD. The carbinolamine or the carbinolamine ether is formed when a nucleophilic solvent ($H_2O$, ROH) adds across the imine bond of the PBD moiety. The balance of these equilibria between these forms depend on the conditions in which the compounds are found, as well as the nature of the moiety itself.

These compounds may be isolated in solid form, for example, by lyophilisation.

Further particular and preferred aspects are set out in the accompanying independent and dependent claims. Features of the dependent claims may be combined with features of the independent claims as appropriate, and in combinations other than those explicitly set out in the claims.

Synthetic Strategies

The compounds of Formula (I) may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations, A Guide to Functional Group Preparations*, 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry*, 4th Edition, (2006) and P. Kocienski, *Protective Groups*, 3rd Edition (2005).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

BRIEF DESCRIPTION OF THE DRAWINGS

Embodiments of the present invention will now be described further, with reference to the accompanying drawings, in which.

EXAMPLES

General Material and Methods

Figure 1:
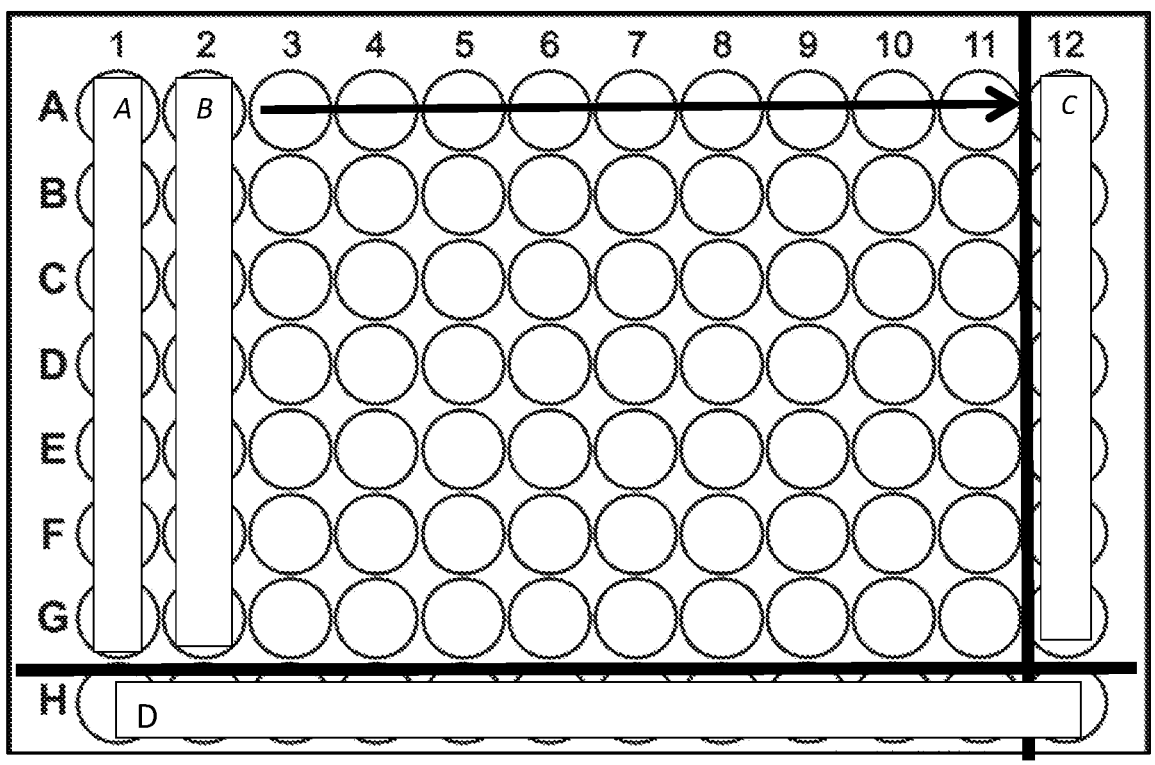
FIG. 1 shows an example plate set up for carrying out the Minimum Inhibitory Concentration (MIC) protocol.

All solvents and reagents for the synthesis were obtained from commercial available sources including among others Sigma-Aldrich, Fisher Scientific, Fluorochem and Alfa Aesar. Thin-layer-chromatography (TLC) analysis was performed on silica gel plates (E. Merck silica gel 60 F254 plates) and visualized by ultra-violet (UV) radiation at 254 nm. Flash chromatography for the purification of compound was performed with silica gel as a stationary phase (Merck 60, 230-400 mesh). $^1$H and $^{13}$C nuclear magnetic resonance (NMR) analyses were performed on a Balker Spectrospin 400 Hz spectrometer. IR spectra were collected with an FT/IR IRAffinity-1S IR spectrophotometer (Shimadzu). HRMS was performed on a Thermo Scientific-Exactive HCD Orbitrap Mass Spectrometer. LC-MS analyses were performed on a Waters Alliance 2695 system, eluting in gradient with a flow rate of 0.5 mL/min according to the condition reported herein:

1) 10 minutes method: flow 0.5 mL/min
Solvents: A) water+0.1% formic acid
B) acetonitrile+0.1% formic acid

| | Time (min) | | | | | |
|---|---|---|---|---|---|---|
| | 0 | 2 | 5 | 6 | 7.5 | 9 | 10 |
| A (%) | 95 | 95 | 50 | 50 | 5 | 95 | 95 |
| B (%) | 5 | 5 | 50 | 50 | 95 | 5 | 5 |

2) 5 minutes method: flow 1 mL/min
Solvents:
A) water+0.1% formic acid
B) acetonitrile+0.1% formic acid

| Time (min) | 0 | 3 | 3.5 | 4.5 | 5 |
|---|---|---|---|---|---|
| A (%) | 95 | 10 | 5 | 5 | 95 |
| B (%) | 5 | 90 | 95 | 95 | 5 |

The analyses were performed on a Monolithic C18 50×4.60 mm column by Phenomenex. UV detection was performed on a Diode Array Detector. Mass spectra were registered in both ESI+ and ESI− mode. The hydrogenation reaction was conducted using a Parr hydrogenation system.

The bacterial strains used in the biological tests were obtained from type culture collections, in particular, ATCC, the National Collection of Culture Types (NCTC) and the Belgium Co-ordinated Collection of Microorganisms. In some cases the strains have been previously described (35, 36 & 37).

General Reaction Scheme for Synthesis of 4C-Alloc-THP-Protected PBD Unit

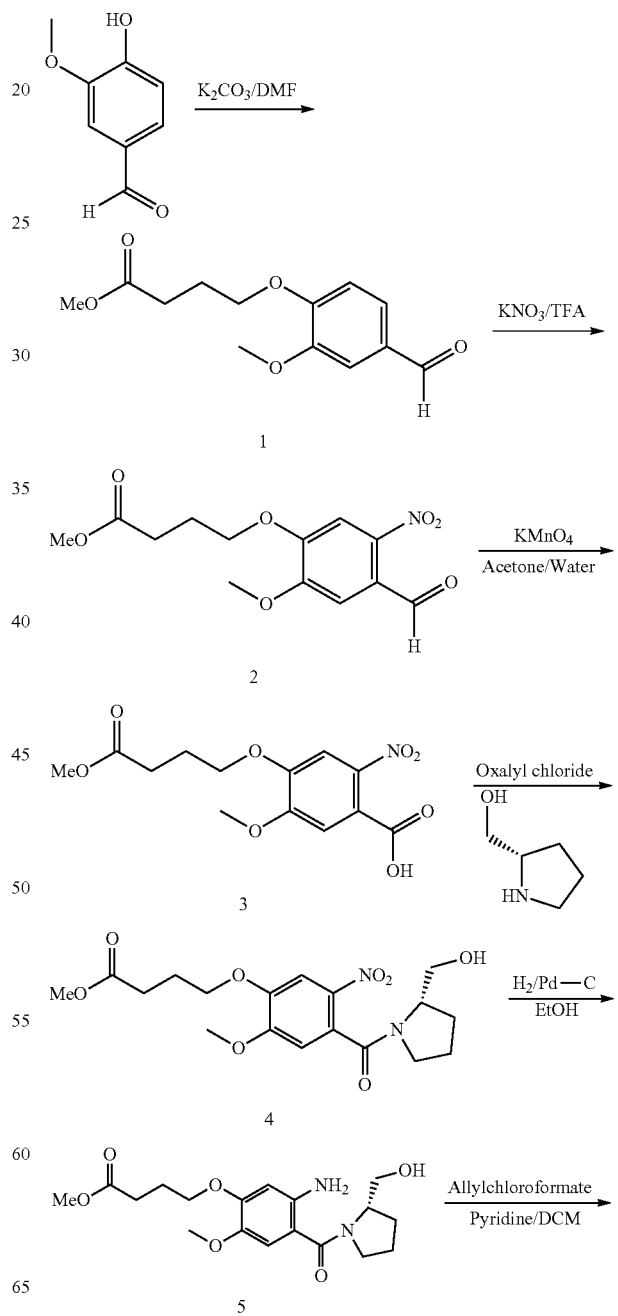

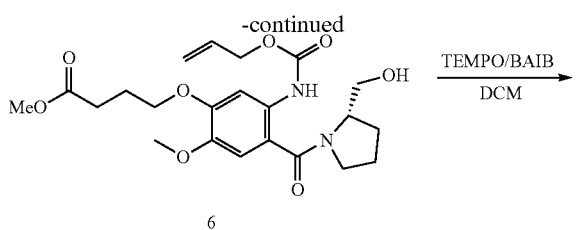

6

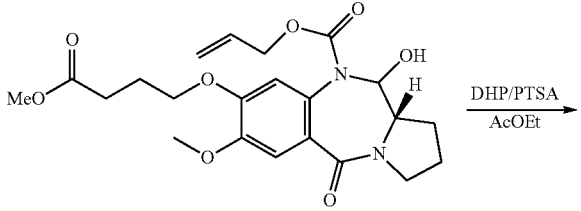

7

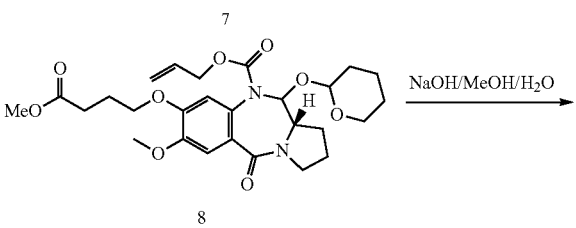

8

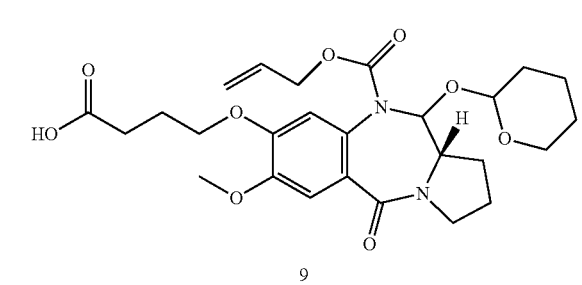

9

Example 1

Synthesis of methyl 4-(4-formyl-2-methoxyphenoxy)butanoate (1)

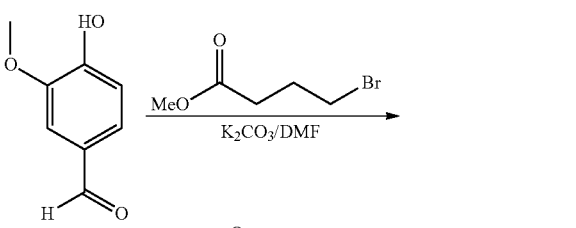

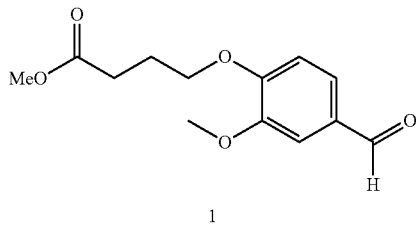

1

Methyl 4-bromobutanoate (17.7 mL, 1.05 eq) and potassium carbonate (30.4 g, 1.5 eq) were added to a solution of vanillin (20 g, 133 mol) in DMF (80 mL). The suspension was stirred at room temperature for 6 hours, until TLC showed completion. At that point water (1000 mL) was added to the reaction, causing the formation of a precipitate that was filtered and collected giving pure 1 (32.05 g, 95%) as a white solid. $^1$H NMR (400 MHz, CHLOROFORM-d) δ: 9.84 (1H, s), 7.40-7.44 (2H, m), 6.98 (1H, d, J=8 Hz), 4.16 (2H, t, J=6.2 Hz), 3.92 (3H, s), 3.69 (3H, s), 2.56 (2H, t, J=7.2 Hz), 2.17-2.23 (2H, m). $^{13}$C NMR (100 MHz, CHLOROFORM-d) δ: 190.9, 173.4, 153.8, 149.9, 130.3, 126.8, 111.5, 109.2, 67.8, 56.0, 51.7, 30.3, 24.2. m/z (+EI) calc. for $C_{13}H_{16}O_5$ (M)$^+$ 252.2 found 253.1 ([M]+H)$^+$

Example 2

Synthesis of methyl 4-(4-formyl-2-methoxy-5-nitrophenoxy)-butanoate (2)

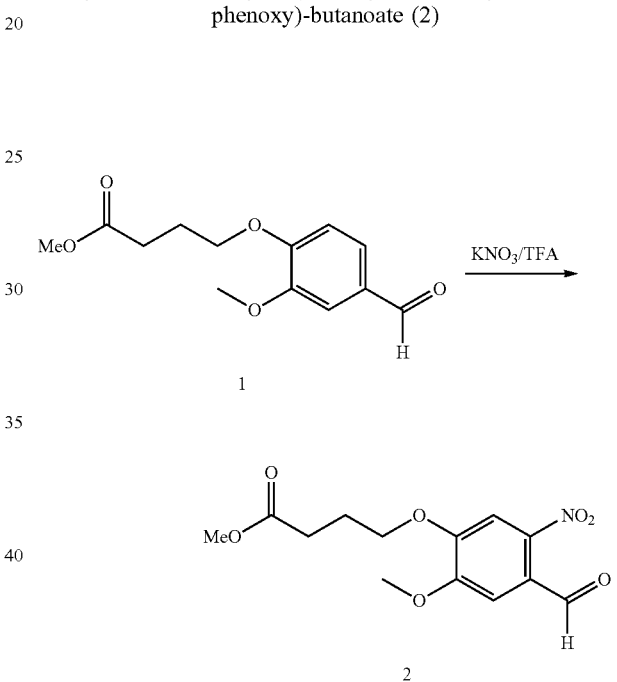

A solution of 1 (10 g, 39 mmol) in trifluoroacetic acid (12 mL) was added dropwise to a solution of KNO$_3$ (5 g, 1.25 equiv.) in trifluroacetic acid (12 mL) kept at 0° C. under magnetic stirrer. After 40 minutes the reaction went to completion by TLC and LCMS. The reaction mixture was evaporated under reduced pressure using a rotary evaporator. The residue was dissolved in EtOAc (50 mL) and the organic phase was washed with brine (3×50 mL). The organic phases were dried over MgSO$_4$ and concentrated by rotary evaporator giving pure 2 (10.65 g, 92%) as an amber oil. $^1$H NMR (400 MHz, CHLOROFORM-d): 10.29 (1H, s), 7.46 (1H, s), 7.11 (1H, s), 4.06 (2H, t, J=6.2 Hz), 3.85 (3H, s), 3.56 (3H, s), 2.42 (2H, t, J=7.2 Hz), 2.04-2.11 (2H, m). $^{13}$C NMR (100 MHz, CHLOROFORM-d) δ: 188.5, 172.8, 152.7, 150.9, 143.5, 124.7, 110.5, 108.2, 67.8, 56.4, 51.3, 29.7, 23.2. m/z (+EI) calc. for $C_{13}H_{15}NO_7$ (M)$^+$ 297.2 found 298.1 ([M]+H)$^+$

Example 3

Synthesis of 5-methoxy-4-(4-methoxy-4-oxobutoxy)-2-nitrobenzoic acid (3)

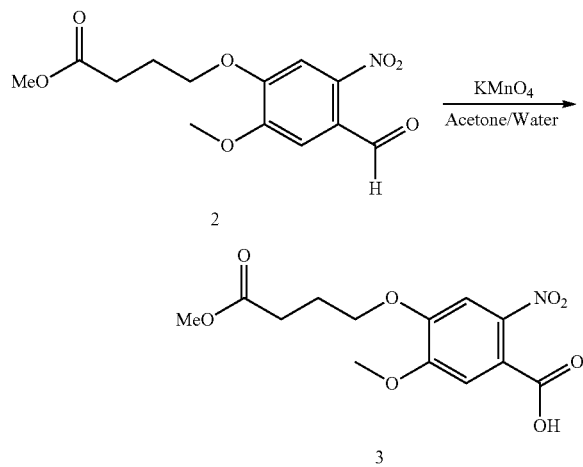 [SMILES: COC(=O)CCCOc1cc([N+](=O)[O-])c(C=O)cc1OC ; "KMnO4" ; COC(=O)CCCOc1cc([N+](=O)[O-])c(C(=O)O)cc1OC]

Compound 2 (10.0 g) was dissolved in acetone (400 mL). A hot solution of 10% potassium permanganate (275 mL) was added to the solution of 2 in a flask fitted with a condenser. The reaction mixture was left under reflux until the reaction went to completion (according to TLC). At that point the reaction mixture was cooled down to room temperature. The brown residue formed was filtered through a celite path and washed with 600 mL hot water. A solution of sodium bisulphite 16% in 1N HCl (400 mL) was added to the filtrate and the pH of the solution was adjusted to 1 using concentrated HCl. This caused the precipitation of a yellow solid that was filtered, collected and dried giving pure 3 (9.01 g, 82%) as a yellow solid. 1H NMR (400 MHz, CHLOROFORM-d) δ: 7.38 (1H, s), 7.21 (1H, s), 4.15 (2H, t, J=5.8 Hz), 3.97 (3H, s), 3.70 (3H, s), 2.56 (2H, t, J=7.2 Hz), 2.17-2.24 (2H, m). $^{13}$C NMR (100 MHz, CHLOROFORM-d) δ: 172.8, 166.0, 151.8, 149.1, 141.2, 121.3, 111.5, 107.2, 68.3, 56.4, 51.3, 29.7, 23.8. m/z (+EI) calc. for $C_{13}H_{15}NO_8$ (M)$^+$ 313.2 found 312.1 ([M]−H)$^-$

Example 4

Synthesis of (S)-methyl 4-(4-(2-(hydroxymethyl)pyrrolidine-1-carbonyl)-2-methoxy-5-nitrophenoxy)butanoate (4)

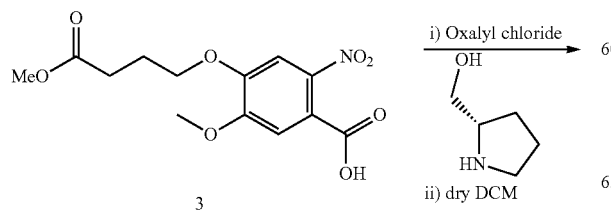

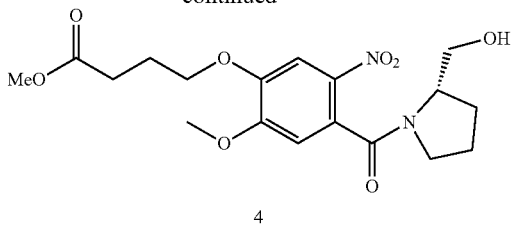

A solution was prepared by dissolving 3 (7.90 g, 25 mmol) in dry DCM (50 mL) in a round bottom flask previously dried in oven. Oxalyl chloride (6.50 mL, 3 eq) and a catalytic amount of DMF (2-3 drops) were added to the solution that started bubbling. The solution was left under magnetic stirrer for 1 hour until ceased the formation of HCl. Dry toluene (15 mL) was added to the reaction mixture that was evaporated under reduced pressure in a rotary evaporator to eliminate the excess of oxalyl chloride. The reaction mixture was dissolved in dry DCM (50 mL and the solution was dropwise added to a solution of triethylamine (10.5 mL, 3 equiv.) and +(S)-pyrrolidinemethanol (3.73 mL, 1.5 equiv.) in dry DCM (30 mL) kept at 0° C. under N$_2$ atmosphere. The reaction mixture was then allowed to stir overnight. After 15 hours TLC showed completion of reaction and the reaction mixture was extracted using 1 N HCl (2×70 mL) and brine (2×70 mL). The combined organic fractions were dried over MgSO$_4$ and concentrated by rotary evaporator to give a yellow oil. The crude was purified by column chromatography (mobile phase: from AcOEt, 100, vv to AcOEt/MeOH, 98/2, v/v) affording pure 4 (5.50 g, 55%) as a pale yellow solid. $^1$H NMR (400 MHz, CHLOROFORM-d) δ: 7.69 (1H, s), 6.79 (1H, s), 4.14 (2H, t, J=4.4 Hz), 3.96 (3H, s), 3.90 (1H, m), 3.78 (1H, m), 3.69 (3H, s), 3.16 (2H, t, J=6.8 Hz), 2.55 (2H, t, J=4.8 Hz), 2.10-2.22 (3H, m), 1.70-1.90 (4H, m). $^{13}$C NMR (100 MHz, CHLOROFORM-d) δ: 173.2, 154.8, 148.4, 109.2, 108.4, 68.4, 66.1, 61.5, 56.7, 51.7, 49.5, 30.3, 28.4, 24.4, 24.2. m/z (+EI) calc. for $C_{18}H_{24}N_2O_8$ (M)$^+$ 396.3 found 397.0 ([M]+H)$^+$

Example 5

Synthesis of (S)-methyl 4-(5-amino-4-(2-(hydroxymethyl)-pyrrolidine-1-carbonyl)-2-methoxyphenoxy)butanoate (5)

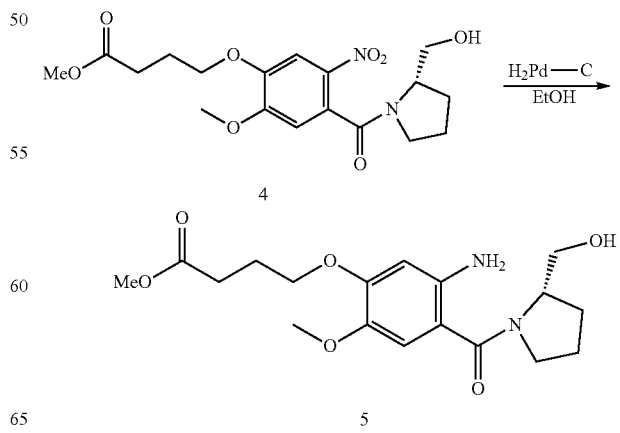

A catalytic amount of Pd/C (10% w/w) was added to a solution of 4 (5.5 g, 13 mmol) in EtOH (100 mL). The reaction mixture was hydrogenated in a Parr hydrogenator at 40 psi until for 4 hours when TLC showed the completion of reaction. At that point the reaction was filtered under vacuum through a path of celite. The resulting solution was evaporated using rotary evaporator giving pure 5 (4.52 g, 95%) as a dark yellow solid. $^1$H NMR (400 MHz, CHLOROFORM-d) δ: 6.76 (1H, s), 6.39 (1H, s), 4.39 (1H, bs), 4.03 (2H, t, J=4.4 Hz), 3.78 (3H, s), 3.69 (3H, s), 3.62 (1H, m), 3.53 (1H, m), 2.54 (2H, t, J=4.8 Hz), 2.15 (3H, m), 1.65-1.87 (4H, m). $^{13}$C NMR (100 MHz, CHLOROFORM-d) δ: 172.5, 170.7, 150.3, 140.5, 140.1, 135.0, 112.3, 110.5, 101.2, 66.5, 59.9, 56.3, 52.4, 50.6, 29.4, 27.5, 23.9, 23.4. m/z (+EI) calc. for $C_{18}H_{26}N_2O_6$ (M)$^+$ 366.4 found 367.2 ([M]+H)$^+$ Example 6

Synthesis of (5)-methyl 4-(5-(allyloxycarbonylamino)-4-(2-(hydroxymethyl)pyrrolidine-1-carbonyl)-2-methoxyphenoxy)butanoate (6)

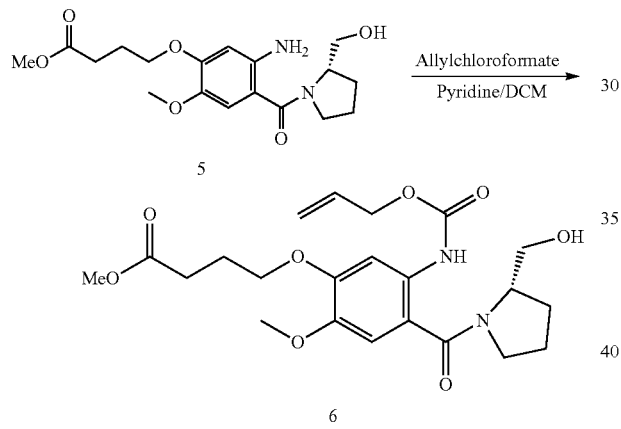

A solution was prepared by dissolving 5 (3.33 g, 9 mmol) in dry DCM (40 mL). To this solution kept at −10° C. under $N_2$ atmosphere were sequentially added dry pyridine (1.69 mL) and a solution of allyl chloroformate (0.91 mL, 0.95 equiv.) in anhydrous DCM (30 mL). The reaction mixture was left under magnetic stirrer at room temperature for 2 hours, until TLC showed completion of reaction. At that point the reaction mixture was extracted with saturated $CuSO_4$ solution (70 mL), saturated aqueous $NaHCO_3$ (100 mL) and brine (100 mL). The organic phase was dried over $MgSO_4$ and concentrated under reduced pressure using a rotary evaporator. The crude of reaction was subsequently purified by column chromatography (mobile phase: AcOEt, 100) affording pure 6 (3.56 g, 88%) as a pale yellow solid. $^1$H NMR (400 MHz, CHLOROFORM-d) δ: 8.72 (1H, bs), 7.77 (1H, s), 6.82 (1H, s), 5.95 (1H, m), 5.35 (1H, dd, J=17.2, 1.2 Hz), 5.23 (1H, dd, J=10.0, 0.8 Hz), 4.63 (2H, dd, J=5.6, 1.2 Hz), 4.40 (1H, bs), 4.11 (2H, t, J=4.4 Hz), 3.82 (3H, s), 3.61 (3H, s), 3.59 (1H, m), 3.50 (1H, m), 2.54 (2H, t, J=4.8 Hz), 2.17 (3H, m), 1.72-1.92 (4H, m). 13C NMR (100 MHz, CHLOROFORM-d) δ: 173.4, 170.9, 153.6, 150.5, 144.0, 132.3, 131.9, 118.2, 115.7, 111.6, 105.6, 67.7, 66.6, 65.7, 61.6, 60.4, 56.6, 51.7, 30.7, 28.3, 25.1, 24.3. m/z (+EI) calc. for $C_{22}H_{30}N_2O_8$ (M)$^+$ 450.4 found 451.2 ([M]+H)$^+$ Example 7

Synthesis of allyl 11-hydroxy-7-methoxy-8-(4-methoxy-4-oxo-butoxy)-5-oxo-2,3,11,11a-hexahydro-1H-pyrrolo[2,1-c][1,4]benzodiazepine-10 (5H)-carboxylate (7)

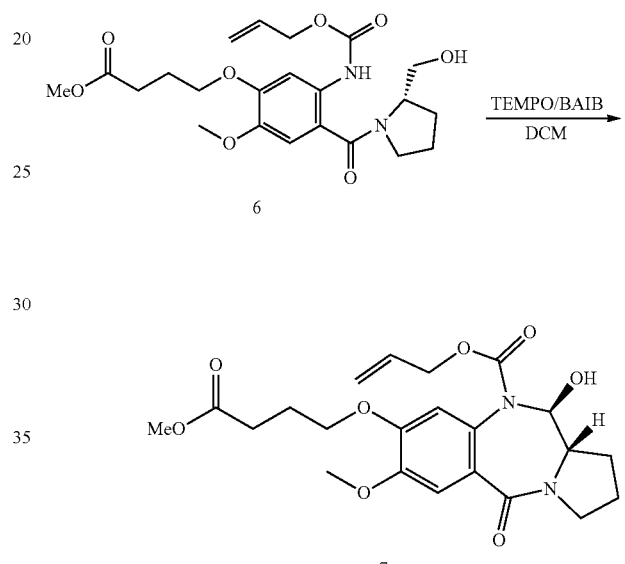

BAIB (3.78 g, 1.2 equiv) and TEMPO (0.152 g, 0.1 equiv.) were sequentially added to a solution of 6 (4.41 g, 9.7 mmol) in DCM (200 mL). The reaction was left under magnetic stirrer 6 hours until TLC showed completion of reaction. At that point the reaction mixture was sequentially washed with saturated sodium metabisulphite (100 mL), saturated aqueous $NaHCO_3$ (2×100 mL) and brine (100 mL). The organic phase was dried over $MgSO_4$ and concentrated under reduced pressure using a rotary evaporation. The crude of reaction was purified by column chromatography (mobile phase: AcOEt/hexane, 50/50, v/v) affording pure 7 (3.34 g, 75%) as a yellow solid. $^1$H NMR (400 MHz, CHLOROFORM-d) δ: 7.22 (1H, s), 6.69 (1H, s), 5.80 (1H, m), 5.62 (1H, d, J=4.0 Hz), 5.07 (2H, d, J=12.0 Hz), 4.61 (1H, dd, J=13.2, 5.6 Hz), 4.41 (1H, bs), 4.21 (2H, d, J=12.0 Hz), 3.89 (3H, s), 3.67 (3H, s), 3.49 (1H, t, J=8.0 Hz), 3.43 (1H, m), 2.475 (2H, t, J=7.2 Hz), 2.12 (4H, m), 1.95 (2H, m). $^{13}$C NMR (100 MHz, CHLOROFORM-d) δ: 173.4, 167.0, 155.9, 149.9, 148.7, 131.8, 128.3, 126.0, 117.9, 114.2, 110.8, 85.9, 67.9, 66.7, 60.3, 60.1, 56.1, 51.6, 46.3, 30.3, 28.7, 24.2, 23.0, 20.9. m/z (+EI) calc. for $C_{22}H_{28}N_2O_8$ (M)$^+$ 448.4 found 449.2 ([M]+H)$^+$

Example 8

Synthesis of allyl 7-methoxy-8-(4-methoxy-4-oxobutoxy)-5-oxo-11-(tetrahydro-2H-pyran-2-yloxy)-2,3,11,11a-hexahydro-1H-pyrrolo-[2,1-c][1,4]benzodiazepine-10(5H)-carboxylate (8)

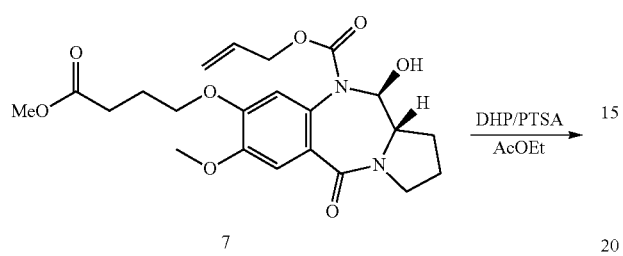

DHP (6.80 mL, 10 equiv.) was added to a solution of 7 (3.31 g, 7.9 mmol) in presence of a catalytic amount of PTSA (33 mg) in ethyl acetate (50 mL). The reaction mixture was left under magnetic stirrer for 2 hours until TLC showed completion of reaction. At that point and the reaction mixture was extracted with saturated aqueous NaHCO$_3$ (2×50 mL) and brine (50 mL). The organic phase was dried over MgSO$_4$, and evaporated using a rotary evaporator under reduced pressure. The crude of reaction was purified by column chromatography (mobile phase: DCM/acetone, 90/10, v/v) affording pure 8 (3.60 g, 85%) as a yellow solid. $^1$H NMR (400 MHz, CHLOROFORM-d) δ: 7.19 (1H, s), 6.88 (1H, s), 6.60 (1H, s), 5.68-5.90 (4H, m), 5.00-5.20 (8H, m), 4.30-4.70 (4H, m), 4.05-4.15 (6H, m), 3.80-3.92 (8H, m), 3.62-3.73 (8H, m), 3.40-3.55 (8H, m), 2.50-2.64 (4H, m), 2.90-2.10 (8H, m), 1.65-1.84 (6H, m), 1.42-1.62 (15H, m). $^{13}$C NMR (100 MHz, CHLOROFORM-d) δ: 173.4, 167.4, 149.1, 132.0, 114.9, 100.0, 98.4, 96.1, 94.6, 91.7, 88.6, 68.0, 67.7, 66.5, 63.6, 62.9, 60.1, 56.1, 51.6, 51.2, 46.3, 30.9, 30.2, 29.0, 25.4, 24.2, 20.0. m/z (+EI) calc. for C$_{27}$H$_{36}$N$_2$O$_9$ (M)$^+$ 532.5 found 533.2 ([M]+H)$^+$

Example 9

Synthesis of 4-(10-(allyloxycarbonyl)-7-methoxy-5-oxo-11-(tetrahydro-2H-pyran-2-yloxy)-2,3,5,10,11,11a-hexahydro-1H-pyrrolo[2,1-c][1,4]benzodiazepine-8-yloxy)butanoic acid (9)

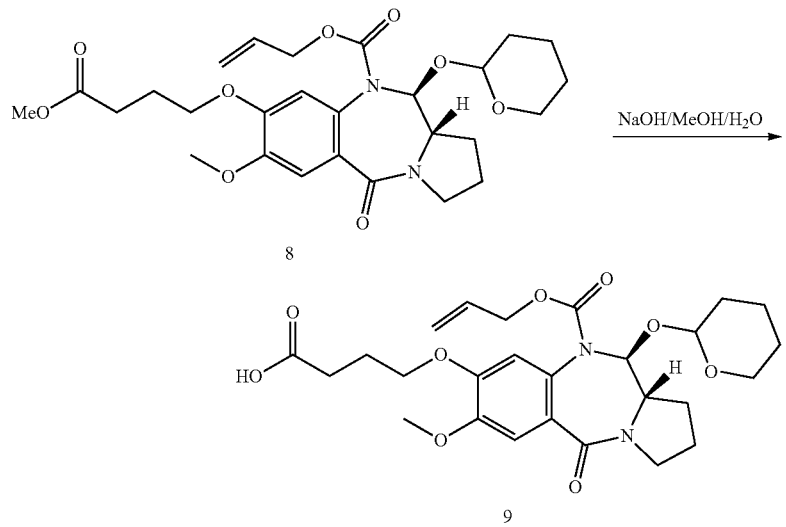

An excess of NaOH 1 M aqueous solution was added to a solution of 8 (3.79 g, 7.1 mmol) in MeOH (60 mL). The reaction mixture was left under magnetic stirrer overnight until TLC showed completion of the reaction. MeOH was evaporated under reduced pressure using a rotary evaporator and water (30 mL) was added to the residue. Citric acid 1 M aqueous solution was added until acid pH is reached. The aqueous layer was extracted with ethyl acetate (2×50 mL). The combined organic layers were dried over MgSO$_4$ and concentrated under reduced pressure using a rotary evaporator, giving pure PBD protected acid core 9 (3.20 g, 87%) as a light yellow solid. $^1$H NMR (400 MHz, CHLOROFORM-d) δ: 7.20 (2H, s), 6.89 (1H, s), 6.58 (1H, s), 5.87 (2H, d, J=9.2 Hz), 5.72 (2H, d, J=9.2 Hz), 4.95-5.18 (5H, m), 4.30-4.60 (5H, m), 4.00-4.15 (7H, m), 3.82-3.91 (7H, m), 3.42-3.69 (9H, m), 2.49-2.60 (4H, m), 1.90-2.20 (12H, m), 1.67-1.81 (4H, m), 1.40-1.60 (8H, m). $^{13}$C NMR (100 MHz, CHLOROFORM-d) δ: 177.6, 167.6, 149.8, 132.1, 131.9, 126.7, 117.3, 114.9, 110.8, 100.7, 96.0, 91.7, 88.5, 67.9, 66.6, 63.6, 60.1, 56.1, 46.5, 31.1, 30.3, 28.8, 25.2, 24.1, 23.2, 20.0. m/z (+EI) calc. for C$_{26}$H$_{34}$N$_2$O$_9$ (M)$^+$ 518.5 found 519.2 ([M]+H)$^+$ -continued

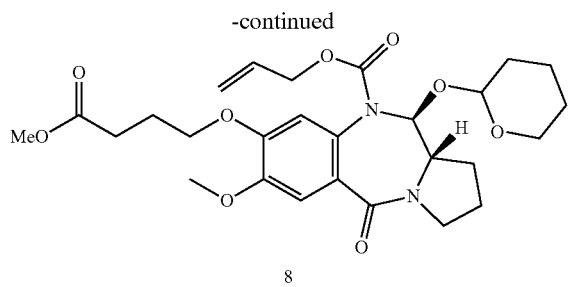

67

Synthesis of Intermediate for PBD C8-Derivatization

Examples 10 & 11

Synthesis of Dimethyl Carboxamido Benzofused Biaryl Derivative

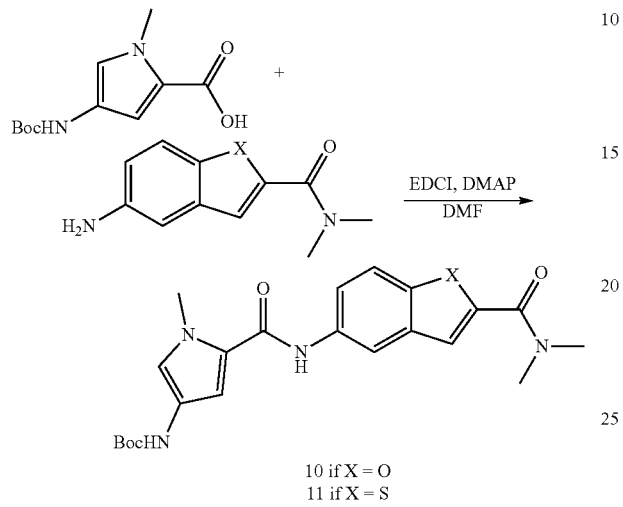

10 if X = O
11 if X = S 4-((tert-butoxycarbonyl)amino)-1-methyl-1H-pyrrole-2-carboxylic acid (150 mg, 1.2 equiv.) was dissolved in DMF (5 mL). EDCI (2.5 equiv.) and DMAP (3 equiv.) were added to the solution that was left under magnetic stirrer in $N_2$ atmosphere for 20 minutes. At that point the corresponding 5-amino-2-dimethyl carboxamido benzofused (1 equiv.) was added to the reaction mixture and left under magnetic stirrer overnight. TLC didn't show total consumption of the starting material. The reaction was quenched by addition of water (15 mL) that was then extracted with ethyl acetate (3×10 mL). The organic phase was then sequentially washed with brine (15 mL), $NaHCO_3$ saturated aqueous solution (15 mL) and citric acid aqueous solution 0.1 M (15 mL). The collected organic phase was dried on $MgSO_4$ and subsequently evaporated using a rotary evaporator giving crude compounds 10 and 11 that were subsequently purified by column chromatography (mobile phase: from 100 DCM to 70/30, v/v, DCM/EA) to give the final products 10 and 11.

Example 10 tert-Butyl (5-((2-(dimethylcarbamoyl)benzofuran-5-yl)-carbamoyl)-1-methyl-1H-pyrrol-3-yl)carbamate (10)

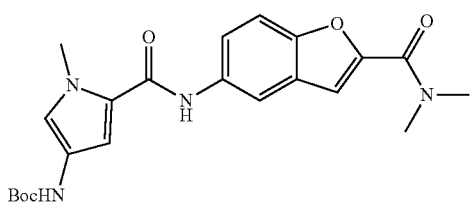

10

68

Obtained 0.190 g (72%), as a yellow solid. 1H NMR (400 MHz, CHLOROFORM-d) δ: 7.99 (d, J=2.01 Hz, 1H), 7.70 (s, 1H), 7.48 (d, J=8.81 Hz, 1H), 7.38 (dd, J=2.14, 8.94 Hz, 1H), 7.25 (d, J=0.76 Hz, 1H), 6.88 (s, 1H), 6.68 (s, 1H), 6.32 (s, 1H), 3.92 (s, 3H), 3.35 (br. s., 3H), 3.15 (br. s., 3H), 1.52 (s, 9H). $^{13}$C NMR (101 MHz, CHLOROFORM-d) δ: 160.9, 159.8, 153.4, 151.5, 150.0, 133.8, 123.4, 120.0, 113.5, 112.1, 111.9, 103.8, 36.8, 28.4. m/z (+EI) calc. for $C_{22}H_{26}N_4O_5$ $(M)^+$ 426.1 found 427.1 $([M]+H)^+$

Example 11 tert-butyl (5-((2-(dimethylcarbamoyl)benzo[b]thiophen-5-yl)carbamoyl)-1-methyl-1H-pyrrol-3-yl)carbamate (11)

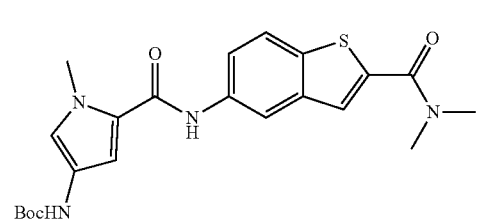

11

Obtained 0.130 g (60%), as a brown solid. $^1$H NMR (400 MHz, CHLOROFORM-d) δ: 8.25 (d, J=2.01 Hz, 1H), 7.70-7.81 (m, 2H), 7.46 (s, 1H), 7.36 (dd, J=2.14, 8.69 Hz, 1H), 6.88 (br. s., 1H), 6.70 (br. s., 1H), 6.33 (br. s., 1H), 3.93 (s, 3H), 3.22 (br. s., 6H), 1.52 (s, 9H). $^{13}$C NMR (101 MHz, CHLOROFORM-d) δ: 164.8, 159.7, 139.4, 138.7, 135.8, 135.2, 125.5, 123.3, 122.7, 119.3, 115.3, 103.9, 36.8, 28.4. m/z (+EI) calc. for $C_{22}H_{26}N_4O_4S$ $(M)^+$ 442.1 found 443.1 $([M]+H)^+$

Examples 12-21

Synthesis of Carboxamido Benzofused Biaryl Derivative

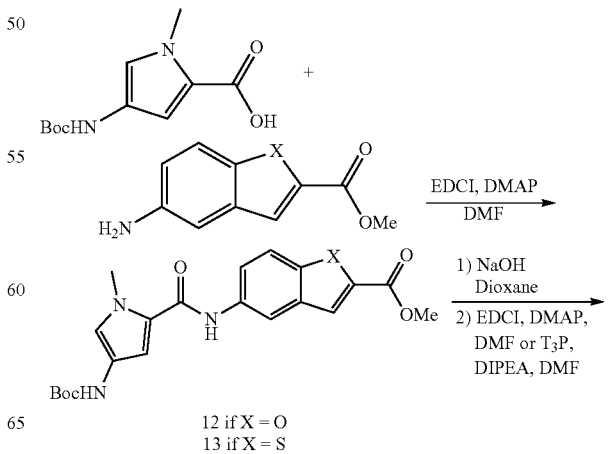

12 if X = O
13 if X = S

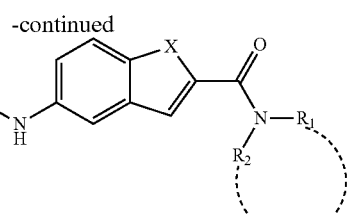

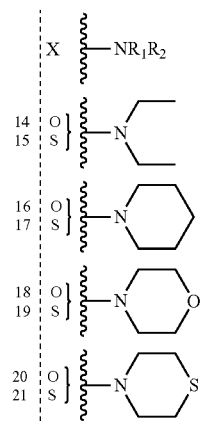

Examples 12 & 13

Synthesis of Methyl Ester Benzofused Intermediate (12,13)

4-((tert-butoxycarbonyl)amino)-1-methyl-1H-pyrrole-2-carboxylic acid (200 mg, 1.2 equiv.) was dissolved in DMF (5 mL). EDCI (2.5 equiv.) and DMAP (3 equiv.) were added to the solution that was left under magnetic stirrer in $N_2$ atmosphere for 20 minutes. At that point the corresponding 5-amino-2-methyl ester benzofused (1 equiv.) was added to the reaction mixture and left under magnetic stirrer overnight. The reaction didn't go to completion. The reaction was quenched by addition of water (15 mL) that was then extracted with ethyl acetate (3×10 mL). The organic phase was then sequentially washed with brine (15 mL), NaHCO$_3$ saturated aqueous solution (15 mL) and citric acid aqueous solution 0.1 M (15 mL). The collected organic phase was dried on MgSO$_4$ and subsequently evaporated using a rotary evaporator giving crude compounds 12 and 13 that were subsequently purified by column chromatography (mobile phase: from 100 DCM to 85/15, v/v, DCM/EA) to give the final products 12 and 13.

Example 12

6-(4-((tert-butoxycarbonyl)amino)-1-methyl-1H-pyrrole-2-carboxamido)benzofuran-2-carboxylate (12)

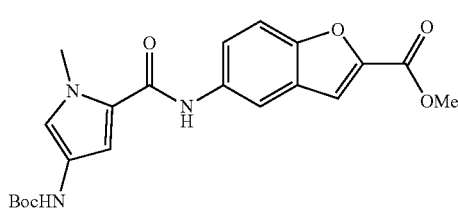

Obtained 0.200 g (70%) as a yellow solid. $^1$H NMR (400 MHz, CHLOROFORM-d) δ: 8.09 (d, J=2.01 Hz, 1H), 7.85 (s, 1H), 7.51 (d, J=9.06 Hz, 1H), 7.47 (s, 1H), 7.40 (dd, J=2.27, 9.06 Hz, 1H), 6.86 (br. s., 1H), 6.70 (br. s., 1H), 6.43 (br. s., 1H), 3.97 (s, 3H), 3.91 (s, 3H), 1.51 (s, 9H). $^{13}$C NMR (101 MHz, CHLOROFORM-d) δ: 171.1, 159.8, 152.5, 146.1, 134.2, 123.3, 122.0, 121.3, 114.1, 113.8, 112.4, 52.3, 36.7, 28.3. m/z (+EI) calc. for $C_{21}H_{23}N_3O_6(M)^+$ 413.1 found 414.0 ([M]+H)$^+$

Example 13

Methyl 5-(4-((tert-butoxycarbonyl)amino)-1-methyl-1H-pyrrole-2-carboxamido) benzo[b]thiophene-2-carboxylate (13)

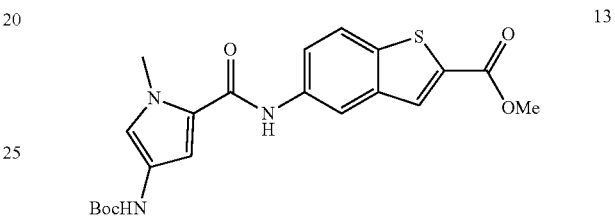

Obtained 0.192 g (65%) as a yellow-orange solid. $^1$H NMR (400 MHz, CHLOROFORM-d) δ: 8.24 (d, J=1.76 Hz, 1H), 7.97 (s, 1H), 7.78-7.76 (m, 2H), 7.49 (dd, J=2.14, 8.69 Hz, 1H), 6.86 (br. s., 1H), 6.70 (br. s., 1H), 6.33 (br. s., 1H), 3.94 (s, 3H), 3.91 (s, 3H), 1.52 (s, 9H). $^{13}$C NMR (100 MHz, CHLOROFORM-d) δ: 163.1, 159.7, 139.3, 137.7, 135.5, 134.4, 130.5, 123.3, 123.0, 122.0, 120.6, 115.9, 104.1, 52.5, 36.7, 28.3. m/z (+EI) calc. for $C_{21}H_{23}N_3O_5S$ (M)$^+$ 429.1 found 430.0 ([M]+H)$^+$

Examples 14 & 15

Synthesis of Diethyl Carboxamido Benzofused Biaryl Derivative (14,15)

An excess of NaOH 1M (aqueous solution) was added to the methyl ester benzofused intermediate 14 or 15 (80 mg, 1 equiv.) dissolved in MeOH (8 mL) and left under magnetic stirrer at room temperature overnight, until TLC showed total disappearance of the starting material and the hydrolysis of the ester is achieved. MeOH was evaporated under reduced pressure using a rotary evaporator and Citric acid 1 M aqueous solution was added until acid pH causing the formation of a precipitate. The solid was filtered using a sintered glass funnel under vacuum, collected and dissolved in DMF (4 mL). Diethyl amine (2 equiv.) and DIPEA (2 equiv.) were added to the solution that was then cooled to 0° C. in an ice bath and added of T$_3$P (50% solution in DMF, 2 equiv.). The reaction mixture was then allowed to reach room temperature and left under magnetic stirrer overnight. The reaction didn't go to completion and was quenched by addition of water (10 mL) and then extracted with ethyl acetate (3×8 mL). The organic phase was then sequentially washed with brine (10 mL) and NaHCO$_3$ saturated aqueous solution (10 mL). The collected organic phase was dried on MgSO$_4$ and subsequently evaporated using a rotary evaporator giving crude compounds 14 and 15 that were subsequently purified by column chromatography (mobile phase: from 100 DCM to 70/30, v/v, DCM/EA) to give the final products 14 and 15.

Example 14 tert-butyl (5-((2-(diethylcarbamoyl)benzofuran-5-yl)-carbamoyl)-1-methyl-1H-pyrrol-3-yl)carbamate (14)

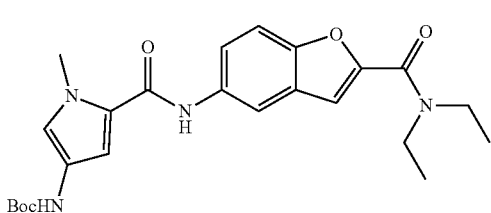

Obtained 0.036 g (40%) as a white solid. $^1$H NMR (400 MHz, CHLOROFORM-d) δ: 7.95 (d, J=2.01 Hz, 1H), 7.80 (s, 1H), 7.34-7.47 (m, 2H), 7.23 (s, 1H), 6.88 (br. s., 1H), 6.68 (br. s., 1H), 6.43 (br. s., 1H), 3.91 (s, 3H), 3.59 (br. s., 4H), 1.51 (s, 9H), 1.29 (br. s., 6H). $^{13}$C NMR (100 MHz, CHLOROFORM-d) δ: 159.9, 159.4, 153.1, 151.1, 150.1, 133.5, 127.1, 123.0, 121.6, 119.6, 118.3, 113.2, 111.6, 111.0, 103.5, 80.0, 36.4, 28.0. m/z (+EI) calc. for $C_{24}H_{30}N_4O_5$ (M)$^+$ 454.2 found 455.1 ([M]+H)$^+$ Example 15 tert-butyl (5-((2-(diethylcarbamoyl)benzo[b]thiophen-5-yl)carbamoyl)-1-methyl-1H-pyrrol-3-yl)carbamate (15)

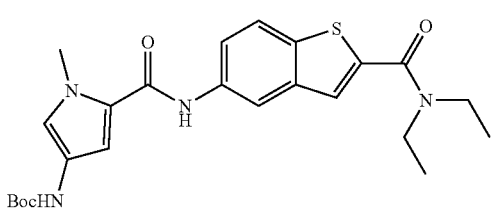

Obtained 0.035 g (41%) as a white solid. $^1$H NMR (400 MHz, CHLOROFORM-d) δ: 8.20 (d, J=2.01 Hz, 1H), 7.92 (br. s., 1H), 7.69 (d, J=8.81 Hz, 1H), 7.37 (s, 1H), 7.31 (d, J=8.81 Hz, 1H), 6.90 (br. s., 1H), 6.70 (br. s., 1H), 6.55 (br. s., 1H), 3.89 (s, 3H), 3.55 (q, J=7.22 Hz, 4H), 1.51 (s, 9H), 1.26 (t, J=7.18 Hz, 6H). $^{13}$C NMR (100 MHz, CHLOROFORM-d) δ: 171.2, 164.2, 159.9, 153.5, 139.4, 138.8, 135.4, 135.3, 124.2, 123.2, 122.5, 122.0, 119.3, 118.9, 115.4, 80.2, 60.4, 36.8, 28.4. m/z (+EI) calc. for $C_{24}H_{30}N_4O_4S$ (M)$^+$ 470.2 found 471.1 ([M]+H)$^+$ Examples 16-21

Synthesis of Aliphatic Ring Carboxamido Benzofused Biaryl Derivative (16-21)

An excess of NaOH 1M (aqueous solution) was added to the methyl ester benzofused intermediate 14 or 15 (80 mg, 1 equiv.) dissolved in MeOH (8 mL) and left under magnetic stirrer at room temperature overnight, until TLC showed total disappearance of the starting material and the hydrolysis of the ester is achieved. MeOH was evaporated under reduced pressure using a rotary evaporator and Citric acid 1 M aqueous solution was added until acid pH causing the formation of a precipitate. The solid was filtered using a sintered glass funnel under vacuum, collected and dissolved in DMF (4 mL). EDCI (2.5 equiv.) and DMAP (3 equiv.) were added to the solution that was left under magnetic stirrer under N$_2$ atmosphere for 20 minutes. At that point the corresponding secondary aliphatic ring amine (1.5 equiv.) was added to the solution and left under magnetic stirrer overnight. The reaction didn't go to completion and was quenched by addition of water (10 mL) that was then extracted with ethyl acetate (3×8 mL). The organic phase was then sequentially washed with brine (10 mL), NaHCO$_3$ saturated aqueous solution (10 mL) and citric acid aqueous solution 0.1 M (10 mL). The collected organic phase was dried on MgSO$_4$ and subsequently evaporated using a rotary evaporator giving crude compounds 16-21 that were subsequently purified by column chromatography (mobile phase: from 100 DCM to 70/30, v/v, DCM/EA, depending on the substrate) to give the final products 16-21.

Example 16 tert-butyl (1-methyl-5-((2-(piperidine-1-carbonyl)benzofuran-5-yl)carbamoyl)-1H-pyrrol-3-yl)carbamate (16)

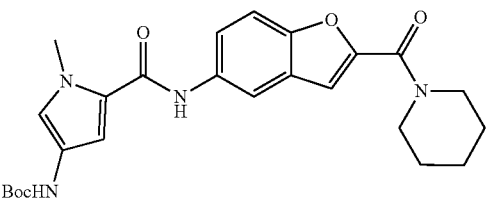

Obtained 0.031 g (34%) as a white solid. $^1$H NMR (400 MHz, CHLOROFORM-d) δ: 7.91-7.93 (m, 2H), 7.42 (d, 1H), 7.34-7.39 (m, 1H), 7.13 (d, J=0.76 Hz, 1H), 6.88 (s, 1H), 6.68 (s, 1H), 6.55 (s, 1H), 3.88 (s, 3H), 3.72 (br. s., 4H), 1.62-1.75 (m, 5H), 1.50 (s, 9H). $^{13}$C NMR (100 MHz, CHLOROFORM-d) δ: 171.2, 159.9, 159.8, 153.5, 151.3, 150.0, 133.9, 127.4, 123.3, 122.0, 120.0, 118.7, 113.5, 111.9, 111.2, 103.9, 80.2, 46.9, 36.7, 28.4, 26.6, 24.6. m/z (+EI) calc. for $C_{25}H_{30}N_4O_5$ (M)$^+$ 466.2 found 467.1 ([M]+H)$^+$ Example 17 tert-butyl (1-methyl-5-((2-(piperidine-1-carbonyl)benzo-[b]thiophen-5-yl)carbamoyl)-1H-pyrrol-3-yl)carbamate (17)

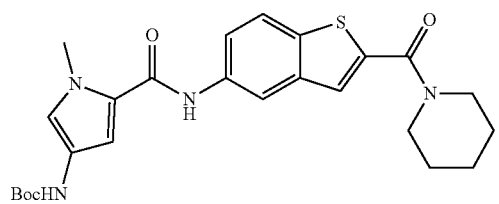

Obtained 0.032 g (33%) as a yellow solid. $^1$H NMR (400 MHz, CHLOROFORM-d) δ: 8.20 (s, 1H), 7.86 (s, 1H), 7.72 (d, J=9.06 Hz, 1H), 7.30-7.37 (m, 2H), 6.90 (br. s., 1H), 6.70 (br. s., 1H), 6.48 (br. s., 1H), 3.91 (s, 3H), 3.68 (br. s., 4H), 1.59-1.75 (m, 5H), 1.52 (s, 9H). $^{13}$C NMR (100 MHz, CHLOROFORM-d) δ: 171.2, 163.7, 159.8, 153.5, 139.3, 138.2, 135.5, 135.3, 124.6, 123.3, 122.6, 122.0, 119.2, 118.8, 115.3, 104.0, 36.8, 28.4, 24.6. m/z (+EI) calc. for $C_{25}H_{30}N_4O_4S$ (M)$^+$ 482.2 found 483.0 ([M]+H)$^+$ Example 18 tert-butyl (1-methyl-5-((2-(morpholine-4-carbonyl)benzofuran-5-yl)carbamoyl)-1H-pyrrol-3-yl)carbamate (18)

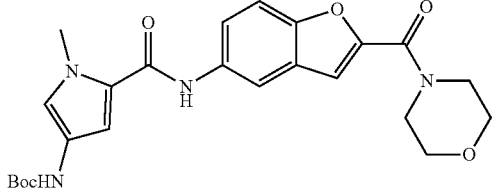

Obtained 0.038 g (40%) as a grey solid. $^1$H NMR (400 MHz, CHLOROFORM-d) δ: 8.01 (d, J=2.01 Hz, 1H), 7.69 (s, 1H), 7.48 (d, J=8.81 Hz, 1H), 7.41 (dd, J=2.14, 8.94 Hz, 1H), 7.31 (d, J=0.76 Hz, 1H), 6.87 (s, 1H), 6.69 (s, 1H), 6.29 (br. s., 1H), 3.93 (s, 3H), 3.89 (br. s., 4H), 3.80 (br. s., 4H), 1.52 (s, 9H). $^{13}$C NMR (100 MHz, CHLOROFORM-d) δ: 171.1, 162.7, 159.7, 151.5, 143.8, 133.7, 128.0, 127.4, 121.8, 120.2, 118.6, 113.5, 112.7, 112.1, 66.9, 36.9, 28.4. m/z (+EI) calc. for $C_{24}H_{28}N_4O_6$ (M)$^+$ 468.2 found 469.2 ([M]+H)$^+$ Example 19 tert-butyl (1-methyl-5-((2-(morpholine-4-carbonyl)benzo[b]-thiophen-5-yl)carbamoyl)-1H-pyrrol-3-yl)carbamate (19)

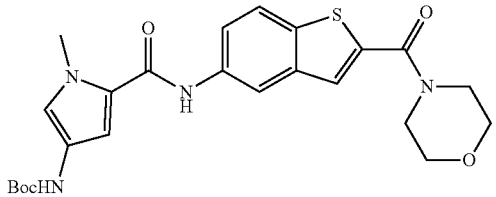

Obtained 0.044 g (48%) as a white solid. $^1$H NMR (400 MHz, CHLOROFORM-d) δ: 8.20 (d, J=2.01 Hz, 1H), 7.92 (br. s., 1H), 7.69 (d, J=8.81 Hz, 1H), 7.37 (s, 1H), 7.31 (d, J=8.81 Hz, 1H), 6.90 (br. s., 1H), 6.70 (br. s., 1H), 6.55 (br. s., 1H), 3.89 (s, 3H), 3.55 (q, J=7.22 Hz, 4H), 1.51 (s, 9H), 1.26 (t, J=7.18 Hz, 6H). $^{13}$C NMR (100 MHz, CHLOROFORM-d) δ: 171.2, 164.2, 159.9, 153.5, 139.4, 138.8, 135.4, 135.3, 124.2, 123.2, 122.5, 122.0, 119.3, 118.9, 115.4, 80.2, 60.4, 36.8, 28.4. m/z (+EI) calc. for $C_{24}H_{28}N_4O_5S$ (M)$^+$ 484.1 found 485.1 ([M]+H)$^+$ Example 20 tert-butyl (1-methyl-5-((2-(thiomorpholine-4-carbonyl)-benzofuran-5-yl)carbamoyl)-1H-pyrrol-3-yl)carbamate (20)

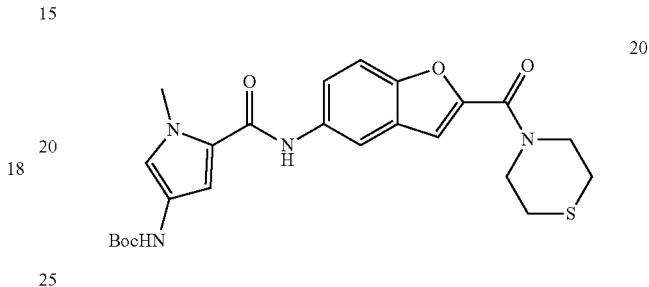

Obtained 0.039 g (41%) as a white solid. $^1$H NMR (400 MHz, CHLOROFORM-d) δ: 8.01 (d, J=2.01 Hz, 1H), 7.67 (s, 1H), 7.48 (d, J=8.81 Hz, 1H), 7.40 (dd, J=2.27, 8.81 Hz, 1H), 6.87 (s, 1H), 6.69 (s, 1H), 6.27 (br. s., 1H), 4.08 (br. s., 4H), 3.93 (s, 3H), 2.73-2.80 (m, 4H), 1.52 (s, 9H). $^{13}$C NMR (100 MHz, CHLOROFORM-d) δ: 159.7, 151.4, 149.6, 134.0, 127.5, 123.3, 122.0, 120.6, 120.1, 113.5, 112.3, 112.1, 80.4, 36.8, 35.0, 28.4. m/z (+EI) calc. for $C_{24}H_{28}N_4O_5S$ (M)$^+$ 484.1 found 485.1 ([M]+H)$^+$ Example 21 tert-butyl (1-methyl-5-((2-(thiomorpholine-4-carbonyl)-benzo[b]thiophen-5-yl)carbamoyl)-1H-pyrrol-3-yl)carbamate (21)

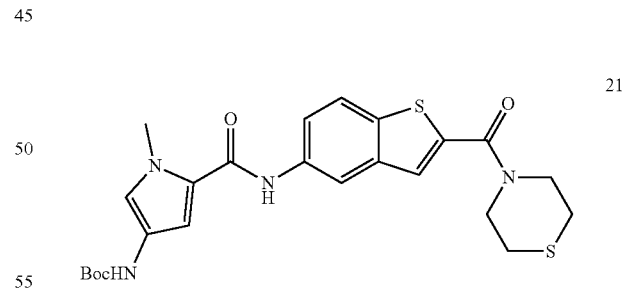

Obtained 0.048 g (50%) as a white solid. $^1$H NMR (400 MHz, CHLOROFORM-d) δ: 8.23 (s, 1H), 7.92 (s, 1H), 7.73 (d, J=10.83 Hz, 1H), 7.33-7.40 (m, 2H), 6.87 (br. s., 1H), 6.71 (br. s., 1H), 6.45 (br. s., 1H), 4.00 (br. s., 4H), 3.91 (s, 3H), 2.71 (br. s., 4H), 1.51 (s, 9H). $^{13}$C NMR (100 MHz, CHLOROFORM-d) δ: 171.3, 164.2, 163.1, 159.8, 153.5, 139.2, 137.3, 135.6, 135.4, 125.0, 123.3, 122.6, 119.5, 116.5, 115.4, 104.1, 80.3, 36.8, 35.6, 28.4. m/z (+EI) calc. for $C_{24}H_{28}N_4O_4S_2$ (M)$^+$ 500.1 found 501.2 ([M]+H)$^+$ Reaction Scheme for Synthesis of PBD C8-Derivates
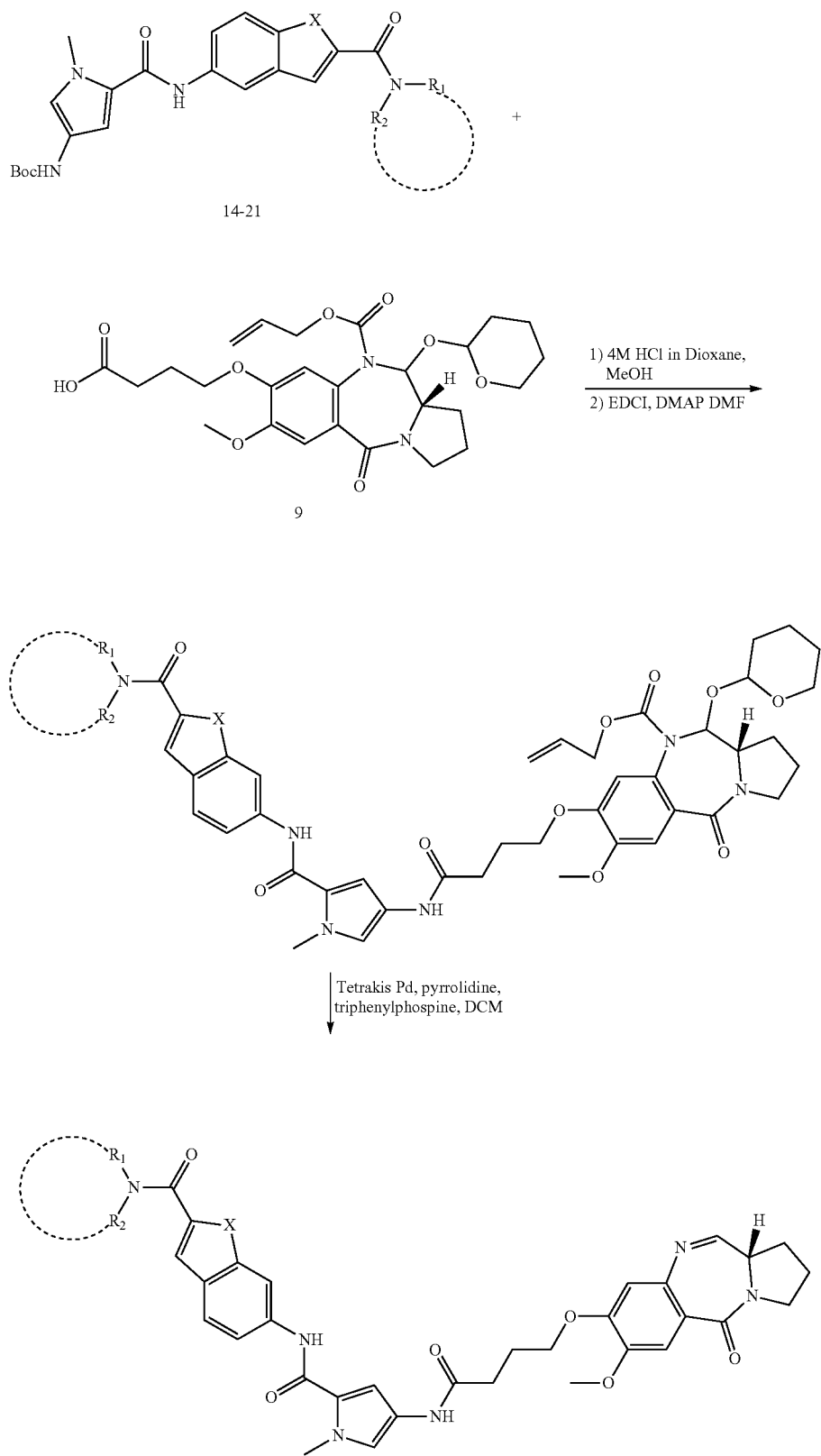

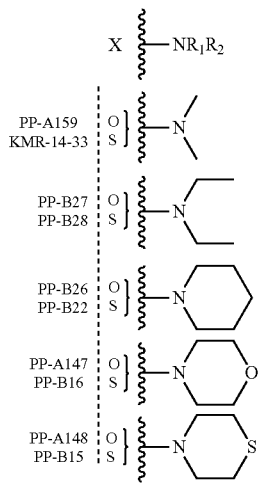

Examples 22-31

Synthesis of PBD C8-Derivatives

As shown in the reaction scheme above, compounds 14-21 (from 30 to 50 mg, 1 equiv.) were boc-deprotected dissolving the desiderate derivative in MeOH (3 ml) and HCl 4M in dioxane (3 mL). The solution was left under magnetic stirrer for 2 hours until TLC showed total cleavage of protecting group. The reaction mixture was subsequently evaporated using a rotary evaporator, obtaining a solid. PBD capping unit 9 (1.2 equiv.) was dissolved in DMF (4 mL) and added of EDCI (2 equiv.) and DMAP (3 equiv.). The reaction mixture was left under magnetic stirrer in $N_2$ atmosphere for 20 minutes. At that point the desiderate deprotected compound was added to the reaction mixture and left under magnetic stirrer overnight for 15 hours until TLC and LC-MS analysis showed formation of the protected PBD-C8 derivative. The reaction was quenched by addition of water (10 mL) that was then extracted with ethyl acetate (3×10 mL). The organic phase was then sequentially washed with brine (10 mL), NaHCO$_3$ saturated aqueous solution (10 mL) and citric acid aqueous solution 0.1M (10 mL). The collected organic phase was dried over MgSO$_4$ and subsequently evaporated using a rotary evaporator. The crude of each reaction was purified by column chromatography (mobile phase: from DCM/acetone, 90/10, v/v to DCM/acetone, 60/40/, v/v depending on the substrate). The protected PBD-conjugates (from 25 to 60 mg, 1 equiv) was dissolved in DCM (4 mL) and added of Tetrakis Pd (0.05 equiv.), triphenylphospine (0.25 equiv.) and pyrrolidine (1.2 equiv). The reaction mixture was kept under magnetic stirrer for 20 minutes when TLC showed completion of reaction. At that point the solvent was evaporated using a rotary evaporator and the crude of reaction was purified by column chromatography (mobile phase: from DCM/acetone, 90/10, v/v to DCM/acetone, 40/60/, v/v, depending on the substrate) affording pure final compounds.

Example 22

(S)—N-(2-(dimethylcarbamoyl)benzofuran-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide (PP-A159)

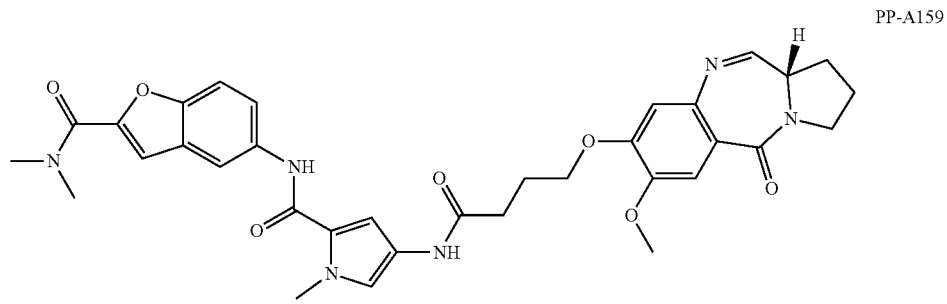 [SMILES: COc1cc2c(cc1OCCCC(=O)Nc1cc(C(=O)Nc3ccc4oc(C(=O)N(C)C)cc4c3)n(C)c1)N=C[C@@H]1CCCN1C2=O]

PP-A159

Obtained 0.045 g (64%) as a white solid. $^1$H NMR (400 MHz, CHLOROFORM-d) δ: 8.28 (s, 1H), 8.27 (s, 1H), 7.99 (d, J=1.76 Hz, 1H), 7.64 (d, J=4.53 Hz, 1H), 7.48 (s, 1H), 7.36-7.46 (m, 2H), 7.20 (s, 1H), 7.15 (d, J=1.76 Hz, 1H), 6.79 (s, 1H), 6.58 (d, J=2.01 Hz, 1H), 3.97-4.08 (m, 2H), 3.87 (s, 3H), 3.84 (s, 3H), 3.76 (m, 1H), 3.66-3.72 (m, 1H), 3.51-3.57 (m, 1H), 3.32 (br. s., 3H), 3.13 (br. s., 3H), 2.24-2.33 (m, 2H), 2.17-2.22 (m, 2H), 1.93-2.08 (m, 4H). $^{13}$C NMR (100 MHz, CHLOROFORM-d) δ: 169.9, 164.7, 162.8, 160.9, 160.0, 151.4, 150.6, 149.7, 147.7, 140.62, 134.1, 127.2, 123.0, 121.7, 120.4, 120.4, 119.9, 113.7, 111.8, 111.6, 110.8, 104.1, 68.1, 56.1, 53.8, 46.7, 36.8, 32.9, 29.5, 29.3, 24.9, 24.2. m/z (HRMS)

Example 23

(S)—N-(2-(dimethylcarbamoyl)benzo[b]thiophen-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide (KMR-14-33)

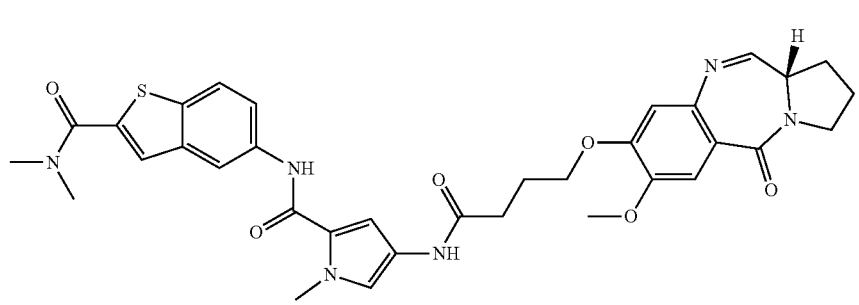

KMR-14-33

Obtained 0.040 g (67%) as a light yellow solid. $^1$H NMR (400 MHz, DMSO-d$_6$) δ: 9.98 (s, 1H), 9.93 (s, 1H), 8.43 (d, J=2.01 Hz, 1H), 7.91 (d, J=8.81 Hz, 1H), 7.76-7.80 (m, 2H), 7.68 (dd, J=2.01, 8.81 Hz, 1H), 7.33 (s, 1H), 7.24 (d, J=1.76 Hz, 1H), 7.01 (d, J=1.76 Hz, 1H), 6.83 (s, 1H), 4.09-4.16 (m, 1H), 4.00-4.07 (m, 1H), 3.85 (s, 3H), 3.83 (s, 3H), 3.65-3.68 (m, 1H), 3.57-3.63 (m, 1H), 3.33-3.42 (m, 1H), 3.25 (br. s., 3H), 3.06 (br. s., 3H), 2.41-2.47 (m, 2H), 2.18-2.29 (m, 2H), 2.02-2.08 (m, 2H), 1.88-1.98 (m, 2H). $^{13}$C NMR (100 MHz, DMSO-d$_6$) δ: 168.8, 164.2, 163.3, 163.2, 159.8, 150.1, 146.8, 140.5, 139.2, 138.5, 136.6, 133.9, 126.0, 122.5, 122.2, 122.0, 119.9, 119.8, 1118.9, 115.3, 111.2, 104.8, 79.3, 78.9, 78.6, 68.5, 67.8, 55.9, 55.6, 54.9, 53.4, 46.3, 36.2, 32.1, 29.6, 28.8. m/z (HRMS)

Example 24

(S)—N-(2-(diethylcarbamoyl)benzofuran-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide (PP-B27)

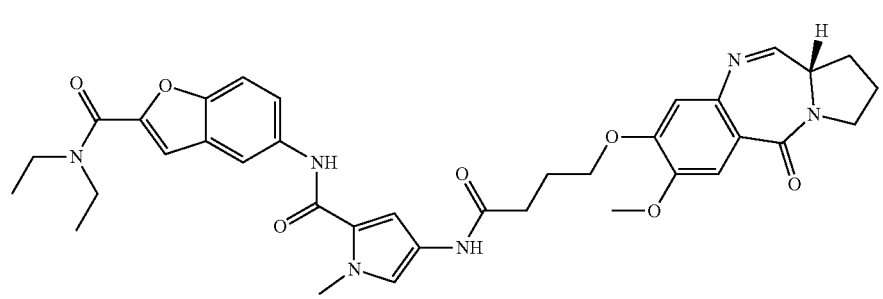

PP-B27

Obtained 0.025 g (56%) as a white solid. $^1$H NMR (400 MHz, CHLOROFORM-d) δ: 8.20 (s, 1H), 8.16 (s, 1H), 7.98 (d, J=1.51 Hz, 1H), 7.65 (d, J=4.28 Hz, 1H), 7.50 (s, 1H), 7.41-7.45 (m, 2H), 7.22 (s, 1H), 7.15 (s, 1H), 6.80 (s, 1H), 6.57 (s, 1H), 4.07 (t, J=5.67 Hz, 2H), 3.88 (s, 3H), 3.86 (s, 3H), 3.73-3.82 (m, 2H), 3.67-3.73 (m, 1H), 3.60 (br. s., 4H), 2.45-2.53 (m, 2H), 2.25-2.34 (m, 2H), 2.18-2.24 (m, 2H), 1.99-2.07 (m, 2H), 1.28 (br. s., 6H). $^{13}$C NMR (100 MHz, CHLOROFORM-d) δ: 169.9, 164.6, 160.3, 159.9, 151.4, 150.7, 150.3, 147.7, 140.6, 134.1, 127.4, 123.0, 121.6, 120.4, 120.2, 119.9, 113.7, 111.8, 111.7, 110.9, 104.8, 69.5, 68.1, 59.1, 53.8, 46.7, 36.8, 31.8, 29.6, 29.3, 24.9, 24.1. m/z (+EI) calc. for $C_{24}H_{28}N_4O_4S_2$ (M)$^+$ 500.1 found 501.2 ([M]+H)$^+$ Example 25

((S)—N-(2-(diethylcarbamoyl)benzo[b]thiophen-5-yl)-4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamide (PP-B28)

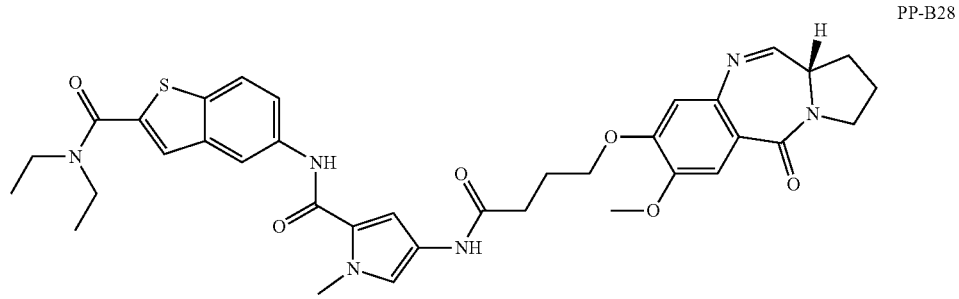 [SMILES: CCN(CC)C(=O)c1cc2cc(NC(=O)c3cc(NC(=O)CCCOc4cc5c(cc4OC)C(=O)N4CCC[C@H]4C=N5)cn3C)ccc2o1]

PP-B28

Obtained 0.031 g (62%) as a yellow solid. $^1$H NMR (400 MHz, DMSO-d$_6$) δ: 9.94 (s, 1H), 9.98 (s, 1H), 8.45 (s, 1H), 7.91 (d, J=8.78 Hz, 1H), 7.75 (d, J=4.40 Hz, 1H), 7.57-7.70 (m, 2H), 7.33 (s, 1H), 7.24 (s, 1H), 7.02 (s, 1H), 6.83 (s, 1H), 4.09-4.20 (m, 1H), 3.96-4.09 (m, 1H), 3.85 (s, 3H), 3.83 (s, 3H), 3.63-3.71 (m, 2H), 3.55-3.63 (m, 1H), 3.49 (br. s., 4H), 2.40-2.46 (m, 2H), 2.16-2.26 (m, 2H), 1.99-2.05 (m, 2H), 1.90-1.95 (m, 2H), 1.19 (br.s., 6H). $^{13}$C NMR (100 MHz, DMSO-d$_6$) δ: 184.2, 168.6, 159.8, 158.3, 154.6, 151.6, 149.9, 147.8, 144.9, 142.2, 141.1, 140.8, 139.1, 138.5, 136.6, 134.9, 136.6, 134.9, 133.7, 129.9, 127.8, 124.4, 124.4, 122.5, 122.2, 119.7, 118.9, 116.4, 115.3, 110.6, 68.5, 55.8, 36.2, 30.7, 29.5. m/z (HRMS)

Example 26

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(2-(piperidine-1-carbonyl)benzofuran-5-yl)-1H-pyrrole-2-carboxamide (PP-B26)

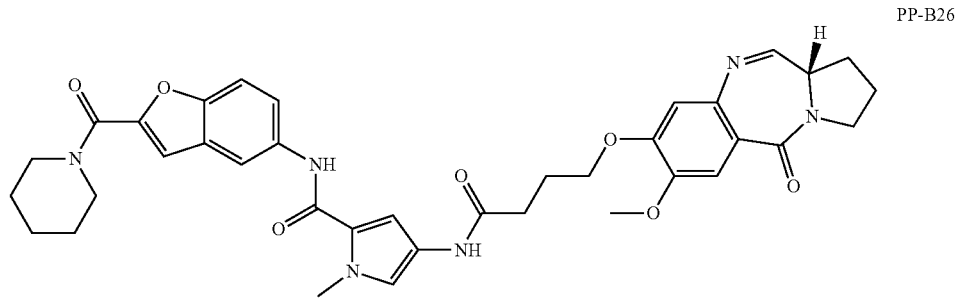 [SMILES: COc1cc2c(cc1OCCCC(=O)Nc1cc(C(=O)Nc3ccc4oc(C(=O)N5CCCCC5)cc4c3)n(C)c1)N=C[C@@H]1CCCN1C2=O]

PP-B26

Obtained 0.020 g (46%) as a white solid. $^1$H NMR (400 MHz, CHLOROFORM-d) δ: 8.18 (s, 1H), 8.13 (s, 1H), 7.98 (s, 1H), 7.65 (d, J=4.28 Hz, 1H), 7.50 (s, 1H), 7.42-7.45 (m, 2H), 7.13-7.16 (m, 2H), 6.80 (s, 1H), 6.56 (d, J=2.01 Hz, 1H), 4.06 (t, J=6.17 Hz, 2H), 3.88 (s, 3H), 3.86 (s, 3H), 3.67-3.78 (m, 6H), 3.52-3.59 (m, 1H), 2.46-2.52 (m, 2H), 2.27-2.32 (m, 2H), 2.19-2.24 (m, 2H), 2.00-2.07 (m, 2H), 1.62-1.71 (m, 6H). $^{13}$C NMR (100 MHz, CHLOROFORM-d) δ: 169.8, 164.65, 162.8, 159.9, 159.8, 151.3, 150.7, 149.9, 147.7, 140.6, 134.1, 127.4, 123.0, 121.6, 120.4, 120.1, 119.8, 113.6, 111.8, 111.7, 111.1, 110.9, 104.5, 69.5, 68.1, 56.1, 53.8, 46.7, 36.7, 31.7, 30.9, 29.5, 29.2, 24.9, 24.6, 24.1. m/z (HRMS)

Example 27

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(2-(piperidine-1-carbonyl)benzo[b]thiophen-5-yl)-1H-pyrrole-2-carboxamide (PP-B22)

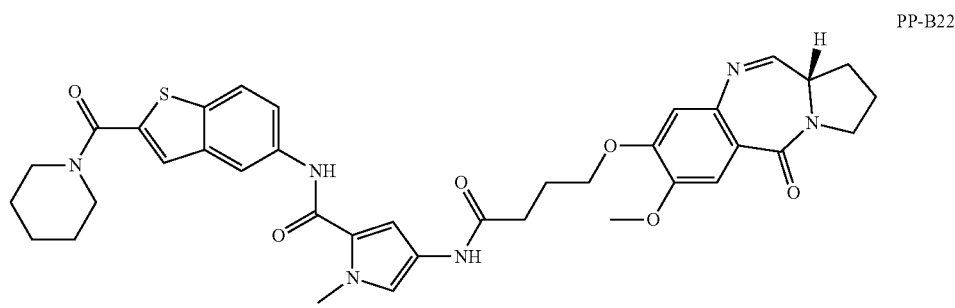 [SMILES: COc1cc2c(cc1OCCCC(=O)Nc1cc(C(=O)Nc3ccc4sc(C(=O)N5CCCCC5)cc4c3)n(C)c1)N=C[C@@H]1CCCN1C2=O]

Obtained 0.030 g (69%) as a yellow solid. $^1$H NMR (400 MHz, CHLOROFORM-d) δ: 8.26 (d, J=1.76 Hz, 1H), 8.10 (s, 1H), 7.99 (s, 1H), 7.75 (d, J=8.56 Hz, 1H), 7.66 (d, J=4.53 Hz, 1H), 7.52 (s, 1H), 7.42 (dd, J=2.14, 8.69 Hz, 1H), 7.38 (s, 1H), 7.15 (d, J=1.51 Hz, 1H), 6.82 (s, 1H), 6.56 (d, J=1.76 Hz, 1H), 4.09 (t, J=6.17 Hz, 2H), 3.90 (s, 3H), 3.89 (s, 3H), 3.68 (br. s., 5H), 3.53-3.58 (m, 2H), 2.48-2.55 (m, 2H), 2.27-2.34 (m, 2H), 2.20-2.27 (m, 2H), 2.00-2.09 (m, 2H), 1.55-1.69 (m, 6H). m/z (HRMS)

Example 28

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(2-(morpholine-4-carbonyl)benzofuran-5-yl)-1H-pyrrole-2-carboxamide (PP-A147)

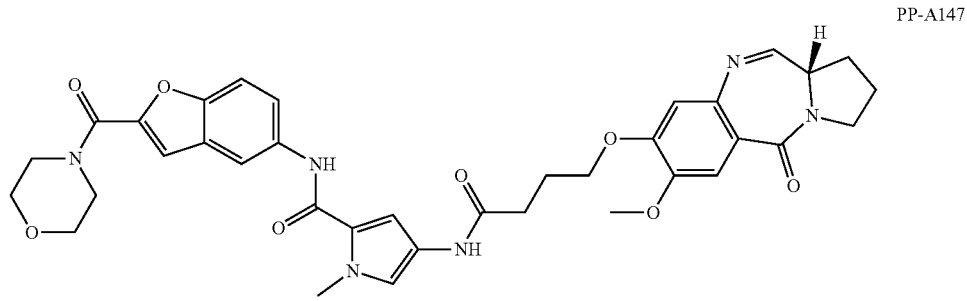 [SMILES: COc1cc2c(cc1OCCCC(=O)Nc1cc(C(=O)Nc3ccc4oc(C(=O)N5CCOCC5)cc4c3)n(C)c1)N=C[C@@H]1CCCN1C2=O]

Obtained 0.030 g (58%) as a white solid. $^1$H NMR (400 MHz, CHLOROFORM-d) δ: 8.04 (d, J=1.51 Hz, 1H), 8.00 (s, 1H), 7.70 (s, 1H), 7.67 (d, J=4.53 Hz, 1H), 7.54 (s, 1H), 7.46-7.50 (m, 2H), 7.30 (s, 1H), 7.12 (d, J=1.76 Hz, 1H), 6.84 (s, 1H), 6.59 (d, J=2.01 Hz, 1H), 4.15 (t, J=5.92 Hz, 2H), 3.92 (s, 3H), 3.91 (s, 3H), 3.76-3.83 (m, 8H), 3.70-3.75 (m, 2H), 3.53-3.60 (m, 1H), 2.56 (t, J=6.80 Hz, 2H), 2.23-2.34 (m, 4H), 2.00-2.10 (m, 2H). $^{13}$C NMR (100 MHz, CHLOROFORM-d) δ: 169.9, 164.5, 162.7, 159.8, 159.6, 151.4, 149.5, 140.7, 134.1, 127.4, 127.3, 123.1, 121.4, 120.4, 119.8, 119.4, 119.3, 118.8, 115.7, 113.9, 113.6, 112.7, 11.9, 11.7, 11.1, 104.0, 68.0, 66.9, 56.2, 53.7, 46.7, 36.8, 29.5, 25.0, 24.2. m/z (HRMS)

Example 29

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(2-(morpholine-4-carbonyl)benzo[b]thiophen-5-yl)-1H-pyrrole-2-carboxamide (PP-B16)

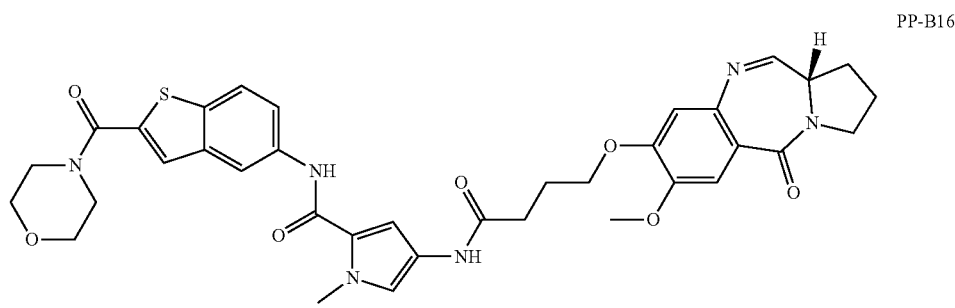 [SMILES: COc1cc2c(cc1OCCCC(=O)Nc1cc(C(=O)Nc3ccc4sc(C(=O)N5CCOCC5)cc4c3)n(C)c1)N=C[C@@H]1CCCN1C2=O]

Obtained 0.030 g (48%) as a yellow solid. $^1$H NMR (400 MHz, CHLOROFORM-d) δ: 8.29 (s, 1H), 8.10 (s, 1H), 7.82 (s, 1H), 7.77 (d, J=8.56 Hz, 1H), 7.67 (d, J=4.28 Hz, 1H), 7.53 (s, 1H), 7.47 (d, J=9.06 Hz, 1H), 7.42 (s, 1H), 7.13 (s, 1H), 6.83 (s, 1H), 6.60 (s, 1H), 4.12 (t, J=5.79 Hz, 2H), 3.91 (s, 3H), 3.90 (s, 3H), 3.79 (br. s., 9H), 3.54-3.62 (m, 2H), 2.50-2.58 (m, 2H), 2.28-2.32 (m, 2H), 2.21-2.27 (m, 2H), 2.00-2.10 (m, 2H). m/z (HRMS)

Example 30

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(2-(thiomorpholine-4-carbonyl)benzofuran-5-yl)-1H-pyrrole-2-carboxamide (PP-A148)

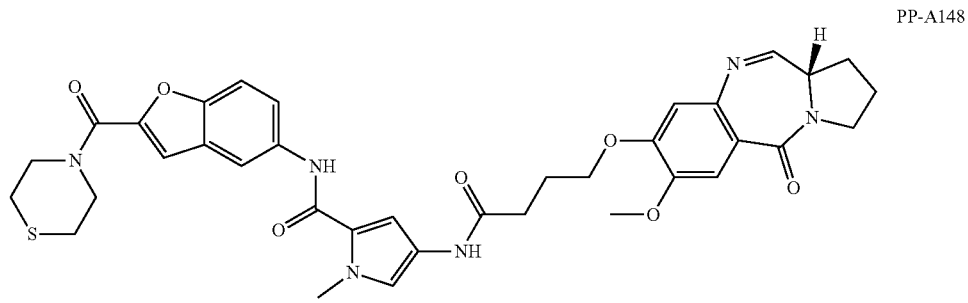

Obtained 0.030 g (48%) as a light yellow solid. ¹H NMR (400 MHz, CHLOROFORM-d) δ: 8.28 (s, 1H), 8.13 (s, 1H), 8.00 (d, J=2.01 Hz, 1H), 7.64 (d, J=4.28 Hz, 1H), 7.45-7.49 (m, 2H), 7.39-7.43 (m, 1H), 7.21 (s, 1H), 7.11 (d, J=1.76 Hz, 1H), 6.79 (s, 1H), 6.60 (d, J=1.76 Hz, 1H), 3.99-4.09 (m, 6H), 3.87 (s, 3H), 3.84 (s, 3H), 3.74-3.81 (m, 1H), 3.66-3.71 (m, 1H), 3.49-3.57 (m, 1H), 2.70-2.77 (m, 4H), 2.46-2.52 (m, 2H), 2.25-2.32 (m, 2H), 1.93-2.08 (m, 4H). ¹³C NMR (100 MHz, CHLOROFORM-d) δ: 169.9, 164.6, 162.7, 160.0, 159.9, 151.3, 150.6, 149.4, 147.7, 140.6, 134.3, 127.2, 123.0, 121.6, 120.5, 120.4, 119.8, 113.6, 112.2, 111.9, 111.7, 110.8, 104.2, 68.0, 56.1, 53.7, 53.4, 46.7, 36.7, 32.9, 29.5, 29.2, 24.9, 24.1. m/z (HRMS)

Example 31

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(2-(thiomorpholine-4-carbonyl)benzo[b]thiophen-5-yl)-1H-pyrrole-2-carboxamide (PP-B15)

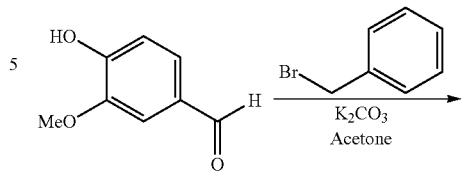

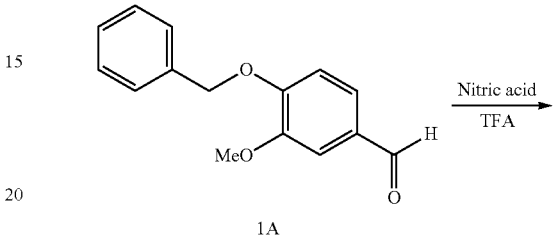

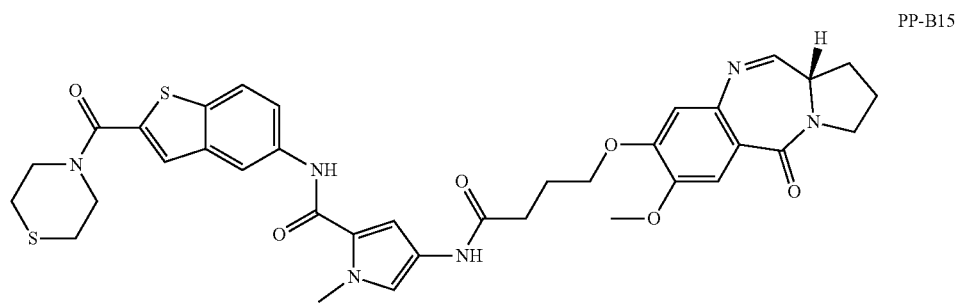 [SMILES: COc1cc2c(cc1OCCCC(=O)Nc1cc(C(=O)Nc3ccc4sc(C(=O)N5CCSCC5)cc4c3)n(C)c1)N=C[C@@H]1CCCN1C2=O]

Obtained 0.024 g (57%) as a yellow solid. ¹H NMR (400 MHz, CHLOROFORM-d) δ: 8.29 (s, 1H), 8.11 (s, 1H), 7.83 (s, 1H), 7.76 (d, J=8.56 Hz, 1H), 7.67 (d, J=4.28 Hz, 1H), 7.53 (s, 1H), 7.44-7.49 (m, 1H), 7.40 (s, 1H), 7.13 (s, 1H), 6.84 (s, 1H), 6.60 (s, 1H), 4.08-4.15 (m, 2H), 4.01 (br. s., 4H), 3.91 (s, 3H), 3.90 (s, 3H), 3.73-3.82 (m, 1H), 3.68-3.74 (m, 1H), 3.52-3.61 (m, 1H), 2.72 (br. s., 4H), 2.49-2.57 (m, 2H), 2.27-2.35 (m, 2H), 2.19-2.26 (m, 2H), 1.98-2.09 (m, 2H). ¹³C NMR (100 MHz, CHLOROFORM-d) δ: 169.9, 164.6, 164.1, 162.7, 150.6, 147.7, 140.6, 139.2, 137.3, 135.7, 135.4, 125.0, 123.0, 122.6, 121.5, 120.6, 120.0, 119.6, 116.1, 115.5, 111.8, 111.1, 104.2, 68.1, 56.2, 53.8, 46.7, 36.8, 33.1, 30.9, 29.6, 29.2, 27.9, 27.3, 25.0, 24.2. m/z (HRMS)

General Reaction Scheme for Synthesis of 4C NH Linker-Alloc-Protected PBD Unit

A PBD unit 9A with a protected amine group as the terminal group attached to the C8 position may be prepared as shown in the reaction scheme below. This PBD unit 9A is suitable for adding ring substituents via an amide bond that runs in the reverse direction to the amide bond of the compounds prepared in Examples 23-29.

-continued

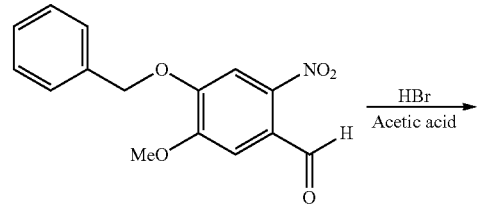

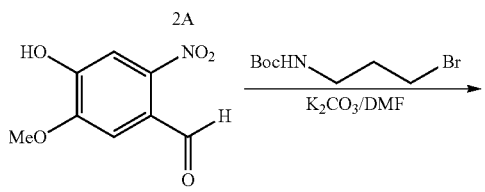

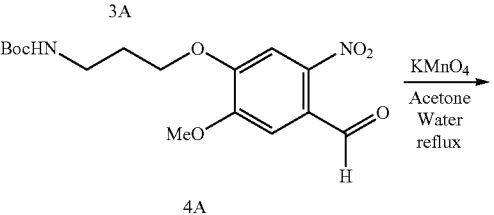

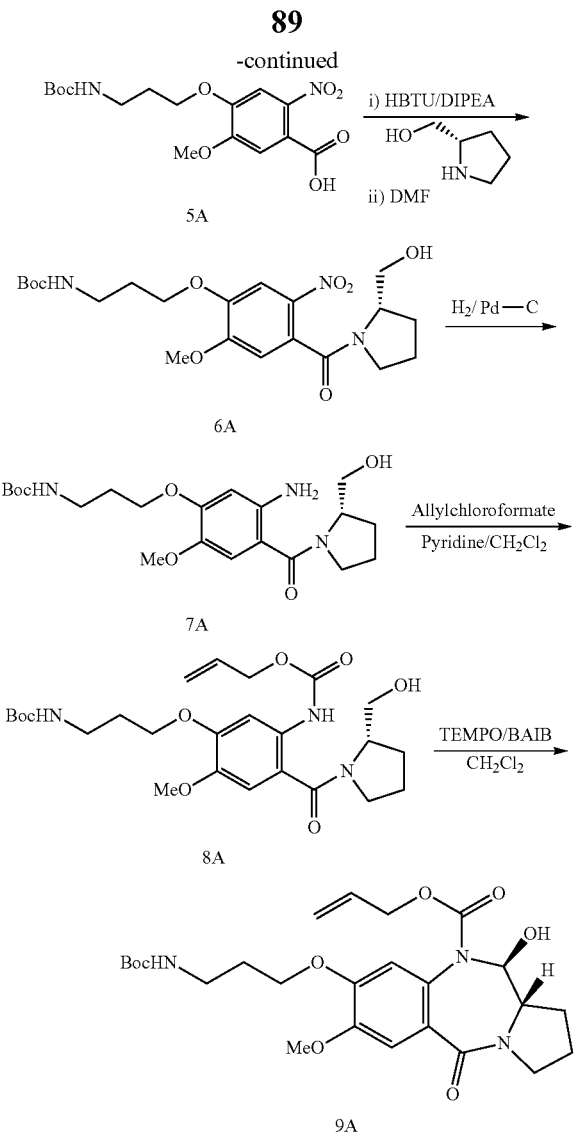

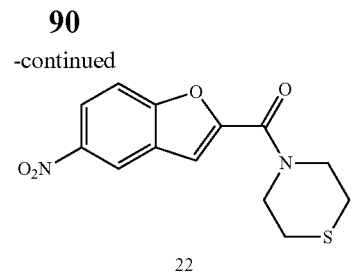

To a solution of 5-nitrobenzofuran-2-carboxylic acid (1.03 g, 1 equiv.) in DMF (10 mL) were sequentially added HATU (1.3 equiv.) and DIPEA (3 equiv.). The reaction mixture was left under magnetic stirrer for 15 minutes and the thiomorpholine (1.5 equiv.) was added. The reaction was left overnight under magnetic stirrer at room temperature. TLC and LC-MS analysis showed formation of the product. The reaction was quenched by addition of water (10 mL) that was then extracted with ethyl acetate (3×10 mL). The organic phase was then sequentially washed with NaHCO$_3$ saturated aqueous solution (20 mL) and brine (20 mL). The collected organic phase was dried over MgSO4 and subsequently evaporated using a rotary evaporator. The crude of reaction was purified by column chromatography (mobile phase: from DCM/EA, 90/10, v/v) affording pure final compound 22 (1.2 g, 80%) as a yellow solid. $^1$H NMR (400 MHz, DMSO-d$_6$) δ: 8.66 (d, J=2.27 Hz, 1H), 8.27 (dd, J=2.52, 9.06 Hz, 1H), 7.88 (d, J=9.57 Hz, 1H), 7.55 (d, J=0.76 Hz, 1H), 3.88 (br. s., 4H), 2.66-2.72 (m, 4H). $^{13}$C NMR (101 MHz, DMSO-d$_6$) δ: 158.4, 156.6, 150.9, 144.1, 127.3, 121.8, 119.0, 112.9, 111.1. m/z (+EI) calc. for C$_{13}$H$_{12}$N$_2$O$_4$S (M)$^+$ 292.0 found 293.0 ([M]+H)$^+$ Examples 33-36

Synthesis of Thiomorpholino-Benzofurane Derivative (23-26)

Synthesis of Thiomorpholine-Benzofused Intermediate for PBD C8-Derivatization

Example 32

Synthesis of (5-nitrobenzofuran-2-yl)(thiomorpholino)-methanone (22)

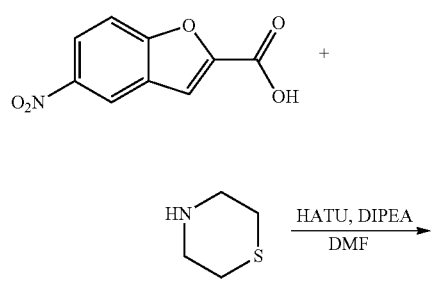

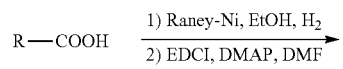

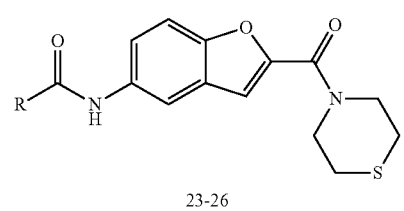

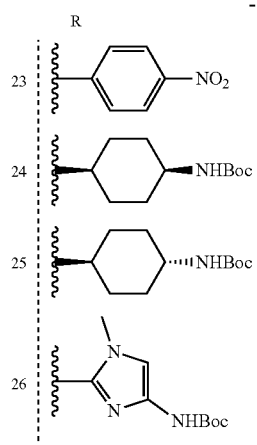

A catalytic amount of Raney-Ni was added to a solution of 22 (1.2 g, 4 mmol) in EtOH (20 mL). The reaction mixture was hydrogenated in a Parr hydrogenator at 40 psi until for 2 hours when TLC showed the completion of reaction. At that point the reaction was filtered under vacuum through a path of celite washing with DCM. The resulting solution was evaporated using rotary evaporator giving pure reduced compound. A solution of the corresponding carboxylic acid R—COOH was prepared dissolving the desiderate acid (from 0.06 g to 0.160 g, 1 equiv.) in DMF (3 mL). The solution was sequentially added of EDCI (2.5 equiv.) and DMAP (3 equiv.) and left under magnetic stirring under $N_2$ atmosphere for 20 minutes. At that point the reduced compound was added to the reaction mixture and left under magnetic stirrer overnight under $N_2$ atmosphere. TLC and LC-MS analysis showed formation of the product. The reaction was quenched by addition of water (10 mL) that was then extracted with ethyl acetate (3×10 mL). The organic phase was then sequentially washed with citric acid saturated solution (20 mL), $NaHCO_3$ saturated aqueous solution (20 mL) and brine (20 mL). The crude of each reaction was purified by column chromatography (mobile phase: from DCM/EA, 90/10, v/v to DCM/EA, 50/50, v/v) affording pure final compound 23-26.

Example 33

4-nitro-N-(2-(thiomorpholine-4-carbonyl)benzofuran-5-yl)benzamide (23)

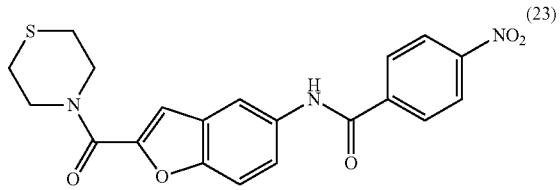 [SMILES: O=C(Nc1ccc2oc(C(=O)N3CCSCC3)cc2c1)c1ccc([N+](=O)[O-])cc1]

Obtained 0.130 g (83%) as a yellow solid. $^1$H NMR (400 MHz, DMSO-$d_6$) δ: 8.33-8.42 (m, J=9.06 Hz, 2H), 8.26 (d, J=2.01 Hz, 1H), 8.17-8.24 (m, J=9.06 Hz, 2H), 7.69-7.76 (m, 1H), 7.67 (d, J=9.06 Hz, 1H), 7.45 (d, J=0.76 Hz, 1H), 3.93 (br. s., 4H), 2.63-2.78 (m, 4H). $^{13}$C NMR (101 MHz, DMSO-$d_6$) δ: 163.8, 159.1, 150.7, 149.1, 148.8, 140.6, 134.7, 129.2, 126.8, 123.6, 120.3, 113.6, 111.8, 111.0, 79.1. m/z (+EI) calc. for $C_{20}H_{17}N_3O_5S$ (M)$^+$ 411.0 found 411.9 ([M]+H)$^+$ Example 34 tert-butyl (Z-4-((2-(thiomorpholine-4-carbonyl)benzofuran-5-yl)carbamoyl)cyclohexyl) carbamate (24)

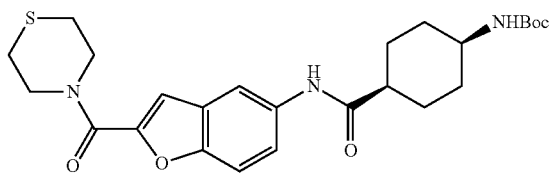

Obtained 0.100 g (54%) as a yellow oil. $^1$H NMR (400 MHz, CHLOROFORM-d) δ: 8.21 (br. s., 1H), 7.94 (s, 1H), 7.38 (s, 2H), 7.17 (s, 1H), 4.04 (br.s., 4H), 3.75 (br. s., 1H), 2.66-2.79 (m, 4H), 2.29-2.42 (m, 1H), 1.68-1.89 (m, 6H), 1.49-1.66 (m, 2H), 1.43 (s, 9H). $^{13}$C NMR (101 MHz, CHLOROFORM-d) δ: 174.1, 160.1, 155.3, 151.3, 149.3, 134.4, 127.1, 120.1, 113.5, 112.2, 111.8, 79.2, 45.7, 43.8, 29.5, 28.4, 24.7. m/z (+EI) calc. for $C_{25}H_{33}N_3O_5S$ (M)$^+$ 487.2 found 488.1 ([M]+H)$^+$ Example 35 tert-butyl (E-4-((2-(thiomorpholine-4-carbonyl)benzofuran-5-yl)carbamoyl)cyclohexyl) carbamate (25)

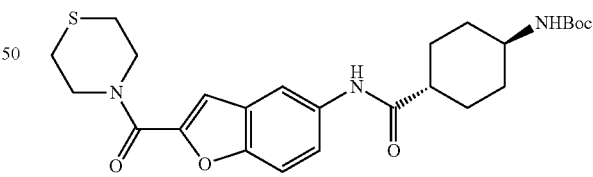

Obtained 0.115 g (62%) as a white solid. $^1$H NMR (400 MHz, CHLOROFORM-d) δ: 7.96 (s, 1H), 7.62 (br. s., 1H), 7.31-7.49 (m, 2H), 7.21 (s, 1H), 4.48 (br. s., 1H), 4.07 (br. s., 4H), 3.47 (br. s., 1H), 2.69-2.79 (m, 4H), 2.07-2.33 (m, 2H), 2.02 (br. s., 2H), 1.63-1.74 (m, 2H), 1.46 (s, 9H), 1.08-1.22 (m, 2H). $^{13}$C NMR (101 MHz, CHLOROFORM-d) δ: 173.8, 160.0, 155.2, 151.4, 149.5, 134.0, 127.3, 120.0, 113.5, 112.2, 111.9, 53.5, 49.0, 45.4, 32.6, 28.5. m/z (+EI) calc. for $C_{25}H_{33}N_3O_5S$ (M)$^+$ 487.2 found 488.1 ([M]+H)$^+$

Example 36 tert-butyl (1-methyl-2-((2-(thiomorpholine-4-carbonyl)-benzofuran-5-yl)carbamoyl)-1H-imidazol-4-yl) carbamate (26)

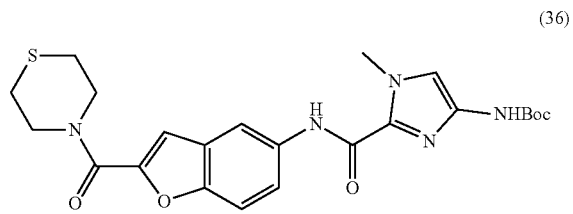 [SMILES: Cn1cc(NC(=O)OC(C)(C)C)nc1C(=O)Nc1ccc2oc(C(=O)N3CCSCC3)cc2c1]

(36)

Obtained 0.080 g (57%) as a yellow solid. $^1$H NMR (400 MHz, CHLOROFORM-d) δ: 9.05 (br. s., 1H), 8.00 (s, 1H), 7.50 (br. s., 1H), 7.32-7.42 (m, 2H), 7.17 (s, 1H), 7.14 (br. s., 1H), 3.99 (s, 7H), 2.61-2.73 (m, 4H), 1.41 (br. s., 9H). $^{13}$C NMR (101 MHz, CHLOROFORM-d) δ: 159.9, 156.7, 152.6, 151.5, 149.7, 136.8, 133.6, 127.3, 119.7, 113.0, 112.9, 112.9, 112.3, 112.0, 81.0, 35.9, 28.3. m/z (+EI) calc. for $C_{23}H_{27}N_5O_5S$ (M)$^+$ 485.2 found 486.0 ([M]+H)$^+$

Examples 37-40

Synthesis of PBD Thiomorpholino-Benzofurane Derivative

Compounds 24-26 (from 40 to 70 mg, 1 equiv.) were boc-deprotected dissolving the desiderate derivative in MeOH (3 ml) and HCl 4M in dioxane (3 mL). The solution was left under magnetic stirrer for 2 hours until TLC showed total cleavage of protecting group. The reaction mixture was subsequently evaporated using a rotary evaporator, obtaining a solid. Compound 23 (70 mg, 1 equiv.) was dissolved in EtOH (10 mL) and reduced in a Parr hydrogenator at 40 psi for 2 hours using Raney-Ni as catalyst until TLC showed the completion of reaction. The reaction mixture was then filtered on a celite path and the organic phases evaporated giving a white-solid. PBD capping unit 9 (1.2 equiv.) was dissolved in DMF (4 mL) and added of EDCI (2 equiv.) and DMAP (3 equiv.). The reaction mixture was left under magnetic stirrer in N$_2$ atmosphere for 20 minutes. At that point the desiderate deprotected compound was added to the reaction mixture and left under magnetic stirrer overnight for 15 hours until TLC and LC-MS analysis showed formation of the protected PBD-C8 derivative. The reaction was quenched by addition of water (10 mL) that was then extracted with ethyl acetate (3×10 mL). The organic phase was then sequentially washed with brine (10 mL), NaHCO$_3$ saturated aqueous solution (10 mL) and citric acid aqueous solution 0.1 M (10 mL). The collected organic phase was dried over MgSO4 and subsequently evaporated using a rotary evaporator. The crude of each reaction was purified by column chromatography (mobile phase: from DCM/acetone, 90/10, v/v to DCM/acetone, 60/40/, v/v depending on the substrate). The protected PBD-conjugates (from 25 to 60 mg, 1 equiv) was dissolved in DCM (4 mL) and added of Tetrakis Pd (0.05 equiv.), triphenylphosphine (0.25 equiv.) and pyrrolidine (1.2 equiv). The reaction mixture was kept under magnetic stirrer for 20 minutes when TLC showed completion of reaction. At that point the solvent was evaporated using a rotary evaporator and the crude of reaction was purified by column chromatography (mobile phase: from DCM/acetone, 90/10, v/v to DCM/acetone, 40/60/, v/v, depending on the substrate) affording pure final compounds.

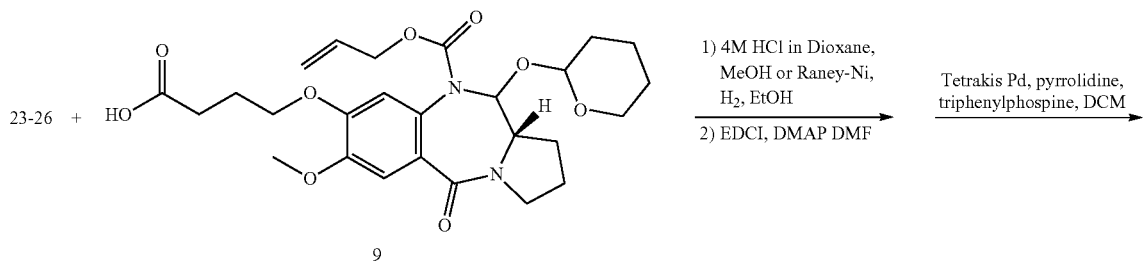

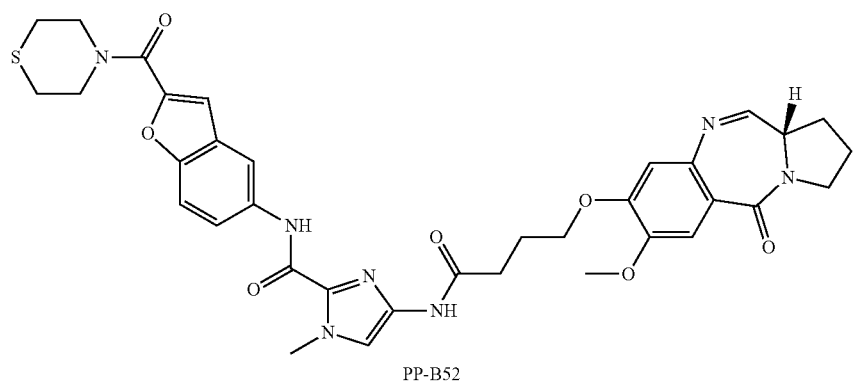

PP-B52

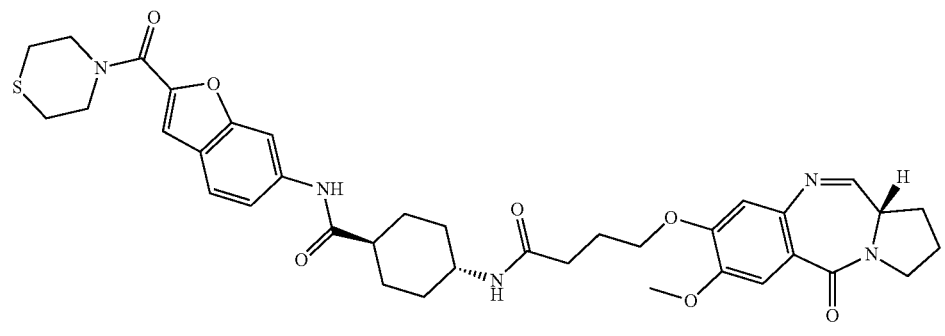
PP-B53
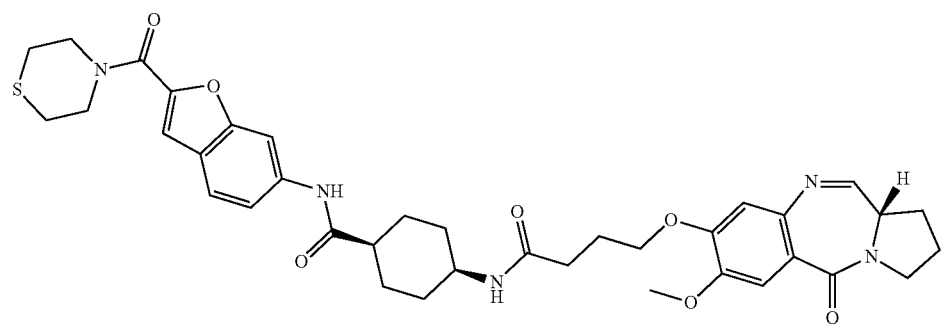
PP-B54
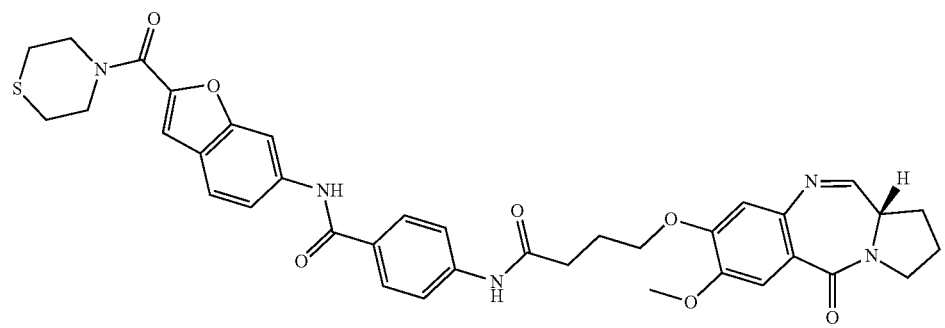
PP-B57

Example 37

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(2-(thiomorpholine-4-carbonyl)benzofuran-5-yl)-1H-imidazole-2-carboxamide (PP-B52)

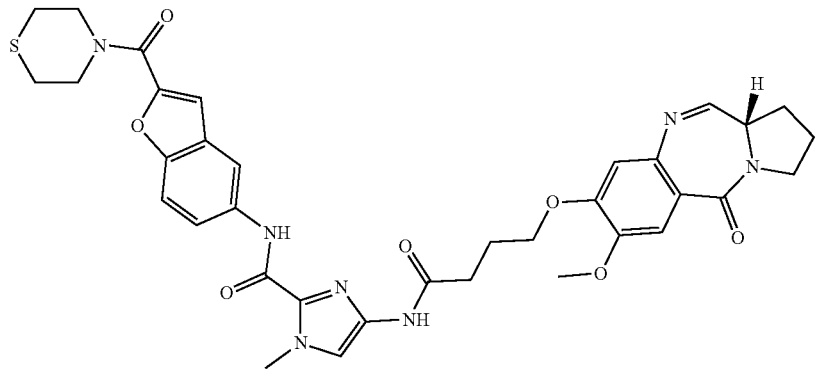

(PP-B52)

Obtained 36 mg (38%) as a transparent oil. $^1$H NMR (400 MHz, CHLOROFORM-d) δ: 8.97 (s, 1H), 8.10 (s, 1H), 8.03 (s, 1H), 7.58 (d, J=4.28 Hz, 1H), 7.47 (s, 1H), 7.37-7.43 (m, 3H), 7.21 (s, 1H), 6.77 (s, 1H), 4.04-4.17 (m, 2H), 3.97-4.03 (m, 7H), 3.88 (s, 3H), 3.66-3.75 (m, 1H), 3.59-3.66 (m, 1H), 3.44-3.51 (m, 1H), 2.65-2.72 (m, 4H), 2.55-2.59 (m, 2H), 2.16-2.27 (m, 4H), 1.91-2.01 (m, 2H). $^{13}$C NMR (101 MHz, CHLOROFORM-d) δ: 169.7, 159.9, 156.7, 151.5, 150.4, 149.7, 147.8, 143.9, 135.9, 134.1, 133.6, 127.4, 120.5, 118.0, 114.9, 112.9, 112.3, 112.2, 69.6, 56.1, 53.8, 53.5, 35.9, 31.8, 29.6, 29.3, 28.0, 24.7. m/z (+EI) calc. for $C_{35}H_{37}N_7O_7S$ (M)$^+$ 699.2 found 700.2 ([M]+H)$^+$.

Example 38

(1S,4R)-4-(4-(((S)-7-methoxy-5-oxo-2,3,5,11a-tetrahydro-1H-benzo[e]pyrrolo[1,2-a][1,4]diazepin-8-yl)oxy)butanamido)-N-(2-(thiomorpholine-4-carbonyl)benzofuran-6-yl)cyclohexane-1-carboxamide (PP-B53)

Obtained 40 mg (40%) as a transparent oil. $^1$H NMR (400 MHz, CHLOROFORM-d) δ: 7.95 (s, 1H), 7.99 (s, 1H), 7.65 (d, J=4.28 Hz, 1H), 7.49 (s, 1H), 7.41 (s, 2H), 7.22 (s, 1H), 6.80 (s, 1H), 6.12 (d, J=8.06 Hz, 1H), 4.04-4.08 (m, 6H), 3.90 (s, 3H), 3.74-3.82 (m, 2H), 3.67-3.73 (m, 1H), 3.50-3.60 (m, 1H), 2.69-2.79 (m, 4H), 2.33-2.44 (m, 3H), 2.25-2.33 (m, 2H), 1.98-2.11 (m, 4H), 1.78-1.86 (m, 2H), 1.74 (d, J=12.09 Hz, 4H), 1.52-1.66 (m, 2H) $^{13}$C NMR (101 MHz, CHLOROFORM-d) δ: 211.0, 173.9, 171.6, 164.7, 162.5, 160.0, 151.4, 150.5, 149.5, 147.7, 140.7, 134.2, 127.2, 120.3, 120.0, 113.5, 112.2, 111.9, 111.5, 110.6, 69.5, 67.8, 56.1, 53.8, 53.7, 53.5, 46.7, 44.7, 43.5, 33.0, 31.8, 29.6, 29.3, 29.1, 25.0, 24.9, 24.2. m/z (+EI) calc. for $C_{37}H_{43}N_5O_7S$ (M)$^+$ 701.2 found 702.2 ([M]+H)$^+$.

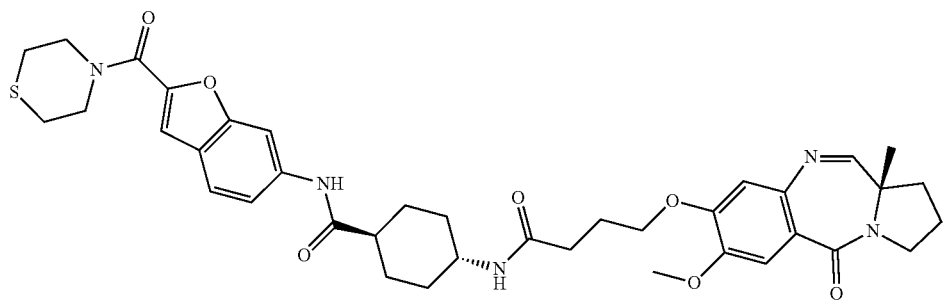 [SMILES: COc1cc2c(cc1OCCCC(=O)N[C@H]1CC[C@H](C(=O)Nc3ccc4cc(C(=O)N5CCSCC5)oc4c3)CC1)N=C[C@]1(C)CCCN1C2=O]

Example 39

(1R,4S)-4-(4-(((S)-7-methoxy-5-oxo-2,3,5,11a-tetrahydro-1H-benzo[e]pyrrolo[1,2-a][1,4]diazepin-8-yl)oxy)butanamido)-N-(2-(thiomorpholine-4-carbonyl)benzofuran-6-yl)cyclohexane-1-carboxamide (PP-B54)

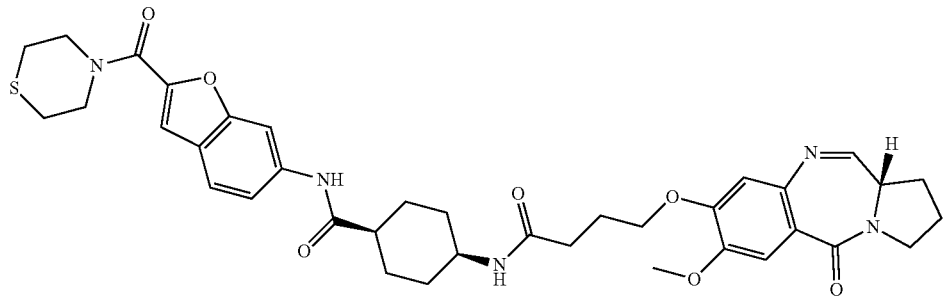

(PP-B54)

Obtained 45 mg (53%) as a white solid. $^1$H NMR (400 MHz, CHLOROFORM-d) δ: 8.37-8.51 (m, 1H), 8.02 (s, 1H), 7.67 (d, J=4.28 Hz, 1H), 7.52 (s, 1H), 7.48 (dd, J=2.14, 8.94 Hz, 1H), 7.38 (d, J=8.81 Hz, 1H), 7.18 (s, 1H), 6.83 (s, 1H), 5.95 (1) r. s., 1H), 4.10-4.20 (m, 1H), 4.04 (br. s., 5H), 3.92 (s, 3H), 3.64-3.83 (m, 4H), 3.54-3.64 (m, 1H), 2.73 (br. s., 4H), 2.28-2.43 (m, 3H), 2.02-2.11 (m, 4H), 1.94-2.02 (m, 4H), 1.55-1.92 (m, 4H), 0.90-1.05 (m, 1H). $^{13}$C NMR (101 MHz, CHLOROFORM-d) δ: 174.2, 171.5, 164.7, 162.8, 160.0, 151.3, 150.9, 149.3, 147.6, 140.8, 134.6, 127.1, 120.4, 119.9, 113.2, 112.2, 111.8, 111.3, 69.5, 68.0, 56.2, 53.8, 53.7, 53.4, 47.3, 46.7, 45.3, 32.9, 31.8, 31.7, 29.5, 29.2, 28.3, 28.2, 25.0, 24.2. m/z (+EI) calc. for $C_{37}H_{43}N_5O_7S$ (M)$^+$ 701.2 found 702.3 ([M]+H)$^+$

Example 40

(S)-4-(4-((7-methoxy-5-oxo-2,3,5,11a-tetrahydro-1H-benzo[e]pyrrolo[1,2-a][1,4]diazepin-8-yl)oxy)butanamido)-N-(2-(thiomorpholine-4-carbonyl)benzofuran-6-yl)benzamide (PP-B57)

Obtained 32 mg (46%) as a yellow solid. $^1$H NMR (400 MHz, CHLOROFORM-d) δ: 8.72 (br. s., 1H), 8.58 (br. s., 1H), 8.06 (s, 1H), 7.79 (d, J=8.81 Hz, 2H), 7.65 (d, J=4.53 Hz, 1H), 7.58 (dd, J=2.14, 8.94 Hz, 1H), 7.54 (d, J=8.56 Hz, 2H), 7.38-7.47 (m, 2H), 7.18 (s, 1H), 6.79 (s, 1H), 4.05 (br. s., 4H), 3.73-3.82 (m, 4H), 3.67-3.73 (m, 1H), 3.51-3.61 (m, 1H), 2.68-2.80 (m, 4H), 2.55-2.62 (m, 2H), 2.27-2.36 (m, 2H), 2.19-2.27 (m, 2H), 1.97-2.12 (m, 2H), 1.89 (br. s., 2H).

$^{13}$C NMR (101 MHz, CHLOROFORM-d) δ: 171.3, 164.6, 162.7, 160.0, 151.5, 150.4, 149.3, 147.6, 140.6, 134.3, 128.2, 127.2, 120.4, 119.3, 114.1, 112.2, 111.9, 111.5, 110.6, 69.5, 67.9, 56.0, 53.7, 46.7, 31.7, 30.9, 29.5, 29.2, 24.6, 24.2. m/z (+EI) calc. for $C_{37}H_{37}N_5O_7S$ (M)$^+$ 695.2 found 696.2 ([M]+H)$^+$ Synthesis of PBD Dimethylcarboxamide-Benzothiophene Imidazole Derivative

Example 41

Synthesis of tert-butyl (2-((2-(dimethylcarbamoyl)benzo[b]-thiophen-5-yl)carbamoyl)-1-methyl-1H-imidazol-4-yl)carbamate (27)

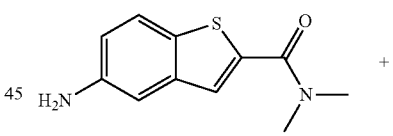

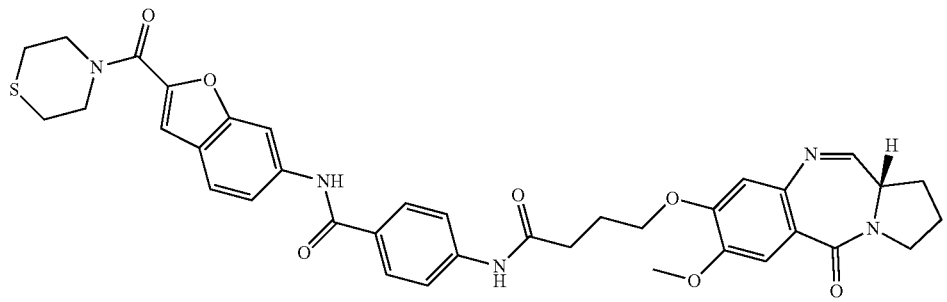 [SMILES: COc1cc2c(cc1OCCCC(=O)Nc1ccc(C(=O)Nc3ccc4cc(C(=O)N5CCSCC5)oc4c3)cc1)N=C[C@@H]1CCCN1C2=O]

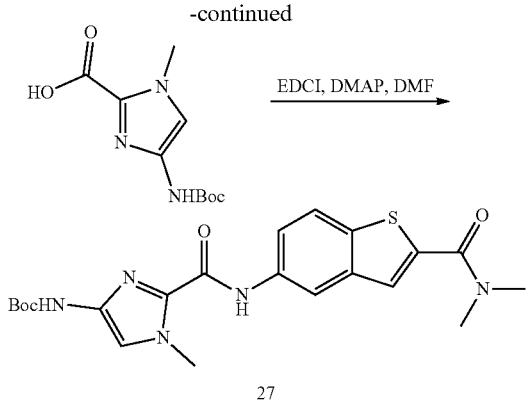

A solution was prepared dissolving 4-((tert-butoxycarbonyl)amino)-1-methyl-1H-imidazole-2-carboxylic acid (0.100 g, 1 equiv.) in DMF (3 mL). The solution was sequentially added of EDCI (2.5 equiv.) and DMAP (3 equiv.) and left under magnetic stirring under N₂ atmosphere for 20 minutes. At that point 5-amino-N,N-dimethyl-benzo[b]thiophene-2-carboxamide (1.2 equiv.) was added to the reaction mixture and left under magnetic stirrer overnight under N₂ atmosphere. TLC and LC-MS analysis showed formation of the product. The reaction was quenched by addition of water (10 mL) that was then extracted with ethyl acetate (3×10 mL). The organic phase was then sequentially washed with citric acid saturated solution (20 mL), NaHCO₃ saturated aqueous solution (20 mL) and brine (20 mL). The crude of each reaction was purified by column chromatography (mobile phase: from DCM/EA, 90/10, v/v to DCM/EA, 70/30, v/v) affording pure final compound 27 (0.097 g, 53%) as a yellow solid. ¹H NMR (400 MHz, CHLOROFORM-d) δ: 9.11 (br. s., 1H), 8.29 (s, 1H), 7.74 (d, J=8.81 Hz, 1H), 7.55 (br. s., 1H), 7.43 (s, 1H), 7.39 (d, J=8.56 Hz, 1H), 7.21 (s, 1H), 4.06 (s, 3H), 3.21 (br. s., 6H), 1.48 (s, 9H). ¹³C NMR (101 MHz, CHLOROFORM-d) δ: 164.6, 156.7, 152.6, 139.3, 138.8, 136.8, 135.9, 134.7, 133.7, 125.4, 122.6, 118.9, 114.9, 112.9, 39.5, 36.3, 35.8, 28.2. m/z (+EI) calc. for $C_{21}H_{25}N_5O_4S$ (M)⁺ 443.1 found 444.0 ([M]+H)⁺.

Example 42

Synthesis of (S)—N-(2-(dimethylcarbamoyl)benzo[b]-thiophen-5-yl)-4-(4-((7-methoxy-5-oxo-2,3,5,11a-tetrahydro-1H-benzo[e]-imidazole[1,2-a][1,4]diazepin-8-yl)oxy)butanamido)-1-methyl-1H-pyrrole-2-carboxamide (PP-B73)

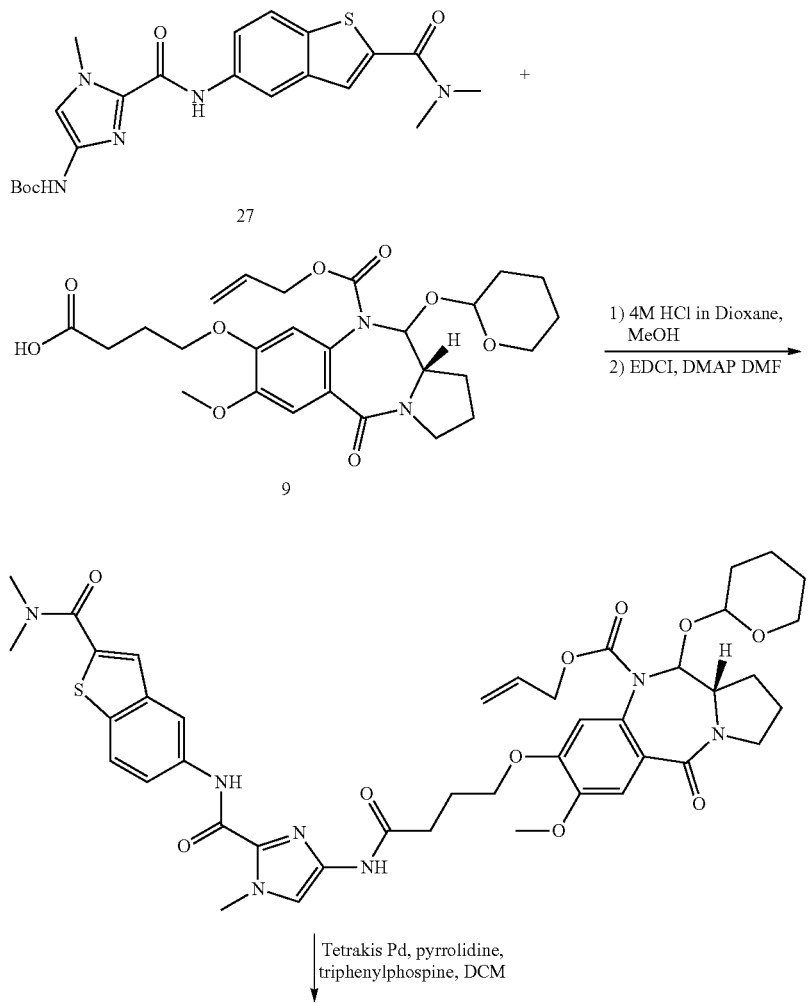

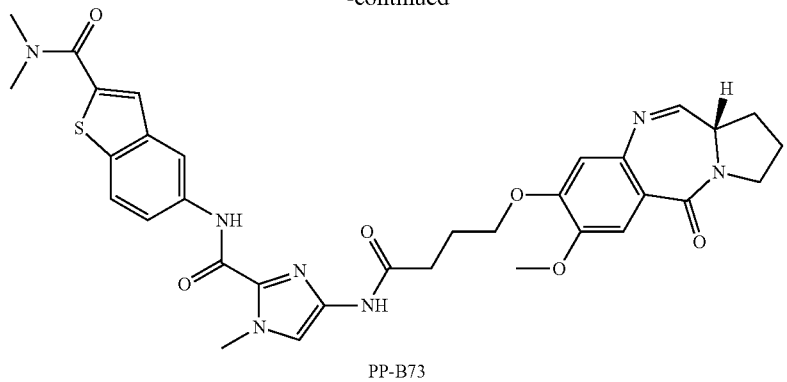

PP-B73

Compounds 27 (50 mg, 1 equiv.) was boc-deprotected dissolving the desiderate derivative in MeOH (3 ml) and HCl 4M in dioxane (3 mL). The solution was left under magnetic stirrer for 2 hours until TLC showed total cleavage of protecting group. The reaction mixture was subsequently evaporated using a rotary evaporator, obtaining a solid. PBD capping unit 9 (1.2 equiv.) was dissolved in DMF (4 mL) and added of EDCI (2 equiv.) and DMAP (3 equiv.). The reaction mixture was left under magnetic stirrer in $N_2$ atmosphere for 20 minutes. At that point the desiderate deprotected compound was added to the reaction mixture and left under magnetic stirrer overnight for 15 hours until TLC and LC-MS analysis showed formation of the protected PBD-C8 derivative. The reaction was quenched by addition of water (10 mL) that was then extracted with ethyl acetate (3×10 mL). The organic phase was then sequentially washed with brine (10 mL), $NaHCO_3$ saturated aqueous solution (10 mL) and citric acid aqueous solution 0.1 M (10 mL). The collected organic phase was dried over MgSO4 and subsequently evaporated using a rotary evaporator. The crude of each reaction was purified by column chromatography (mobile phase: from DCM/acetone, 90/10, v/v to DCM/acetone, 60/40/, v/v). The protected PBD-conjugates (from 25 to 60 mg, 1 equiv) was dissolved in DCM (4 mL) and added of Tetrakis Pd (0.05 equiv.), triphenylphospine (0.25 equiv.) and pyrrolidine (1.2 equiv). The reaction mixture was kept under magnetic stirrer for 20 minutes when TLC showed completion of reaction. At that point the solvent was evaporated using a rotary evaporator and the crude of reaction was purified by column chromatography (mobile phase: from DCM/acetone, 90/10, v/v to DCM/acetone, 40/60/, v/v) affording pure final compounds PP-B73 (0.035 g, 48%). $^1H$ NMR (400 MHz, CHLOROFORM-d) δ: 9.06 (s, 1H), 8.32 (s, 1H), 8.19 (s, 1H), 7.79 (d, J=8.56 Hz, 1H), 7.65 (d, J=4.53 Hz, 1H), 7.55 (s, 1H), 7.50 (s, 1H), 7.41-7.48 (m, 2H), 6.84 (s, 1H), 4.10-4.22 (m, 2H), 4.08 (s, 3H), 3.96 (s, 3H), 3.79 (dd, J=4.41, 11.71 Hz, 1H), 3.65-3.73 (m, 1H), 3.50-3.59 (m, 1H), 3.22 (br. s., 6H), 2.59-2.67 (m, 2H), 2.20-2.39 (m, 4H), 1.96-2.08 (m, 2H). $^{13}C$ NMR (101 MHz, CHLOROFORM-d) δ: 169.7, 164.6, 164.5, 162.5, 156.7, 150.4, 147.7, 140.6, 139.4, 138.9, 136.0, 135.8, 134.7, 133.5, 125.4, 122.8, 120.6, 118.8, 114.8, 111.5, 110.9, 67.7, 56.1, 46.6, 35.8, 32.9, 29.2, 24.7, 24.1. m/z (+EI) calc. for $C_{33}H_{35}N_7O_6S$ (A)+657.2 found 658.2 ($[M]+H)^+$.

Other PBD C8 Derivative
GWL-78 Type Intermediate Derivatives

Example 43

Synthesis of methyl 4-(4-((tert-butoxycarbonyl)amino)-1-methyl-1H-pyrrole-2-carboxamido)-1-methyl-1H-pyrrole-2-carboxylate (28)

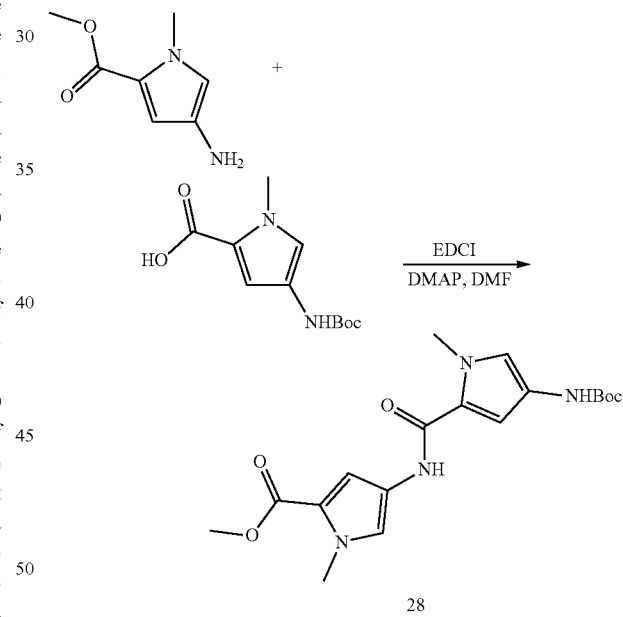

28

4-((tert-butoxycarbonyl)amino)-1-methyl-1H-pyrrole-2-carboxylic acid (0.754 g, 1.2 equiv.) was dissolved in DMF (7 mL). EDCI (0.976 g, 2.4 equiv.) and DMAP (0.960 g, 3 equiv.) were added to the solution that was left to stir in $N_2$ atmosphere for 30 minutes. At that point methyl 4-amino-1-methyl-1H-pyrrole-2-carboxylate (0.500 g, 2.62 mmols) was added to the reaction mixture and left under magnetic stirrer in $N_2$ atmosphere overnight. After 17 hours LC-MS showed the formation of the product. The reaction was quenched by the addition of water (10 mL) that was then extracted with AcOEt (3×10 mL). The collected organic phase was sequentially washed with Citric Acid 0.1 M aqueous solution (10 mL), saturated $NaHCO_3$ aqueous solution (10 mL) and Brine (10 mL). The collected organic phase was dried over MgSO₄ and subsequently evaporated using a rotary evaporator giving crude compound 28 that was then purified by column chromatography (mobile phase: DCM/AcOEt, 80/20, v/v), giving pure 10 (0.940 g, 95%) as an amber oil. ¹H NMR (400 MHz, CHLOROFORM-d) δ: 7.58 (s, 1H), 7.40 (d, J=2.01 Hz, 1H), 6.83 (br. s, 1H), 6.73 (d, J=2.01 Hz, 1H), 6.56 (br. s., 1H), 6.30 (br. s., 1H), 3.89 (s, 6H), 3.81 (s, 3H), 1.51 (s, 9H). ¹³C NMR (101 MHz, CHLOROFORM-d) δ: 161.5, 159.0, 153.6, 123.1, 121.9, 120.9, 119.6, 118.5, 108.4, 103.8, 80.0, 51.0, 36.6, 36.5, 28.3. m/z (+EI) calc. for $C_{18}H_{24}N_4O_5$ (M)⁺ 376.1 found 376.9 ([M]+H)⁺.

Examples 44-47

Synthesis of Pyrrole-Pyrrole Amido Derivatives (29-32)

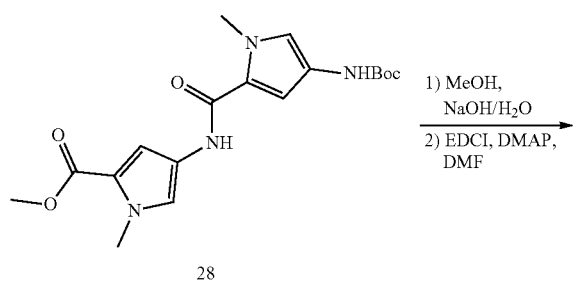

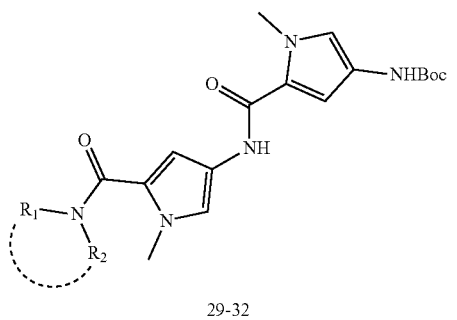

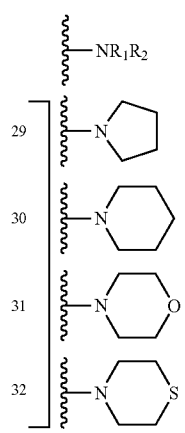

An excess of NaOH 1M aqueous solution was added to the intermediate 28 (0.120 g, 0.33 mmols) dissolved in MeOH (10 mL) and left under magnetic stirrer at room temperature overnight, until TLC showed total disappearance of the starting material. MeOH was evaporated under reduced pressure using a rotary evaporator and Citric Acid 1 M aqueous solution was added until acid pH, causing the formation of a light yellow precipitate. The aqueous layer was then extracted with AcOEt (2×50 mL). The combined organic layers were dried over MgSO₄ and concentrated under reduced pressure using a rotary evaporator. The collected acid was dissolved in DMF (7 mL) and EDCI (0.102 g, 2.4 equiv.) and DMAP (0.121 g, 3 equiv.) were sequentially added. The solution was left to stir under N₂ atmosphere for 30 minutes. At that point the corresponding amine (1.2 equiv.) was added to the reaction mixture and left under magnetic stirrer under N₂ atmosphere overnight. After 17 hours LC-MS showed the formation of the product. The reaction was quenched by the addition of H₂O (10 mL) that was then extracted with AcOEt (3×10 mL). The organic phase was sequentially washed with Citric Acid 0.1 M aqueous solution (10 mL), saturated NaHCO₃ aqueous solution (10 mL) and Brine (10 mL). The collected organic phase was dried over MgSO₄ and subsequently evaporated using a rotary evaporator giving crude compound that was then purified by column chromatography (mobile phase: DCM/AcOEt, 50/50 until 30/70, v/v) to give the final corresponding products 29-32.

Example 44 tert-butyl (1-methyl-5-((1-methyl-5-(pyrrolidine-1-carbonyl)-1H-pyrrol-3-yl)carbamyl)-1H-pyrrol-3-yl) carbamate (29)

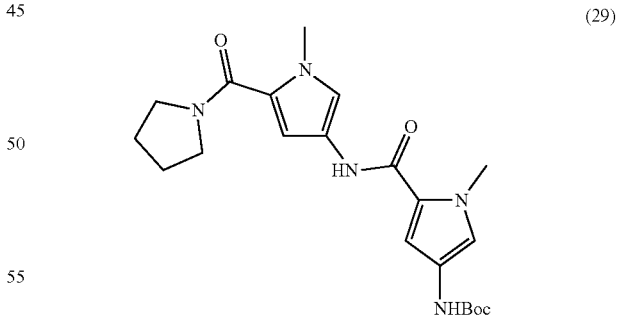

Obtained 0.080 g (58%) as a light yellow solid. ¹H NMR (400 MHz, CHLOROFORM-d) δ: 7.99 (s, 1H), 7.12 (s, 1H), 6.82 (s, 1H), 6.67 (br. s., 1H), 6.58 (br. s., 1H), 6.44 (s, 1H), 3.85 (s, 3H), 3.77 (s, 3H), 3.58 (br. s., 4H), 1.80-1.92 (m, 4H), 1.46 (s, 9H). ¹³C NMR (101 MHz, CHLOROFORM-d) δ: 161.6, 159.0, 153.8, 124.0, 123.1, 121.8, 121.0, 118.2, 105.2, 103.3, 80.2, 49.7, 46.7, 28.6, 26.9, 24.0. m/z (+EI) calc. for $C_{21}H_{29}N_5O_4$ (M)⁺ 415.2 found 416.1 ([M]+H)⁺.

Example 45 tert-butyl (1-methyl-5-((1-methyl-5-(piperidine-1-carbonyl)-1H-pyrrol-3-yl)carbamoyl)-1H-pyrrol-3-yl)carbamate (30)

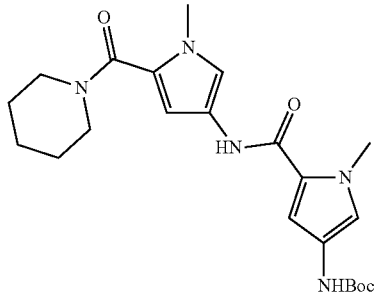

(30)

Obtained 0.064 g (45%) as a light brown solid. $^1$H NMR (400 MHz, CHLOROFORM-d) δ: 7.95 (br. s., 1H), 7.13 (s, 1H), 6.81 (s, 1H), 6.69 (br. s., 1H), 6.53 (br. s., 1H), 6.20 (s, 1H), 3.84 (s, 3H), 3.65 (s, 3H), 3.56-3.63 (m, 4H), 1.60-1.69 (m, 2H), 1.51-1.60 (m, 4H), 1.46 (s, 9H). $^{13}$C NMR (101 MHz, CHLOROFORM-d) δ: 162.5, 159.5, 153.9, 123.4, 123.2, 122.1, 121.3, 118.4, 116.9, 104.2, 103.5, 80.4, 36.5, 35.6, 28.5, 26.2, 25.0. m/z (+EI) calc. for $C_{22}H_{31}N_5O_4$ (M)$^+$ 429.2 found 430.0 ([M]+H)$^+$.

Example 46 tert-butyl (1-methyl-5-((1-methyl-5-(morpholine-4-carbonyl)-1H-pyrrol-3-yl)carbamoyl)-1H-pyrrol-3-yl]carbamate (31)

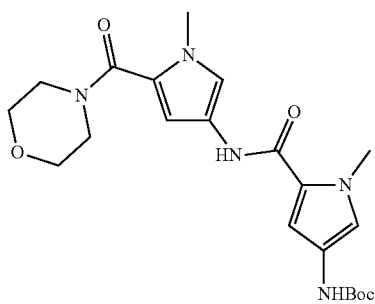

(31)

Obtained 0.091 g (64%) as a light yellow solid. $^1$H NMR (400 MHz, CHLOROFORM-d) δ: 8.13 (br. s., 1H), 7.11 (s, 1H), 6.78 (d, J=8.31 Hz, 2H), 6.58 (br. s., 1H), 6.24 (s, 1H), 3.82 (s, 3H), 3.59-3.70 (m, 11H), 1.45 (s, 9H). $^{13}$C NMR (101 MHz, CHLOROFORM-d) δ: 162.8, 159.1, 153.5, 123.1, 122.2, 121.8, 121.4, 118.3, 117.5, 104.9, 103.8, 80.0, 66.8, 36.5, 35.5, 28.3. m/z (+EI) calc. for $C_{21}H_{29}N_5O_5$ (M)$^+$ 431.2 found 432.0 ([M]+H)$^+$.

Example 47 tert-butyl (1-methyl-5-((1-methyl-5-(thiomorpholine-4-carbonyl)-1H-pyrrol-3-yl)carbamoyl)-1H-pyrrol-3-yl)carbamate (32)

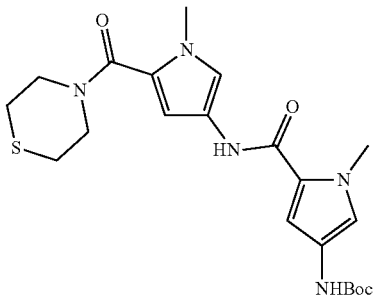

(32)

Obtained 0.088 g, (59%) as a yellow solid. $^1$H NMR (400 MHz, CHLOROFORM-d) δ: 7.80 (br. s., 1H), 7.18 (d, J=1.76 Hz, 1H), 6.80 (s, 1H), 6.59 (s, 1H), 6.52 (br. s., 1H), 6.12-6.30 (m, 1H), 3.95 (td, J=2.58, 4.91 Hz, 4H), 3.87 (s, 3H), 3.68 (s, 3H), 2.59-2.70 (m, 4H), 1.48 (s, 9H). $^{13}$C NMR (101 MHz, CHLOROFORM-d) δ: 163.2, 159.2, 153.7, 123.5, 122.9, 122.1, 121.5, 118.3, 117.6, 104.4, 103.7, 80.4, 36.5, 35.6, 28.6, 28.1. m/z (+EI) calc. for $C_{21}H_{29}N_5O_4S$ (M)$^+$ 447.19 found 448.0 ([M]+H)$^+$.

Examples 48-49

Synthesis of Nitro Pyrrole Carboxyamido Derivatives (33,34)

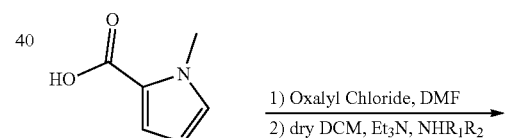

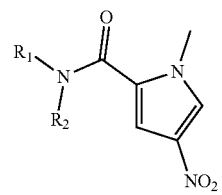

33,34

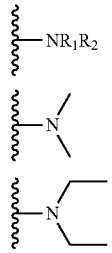

1-methyl-4-nitro-1H-pyrrole-2-carboxylic acid (0.400 g, 2.35 mmols) was dissolved in dry DCM (20 mL) in a round bottom flask previously dried in oven. Oxalyl chloride (0.605 mL, 3 equiv.) and a catalytic amount of dry DMF (2-3 drops) were added to the solution that started bubbling. The reaction mixture was left under magnetic stirrer for 1 hour until ceased the formation of gas. The solution was then evaporated using a rotary evaporator to eliminate the excess of oxalyl chloride. The reaction mixture was subsequently dissolved in dry DCM (20 mL). The obtained solution was then added dropwise to a solution of triethylamine (1.02 mL, 3 equiv.) and the corresponding amine (1.5 equiv.) in dry DCM (2.82 mL) kept at 0° C. under $N_2$ atmosphere during the addition. The addition of the first solution to the second one caused the formation of steam. The reaction mixture was left to stir overnight under $N_2$ atmosphere. After 16 hours TLC and LC-MS showed completion of the reaction. At that point DCM was evaporated using a rotary evaporator. The reaction was quenched by the addition of water (10 mL) that was then extracted with AcOEt (3×10 mL). The collected organic phases were sequentially washed with Citric Acid 0.1 M aqueous solution (10 mL), saturated $NaHCO_3$ aqueous solution (10 mL) and Brine (10 mL). The collected organic phase was dried over $MgSO_4$ and subsequently evaporated using a rotary evaporator giving crude of reaction that was then purified by column chromatography (mobile phase: DCM/AcOEt, 80/20, v/v), giving pure compounds 33 and 34.

Example 48

N,N,1-trimethyl-4-nitro-1H-pyrrole-2-carboxamide (33)

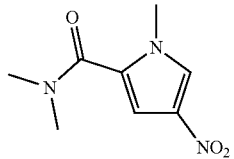

(33)

Obtained 0.283 g (61%) as a light brown solid. $^1$H NMR (400 MHz, CHLOROFORM-d) δ: 7.55 (d, J=1.76 Hz, 1H), 6.88 (d, J=2.01 Hz, 1H), 3.83 (s, 3H), 3.02-3.29 (m, 6H). $^{13}$C NMR (101 MHz, CHLOROFORM-d) δ: 161.4, 134.6, 125.5, 125.2, 107.8, 36.7. m/z (+EI) calc. for $C_8H_{11}N_3O_3$ (M)$^+$ 197.0 found 197.9 ([M]+H)$^+$.

Example 49

N,N-diethyl-1-methyl-4-nitro-1H-pyrrole-2-carboxamide (34)

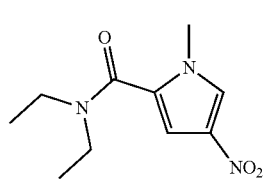

(34)

Obtained 0.048 g (48%) as a light yellow solid. 1H NMR (400 MHz, CHLOROFORM-d) δ: 7.53 (d, J=2.01 Hz, 1H), 6.77 (d, J=2.01 Hz, 1H), 3.74 (s, 3H), 3.47 (q, J=7.13 Hz, 4H), 1.19 (t, J=7.05 Hz, 6H). $^{13}$C NMR (101 MHz, CHLOROFORM-d) δ: 160.9, 134.5, 126.4, 124.7, 105.4, 43.3, 39.9, 36.2, 14.1, 12.9.

Examples 50-51

Synthesis of Pyrrole-Pyrrole Dimethyl and Diethyl Amido Derivatives (35,36)

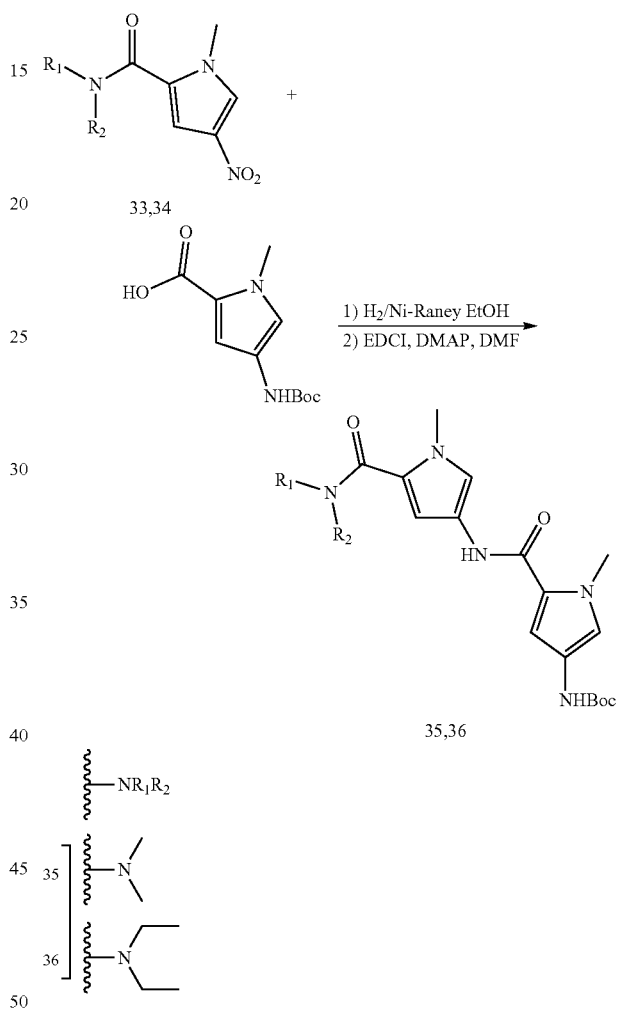

A solution of the corresponding nitro pyrrole carboxamide (33 0.263 g, 1.33 mmols or 34 0.228 g, 1.01 mmols) in EtOH absolute (14.5 mL) was prepared. A catalytic amount of Raney-Nickel was then added to the solution. The reaction mixture was hydrogenated in a Parr hydrogenator at 60 psi for 1 hour until TLC showed the completion of the reaction. At that point the reaction mixture was filtered under vacuum through a path of celite previously washed with DCM. The resulting solution, brown in colour, was evaporated using a rotary evaporator giving the reduced corresponding intermediated with no further purification.

4-((tert-butoxycarbonyl)amino)-1-methyl-1H-pyrrole-2-carboxylic acid (1.2 equiv.) was dissolved in DMF (3 mL). EDCI (0.334 g, 2.4 equiv.) and DMAP (0.319 g, 3 equiv.) were sequentially added to the solution that was left to stir in $N_2$ atmosphere for 30 minutes. At that point the reduced corresponding intermediate was added to the reaction mixture and left to stir overnight in $N_2$ atmosphere. After 17 hours LC-MS showed the formation of the product. The reaction was quenched by the addition of water (10 mL) that was then extracted with AcOEt (3×10 mL). The collected organic phases were sequentially washed with Citric Acid 0.1 M aqueous solution (10 mL), saturated $NaHCO_3$ aqueous solution (10 mL) and Brine (10 mL). The collected organic phase was dried over $MgSO_4$ and subsequently evaporated using a rotary evaporator giving crude of reaction that was then purified by column chromatography (mobile phase: DCM/AcOEt, 30/70, v/v) giving corresponding pure compounds 35 and 36.

Example 50 tert-butyl (5-((5-(dimethylcarbamoyl)-1-methyl-1H-pyrrol-3-yl)carbamoyl)-1-methyl-1H-pyrrol-3-yl)carbamate (35)

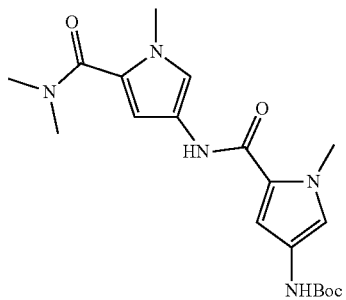

(35)

Obtained 0.240 g (70%) as a yellow solid. 1H NMR (400 MHz, CHLOROFORM-d) δ: 8.12 (br. s., 1H), 7.09 (br. s., 1H), 6.79 (br. s., 1H), 6.53 (br. s., 1H), 6.27 (s, 1H), 3.81 (s, 3H), 3.64 (s, 3H), 3.04 (br. s., 6H), 1.43 (s, 9H). $^{13}$C NMR (101 MHz, CHLOROFORM-d) δ: 163.7, 158.9, 153.4, 123.0, 122.8, 121.7, 121.1, 118.1, 116.9, 105.0, 103.5, 79.7, 36.7, 35.5, 28.2. m/z (+EI) calc. for $C_{19}H_{27}N_5O_4$ (M)$^+$ 389.2 found 390.0 ([M]+H)$^+$.

Example 51 tert-butyl (5-((5-(diethylcarbamoyl)-1-methyl-1H-pyrrol-3-yl)carbamoyl)-1-methyl-1H-pyrrol-3-yl)carbamate (36)

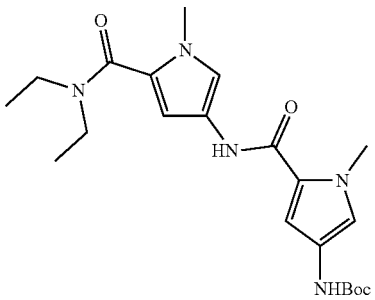

(36)

Obtained 0.204 g (59%) as a light yellow solid. $^1$H NMR (400 MHz, CHLOROFORM-d) δ: 7.56 (br. s., 1H), 7.21 (d, J=1.76 Hz, 1H), 6.80 (s, 1H), 6.58 (s, 1H), 6.34 (br. s., 1H), 6.21 (d, J=1.51 Hz, 1H), 3.90 (s, 3H), 3.70 (s, 3H), 3.53 (q, J=7.22 Hz, 4H), 1.51 (s, 9H), 1.22 (t, J=7.05 Hz, 6H). $^{13}$C NMR (101 MHz, CHLOROFORM-d) δ: 163.3, 158.8, 151.7, 124.0, 123.4, 121.8, 120.9, 116.4, 103.3, 102.5, 80.2, 36.5, 35.6, 28.3, 14.2. m/z (+EI) calc. for $C_{21}H_{31}N_5O_4$ (M)$^+$ 417.2 found 418.0 ([M]+H)$^+$.

MPB Type Intermediate Derivatives

Example 52

Synthesis of methyl 4-(4-((tert-butoxycarbonyl)amino)-phenyl)-1-methyl-1H-pyrrole-2-carboxylate (37)

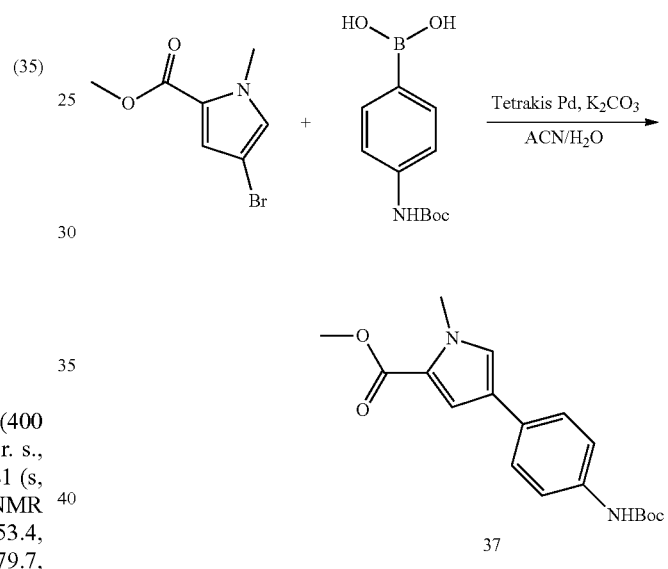

Methyl 4-bromo-1-methyl-1H-pyrrole-2-carboxylate (1 g, 4.60 mmols), (4-((tert-butoxycarbonyl)amino)phenyl)boronic acid (1.2 g, 1.1 equiv.), $K_2CO_3$ (1.7 g, 3 equiv.) were solubilized in a mixture of ACN (40 mL) and $H_2O$ (36 mL) in a microwave vial. The reaction mixture was left under magnetic stirrer in $N_2$ atmosphere for 5 minutes. At that point Tetrakis Pd (0.280 g, 0.05 equiv.) was added. The reaction mixture was then heated at MW radiation at 100° C. for 6 minutes. LC-MS showed the formation of the product. The reaction mixture was filtered under vacuum through a path of celite previously washed with AcOEt. The resulting solution, brown in colour, was then evaporated using a rotary evaporator. The obtained residue was purified by column chromatography (mobile phase: DCM/AcOEt, 80/20, v/v) giving pure 37 (0.635 g, 42%) as an amber oil. $^1$H NMR (400 MHz, CHLOROFORM-d) δ: 7.47-7.52 (m, 1H), 7.41-7.44 (m, 2H), 7.32-7.38 (m, 2H), 7.17 (d, J=2.01 Hz, 1H), 7.04 (d, J=2.27 Hz, 1H), 3.96 (s, 3H), 3.85 (s, 3H), 1.53 (s, 9H). $^{13}$C NMR (101 MHz, CHLOROFORM-d) δ: 161.9, 153.1, 136.8, 135.7, 129.4, 127.2, 126.2, 123.5, 119.2, 114.7, 80.5, 51.1, 37.2, 28.4. m/z (+EI) calc. for $C_{18}H_{22}N_2O_4$ (M)$^+$ 330.1 found 331.0 ([M]+H)$^+$.

Example 53

Synthesis of methyl 4-(4-(4-((tert-butoxycarbonyl)amino)-1-methyl-1H-pyrrole-2-carboxamido)phenyl)-1-methyl-1H-pyrrole-2-carboxylate (38)

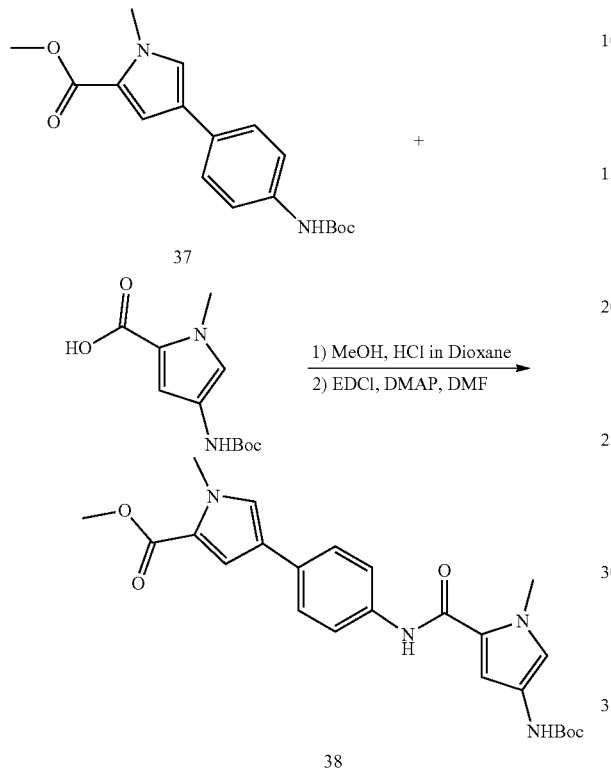

Compound 37 (1.1 g, 1.2 equiv.) was dissolved in MeOH (7 mL) and HCl 4M in Dioxane (7 mL) was added. The solution was left to stir for 2 hours until TLC showed the total cleavage of the Boc group. At that point the reaction mixture was evaporated using a rotary evaporator obtaining a light brown solid of the deprotected compound 37. 4-((tert-butoxycarbonyl)amino)-1-methyl-1H-pyrrole-2-carboxylic acid (0.667 g, 2.78 mmols) was dissolved in DMF (7 mL). EDCI (1.064 g, 2.4 equiv.) and DMAP (1.017 g, 3 equiv.) were added to the solution that was left to stir in $N_2$ atmosphere for 30 minutes. At that point the deprotected compound 37 was added to the reaction mixture and left to stir overnight in $N_2$ atmosphere. After 17 hours LC-MS showed the formation of the product. The reaction was quenched by the addition of $H_2O$ (10 mL) that was then extracted with AcOEt (3×10 mL). The organic phase was sequentially washed with Citric Acid 0.1 M aqueous solution (10 mL), saturated $NaHCO_3$ aqueous solution (10 mL) and Brine (10 mL). The collected organic phase was dried over $MgSO_4$ and subsequently evaporated using a rotary evaporator giving the crude of reaction that was purified by column chromatography (mobile phase: DCM/AcOEt, 60/40, v/v) giving pure compound 38. $^1H$ NMR (400 MHz, CHLOROFORM-d) δ: 7.64 (s, 1H), 7.53 (d, J=8.81 Hz, 2H), 7.45 (d, J=8.81 Hz, 2H), 7.19 (d, J=2.01 Hz, 1H), 7.06 (d, J=2.27 Hz, 1H), 6.85 (br. s., 1H), 6.64 (br. s., 1H), 6.31 (br. s., 1H), 3.96 (s, 3H), 3.91 (s, 3H), 3.85 (s, 3H), 1.52 (s, 9H). $^{13}C$ NMR (101 MHz, CHLOROFORM-d) δ: 161.7, 159.7, 153.4, 136.3, 130.4, 126.2, 123.6, 123.0, 122.0, 118.9, 114.8, 103.8, 80.3, 50.9, 37.0, 28.2. m/z (+EI) calc. for $C_{24}H_{28}N_4O_5$ $(M)^+$ 452.2 found 453.1 $([M]+H)^+$.

Examples 54-57

Synthesis of mpb-Pyrrole Amido Derivatives (21-24)

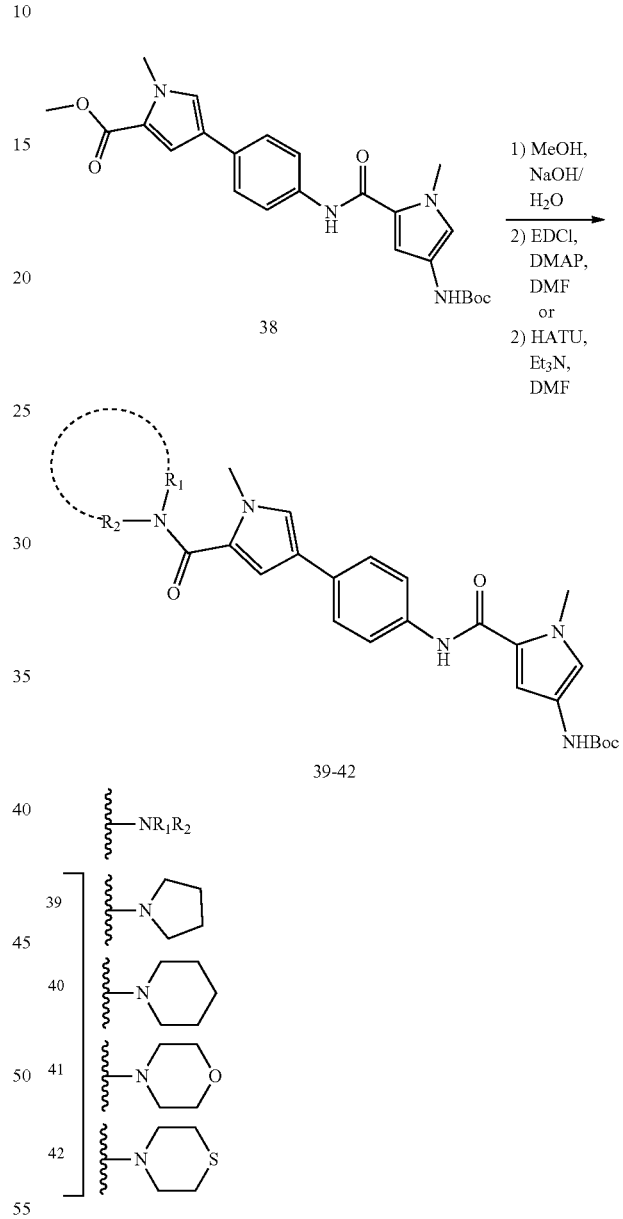

An excess of NaOH 1M (aqueous solution) was added to the methyl ester intermediate 38 (0.120 g, 1.2 equiv.) dissolved in MeOH (10 mL) and left under magnetic stirrer at room temperature overnight, until TLC showed total disappearance of the starting material and the hydrolysis of the ester was achieved. MeOH was evaporated under reduced pressure using a rotary evaporator and Citric Acid 1 M aqueous solution was added until acidic pH, causing the formation of a light yellow precipitate. The aqueous layer was then extracted with AcOEt (2×50 mL). The combined organic layers were dried over $MgSO_4$ and concentrated under reduced pressure using a rotary evaporator. The compound was collected and coupled with the corresponding amine following either method A or method B giving compounds 39-42 as provided below.

Method A:
Hydrolysed compound 38 (1 equiv.) was dissolved in DMF (7 mL). EDCI (2.4 equiv.) and DMAP (3 equiv.) were added to the solution that was left to stir in $N_2$ atmosphere for 30 minutes. At that point the corresponding amine (1.2 equiv.) was added to the reaction mixture and left to stir overnight in $N_2$ atmosphere. After 17 hours LC-MS showed formation of the product. The reaction was quenched by the addition of water (10 mL) that was then extracted with AcOEt (3×10 mL). The organic phase was sequentially washed with Citric Acid 0.1 M aqueous solution (10 mL), saturated $NaHCO_3$ aqueous solution (10 mL) and Brine (10 mL). The organic phase was dried over $MgSO_4$ and subsequently evaporated using a rotary evaporator giving crude compounds that were then purified by column chromatography (mobile phase: DCM/AcOEt, 60/40, v/v) giving the pure corresponding compound.

Method B:
Hydrolysed compound 38 (1 equiv.) was dissolved in DMF (7 mL). HATU (1.5 equiv.) and triethylamine (5 equiv.) were added to the solution that was left to stir for 15 minutes. At that point the corresponding amine (1.2 equiv.) was added to the reaction mixture and left to stir overnight in $N_2$ atmosphere. After 17 hours LC-MS showed e formation of the product. The reaction was quenched by the addition of water (10 mL) that was then extracted with AcOEt (3×10 mL). The organic phase was sequentially washed with Citric Acid 0.1 M aqueous solution (10 mL), saturated $NaHCO_3$ aqueous solution (10 mL) and Brine (10 mL). The organic phase was dried over $MgSO_4$ and subsequently evaporated using a rotary evaporator giving crude compound that was then purified by column chromatography (mobile phase: DCM/AcOEt, 60/40, v/v) giving pure corresponding compound.

Example 54 tert-butyl (1-methyl-5-((4-(1-methyl-5-(pyrrolidine-1-carbonyl)-1H-pyrrol-3-yl)phenyl)carbamoyl)-1H-pyrrol-3-yl)carbamate (39)

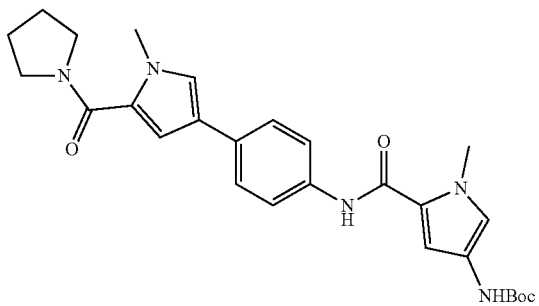

(39)

Method B was followed. Obtained 0.030 g (38%) as a light yellow solid. $^1$H NMR (400 MHz, CHLOROFORM-d) δ: 7.71 (s, 1H), 7.51 (d, J=8.81 Hz, 2H), 7.41 (d, J=8.56 Hz, 2H), 6.94 (d, J=1.76 Hz, 1H), 6.86 (br. s., 1H), 6.74 (d, J=1.76 Hz, 1H), 6.65 (br. s., 1H), 6.52 (br. s., 1H), 3.90 (s, 3H), 3.89 (s, 3H), 3.74 (br. s., 2H), 3.64 (br. s., 2H), 1.86-2.02 (m, 4H), 1.50 (s, 9H). $^{13}$C NMR (101 MHz, CHLOROFORM-d) δ: 161.8, 159.5, 153.4, 135.9, 130.9, 127.0, 125.4, 123.5, 123.1, 122.6, 121.9, 120.3, 118.5, 110.6, 103.7, 80.4, 38.6, 36.7, 36.6, 28.3. m/z (+EI) calc. for $C_{27}H_{33}N_5O_4$ (M)$^+$ 491.2 found 492.1 ([M]+H)$^+$.

Example 55 tert-butyl (1-methyl-5-((4-(1-methyl-5-(piperidine-1-carbonyl)-1H-pyrrol-3-yl)phenyl)carbamoyl)-1H-pyrrol-3-yl)carbamate (40)

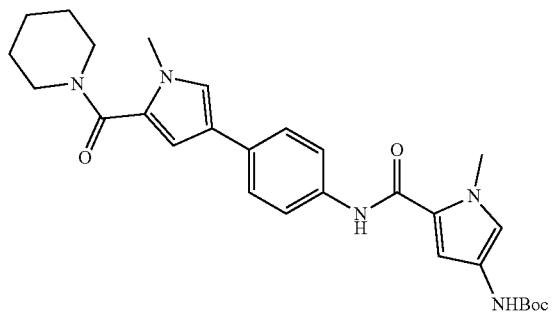

(40)

Method A was followed. Obtained 0.060 g (50%) as light yellow solid. $^1$H NMR (400 MHz, CHLOROFORM-d) δ: 7.67 (s, 1H), 7.45-7.54 (m, 2H), 7.40 (d, J=8.56 Hz, 2H), 6.93 (d, J=1.76 Hz, 1H), 6.87 (br. s., 1H), 6.62 (br. s., 1H), 6.54 (d, J=1.76 Hz, 1H), 6.47 (br. s., 1H), 3.90 (s, 3H), 3.77 (s, 3H), 3.65-3.73 (m, 4H), 1.71 (br. s., 2H), 1.60-1.66 (m, 4H), 1.51 (s, 9H). $^{13}$C NMR (101 MHz, CHLOROFORM-d) δ: 162.7, 159.5, 153.4, 135.8, 130.9, 126.6, 125.4, 123.5, 122.8, 122.28, 121.9, 120.3, 118.5, 109.2, 103.7, 80.2, 60.4, 47.9, 36.7, 35.7, 28.3, 25.7, 24.7. m/z (+EI) calc. for $C_{28}H_{35}N_5O_4$ (M)$^+$ 505.2 found 506.2 ([M]+H)$^+$.

Example 56 tert-butyl (1-methyl-5-((4-(1-methyl-5-(morpholine-4-carbonyl)-1H-pyrrol-3-yl)phenyl)carbamoyl)-1H-pyrrol-3-yl)carbamate (41)

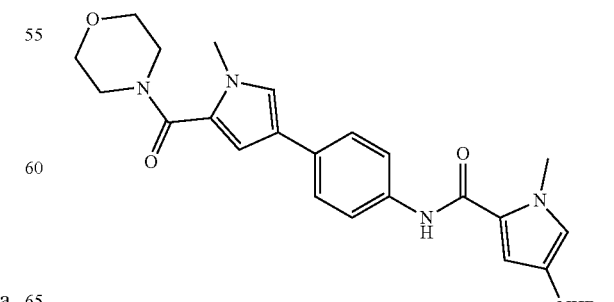

(41)

Method B was followed. Obtained 0.087 g, (72%) as a yellow-orange solid. $^1$H NMR (400 MHz, CHLOROFORM-d) δ: 7.70 (br. s., 1H), 7.46-7.57 (m, J=7.05 Hz, 2H), 7.34-7.45 (m, J=7.55 Hz, 2H), 6.97 (br. s., 1H), 6.85 (br. s., 1H), 6.65 (br. s., 1H), 6.55 (br. s., 1H), 6.46 (br. s., 1H), 3.90 (br. s., 3H), 3.80 (br. s., 7H), 3.74 (br. s., 4H), 1.51 (br. s., 9H). $^{13}$C NMR (101 MHz, CHLOROFORM-d) δ: 163.1, 159.5, 153.8, 136.2, 130.7, 125.4, 123.5, 122.9, 122.0, 120.3, 118.5, 110.2, 103.8, 80.3, 67.1, 38.6, 36.5, 35.7, 28.4. m/z (+EI) calc. for $C_{27}H_{33}N_5O_5$ (M)$^+$ 507.2 found 508.1 ([M]+H)$^+$.

Example 57 tert-butyl (1-methyl-5-((4-(1-methyl-5-(thiomorpholine-4-carbonyl)-1H-pyrrol-3-yl)phenyl)carbamoyl)-1H-pyrrol-3-yl)carbamate (42)

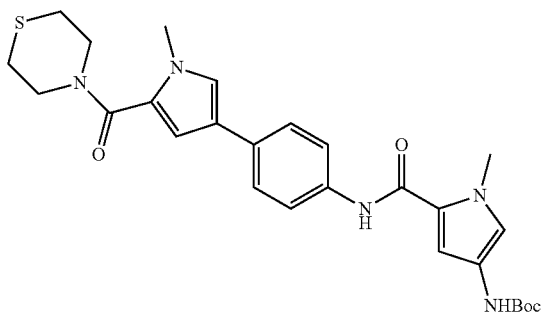

Method A was followed. Obtained 0.040 g (86%) as a yellow oil. $^1$H NMR (400 MHz, CHLOROFORM-d) δ: 7.64 (br. s., 1H), 7.47-7.57 (m, J=8.06 Hz, 2H), 7.32-7.47 (m, J=8.06 Hz, 2H), 6.97 (s, 1H), 6.85 (br. s., 1H), 6.64 (br. s., 1H), 6.54 (s, 1H), 6.38 (br. s., 1H), 4.04 (br. s., 4H), 3.91 (s, 3H), 3.78 (s, 3H), 2.71 (br. s., 4H), 1.51 (br. s., 9H). $^{13}$C NMR (101 MHz, CHLOROFORM-d) δ: 163.1, 159.5, 153.4, 135.9, 130.6, 125.8, 125.5, 123.5, 123.0, 122.9, 121.8, 120.3, 118.6, 109.6, 103.7, 80.4, 60.4, 36.7, 35.8, 28.3. m/z (+EI) calc. for $C_{27}H_{33}N_5O_4S$ (M)$^+$ 523.2 found 524.1 ([M]+H)$^+$.

Examples 58-59

Synthesis of Bromo-Pyrrole Carboxyamido Derivatives (43, 44)

4-bromo-1-methyl-1H-pyrrole-2-carboxylic acid (0.500 g, 2.45 mmols) was dissolved in dry DCM (25 mL) in a round bottom flask previously dried in oven. Oxalyl chloride (0.630 mL, 3 equiv.) and a catalytic amount of dry DMF (2-3 drops) were added to the solution that started bubbling. The reaction mixture was left under magnetic stirrer for 1 hour until ceased the formation of gas. At that point, the solution was evaporated using a rotary evaporator to eliminate the excess of oxalyl chloride. The reaction mixture was then dissolved in dry DCM (10 mL). The obtained solution was then added dropwise to a solution made of triethylamine (1.06 mL, 3 equiv.) and the corresponding amine (1.5 equiv.) in dry DCM (3 mL) kept at 0° C. under N$_2$ atmosphere during the addition. The addition of the first solution to the second one caused the formation of steam. The reaction mixture was left to stir overnight under N$_2$ atmosphere. After 16 hours TLC and LC-MS showed completion of the reaction. At that point DCM was evaporated using a rotary evaporator. The reaction was quenched by the addition of water (10 mL) that was then extracted with AcOEt (3×10 mL). The organic phase was sequentially washed with Citric Acid 0.1 M aqueous solution (10 mL), saturated NaHCO$_3$ aqueous solution (10 mL) and Brine (10 mL). The collected organic phase was dried over MgSO$_4$ and subsequently evaporated using a rotary evaporator giving crude compounds, that were then purified by column chromatography (mobile phase: DCM/AcOEt, 80/20, v/v), giving pure compounds 43 and 44.

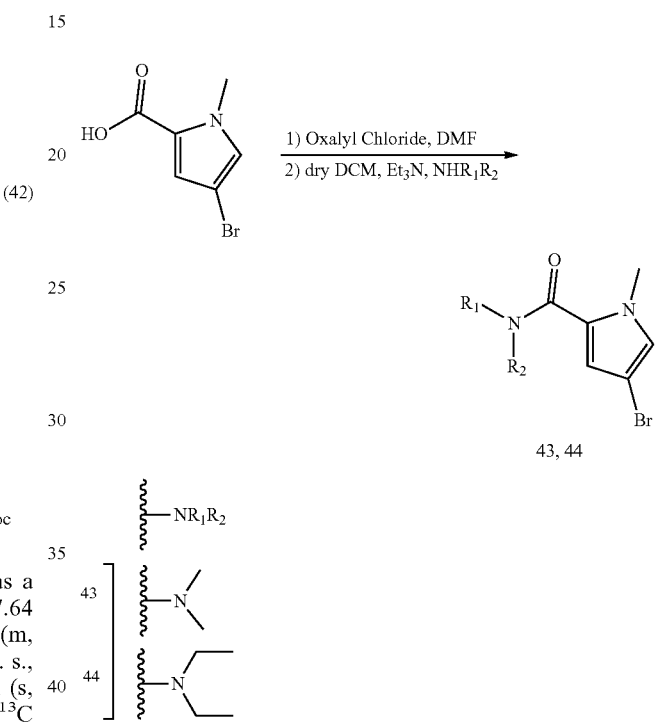

Example 58

4-bromo-N,N,1-trimethyl-1H-pyrrole-2-carboxamide (43)

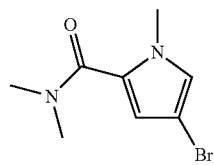

Obtained 0.420 g (74%) as a light yellow solid. $^1$H NMR (400 MHz, CHLOROFORM-d) δ: 6.67 (s, 1H), 6.34 (s, 1H), 3.74 (s, 3H), 3.12 (br. s., 6H). $^{13}$C NMR (101 MHz, CHLOROFORM-d) δ: 163.1, 126.2, 125.2, 114.9, 94.0, 35.8. m/z (+EI) calc. for $C_8H_{11}BrN_2O$ (M)$^+$ 230.0 found 230.9 ([M]+H)$^+$.

Example 59

4-bromo-N,N-diethyl-1-methyl-1H-pyrrole-2-carboxamide (44)

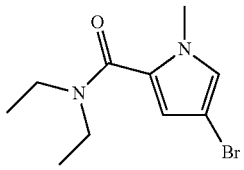

(44)

Obtained 0.484 g (77%) as a light brown solid. $^1$H NMR (400 MHz, CHLOROFORM-d) δ: 6.65 (d, J=1.76 Hz, 1H), 6.28 (d, J=1.76 Hz, 1H), 3.68 (s, 3H), 3.49 (q, J=7.22 Hz, 4H), 1.19 (t, J=7.18 Hz, 6H). $^{13}$C NMR (101 MHz, CHLOROFORM-d) δ: 162.7, 126.7, 124.9, 112.6, 94.2, 35.9. m/z (+EI) calc. for $C_{10}H_{15}BrN_2O$ (M)$^+$ 258.0 found 260.9 ([M]+H)$^+$.

Examples 60-61

Synthesis of Amido mpb Derivatives (26, 29)

In a microwave vial were sequentially added the corresponding bromo pyrrole carboxamide 43 (0.400 g, 1.73 mmols) or 44 (0.484 g, 1.87 mmols), (4-((tert-butoxycarbonyl)amino)phenyl)boronic acid (1.1 equiv.), $K_2CO_3$ (3 equiv.), ACN (15 mL) and $H_2O$ (13 mL). The reaction mixture was left under magnetic stirrer in $N_2$ atmosphere for 5 minutes. At that point Tetrakis Pd (0.05 equiv.) was added. The reaction mixture was then heated at MW radiation at 100° C. for 6 minutes. LC-MS showed the formation of the product. At that point the reaction mixture was filtered under vacuum through a path of celite previously washed with AcOEt. The resulting solution, brown in colour, was then evaporated using a rotary evaporator. At that point the reaction mixture was purified by column chromatography (mobile phase: DCM/AcOEt, 80/20, v/v) giving pure compounds 45 and 46.

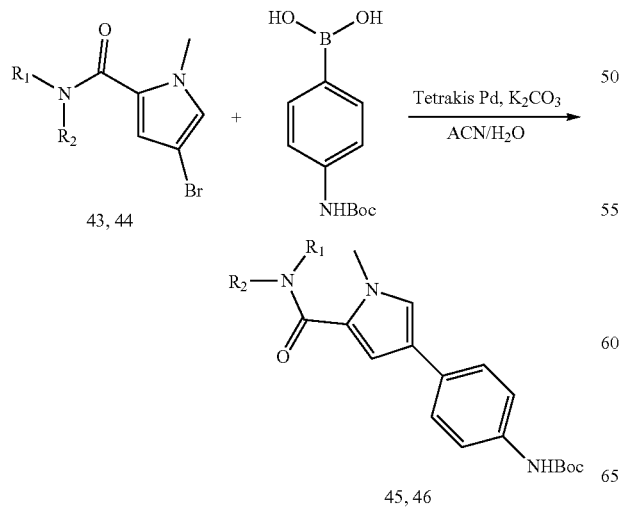

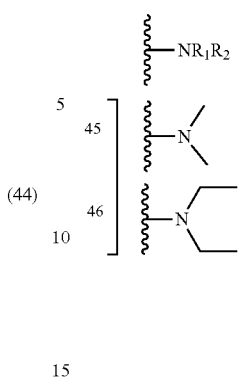

Example 60 tert-butyl (4-(5-(dimethylcarbamoyl)-1-methyl-1H-pyrrol-3-yl)phenyl) carbamate (45)

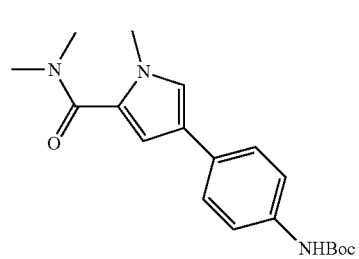

(45)

Obtained 0.360 g (61%) as a orange-brown solid. $^1$H NMR (400 MHz, CHLOROFORM-d) δ: 7.36-7.41 (m, 2H), 7.30-7.36 (m, 2H), 6.93 (d, J=2.01 Hz, 1H), 6.60 (d, J=2.01 Hz, 1H), 6.52 (s, 1H), 3.81 (s, 3H), 3.17 (s, 6H), 1.53 (s, 9H). $^{13}$C NMR (101 MHz, CHLOROFORM-d) δ: 164.1, 152.8, 136.2, 130.0, 126.2, 125.2, 122.8, 122.7, 119.1, 110.4, 80.5, 36.2, 28.4. m/z (+EI) calc. for $C_{19}H_{25}N_3O_3$ (M)$^+$ 343.1 found 344.0 ([M]+H)$^+$.

Example 61 tert-butyl (4-(5-(diethylcarbamoyl)-1-methyl-1H-pyrrol-3-yl)phenyl)carbamate (46)

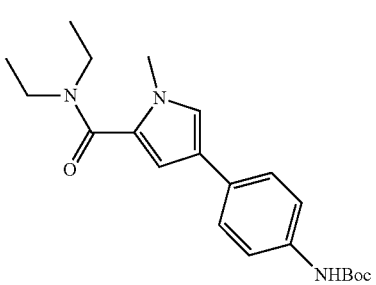

(46)

Obtained 0.313 g (46%) ad a light yellow solid. $^1$H NMR (400 MHz, CHLOROFORM-d) δ: 7.72-7.76 (m, 2H), 7.66-7.72 (m, 2H), 7.27 (s, 1H), 7.03 (s, 1H), 6.91 (d, J=2.01 Hz, 1H), 4.12 (s, 3H), 3.93 (q, J=7.05 Hz, 4H), 1.89 (s, 9H), 1.61 (t, J=7.18 Hz, 6H). $^{13}$C NMR (101 MHz, CHLOROFORM-d) δ: 163.7, 152.7, 135.8, 129.9, 127.0, 125.7, 123.1, 121.6, 118.7, 108.4, 80.2, 35.5, 28.4, 13.7. m/z (+EI) calc. for $C_{21}H_{29}N_3O_3$ (M)$^+$ 371.22 found 372.1 ([M]+H)$^+$.

Examples 62-63

Synthesis of Amido mpb Pyrrole Derivatives (47, 48)

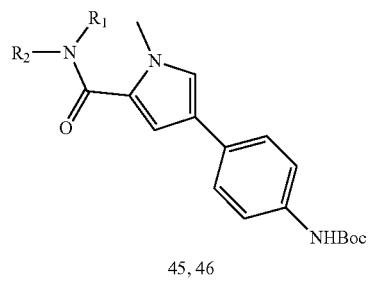

45, 46

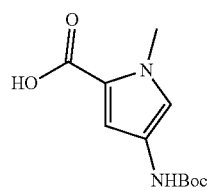

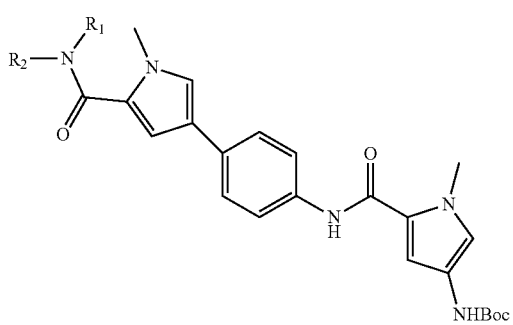

47, 48

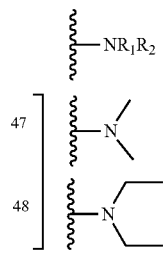

Corresponding amino-mpb intermediate 45 (0.170 g, 1.2 equiv.) or 46 (0.125 g, 1.2 equiv.) was dissolved in MeOH (7 mL) and HCl 4M in Dioxane (7 mL) was added. The solution was left to stir for 2 hours until TLC showed the total cleavage of the Boc group. At that point the reaction mixture was evaporated using a rotary evaporator obtaining a brown solid that was coupled to 4-((tert-butoxycarbonyl) amino)-1-methyl-1H-pyrrole-2-carboxylic acid following either Method A or Method B, giving compounds 47 and 48.

Example 62 tert-butyl (5-((4-(5-(dimethylcarbamoyl)-1-methyl-1H-pyrrol-3-yl)phenyl)carbamoyl)-1-methyl-1H-pyrrol-3-yl)carbamate (47)

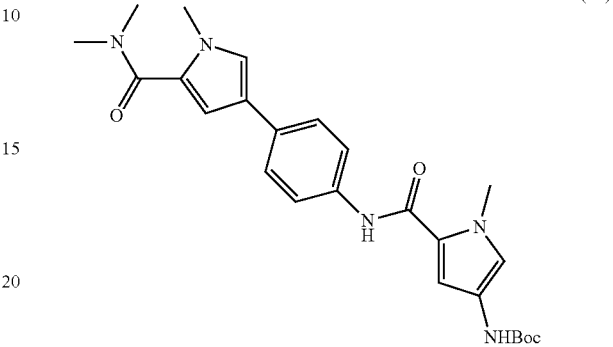

(47)

Method A was followed. Obtained 0.185 g (95%) as a brown solid. $^1$H NMR (400 MHz, CHLOROFORM-d) δ: 7.65 (s, 1H), 7.46-7.53 (m, J=8.56 Hz, 2H), 7.36-7.45 (m, J=8.56 Hz, 2H), 6.94 (d, J=1.76 Hz, 1H), 6.86 (s, 1H), 6.62 (d, J=2.01 Hz, 1H), 6.43 (br. s., 1H), 3.90 (s, 3H), 3.80 (s, 3H), 3.18 (br. s., 6H), 1.51 (s, 9H). $^{13}$C NMR (101 MHz, CHLOROFORM-d) δ: 163.9, 159.7, 153.6, 136.0, 130.8, 126.4, 125.5, 123.5, 122.6, 121.9, 120.6, 118.6, 110.4, 103.5, 80.4, 37.0, 35.8, 28.2. m/z (+EI) calc. for $C_{25}H_{31}N_5O_4$ (M)$^+$ 465.2 found 466.1 ([M]+H)$^+$.

Example 63 tert-butyl (5-((4-(5-(diethylcarbamoyl)-1-methyl-1H-pyrrol-3-yl)phenyl)carbamoyl)-1-methyl-1H-pyrrol-3-yl)carbamate (48)

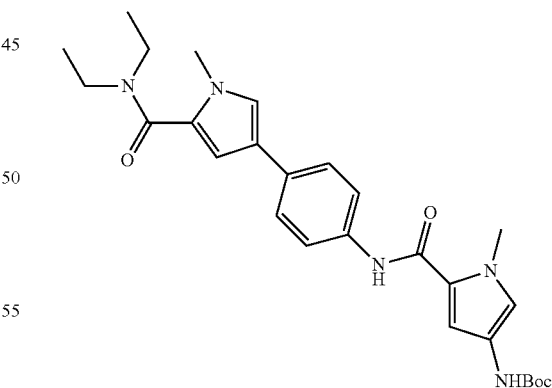

(48)

Method B was followed. Obtained 0.090 g (53%) as a light yellow solid. $^1$H NMR (400 MHz, CHLOROFORM-d) δ: 7.64 (s, 1H), 7.45-7.52 (m, J=8.56 Hz, 2H), 7.37-7.42 (m, J=8.56 Hz, 2H), 6.93 (d, J=2.01 Hz, 1H), 6.86 (s, 1H), 6.61 (s, 1H), 6.57 (d, J=2.01 Hz, 1H), 6.47 (br. s., 1H), 3.90 (s, 3H), 3.76 (s, 3H), 3.58 (q, J=6.88 Hz, 4H), 1.51 (s, 9H), 1.22-1.27 (m, 6H). $^{13}$C NMR (101 MHz, CHLOROFORM-d) δ: 163.3, 159.8, 153.8, 136.0, 131.4, 127.1, 124.9, 124.0, 122.7, 122.0, 120.2, 118.7, 108.0, 103.8, 80.3, 37.3, 35.4, 28.3. m/z (+EI) calc. for $C_{27}H_{35}N_5O_4$ (M)$^+$ 493.2 found 494.1 ([M]+H)$^+$.

Examples 64-69

Synthesis of PBD GWL-78 C8-Derivatives

Compounds 29-32, 35, 36 (from 0.047 g to 0.090 g, 1 equiv.) were Boc-deprotected dissolving the desiderate derivative in MeOH (6 mL) and HCl 4M in Dioxane (6 mL). The solution was left under magnetic stirrer for 2 hours until TLC showed total cleavage of protecting group. The reaction mixture was subsequently evaporated using a rotary evaporator, obtaining a solid. PBD capping unit 9 (1.2 equiv.) was dissolved in DMF (7 mL) and added of EDCI

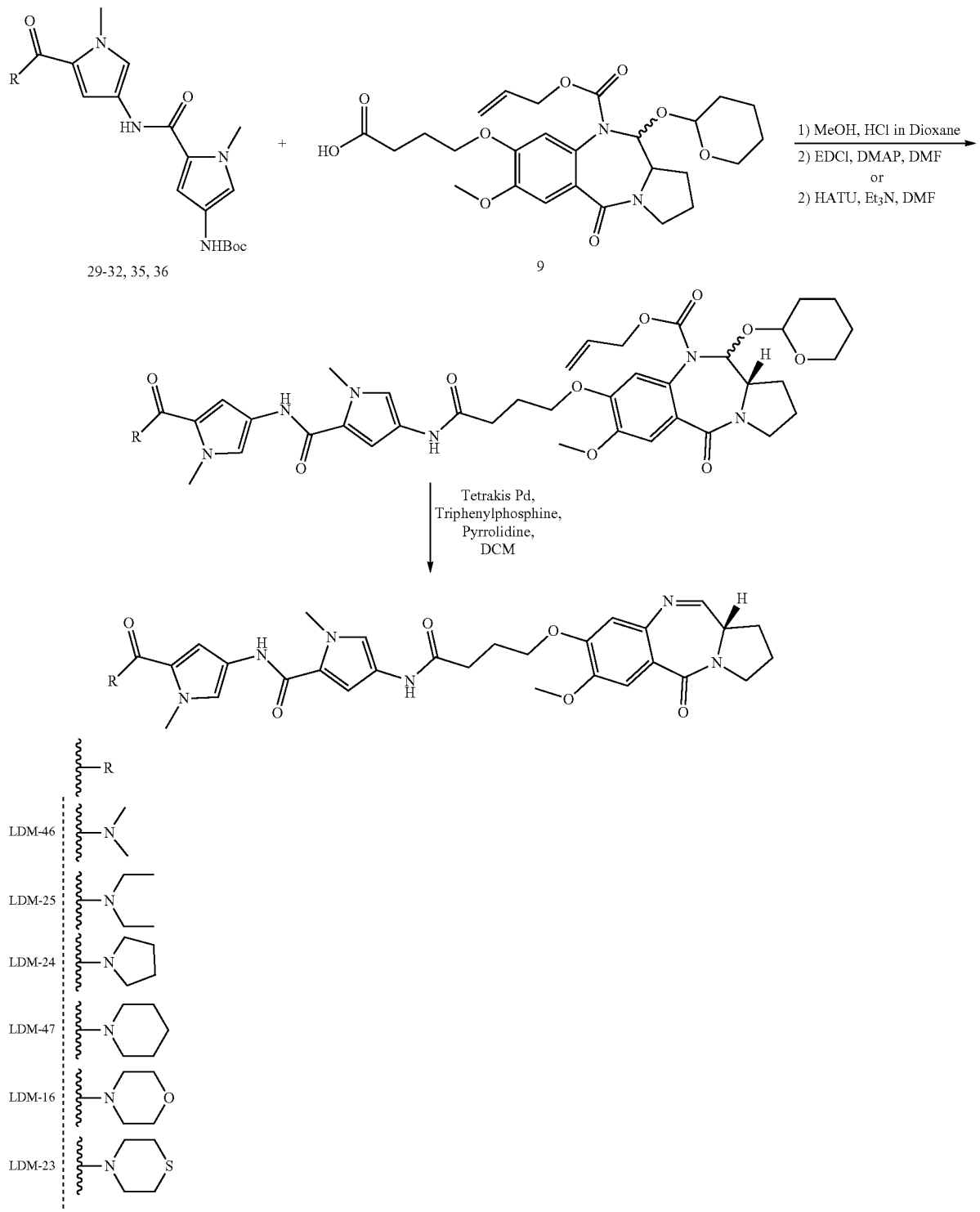

(2.4 equiv.) and DMAP (3 equiv.). The reaction mixture was left under magnetic stirrer in $N_2$ atmosphere for 30 minutes. At that point the desiderate deprotected compound was added to the reaction mixture and left under magnetic stirrer overnight for 15 hours until TLC and LC-MS analysis showed formation of the protected PBD-C8 derivative. The reaction was quenched by addition of water (10 mL) that was then extracted with AcOEt (3×10 mL). The organic phase was then sequentially washed with Citric Acid 0.1 M aqueous solution (10 mL), saturated $NaHCO_3$ aqueous solution (10 mL) and Brine (10 mL). The collected organic phase was dried over MgSO4 and subsequently evaporated using a rotary evaporator. The crude of each reaction was purified by column chromatography (mobile phase: from DCM/acetone, 90/10, v/v to DCM/acetone, 60/40/, v/v depending on the substrate). The protected PBD-conjugates (from 0.043 g to 0.055 g, 1 equiv.) was dissolved in DCM (7 mL) and added of Tetrakis Pd (0.05 equiv.), triphenylphosphine (0.25 equiv.) and pyrrolidine (1.2 equiv.). The reaction mixture was kept under magnetic stirrer for 20 minutes when TLC showed completion of reaction. At that point the solvent was evaporated using a rotary evaporator and the crude of reaction was purified by column chromatography (mobile phase: from DCM/acetone, 30/70, v/v to DCM/acetone, 10/90/, v/v, depending on the substrate) affording pure final compounds.

Example 64

(S)-4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)-N,N,1-trimethyl-1H-pyrrole-2-carboxamide (LDM-46)

1H), 7.19 (d, J=1.51 Hz, 1H), 7.11 (d, J=1.76 Hz, 1H), 6.82 (s, 1H), 6.36-6.38 (m, 1H), 4.10 (t, J=5.92 Hz, 2H), 3.88 (s, 3H), 3.87 (s, 3H), 3.75-3.84 (m, 2H), 3.71 (s, 3H), 3.51-3.61 (m, 1H), 3.12 (br. s., 6H), 2.48-2.55 (m, 2H), 2.27-2.33 (m, 2H), 2.22 (t, J=6.29 Hz, 2H), 1.97-2.10 (m, 2H). $^{13}$c NMR (101 MHz, CHLOROFORM-d) δ: 170.1, 164.9, 164.1, 163.0, 159.3, 151.0, 148.0, 141.0, 123.3, 121.5, 121.2, 120.5, 119.2, 117.5, 112.1, 111.3, 105.0, 103.6, 68.4, 56.4, 53.4, 47.0, 36.6, 35.8, 33.0, 31.7, 29.6, 29.2, 24.9, 24.1. HRMS (EL m/z): calc. for $C_{31}H_{37}N_7O_6$ $([M]+H)^+$ 604.2878 found 604.2881.

Example 65

(S)—N,N-diethyl-4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)-1-methyl-1H-pyrrole-2-carboxamide (LDM-25)

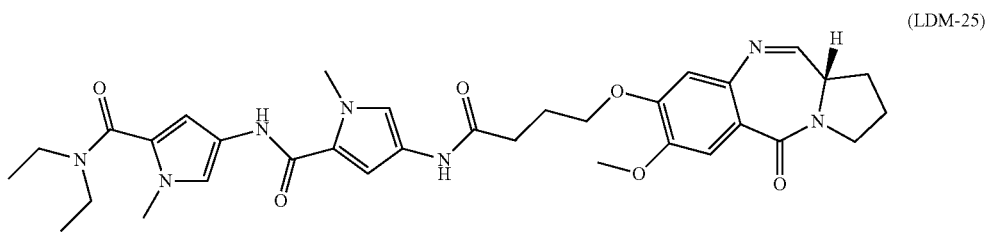 [SMILES: CCN(CC)C(=O)c1cc(NC(=O)c2cc(NC(=O)CCCOc3cc4c(cc3OC)C(=O)N3CCC[C@H]3C=N4)cn2C)cn1C]
(LDM-25)

Obtained 0.030 g (83%) as a light yellow solid. $^1$H NMR (400 MHz, DMSO-$d_6$) δ: 9.87 (s, 1H), 9.79 (s, 1H), 7.78 (d, J=4.53 Hz, 1H), 7.33 (s, 1H), 7.24 (d, J=1.51 Hz, 1H), 7.13 (d, J=1.76 Hz, 1H), 6.86 (d, J=1.76 Hz, 1H), 6.82 (s, 1H), 6.38 (d, J=1.76 Hz, 1H), 4.08-4.18 (m, 1H), 4.00-4.08 (m, 1H), 3.82 (d, J=2.27 Hz, 6H), 3.63-3.72 (m, 2H), 3.59 (s, 3H), 3.41-3.47 (m, 4H), 3.36-3.39 (m, 1H), 2.43 (t, J=7.43 Hz, 2H), 2.17-2.33 (m, 2H), 2.00-2.08 (m, 2H), 1.89-1.97 (m, 2H), 1.12-1.16 (m, 6H). $^{13}$C NMR (101 MHz, DMSO-$d_6$) δ: 168.7, 164.4, 163.4, 162.7, 158.3, 150.2, 146.7, 140.6, 123.2, 122.8, 121.9, 119.7, 117.9, 115.8, 111.1, 110.1, 103.8,

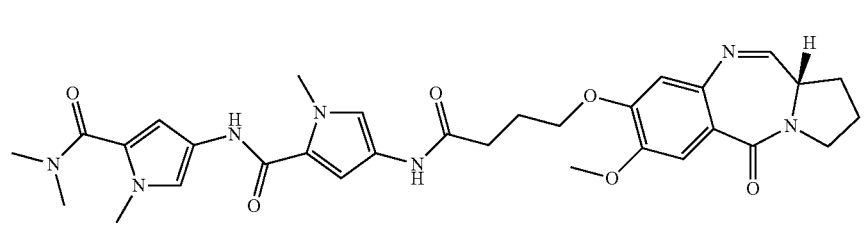
(LDM-26)

Obtained 0.021 g (61%) as a light brown solid. $^1$H NMR (400 MHz, CHLOROFORM-d) δ: 8.10 (d, J=17.63 Hz, 1H), 7.98 (d, J=12.34 Hz, 1H), 7.65 (d, J=4.28 Hz, 1H), 7.51 (s, 102.4, 68.4, 67.8, 55.8, 55.5, 53.3, 46.3, 36.0, 34.8, 31.9, 29.5, 28.8, 24.4, 23.6, 13.5. HRMS (EL m/z): calc. for $C_{33}H_{41}N_7O_6$ $([M]+H)^+$ 632.3191 found 632.3194.

Example 66

(S)-4-(4-((7-methoxy-5-oxo-2,3,5,11a-tetrahydro-1H-benzo[e]pyrrolo[1,2-a][1,4]diazepin-8-yl)oxy]butanamido)-1-methyl-N-(1-methyl-5-(pyrrolidine-1-carbonyl)-1H-pyrrol-3-yl)-1H-pyrrole-2-carboxamide (LDM-24)

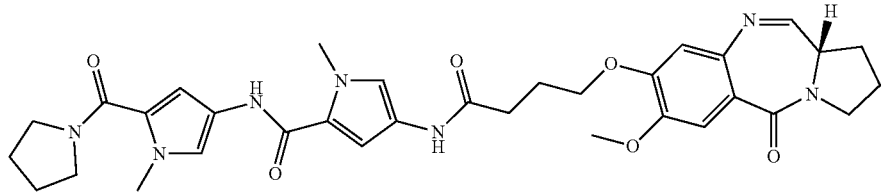

(LDM-24)

Obtained 0.028 g (66%) as a light grey solid. $^1$H NMR (400 MHz, DMSO-d$_6$) δ: 9.87 (s, 1H), 9.80 (s, 1H), 7.77 (d, J=4.28 Hz, 1H), 7.33 (s, 1H), 7.24 (d, J=1.76 Hz, 1H), 7.14 (d, J=1.76 Hz, 1H), 6.87 (d, J=1.76 Hz, 1H), 6.82 (s, 1H), 6.58 (d, J=1.76 Hz, 1H), 4.08-4.16 (m, 1H), 3.99-4.07 (m, 1H), 3.81 (d, J=1.76 Hz, 6H), 3.71 (s, 3H), 3.66 (td, J=3.84, 7.93 Hz, 1H), 3.35-3.63 (m, 6H), 2.43 (t, J=7.43 Hz, 2H), 2.15-2.33 (m, 2H), 2.00-2.06 (m, 2H), 1.89-1.97 (m, 2H), 1.85 (t, J=6.55 Hz, 4H). $^{13}$C NMR (101 MHz, DMSO-d$_6$) δ: 168.7, 164.3, 163.2, 160.7, 158.2, 150.4, 146.8, 140.7, 123.1, 122.3, 122.0, 119.6, 118.1, 116.7, 111.3, 109.9, 103.8, 68.5, 53.3, 46.3, 32.3, 28.7, 24.7, 23.8. HRMS (EL m/z): calc. for $C_{33}H_{39}N_7O_6$ ([M]+H)$^+$ 630.3035 found 630.3032.

Example 67

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(1-methyl-5-(piperidine-1-carbonyl)-1H-pyrrol-3-yl)-1H-pyrrole-2-carboxamide (LDM-47)

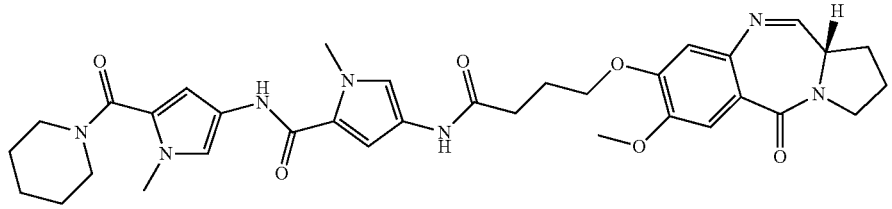

(LDM-47)

Obtained 0.050 g (94%) as a light yellow solid. $^1$H NMR (400 MHz, CHLOROFORM-d) δ: 8.16 (s, 1H), 7.96 (s, 1H), 7.65 (d, J=4.53 Hz, 1H), 7.50 (s, 1H), 7.19 (d, J=1.76 Hz, 1H), 7.11 (d, J=1.76 Hz, 1H), 6.81 (s, 1H), 6.34 (d, J=1.76 Hz, 1H), 6.28 (d, J=1.76 Hz, 1H), 4.10 (t, J=6.17 Hz, 2H), 3.88 (s, 3H), 3.86 (s, 3H), 3.80 (ddd, J=4.28, 7.24, 11.65 Hz, 1H), 3.69-3.73 (m, 1H), 3.68 (s, 3H), 3.61-3.66 (m, 4H), 3.51-3.60 (m, 1H), 2.48-2.54 (m, 2H), 2.27-2.33 (m, 2H), 2.21 (quin, J=6.55 Hz, 2H), 2.01-2.08 (m, 2H), 1.63-1.71 (m, 2H), 1.55-1.62 (m, 4H). $^{13}$C NMR (101 MHz, CHLOROFORM-d) δ: 169.8, 164.7, 162.8, 159.4, 150.7, 147.8, 144.3, 140.7, 123.6, 122.9, 121.6, 120.3, 119.4, 117.0, 112.3, 111.2, 104.2, 68.1, 56.2, 46.7, 36.4, 35.7, 32.9, 29.8, 26.2, 25.2, 24.3. HRMS (EI, m/z): calc. for $C_{34}H_{41}N_7O_6$ ([M]+H)$^+$ 644.3191 found 644.3194.

Example 68

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(1-methyl-5-(morpholine-4-carbonyl)-1H-pyrrol-3-yl)-1H-pyrrole-2-carboxamide (LDM-16)

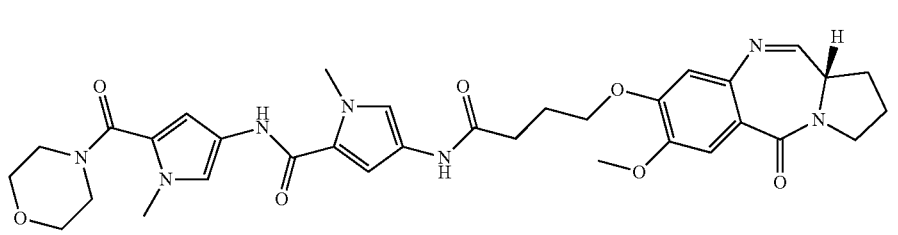

(LDM-16)

Obtained 0.040 g (80%) as a light brown solid. $^1$H NMR (400 MHz, CHLOROFORM-d) δ: 8.22 (br. s., 1H), 8.20 (br. s., 1H), 7.65 (d, J=4.53 Hz, 1H), 7.48 (s, 1H), 7.20 (d, J=1.76 Hz, 1H), 7.09 (d, J=1.51 Hz, 1H), 6.80 (s, 1H), 6.44 (d, J=1.76 Hz, 1H), 6.32 (d, J=1.76 Hz, 1H), 4.07 (t, J=6.04 Hz, 2H), 3.86 (s, 3H), 3.83 (s, 3H), 3.74-3.80 (m, 1H), 3.64-3.74 (m, 12H), 3.50-3.60 (m, 1H), 2.44-2.51 (m, 2H), 2.29 (t, J=6.80 Hz, 2H), 2.17-2.24 (m, 2H), 2.00-2.08 (m, 2H). $^{13}$C NMR (101 MHz, CHLOROFORM-d) δ: 169.8, 164.9, 162.7, 159.0, 150.7, 147.6, 140.7, 122.9, 122.3, 121.6, 120.4, 119.4, 117.6, 111.8, 110.9, 104.8, 103.6, 69.5, 68.1, 67.0, 56.0, 53.5, 46.6, 36.6, 35.6, 32.9, 31.8, 29.6, 29.2, 24.9, 24.2. HRMS (EI, m/z): calc. for $C_{33}H_{39}N_7O_7$ ([M]+H)$^+$ 646.2984 found 646.2990.

Example 69

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(1-methyl-5-(thiomorpholine-4-carbonyl)-1H-pyrrol-3-yl)-1H-pyrrole-2-carboxamide (LDM-23)

Obtained 0.030 g (90%) as a light grey solid. $^1$H NMR (400 MHz, CHLOROFORM-d) δ: 8.22 (s, 1H), 8.16 (s, 1H), 7.65 (d, J=4.53 Hz, 1H), 7.49 (s, 1H), 7.22 (d, J=1.76 Hz, 1H), 7.09 (d, J=1.76 Hz, 1H), 6.80 (s, 1H), 6.45 (d, J=1.76 Hz, 1H), 6.30 (d, J=1.76 Hz, 1H), 4.08 (t, J=6.04 Hz, 2H), 3.92-3.98 (m, 4H), 3.87 (s, 3H), 3.84 (s, 3H), 3.76-3.80 (m, 1H), 3.69-3.73 (m, 1H), 3.68 (s, 3H), 3.49-3.61 (m, 1H), 2.63 (t, J=5.04 Hz, 4H), 2.44-2.52 (m, 2H), 2.26-2.33 (m, 2H), 2.18-2.22 (m, 2H), 2.00-2.09 (m, 2H). $^{13}$C NMR (101 MHz, CHLOROFORM-d) δ: 170.1, 164.9, 162.7, 162.4, 159.1, 150.8, 147.5, 140.4, 123.0, 122.3, 121.5, 120.5, 119.4, 117.4, 111.8, 110.9, 104.3, 103.8, 97.4, 68.1, 56.1, 53.4, 46.9, 36.3, 32.6, 27.5, 24.6, 23.8. HRMS (EI, m/z): calc. for $C_{33}H_{39}N_7O_6S$ ([M]+H)$^+$ 662.2755 found 662.2761.

Examples 70-75

MPB Derivatives

Compounds 39-42, 47 and 48 (from 0.030 g to 0.070 g, 1 equiv.) were Boc-deprotected dissolving the desiderate derivative in MeOH (6 mL) and HCl 4M in Dioxane (6 mL). The solution was left under magnetic stirrer for 2 hours until TLC showed total cleavage of protecting group. The reaction mixture was subsequently evaporated using a rotary evaporator, obtaining a solid. PBD capping unit 9 was coupled with desiderate deprotected compound (1.2 equiv.) either with Method A or Method B.

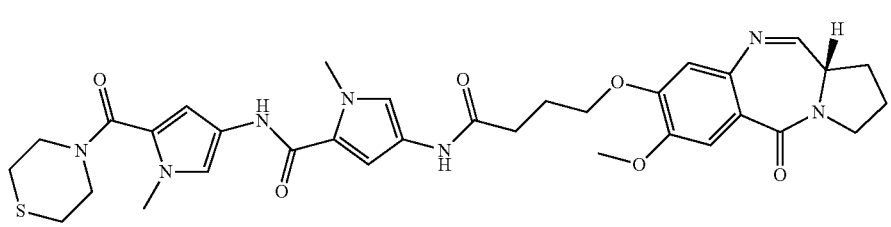

(LDM-23)

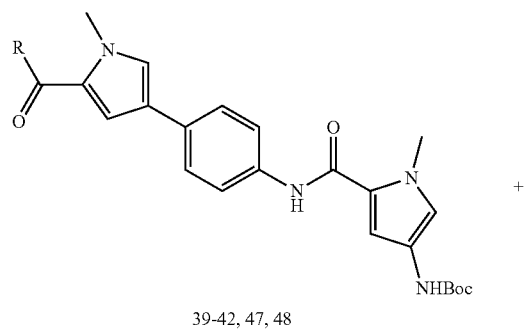
39-42, 47, 48
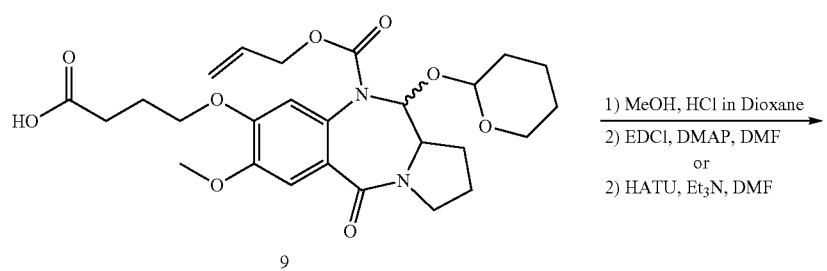
1) MeOH, HCl in Dioxane
2) EDCl, DMAP, DMF
or
2) HATU, Et₃N, DMF
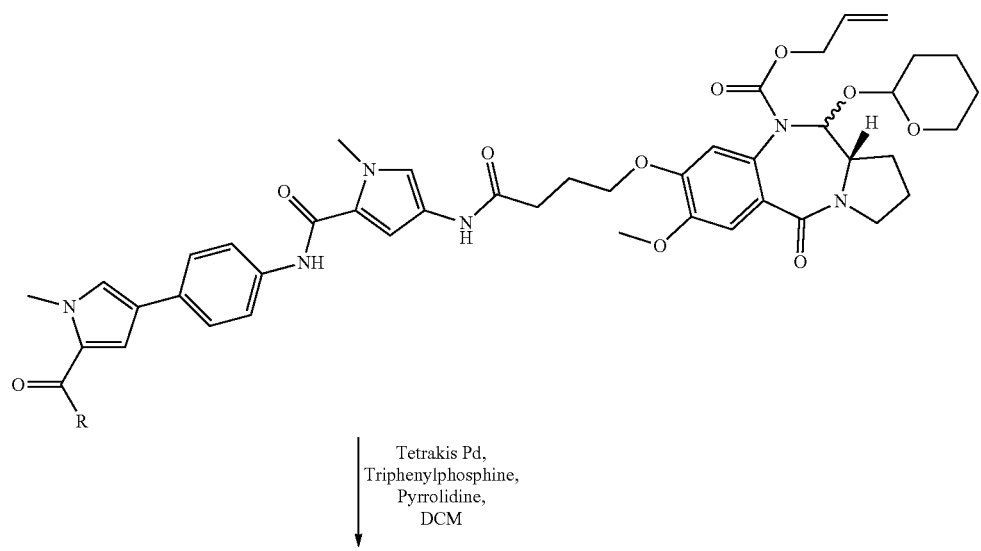
Tetrakis Pd,
Triphenylphosphine,
Pyrrolidine,
DCM
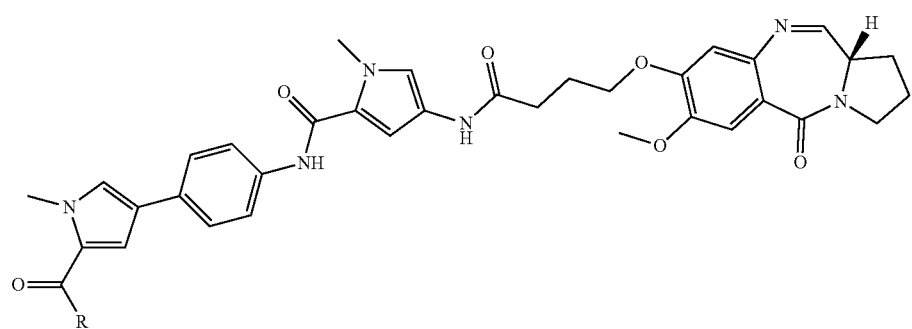

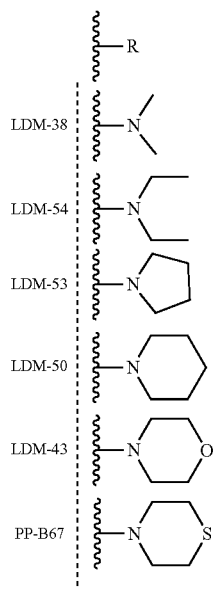

The protected PBD-conjugates (from 0.021 g to 0.080 g, 1 equiv.) was dissolved in DCM (7 mL) and added of Tetrakis Pd (0.05 equiv.), triphenylphosphine (0.25 equiv.) and pyrrolidine (1.2 equiv.). The reaction mixture was kept under magnetic stirrer for 20 minutes when TLC showed completion of reaction. At that point the solvent was evaporated using a rotary evaporator and the crude of reaction was purified by column chromatography (mobile phase: from DCM/acetone, 30/70, v/v to DCM/acetone, 10/90/, v/v, depending on the substrate) affording pure final compounds.

Example 70

(S)-4-(4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)phenyl)-N,N,1-trimethyl-1H-pyrrole-2-carboxamide (LDM-38)

Method A was followed. Obtained 0.044 g (70%) as a light yellow solid. $^1$H NMR (400 MHz, DMSO-$d_6$) δ: 9.90 (s, 1H), 9.76 (s, 1H), 7.77 (d, J=4.53 Hz, 1H), 7.62-7.69 (m, J=8.81 Hz, 2H), 7.44-7.50 (m, J=8.56 Hz, 2H), 7.33 (s, 1H), 7.30 (d, J=1.76 Hz, 1H), 7.20 (d, J=1.76 Hz, 1H), 6.95 (d, J=1.76 Hz, 1H), 6.82 (s, 1H), 6.75 (d, J=1.76 Hz, 1H), 4.08-4.17 (m, 1H), 3.99-4.08 (m, 1H), 3.82 (s, 6H), 3.68 (s, 3H), 3.65 (d, J=3.53 Hz, 1H), 3.55-3.63 (m, 1H), 3.07 (br. s., 6H), 2.47 (s, 1H), 2.44 (t, J=7.43 Hz, 2H), 2.15-2.33 (m, 2H), 2.00-2.07 (m, 2H), 1.92 (d, J=5.54 Hz, 2H). $^{13}$C NMR (101 MHz, DMSO-$d_6$) δ: 168.6, 164.4, 163.3, 162.4, 159.3, 150.4, 146.7, 140.7, 136.9, 129.6, 126.2, 124.1, 122.7, 121.8, 120.5, 119.8, 110.1, 109.2, 104.5, 67.3, 46.2, 36.0, 31.8, 28.5, 24.7, 23.4. HRMS (EL m/z): calc. for $C_{37}H_{41}N_7O_6$ ([M]+H)$^+$ 680.3191 found 680.3196.

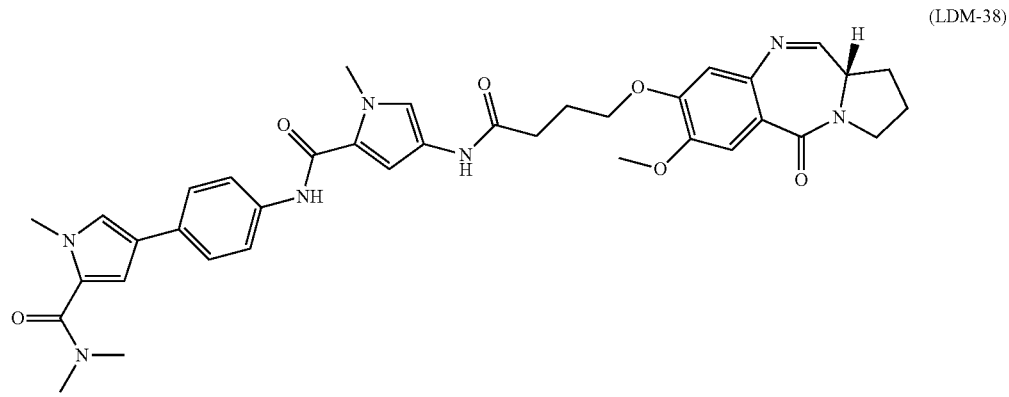 [SMILES: COc1cc2c(cc1OCCCC(=O)Nc1cc(C(=O)Nc3ccc(-c4cc(C(=O)N(C)C)n(C)c4)cc3)n(C)c1)N=C[C@@H]1CCCN1C2=O]
(LDM-38)

Example 71

(S)—N,N-diethyl-4-(4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)phenyl)-1-methyl-1H-pyrrole-2-carboxamide (LDM-54)

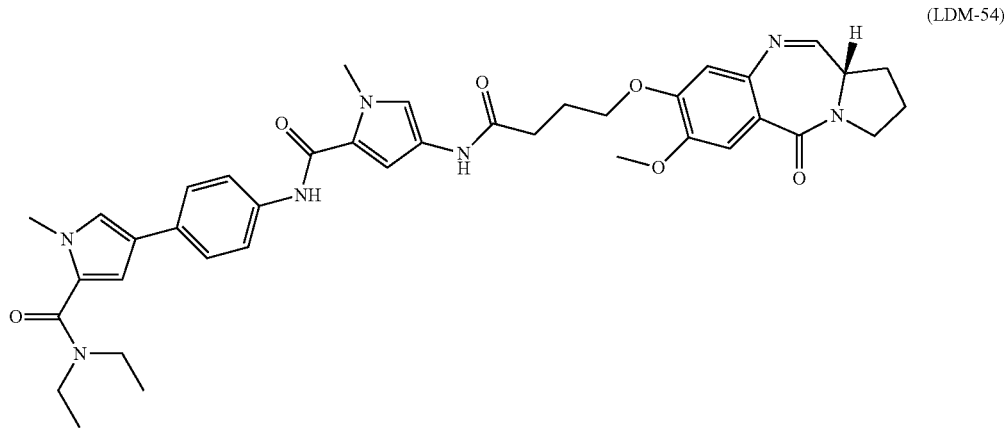 [SMILES: CCN(CC)C(=O)c1cc(-c2ccc(NC(=O)c3cc(NC(=O)CCCOc4cc5c(cc4OC)C(=O)N4CCC[C@H]4C=N5)cn3C)cc2)cn1C]

(LDM-54)

Method B was followed. Obtained 0.029 g (64%) as a white solid. $^1$H NMR (400 MHz, CHLOROFORM-d) δ: 8.22 (br. s., 1H), 7.86 (br. s., 1H), 7.66 (d, J=4.53 Hz, 1H), 7.51 (s, 1H), 7.44-7.49 (m, J=8.56 Hz, 2H), 7.33-7.41 (m, J=8.81 Hz, 2H), 7.17 (d, J=1.76 Hz, 1H), 6.94 (d, J=1.51 Hz, 1H), 6.82 (s, 1H), 6.59 (d, J=2.01 Hz, 1H), 6.35 (d, J=1.51 Hz, 1H), 4.10 (t, J=6.17 Hz, 2H), 3.89 (s, 6H), 3.80 (ddd, J=4.15, 7.43, 11.83 Hz, 1H), 3.74 (s, 2H), 3.68-3.72 (m, 1H), 3.53-3.62 (m, 6H), 2.53 (dt, J=3.65, 6.99 Hz, 2H), 2.26-2.33 (m, 2H), 2.23 (t, J=6.67 Hz, 2H), 1.98-2.09 (m, 2H), 1.25 (t, J=7.05 Hz, 6H); $^{13}$C NMR (101 MHz, CHLOROFORM-d) δ: 170.0, 165.0, 163.7, 162.8, 160.0, 150.7, 147.9, 140.6, 136.1, 130.6, 127.3, 125.5, 122.9, 121.4, 119.6, 112.1, 110.8, 108.4, 10.40, 68.1, 56.4, 53.6, 47.0, 36.9, 35.8, 33.0, 29.9, 25.1, 24.2. HRMS (EI, m/z): calc. for $C_{39}H_{45}N_7O_6$ ([M]+H)$^+$ 708.3504 found 708.3508.

Example 72

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(4-(1-methyl-5-(pyrrolidine-1-carbonyl)-1H-pyrrol-3-yl)phenyl)-1H-pyrrole-2-carboxamide (LDM-53)

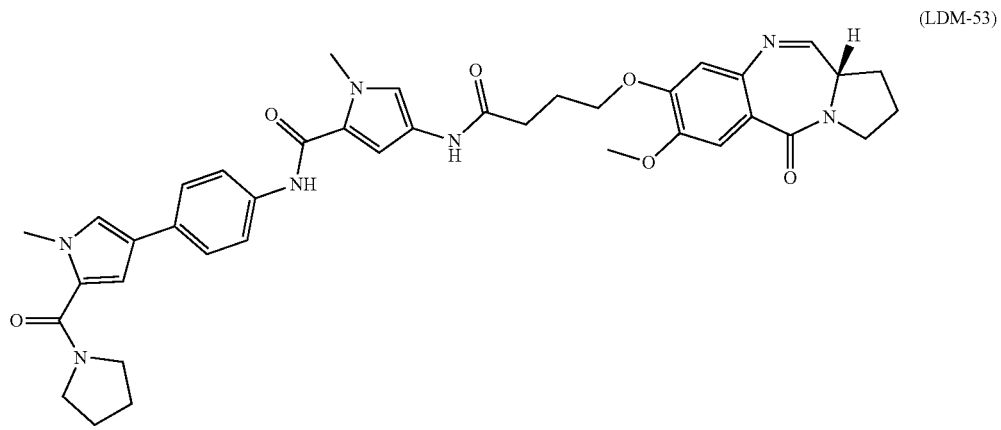 [SMILES: COc1cc2c(cc1OCCCC(=O)Nc1cc(C(=O)Nc3ccc(-c4cc(C(=O)N5CCCC5)n(C)c4)cc3)n(C)c1)N=C[C@@H]1CCCN1C2=O]

(LDM-53)

Method B was followed. Obtained 0.017 g (91%) as a light brown solid. $^1$H NMR (400 MHz, CHLOROFORM-d) δ: 7.97 (br. s., 1H), 7.82 (s, 1H), 7.66 (d, J=4.53 Hz, 1H), 7.53 (s, 1H), 7.51 (d, J=8.56 Hz, 2H), 7.39 (d, J=8.56 Hz, 2H), 7.15 (d, J=1.76 Hz, 1H), 6.96 (d, J=1.76 Hz, 1H), 6.83 (s, 1H), 6.76 (d, J=2.01 Hz, 1H), 6.42 (S, 1H), 4.09-4.16 (m, 2H), 3.90 (s, 6H), 3.88 (s, 3H), 3.76-3.84 (m, 2H), 3.68-3.74 (m, 2H), 3.64 (br. s., 1H), 3.57 (td, J=7.68, 11.83 Hz, 2H), 2.52-2.57 (m, 2H), 2.22-2.39 (m, 3H), 2.00-2.08 (m, 3H), 1.92-1.98 (m, 4H). $^{13}$C NMR (101 MHz, CHLOROFORM-d) δ: 169.8, 164.6, 163.2, 159.7, 147.7, 127.5, 125.7, 123.6, 121.6, 112.2, 111.0, 103.8, 68.5, 55.8, 49.8, 46.5, 35.2, 32.9, 29.4, 26.4, 25.1, 24.2. HRMS (EI, m/z): calc. for $C_{39}H_{43}N_7O_6$ ([M]+H)$^+$ 706.3348 found 706.3353.

Example 73

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(4-(1-methyl-5-(piperidine-1-carbonyl)-1H-pyrrol-3-yl)phenyl)-1H-pyrrole-2-carboxamide (LDM-50)

(LDM-50)

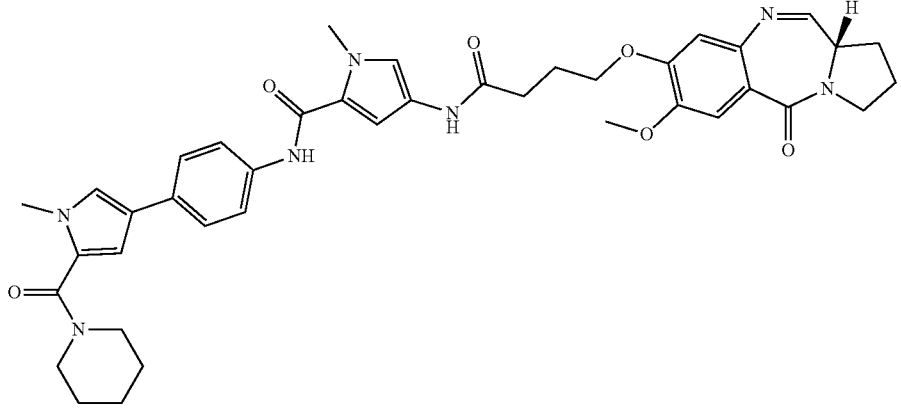

Method B was followed. Obtained 0.021 g (81%) as a light brown solid. $^1$H NMR (400 MHz, CHLOROFORM-d) δ: 8.06 (s, 1H), 7.84 (s, 1H), 7.66 (d, J=4.53 Hz, 1H), 7.52 (s, 1H), 7.46-7.51 (m, J=8.31 Hz, 2H), 7.34-7.43 (m, J=8.56 Hz, 2H), 7.13-7.19 (m, 1H), 6.95 (d, J=1.76 Hz, 1H), 6.83 (s, 1H), 6.56 (d, J=1.51 Hz, 1H), 6.40 (d, J=1.51 Hz, 1H), 4.11 (t, J=5.92 Hz, 2H), 3.90 (s, 6H), 3.78-3.84 (m, 1H), 3.76 (s, 3H), 3.69-3.73 (m, 4H), 3.57 (td, J=7.71, 12.02 Hz, 2H), 2.50-2.57 (m, 2H), 2.27-2.35 (m, 2H), 2.20-2.26 (m, 2H), 1.98-2.09 (m, 2H), 1.73 (dd, J=7.18, 17.25 Hz, 6H). $^{13}$C NMR (101 MHz, CHLOROFORM-d) δ: 169.9, 164.6, 162.8, 160.3, 159.7, 150.7, 147.8, 140.7, 136.1, 130.7, 126.8, 125.4, 123.3 123.0, 122.4, 121.6, 120.7, 119.8, 111.9, 111.1, 109.1, 103.5, 100.0, 68.5, 61.4, 56.4, 53.7, 46.6, 36.9, 35.6, 32.8, 29.7, 25.0, 24.7, 24.3. HRMS (EI, m/z): calc. for $C_{40}H_{46}N_7O_6$ ([M]+H)$^+$ 720.3504 found 720.3505.

Example 74

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(4-(1-methyl-5-(morpholine-4-carbonyl)-1H-pyrrol-3-yl)phenyl)-1H-pyrrole-2-carboxamide (LDM-43)

(LDM-43)

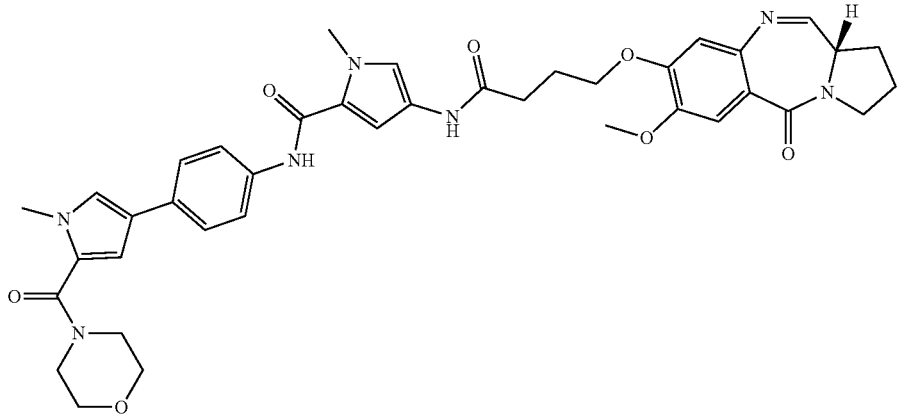

Method B was followed. Obtained 0.032 g (50%) as a light yellow solid. $^1$H NMR (400 MHz, DMSO-$d_6$) δ: 9.91 (s, 1H), 9.78 (s, 1H), 7.78 (br. s., 1H), 7.61-7.71 (m, J=8.06 Hz, 2H), 7.44-7.52 (m, J=7.81 Hz, 2H), 7.34 (br. s., 2H), 7.21 (s, 1H), 6.96 (s, 1H), 6.83 (s, 1H), 6.71 (s, 1H), 4.13 (q, J=8.14 Hz, 1H), 4.00-4.08 (m, 1H), 3.83 (s, 6H), 3.70 (s, 3H), 3.64 (br. s., 8H), 3.56-3.60 (m, 1H), 2.44 (t, J=7.05 Hz, 2H), 2.25-2.35 (m, 1H), 2.15-2.25 (m, 1H), 1.99-2.15 (m, 4H), 1.88-1.98 (m, 2H). $^{13}$C NMR (101 MHz, DMSO-$d_6$) δ: 168.9, 164.3, 163.4, 161.9, 159.5, 150.3, 146.9, 140.6, 137.0, 129.5, 125.4, 124.4, 123.1, 122.7, 122.0, 120.2, 119.7, 111.2, 109.9, 109.8, 104.6, 67.8, 66.2, 55.4, 53.4, 46.5, 36.4, 31.8, 29.7, 28.7, 24.8, 23.7, HRMS (EI, m/z): calc. for $C_{39}H_{43}N_7O_7$ ([M]+H)$^+$ 722.3297 found 722.3302.

Example 75

(S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(4-(1-methyl-5-(thiomorpholine-4-carbonyl)-1H-pyrrol-3-yl)phenyl)-1H-pyrrole-2-carboxamide (PP-B67)

Synthesis C7 Fluorine PBD Derivative.

Examples 76-84

General Reaction Scheme for Synthesis of 4C-Alloc-THP-Protected C7 Fluorine PBD Unit

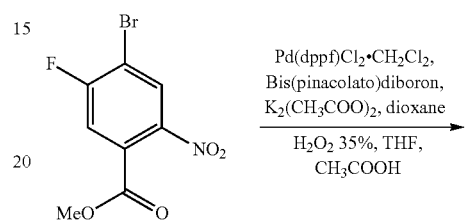

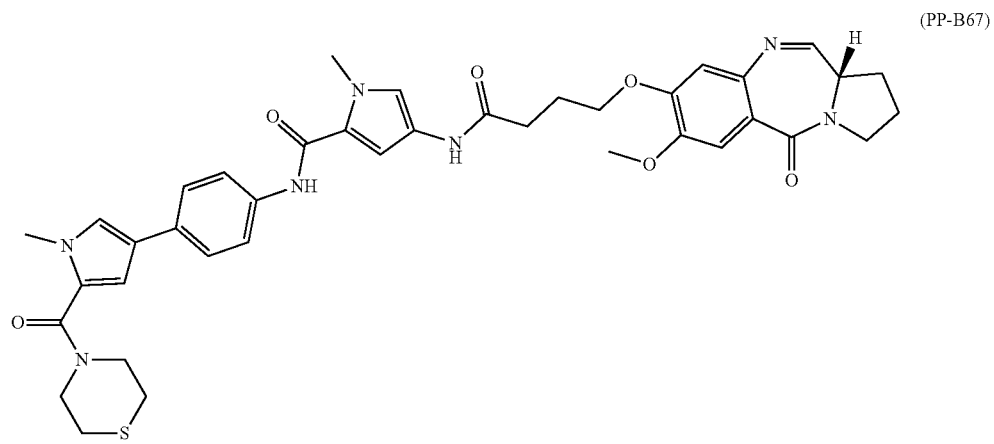 [SMILES: COc1cc2c(cc1OCCCC(=O)Nc1cc(C(=O)Nc3ccc(-c4cc(C(=O)N5CCSCC5)n(C)c4)cc3)n(C)c1)N=C[C@@H]1CCCN1C2=O]

Method A was followed. Obtained 0.077 g (96%) as a light brown solid. $^1$H NMR (400 MHz, CHLOROFORM-d) δ: 7.98 (s, 1H), 7.92 (s, 1H), 7.66 (d, J=4.53 Hz, 1H), 7.53 (d, J=8.56 Hz, 2H), 7.51 (s, 1H), 7.38 (d, J=8.56 Hz, 2H), 7.14 (d, J=1.76 Hz, 1H), 6.97 (d, J=1.76 Hz, 1H), 6.82 (s, 1H), 6.55 (d, J=1.76 Hz, 1H), 6.45 (d, J=2.01 Hz, 1H), 4.09 (t, J=6.42 Hz, 2H), 4.03 (dd, J=2.77, 7.05 Hz, 4H), 3.89 (s, 3H), 3.88 (s, 3H), 3.78-3.83 (m, 1H), 3.77 (s, 3H), 3.68-3.74 (m, 1H), 3.51-3.61 (m, 1H), 2.67-2.73 (m, 4H), 2.48-2.54 (m, 2H), 2.27-2.35 (m, 2H), 2.20-2.26 (m, 2H), 2.00-2.08 (m, 2H). $^{13}$C NMR (101 MHz, CHLOROFORM-d) δ: 169.8, 164.6, 163.1, 162.7, 159.6, 150.6, 147.7, 140.6, 136.1, 130.4, 125.8, 125.4, 123.3, 123.0, 122.9, 121.5, 120.5, 120.4, 119.8, 111.6, 110.9, 109.5, 103.7, 68.1, 64.5, 56.1, 46.7, 36.7, 35.8, 32.9, 29.5, 29.2, 27.9, 24.9, 24.2. HRMS (EI, m/z): calc. for $C_{39}H_{43}N_7O_7$ ([M]+H)$^+$ 738.3068 found 738.3075.

-continued

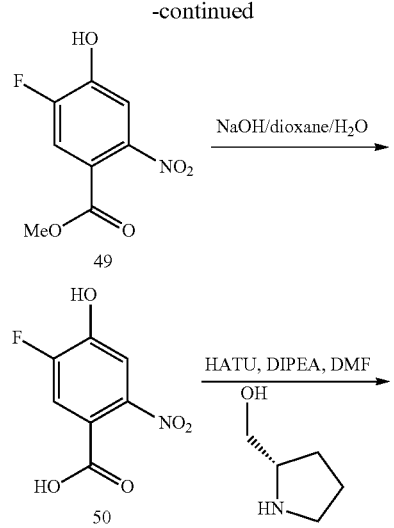

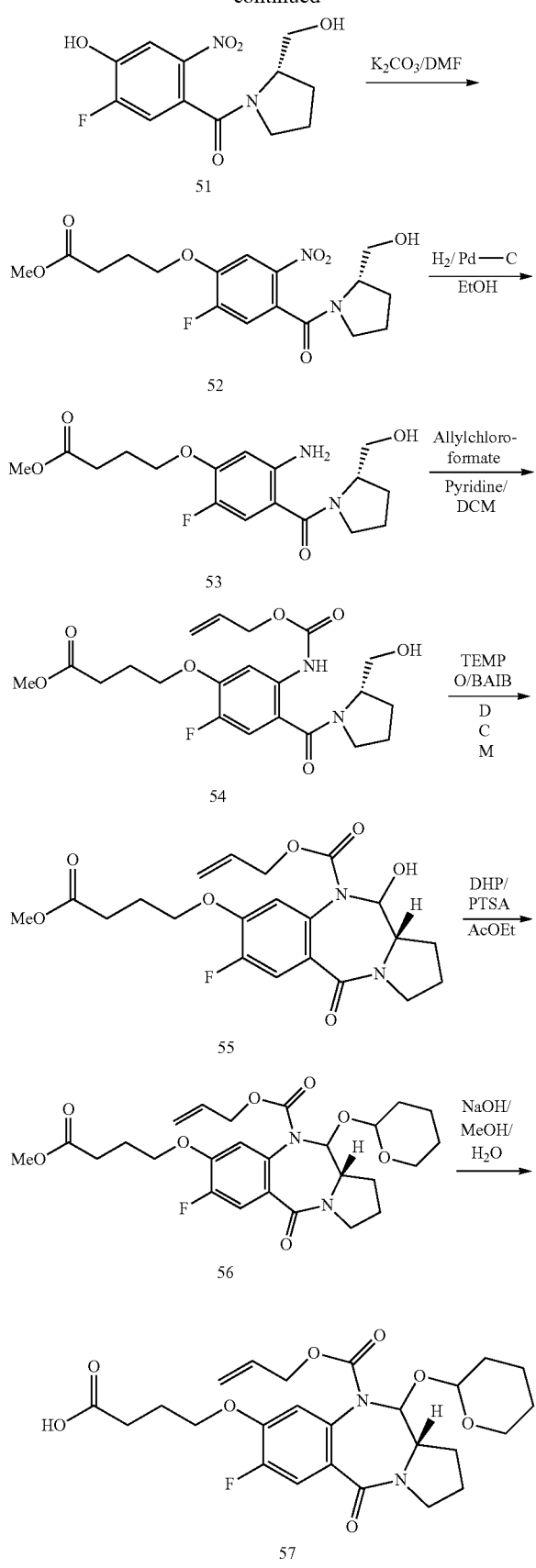

Procedure:

Example 76

Synthesis of Methyl 5-fluoro-4-hydroxy-2-nitrobenzoate (49)

Methyl 4-bromo-5-fluoro-2-nitrobenzoate (5.0 g, 1 equiv.) was dissolved in dioxane (40 mL) and sequentially added of bis(pinacolato)diboron (5.04 g, 1.1 equiv.), Pd(dppeCl$_2$.CH$_2$Cl$_2$ (0.44 g, 0.03 equiv.) and potassium acetate (5.2 g, 3 equiv.). The reaction mixture was left heating at reflux, under magnetic stirrer and N$_2$ atmosphere overnight until TLC showed the total consumption of the starting material. The reaction mixture was then filtered on celite path eluting with DCM, the solvent evaporated under reduced pressure and the crude purified by filtration on silica gel eluting with DCM. The collected organic solvent was filtrated under reduced pressure giving a black oil. The crude of reaction was dissolved in THF (100 mL) and added of acetic acid (8 mL). The solution was kept at 0° C. and H$_2$O$_2$ 35% (15 mL) added dropwise. The reaction mixture was then left under magnetic stirrer at r.t. for 1 hour until TLC showed total consumption of the starting material. Iced water (50 mL) was then added to the reaction mixture along with sodium metabisulphite (10 g). The reaction mixture was washed with ethyl acetate (3×50 mL) and the collected organic phases dried over dried over MgSO$_4$ and concentrated by rotary evaporator to give a yellow oil. The crude was purified by column chromatography (mobile phase: 100% DCM) affording pure 49 as orange solid (2.3 g, 59%). $^1$H NMR (400 MHz, METHANOL-d$_4$) δ: 7.56 (d, J=10.58 Hz, 1H), 7.39 (d, J=7.30 Hz, 1H), 3.85 (s, 3H). $^{13}$C NMR (101 MHz, METHANOL-d$_4$) δ: 164.2, 153.5, 151.1, 148.6, 117.5, 117.2, 113.0, 51.9. m/z (+EI) calc. for C$_8$H$_6$FNO$_5$ (M)+ 215.0 found 214.0 ([M]−H)$^-$ Example 77

Synthesis of 5-fluoro-4-hydroxy-2-nitrobenzoic acid (50)

NaOH 1 M aqueous solution in excess was added to a solution of 49 (2.1 g, 9.7 mmol) in dioxane (60 mL). The reaction mixture was left at r.t. under magnetic stirrer overnight until TLC showed completion of the reaction. Dioxane was evaporated under reduced pressure and water (40 mL) was added to the crude. Citric acid 1 M aqueous solution was added until acid pH is reached. The aqueous layer was extracted with ethyl acetate (2×70 mL). The combined organic layers were dried over MgSO$_4$ and concentrated under reduced pressure, giving pure 50 (1.9 g, >95%) as light yellow solid. $^1$H NMR (400 MHz, METHANOL-d$_4$) δ: 7.30 (d, J=10.83 Hz, 1H), 7.03 (d, J=7.30 Hz, 1H). $^{13}$C NMR (101 MHz, METHANOL-d$_4$) δ: 175.1, 171.8, 164.7, 153.0, 117.2, 112.6, 72.4. m/z (+EI) calc. for C$_7$H$_4$FNO$_5$ (M)+ 201.0 found 200.0 ([M]−H)$^-$ Example 78

Synthesis of (S)-(5-fluoro-4-hydroxy-2-nitrophenyl) (2-(hydroxymethyl)pyrrolidin-1-yl)methanone (51)

HATU (4.5 g, 1.2 equiv.) and DIPEA (3.6 mL, 2 equiv.) were sequentially added to a solution of 50 (2.0 g, 1 equiv.) in DMF (30 mL) and the reaction mixture was left under magnetic stirrer for 30 minutes. (S)-pyrrolidinemethanol (0.97 mL, 1 equiv.) was then added to the solution and the reaction mixture was left under magnetic stirrer overnight until no changes by TLC were observed. The reaction did not go to completion. The reaction mixture was added of ethyl acetate (40 mL) and extracted with citric acid 0.1 M aqueous solution (3×50 mL). The organic phase was then dried over MgSO$_4$ and concentrated under reduced pressure. The crude was further purified by column chromatography (mobile phase: 100% ethyl acetate) affording pure 51 (2.0 g, 71%) as yellow oil. $^1$H NMR (400 MHz, METHANOL-d$_4$) δ: 7.77 (d, J=7.55 Hz, 1H), 7.38 (d, J=10.32 Hz, 1H), 4.23-4.31 (m, 1H), 3.73-3.88 (m, 2H), 3.28 (t, J=6.80 Hz, 2H), 2.04-2.15 (m, 2H), 1.96-2.02 (m, 1H), 1.81-1.91 (m, 1H). m/z (+EI) calc. for C$_{12}$H$_{13}$FN$_2$O$_5$ (M)+ 284.0 found 285.0 ([M]+H)+

Example 79

Synthesis of (methyl (S)-4-(2-fluoro-4-(2-(hydroxymethyl)-pyrrolidine-1-carbonyl)-5-nitrophenoxy)butanoate (52)

Methyl 4-bromobutanoate (0.81 mL, 1.1 equiv.) and potassium carbonate (1.2 g, 3 equiv.) were added to a solution of 51 (1.7 g, 5.9 mmol) in DMF (20 mL). The suspension was stirred at room temperature overnight, until TLC showed completion. Iced water (60 mL) was added to the reaction mixture that was subsequently extracted with ethyl acetate (3×50 mL). The collected organic phases were dried over MgSO4 and concentrated under reduced pressure. The crude was then purified by column chromatography (mobile phase: ethyl acetate/MeOH, 99/1, v/v) affording pure 52 (1.7 g, 74%) as yellow oil. $^1$H NMR (400 MHz, CHLOROFORM-d) δ: 7.70 (d, J=7.30 Hz, 1H), 7.11 (d, J=9.82 Hz, 1H), 4.36 (dd, J=4.28, 7.05 Hz, 1H), 4.16-4.25 (m, 1H), 4.10 (t, J=6.40 Hz, 2H), 3.65-3.71 (m, 1H), 3.59 (s, 3H), 3.10 (t, J=6.29 Hz, 2H), 2.46 (t, J=7.05 Hz, 2H), 1.98-2.13 (m, 3H), 1.78-1.88 (m, 1H), 1.65-1.77 (m, 2H). $^{13}$C NMR (101 MHz, CHLOROFORM-d) δ: 173.2, 166.5, 156.8, 154.2, 147.5, 140.5, 127.2, 115.5, 110.6, 68.7, 64.7, 51.7, 49.5, 38.5, 30.0, 28.0, 24.0. m/z (+EI) calc. for C$_{17}$H$_{21}$FN$_2$O$_7$ (M)+ 384.1 found 385.0 ([M]+H)$^+$ Example 80

Synthesis of methyl (S)-4-(5-amino-2-fluoro-4-(2-(hydroxy-methyl)pyrrolidine-1-carbonyl)phenoxy)butanoate (53)

A solution of the starting nitro derivative was prepared dissolving 53 (1.6 g, 4.1 mmol) in EtOH (30 mL). A catalytic amount of Pd/C (10% w/w) was added to the solution that was hydrogenated in a Parr hydrogenator at 60 psi until TLC showed the completion of the reaction. The reaction mixture was then filtered on celite path eluting with DCM. The organic phase was evaporated under reduced pressure to give pure 53 (1.4 g, >95%) as transparent oil. $^1$H NMR (400 MHz, CHLOROFORM-d) δ: 6.94 (d, J=11.58 Hz, 1H), 6.26 (d, J=7.30 Hz, 1H), 4.65 (br. s., 2H), 4.28-4.43 (m, 1H), 4.02 (t, J=6.04 Hz, 2H), 3.73-3.82 (m, 1H), 3.68 (s, 3H), 3.55-3.66 (m, 2H), 3.44-3.53 (m, 1H), 2.53 (t, J=7.18 Hz, 2H), 2.05-2.21 (m, 3H), 1.81-1.94 (m, 1H), 1.56-1.81 (n, 2H). $^{13}$C NMR (101 MHz, CHLOROFORM-d) δ: 173.5, 171.1, 149.0, 145.6, 143.9, 143.2, 115.4, 110.7, 102.4, 67.8, 61.0, 51.7, 38.6, 30.3, 28.4, 25.0, 24.3. m/z (+EI) calc. for C$_{17}$H$_{23}$FN$_2$O$_5$ (M)+ 354.1 found 355.0 ([M]+H)$^+$ Example 81

Synthesis of methyl (S)-4-(5-(((allyloxy)carbonyl)amino)-2-fluoro-4-(2-(hydroxymethyl)pyrrolidine-1-carbonyl)phenoxy)butanoate (54)

Compound 53 (0.9 g, 2.5 mmol) was dissolved in dry DCM (50 mL) and the solution was kept at −10° C. under N$_2$ atmosphere. Dry pyridine (2.0 mL) and a solution of allyl chloroformate (0.3 mL, 0.95 equiv.) in anhydrous DCM (5 mL) were sequentially added to the obtained solution. The reaction mixture was left under magnetic stirrer at room temperature for 2 hours, until TLC showed completion of reaction. The reaction mixture was then sequentially washed with saturated CuSO$_4$ solution (70 mL), saturated aqueous NaHCO$_3$ (100 mL) and brine (100 mL). The organic phase was dried over MgSO$_4$ and concentrated under reduced pressure using a rotary evaporator. The crude of reaction was subsequently purified by column chromatography (mobile phase: Ethyl acetate/MeOH, 99/1, v/v) giving pure 54 (0.86 g, 78%) as transparent oil. $^1$H NMR (400 MHz, CHLOROFORM-d) δ: 9.02 (br. s., 1H), 7.81 (d, J=7.81 Hz, 1H), 7.06 (d, J=11.33 Hz, 1H), 5.80-6.03 (m, 1H), 5.32 (qd, J=1.51, 17.37 Hz, 1H), 5.22 (qd, J=1.30, 10.45 Hz, 1H), 4.60 (qd, J=1.48, 5.63 Hz, 2H), 4.34 (br. s., 1H), 4.24 (br. s., 1H), 4.09 (t, J=6.80 Hz, 2H), 3.81 (br. s., 1H), 3.58-3.70 (m, 4H), 3.42-3.57 (m, 2H), 2.51 (t, J=7.30 Hz, 2H), 2.09-2.16 (m, 3H), 1.83-1.92 (m, 1H), 1.66-1.77 (m, 2H). $^{13}$C NMR (101 MHz, CHLOROFORM-d) δ: 173.4, 171.2, 153.5, 148.7, 148.6, 147.9, 145.5, 136.6, 132.3, 118.2, 115.2, 106.4, 67.9, 65.8, 65.6, 60.9, 51.7, 30.4, 28.0, 25.1, 24.3. m/z (+EI) calc. for C$_{21}$H$_{27}$FN$_2$O$_7$ (M)+ 438.1 found 439.0 ([M]+H)$^+$ Example 82

Synthesis of allyl (11aS)-7-fluoro-11-hydroxy-8-(4-methoxy-4-oxobutoxy)-5-oxo-2,3,11,11a-tetrahydro-1H-benzo[e]pyrrolo[1,2-a][1,4]-diazepine-10(5H)-carboxylate (55)

Compound 54 (0.8 g, 1.8 mmol) was dissolved in DCM (25 mL) and sequentially added of BAIB (0.67 g, 1.2 equiv.) and a catalytic amount of TEMPO (0.03 g, 0.1 equiv.). The reaction mixture was left overnight under magnetic stirrer until TLC showed total disappearance of the starting material. The reaction mixture was the sequentially washed by saturated sodium metabisulphite aqueous solution (20 mL), saturated aqueous NaHCO$_3$ solution (20 mL) and brine (20 mL). The organic phase was dried over MgSO$_4$ and concentrated under reduced pressure using a rotary evaporation. The crude of reaction was further purified by column chromatography (mobile phase: from ethyl acetate 100% to ethyl acetate/MeOH, 99/1, v/v) affording pure 55 (0.65 g, 81%) as a transparent oil. $^1$H NMR (400 MHz, CHLOROFORM-d) δ: 7.44 (d, J=11.08 Hz, 1H), 6.79 (d, J=6.29 Hz, 1H), 5.69-5.91 (m, 1H), 5.52-5.69 (m, 1H), 5.14 (br. s., 2H), 4.50-4.70 (m, 2H), 4.32-4.49 (m, 1H), 3.99-4.09 (m, 2H), 3.61-3.70 (m, 4H), 3.35-3.57 (m, 2H), 2.52 (m, 2H), 2.04-2.19 (m, 4H), 1.91-2.01 (m, 2H). $^{13}$C NMR (101 MHz, CHLOROFORM-d) δ: 173.4, 165.9, 155.6, 152.6, 150.1, 148.8, 131.7, 126.4, 118.1, 116.1, 115.8, 85.8, 68.2, 66.8, 60.4, 57.7, 46.4, 30.2, 28.7, 24.2, 23.0. m/z (+EI) calc. for C$_{21}$H$_{25}$FN$_2$O$_7$ (M)+ 436.1 found 437.0 ([M]+H)$^+$

Example 83

Synthesis of allyl (11aS)-7-fluoro-8-(4-methoxy-4-oxobutoxy)-5-oxo-11-((tetrahydro-2H-pyran-2-yl)oxy)-2,3,11,11a-tetrahydro-1H-benzo[e]pyrrolo[1,2-a][1,4]diazepine-10 (5H)-carboxylate (56)

DHP (1.1 mL, 10 equiv.) along with a catalytic amount of PTSA (10 mg) was added to a solution of 55 (0.55 g, 1.2 mmol) in ethyl acetate (20 mL). The reaction mixture was left under magnetic stirrer for 4 hours until TLC showed completion of reaction and then washed with saturated aqueous $NaHCO_3$ (2×20 mL) and brine (20 mL). The organic phase was dried over $MgSO_4$, and evaporated using a rotary evaporator under reduced pressure. The crude of reaction was purified by column chromatography (mobile phase: ethyl acetate 100%) affording pure 56 (0.57 g, 91%) as a transparent oil. 1H NMR (400 MHz, CHLOROFORM-d, mix of isomers) δ: 7.32-7.44 (m, 2H),6.91 (d, J=6.80 Hz, 1H), 6.63 (d, J=6.80 Hz, 1H), 5.58-5.87 (m, 4H), 4.92-5.09 (m, 5H), 4.80 (br. s., 1H), 4.34-4.64 (m, 2H), 3.90-3.96 (m, 1H), 3.83-3.87 (m, 2H), 3.62 (s, 6H), 3.54-3.60 (m, 3H), 3.37-3.50 (m, 6H), 2.49 (t, J=7.05 Hz, 4H), 2.03-2.13 (m, 7H), 1.91-1.96 (m, 4H), 1.64-1.74 (m, 5H), 1.38-1.55 (m, 13H). $^{13}$C NMR (101 MHz, CHLOROFORM-d, mix of isomers) δ: 173.3, 166.0, 155.4, 152.9, 150.5, 148.9, 148.6, 131.8, 127.2, 117.4, 117.2, 116.6, 116.0, 115.5, 100.3, 96.0, 94.3, 91.6, 88.2, 68.2, 67.9, 66.6, 66.4, 64.2, 63.8, 63.6, 59.9, 59.8, 51.6, 32.0, 31.1, 30.8, 30.2, 30.0, 29.0, 28.7, 25.1, 24.2, 24.1, 23.2, 20.4, 19.9. m/z (+EI) calc. for $C_{26}H_{33}FN_2O_8$ (M)+ 520.2 found 521.1 ([M]+H)$^+$

Example 84

Synthesis of 4-(((11aS)-10-((allyloxy)carbonyl)-7-fluoro-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)butanoic acid (57)

NaOH 1 M aqueous solution in excess was added to a solution of 56 (0.6 g, 1.1 mmol) in dioxane (20 mL). The reaction mixture was left at r.t. under magnetic stirrer overnight until TLC showed completion of the reaction. Dioxane was evaporated under reduced pressure and water (20 mL) was added to the crude. Citric acid 1 M aqueous solution was added until acid pH is reached. The aqueous layer was extracted with ethyl acetate (2×35 mL). The combined organic layers were dried over $MgSO_4$ and concentrated under reduced pressure, giving pure 57 (0.56 g, >95%) as yellowish solid. $^1$H NMR (400 MHz, CHLOROFORM-d, mix of isomers) δ: 7.40-7.51 (m, 2H), 6.98 (d, J=7.30 Hz, 1H), 6.62-6.70 (m, 1H), 5.89 (d, J=9.06 Hz, 1H), 5.75 (d, J=9.32 Hz, 2H), 4.99-5.16 (m, 4H), 4.88-4.99 (m, 1H), 4.52-4.71 (m, 2H), 4.36-4.52 (m, 1H), 4.00-4.10 (m, 3H), 3.86-3.97 (m, 2H), 3.59-3.73 (m, 4H), 3.42-3.59 (m, 6H), 2.55-2.64 (m, 4H), 2.09-2.20 (m, 7H), 1.96-2.04 (m, 5H), 1.71-1.83 (m, 5H), 1.42-1.62 (m, 11H). 13C NMR (100 MHz, CHLOROFORM-d) δ: 177.4, 177.3, 166.4, 166.2, 155.5, 153.1, 150.6, 132.0, 131.8, 127.3, 117.3, 116.8, 116.2, 115.9, 100.5, 96.1, 94.5, 91.6, 88.3, 68.2, 67.9, 66.5, 64.4, 63.8, 63.6, 60.4, 46.5, 31.8, 31.1, 30.9, 30.2, 30.1, 29.0, 28.8, 25.2, 25.1, 24.1, 24.0, 23.2, 23.1, 20.2, 19.9. m/z (+EI) calc. for $C_{25}H_{31}FN_2O_8$ (M)+ 506.2 found 507.0 ([M]+H)$^+$

Examples 85-86

Synthesis of Final Product PBD Fluorine Derivative PP-68 and PP-B82

Compounds 11 or 20 (from 30 to 50 mg, 1 equiv.) were boc-deprotected dissolving the desiderate derivative in MeOH (3 ml) and HCl 4M in dioxane (3 mL). The solution was left under magnetic stirrer for 2 hours until TLC showed total cleavage of protecting group. The reaction mixture was subsequently evaporated using a rotary evaporator, obtaining a solid. PBD fluorine unit 57 (1.2 equiv.) was dissolved in DMF (4 mL) and added of EDCI (2 equiv.) and DMAP (3 equiv.). The reaction mixture was left under magnetic stirrer in $N_2$ atmosphere for 20 minutes. At that point the desiderate deprotected compound was added to the reaction mixture and left under magnetic stirrer overnight for 15 hours until TLC and LC-MS analysis showed formation of the protected PBD-C8 derivative. The reaction was quenched by addition of water (10 mL) that was then extracted with ethyl acetate (3×10 mL). The organic phase was then sequentially washed with brine (10 mL), $NaHCO_3$ saturated aqueous solution (10 mL) and citric acid aqueous solution 0.1 M (10 mL). The collected organic phase was dried over $MgSO_4$ and subsequently evaporated using a rotary evaporator. The crude of each reaction was purified by column chromatography (mobile phase: from DCM/acetone, 90/10, v/v to DCM/acetone, 60/40/, v/v depending on the substrate). The protected PBD-conjugates (from 25 to 60 mg, 1 equiv) was dissolved in DCM (4 mL) and added of Tetrakis Pd (0.05 equiv.), triphenylphospine (0.25 equiv.) and pyrrolidine (1.2 equiv). The reaction mixture was kept under magnetic stirrer for 20 minutes when TLC showed completion of reaction. At was purified by column chromatography (mobile phase: from DCM/acetone, 90/10, v/v to DCM/acetone, 40/60/, v/v, depending on the substrate) affording pure final compounds.

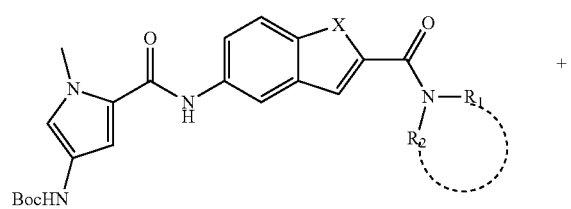

11 or 20

-continued
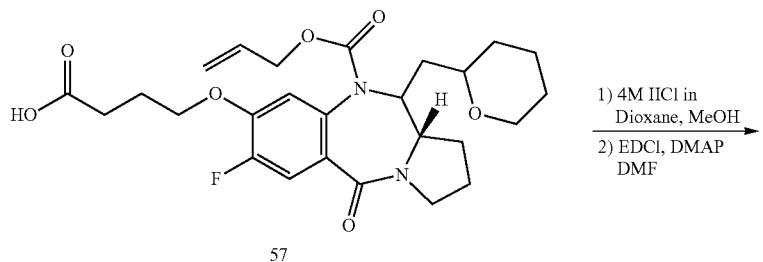
57
1) 4M HCl in Dioxane, MeOH
2) EDCl, DMAP DMF
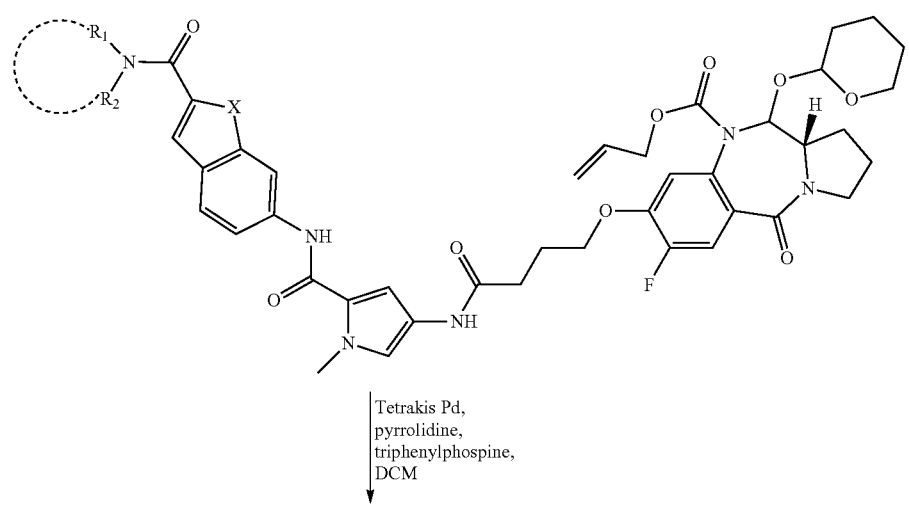
Tetrakis Pd, pyrrolidine, triphenylphospine, DCM
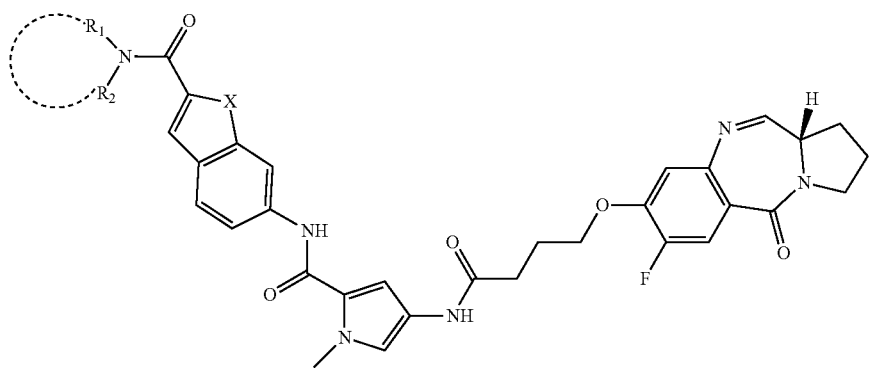
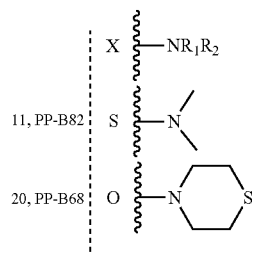

Example 85

(S)—N-(2-(dimethylcarbamoyl)benzo[b]thiophen-5-yl)-4-(4-((7-fluoro-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide (PP-B82)

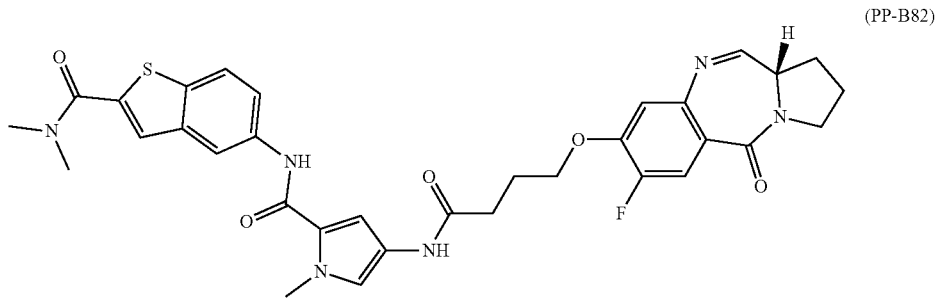 [SMILES: CN(C)C(=O)c1cc2cc(NC(=O)c3cc(NC(=O)CCCOc4cc5c(cc4F)C(=O)N4CCC[C@H]4C=N5)cn3C)ccc2s1]

(PP-B82)

Obtained 20 mg (27%) as a yellow solid. $^1$H NMR (400 MHz, CHLOROFORM-d) δ 8.24 (d, J=2.01 Hz, 1H), 8.00 (s, 1H), 7.96 (s, 1H), 7.76 (s, 1H), 7.73 (d, J=4.53 Hz, 1H), 7.70 (d, J=4.53 Hz, 1H), 7.45 (s, 1H), 7.39 (dd, J=2.14, 8.69 Hz, 1H), 7.15 (d, J=1.76 Hz, 1H), 6.87 (d, J=7.81 Hz, 1H), 6.62 (d, J=1.76 Hz, 1H), 4.11 (t, J=5.92 Hz, 2H), 3.90 (s, 3H), 3.75-3.82 (m, 1H), 3.70-3.75 (m, 1H), 3.49-3.58 (m, 1H), 3.19 (br. s., 6H), 2.49-2.58 (m, 2H), 2.21-2.33 (m, 2H), 2.00-2.11 (m, 4H). m/z (+EI) calc. for $C_{33}H_{33}FN_6O_5S$ (M)$^+$ 644.2 found 645.2 ([M]+H)$^+$

Example 86

(S)-4-(4-((7-fluoro-5-oxo-2,3,5,11a-tetrahydro-1H-benzo[e]pyrrolo[1,2-a][1,4]diazepin-8-yl)oxy)butanamido)-1-methyl-N-(2-(thiomorpholine-4-carbonyl)benzofuran-5-yl)-1H-pyrrole-2-carboxamide (PP-B68)

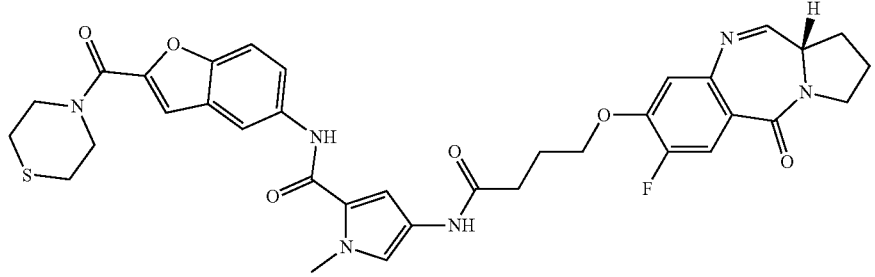

(PP-B68)

Obtained 13 mg (30%) as a yellow solid. $^1$H NMR (400 MHz, CHLOROFORM-d) δ: 8.03 (s, 1H), 7.86 (s, 1H), 7.74-7.79 (m, 1H), 7.70-7.74 (m, 1H), 7.39-7.52 (m, 4H), 7.13 (s, 1H), 6.90 (d, J=7.81 Hz, 1H), 6.66 (s, 1H), 4.12-4.23 (m, 2H), 4.07 (br. s., 4H), 3.93 (s, 3H), 3.77-3.83 (m, 1H), 3.71-3.75 (m, 1H), 3.51-3.61 (m, 1H), 2.69-2.82 (m, 4H), 2.54-2.62 (m, 2H), 2.21-2.40 (m, 4H), 1.99-2.09 (m, 2H). $^{19}$F NMR (376 MHz, CHLOROFORM-d) δ: −135.7. m/z (+EI) calc. for $C_{35}H_{35}FN_6O_6S$ (M)$^+$ 686.2 found 687.3 ([M]+H)$^+$

Example 87

Synthesis of C8 Benzofused-Glucose PBD Derivative

NaOH 1 M aqueous solution in excess was added to a solution of 58 (0.1 g, 1 equiv) in dioxane (5 mL). The reaction mixture was left at r.t. under magnetic stirrer overnight until TLC showed completion of the reaction. Dioxane was evaporated under reduced pressure and water (20 mL) was added to the crude. Citric acid 1M aqueous solution was added until acid pH is reached. The aqueous layer was extracted with ethyl acetate (2×10 mL). The combined organic layers were dried over MgSO$_4$ and concentrated under reduced pressure, giving the corresponding carboxylic acid that was immediately dissolved in DMF (5 mL). The solution was sequentially added of EDCI (0.05 g, 2 equiv.), HOBt (0.04 g, 2 equiv.) and Et$_3$N (0.036 mL, 2 equiv.). The reaction was left under magnetic stirrer in N$_2$ atmosphere for 20 minutes. At that point β-D-Glucopyranose, 2-amino-2-deoxy-, 1,3,4,6-tetraacetate (0.06 g, 1.2 equiv.) was added to the solution that was left under magnetic stirrer overnight. TLC and LC-MS analysis showed formation of the protected PBD-C8 derivative. The reaction was quenched by addition of water (10 mL) that was then extracted with ethyl acetate (3×10 mL). The organic phase was then sequentially washed with brine (10 mL), NaHCO$_3$ saturated aqueous solution (10 mL) and citric acid aqueous solution 0.1 M (10 mL). The collected organic phase was dried over MgSO₄ and subsequently evaporated using a rotary evaporator. The crude of reaction was purified by column chromatography (mobile phase: DCM/acetone, 50/50, v/v) giving the protected PBD-glucose C8 derivative. The protected PBD-conjugates (0.04 g, 1 equiv.) was dissolved in DCM (4 mL) and added of Tetrakis Pd (0.05 equiv.), triphenylphospine (0.25 equiv.) and pyrrolidine (1.2 equiv). The reaction mixture was kept under magnetic stirrer for 20 minutes when TLC showed completion of reaction. At was purified by column chromatography (mobile phase: from DCM/acetone, 70/30, v/v to DCM/acetone, 30/70, v/v) affording pure final compound PP-B 10 2 (0.033 g, 28%) as a white solid. ¹H NMR (400 MHz, CHLOROFORM-d) δ 8.43 (s, 1H), 8.23 (s, 1H), 7.84 (s, 1H), 7.65 (d, J=4.28 Hz, 1H), 7.49 (s, 1H), 7.44 (d, J=9.82 Hz, 1H), 7.37 (dd, J=2.14, 8.94 Hz, 1H), 7.30 (s, 1H), 7.08 (s, 1H), 7.06 (d, J=9.06 Hz, 1H), 6.80 (s, 1H), 6.64 (s, 1H), 5.97 (d, J=8.81 Hz, 1H), 5.44-5.55 (m, 1H), 5.18 (t, J=9.69 Hz, 1H), 4.52-4.62 (m, 1H), 4.30 (dd, J=4.41, 12.46 Hz, 1H), 4.14 (d, J=12.34 Hz, 1H), 4.07 (t, J=5.92 Hz, 2H), 3.76-3.91 (m, 8H), 3.67-3.73 (m, 1H), 3.50-3.59 (m, 1H), 2.50 (t, J=6.92 Hz, 2H), 2.25-2.35 (m, 2H), 2.17-2.23 (m, 4H), 1.98-2.11 (m, 12H). ¹³C NMR (100 MHz, CHLOROFORM-d) δ: 171.2, 170.8, 170.1, 169.6, 169.4, 164.6, 162.8, 160.1, 158.9, 151.4, 150.7, 148.3, 147.7, 140.7, 134.3, 127.5, 121.5, 121.3, 121.4, 119.9, 114.2, 111.7, 111.3, 110.8, 104.5, 92.4, 72.8, 68.1, 68.1, 61.1, 56.0, 53.8, 52.4, 46.8, 36.7, 32.9, 30.9, 29.5, 29.3, 24.9, 24.2, 20.9, 20.7, 20.6, 20.5. m/z (+EI) calc. for $C_{46}H_{50}N_6O_{16}$ (M)⁺ 942.3 found 943.2 ([M]+H)⁺.

Compound PP-B 10 2 (0.02 g, 1 equiv.) was dissolved in MeOH (4 mL) and added of $K_2CO_3$ (3 equiv.). The reaction mixture was left under magnetic stirrer at r.t. for 30 minutes when TLC confirmed the completion of reaction. The solvent was evaporated using a rotary evaporator and the crude of reaction dissolved in Ethyl Acetate (10 mL). The organic phase was washed with citric acid aqueous solution 0.1 M (10 mL) and brine (10 mL) and then evaporated under reduced pressure to give the final product PP-B 10 2 de protected (0.014 g, 87%) as a white solid. m/z (+EI) calc. for $C_{38}H_{42}N_6O_{12}$ (M)⁺ 774.2 found 775.1 ([M]+H)⁺.

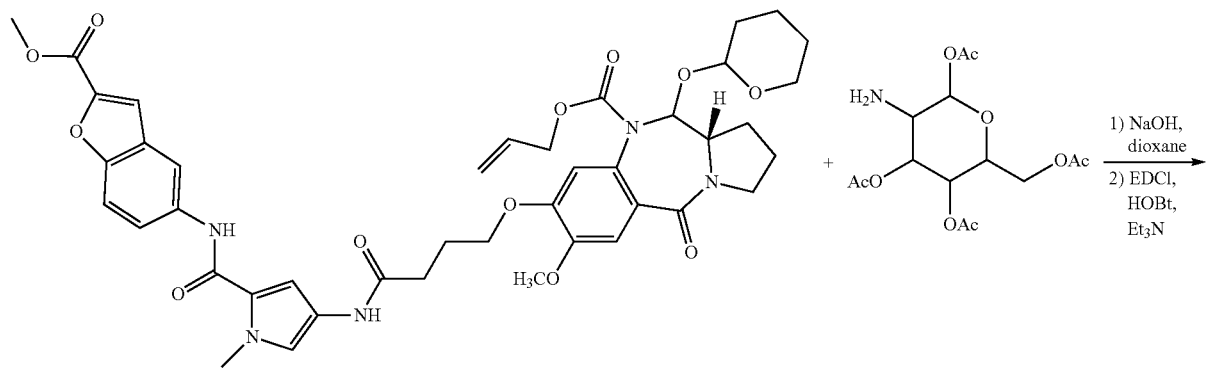

58

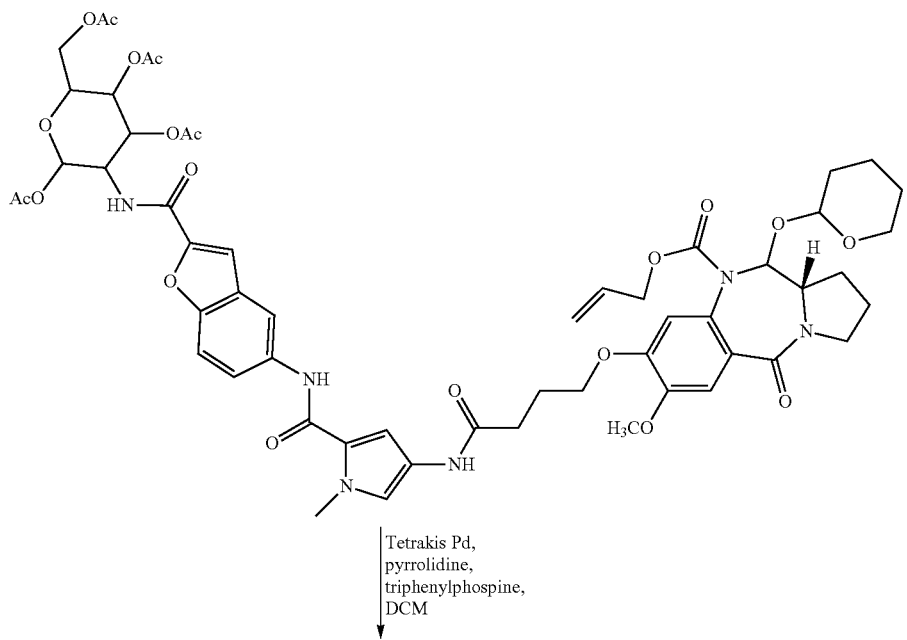

-continued
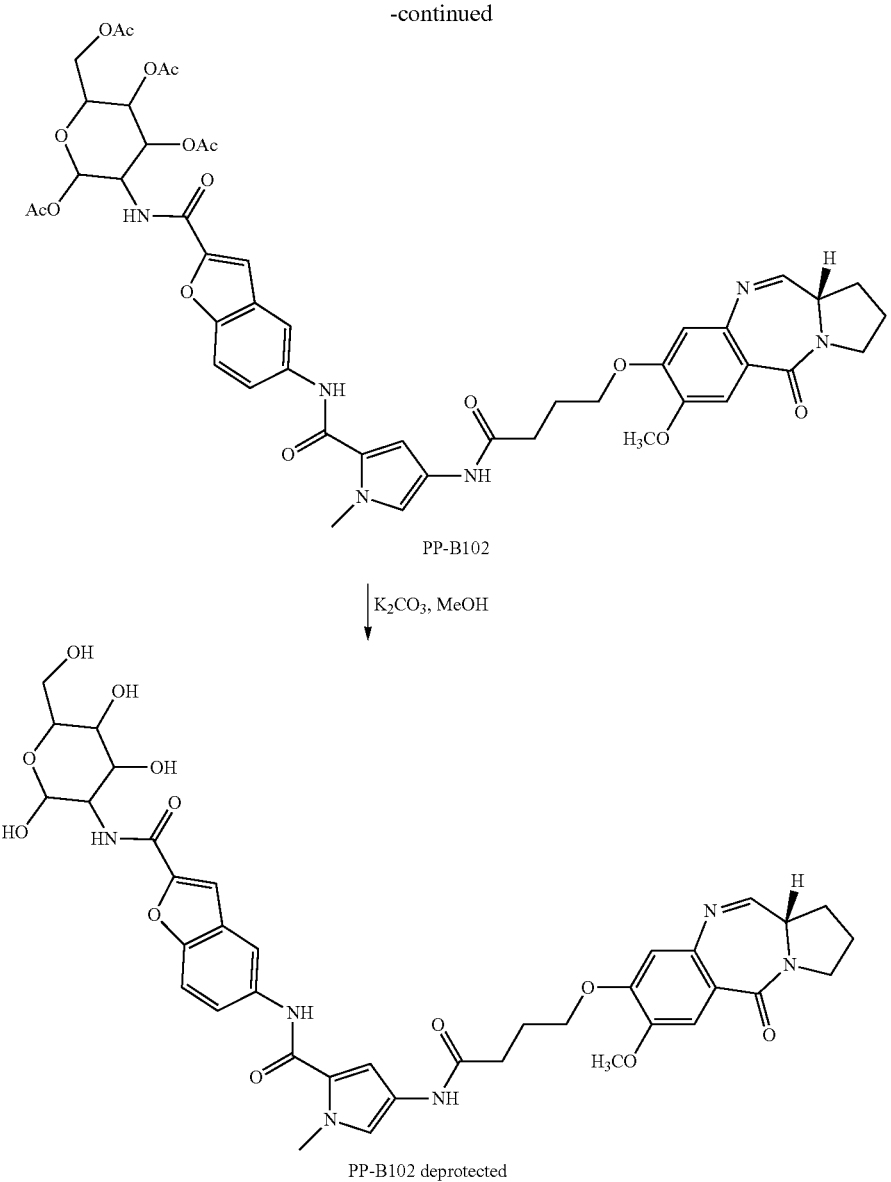
PP-B102
↓ K₂CO₃, MeOH
PP-B102 deprotected
Synthesis of N10 PBD Prodrugs
Reaction Scheme—Aminopeptidase Prodrugs
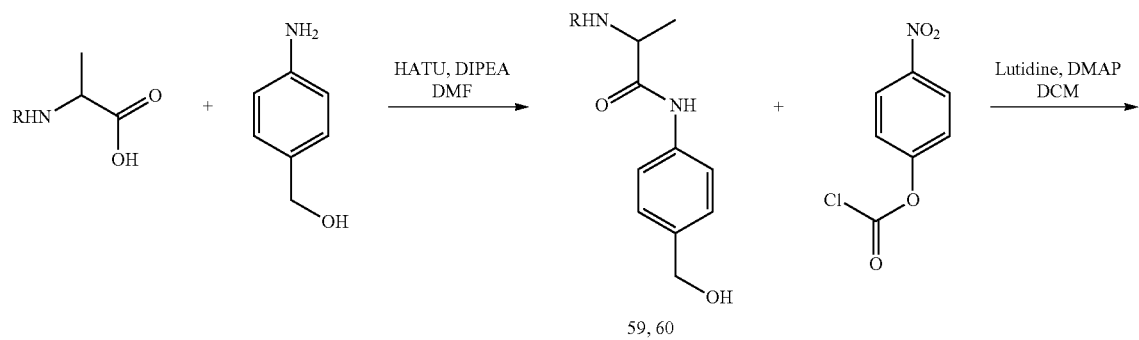
59, 60

-continued
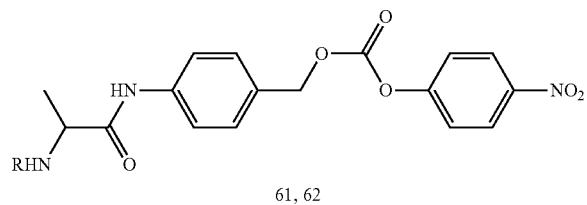
61, 62
61, 62 + 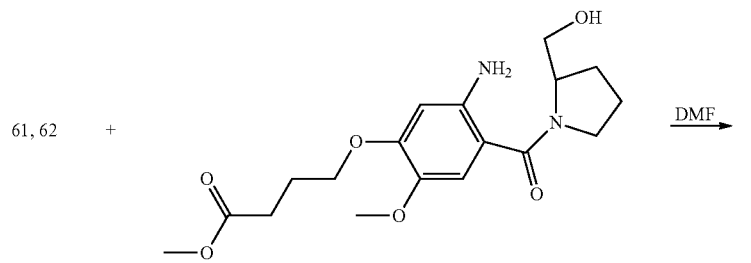 →
5
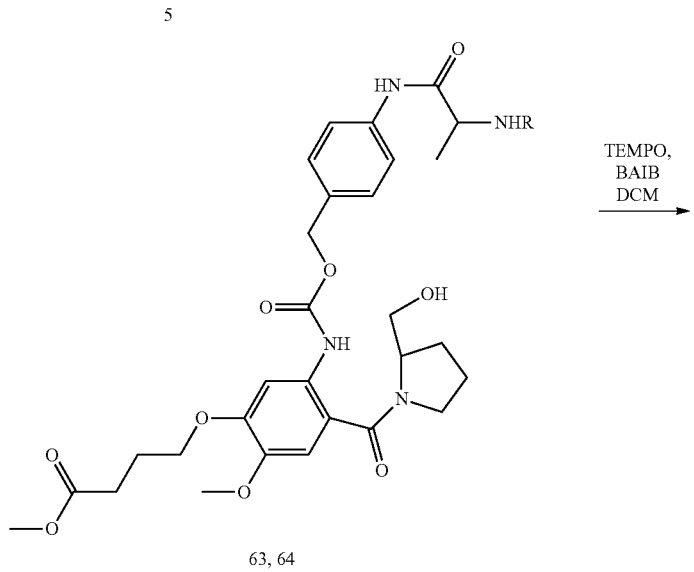
63, 64
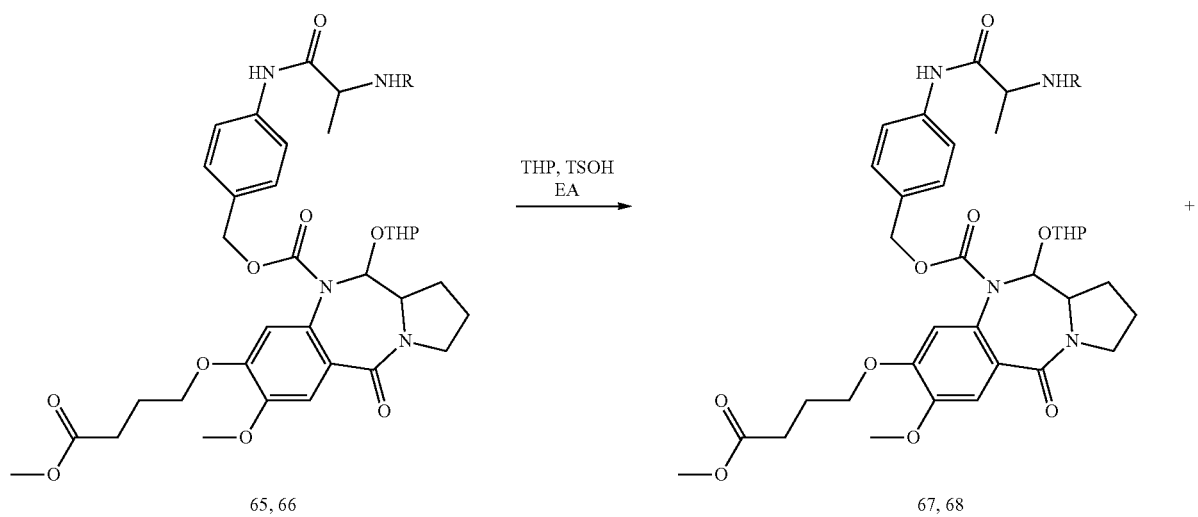
65, 66 → 67, 68 +

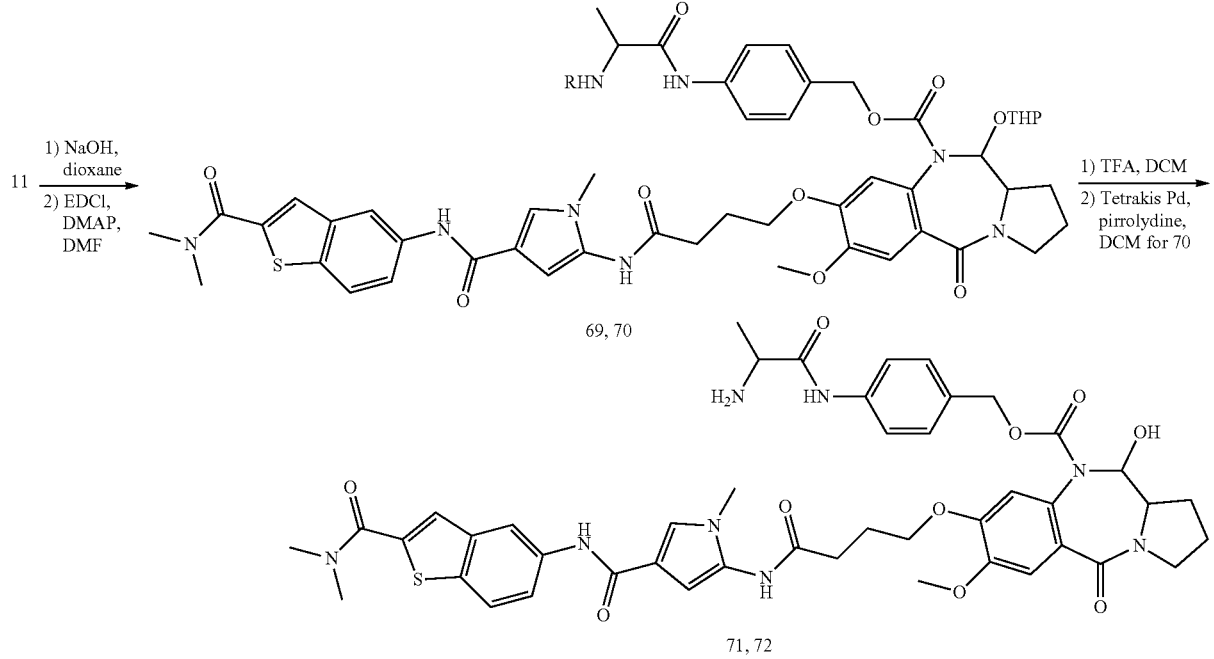

59, 61, 63, 65, 67, 69 R = Boc
60, 62, 64, 66, 68, 70 R = Alloc

Examples 88 & 89

Synthesis of Alanine-Benzyl Alcohol Derivative (59, 60)

Alloc- or Boc-protected aniline (3 g, 1 equiv.) was solubilized in DMF (10 mL) and subsequently added of HATU (1.2 equiv.) and DIPEA (3 equiv.). The solution was left under magnetic stirrer for 15 minutes and then added of (4-aminophenyl)methanol (1.2 equiv.). The reaction was left under magnetic stirrer overnight with LC-MS confirming formation of the product. The reaction was quenched by addition of water (10 mL) that was then extracted with ethyl acetate (3×10 mL). The organic phase was then sequentially washed with brine (10 mL), NaHCO$_3$ saturated aqueous solution (10 mL) and citric acid aqueous solution 0.1 M (10 mL). The collected organic phase was dried over MgSO$_4$ and subsequently evaporated using a rotary evaporator. The crude of reaction was purified by column chromatography (mobile phase: DCM/EA, 70/30, v/v) giving pure product 59 and 60.

Example 88 tert-butyl (1-((4-(hydroxymethyl)phenyl)amino)-1-oxopropan-2-yl)carbamate (59)

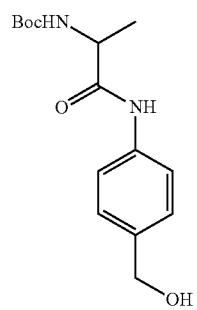
(59)

Obtained 3.5 g (79%) as white solid. $^1$H NMR (400 MHz, CHLOROFORM-d) δ 8.74 (br. s., 1H), 7.38-7.53 (m, J=8.31 Hz, 2H), 7.16-7.26 (m, J=7.81 Hz, 2H), 5.23 (br. s., 1H), 4.61 (s, 2H), 4.35 (br. s., 1H), 1.42-1.47 (m, 12H). $^{13}$C NMR (100 MHz, CHLOROFORM-d) δ: 137.3, 136.7, 127.7, 119.9, 64.9, 55.8, 38.6, 28.3, 18.6, 17.6, 17.2, 14.2. m/z (+EI) calc. for C$_{15}$H$_{22}$N$_2$O$_4$ (M)$^+$ 294.1 found 293.1 ([M]−H)$^−$.

Example 89 allyl (1-((4-(hydroxymethyl)phenyl)amino)-1-oxopropan-2-yl)carbamate (60)

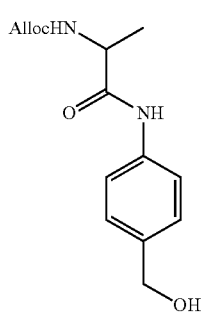
(60)

Obtained 1.3 g (27%) as white solid. $^1$H NMR (400 MHz, CHLOROFORM-d) δ $^1$H NMR (400 MHz, CHLOROFORM-d) δ: 8.48 (br. s., 1H), 7.49 (d, J=8.56 Hz, 2H), 7.28 (d, J=7.81 Hz, 2H), 5.91 (tdd, J=5.54, 11.02, 16.93 Hz, 1H), 5.51 (br. s., 1H), 5.32 (d, J=18.38 Hz, 1H), 5.23 (d, J=10.32 Hz, 1H), 4.63 (s, 2H), 4.59 (d, J=7.05 Hz, 2H), 4.38 (t, J=6.17 Hz, 1H), 1.47 (d, J=7.05 Hz, 3H); m/z (+EI) calc. for C$_{14}$H$_{18}$N$_2$O$_4$(M)$^+$ 278.1 found 279.1 ([M]+H)+.

Example 90 & 91

Synthesis of Para-Nitro Phenil Anhydride Derivative (61, 62)

Compounds 59 or 60 (3 g, 1 equiv.) was solubilized in DCM (40 mL) and subsequently added of lutidine (1.3 equiv.), 4-nitrophenylchloroformate (1.3 equiv.) and a catalytic amount of DMAP. The reaction was left under magnetic stirrer at r.t. overnight until TLC showed completion of the reaction. The solvent was evaporated and the crude of reaction was purified by column chromatography (mobile phase: DCM/EA, 90/10, v/v) giving pure product 61 and 62.

Example 90 tert-butyl (1-((4-((((4-nitrophenoxy)carbonyl)oxy) methyl)-phenyl)amino)-1-oxopropan-2-yl)carbamate (61)

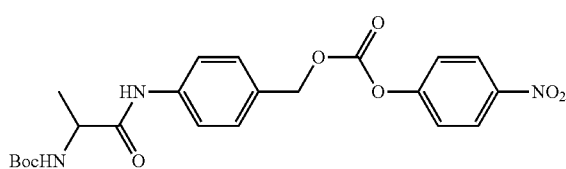

(61)

Obtained 2.1 g (30%) as a yellow oil. $^1$H NMR (400 MHz, CHLOROFORM-d) δ 8.80 (br. s., 1H), 8.27 (d, J=9.06 Hz, 2H), 7.54 (d, J=8.56 Hz, 2H), 7.32-7.39 (m, 4H), 5.23 (s, 2H), 5.17 (d, J=7.55 Hz, 1H), 4.37 (br. s., 1H), 1.42-1.48 (m, 12H). $^{13}$C NMR (101 MHz, CHLOROFORM-d) δ 171.2, 155.5, 152.4, 145.4, 138.7, 129.7, 129.3, 125.3, 121.8, 119.9, 80.9, 70.7, 50.8, 46.0, 28.3, 17.4. m/z (+EI) calc. $C_{22}H_{25}N_3O_8$ for (M)$^+$ 459.1 found 460.0 ([M]+H)$^+$.

Example 91 allyl (1-((4-((((4-nitrophenoxy)carbonyl)oxy) methyl)-phenyl)amino)-1-oxopropan-2-yl)carbamate (62)

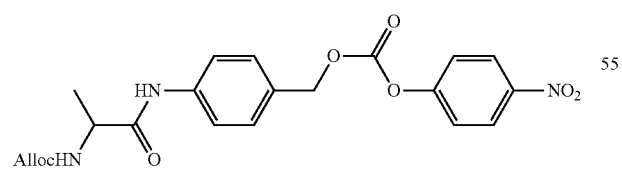

(62)

Obtained 2.9 g (62%) as a yellow oil. $^1$H NMR (400 MHz, CHLOROFORM-d) δ 8.70 (br. s., 1H), 8.26 (d, J=9.32 Hz, 2H), 7.57 (d, J=8.31 Hz, 2H), 7.32-7.40 (m, 4H), 5.84-5.98 (m, 1H), 5.59 (d, J=7.81 Hz, 1H), 5.32 (d, J=17.12 Hz, 1H), 5.17-5.26 (m, 1H), 4.61 (br. s., 2H), 4.38-4.52 (m, 1H), 1.48 (d, J=7.05 Hz, 3H). $^{13}$C NMR (101 MHz, CHLOROFORM-d) δ 156.5, 155.5, 152.4, 145.4, 138.5, 132.2, 130.0, 129.8, 129.7, 129.4, 125.3, 121.8, 120.0, 118.2, 70.6, 66.2, 51.2, 45.9, 18.1, 14.2; m/z (+EI) calc. $C_{21}H_{21}N_3O_8$ for (M)$^+$ 443.1 found 443.9 ([M]+H)$^+$.

Examples 92 & 93

Addition of Cleavable Substrate to N10 position (63, 64)

Compound 5 (1 g, 1 equiv.) was dissolved in DMF (1.5 mL) and added of either compound 61 or 62. The reaction mixture was left for 2 days at 50° C. and then quenched by addition of water (10 mL) that was then extracted with ethyl acetate (3×10 mL). The organic phase was then sequentially washed with brine (10 mL), NaHCO$_3$ saturated aqueous solution (10 mL) and citric acid aqueous solution 0.1 M (10 mL). The collected organic phase was dried over MgSO$_4$ and subsequently evaporated using a rotary evaporator. The crude of reaction was purified by column chromatography (mobile phase: DCM/EA, 30/70, v/v) giving product 63 and 64 as mixed fraction. NMR analysis was not performed due to impurities presented by the compounds. LC-MS showed formation of the product.

Example 92 methyl 4-(5-((((4-(2-((tert-butoxycarbonyl)amino) propanamido)benzyl)oxy)carbonyl)amino)-4-(2-(hydroxymethyl)pyrrolidine-1-carbonyl)-2-methoxyphenoxy)butanoate (63)

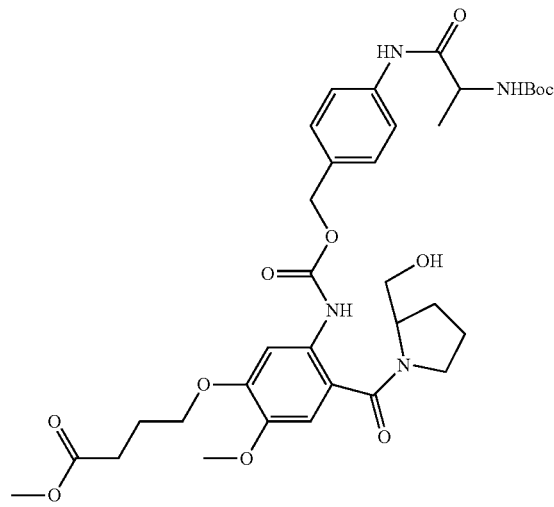

(63)

m/z (+EI) calc. $C_{34}H_{46}N_4O_{11}$ for (M)$^+$ 686.3 found 687.0 ([M]+H)$^+$.

Example 93 methyl 4-(5-((((4-(2-(((allyloxy)carbonyl)amino)propanamido)benzyl)oxy)carbonyl)amino)-4-(2-(hydroxymethyl)pyrrolidine-1-carbonyl)-2-methoxyphenoxy)butanoate (64)

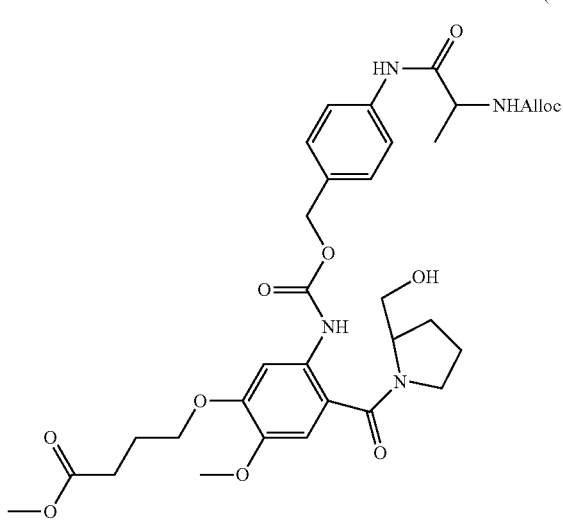

m/z (+EI) calc. $C_{33}H_{42}N_4O_{11}$ for (M)$^+$ 670.2 found 671.1 ([M]+H)$^+$.

Example 94

4-(2-((tert-butoxycarbonyl)amino)propanamido)benzyl 11-hydroxy-7-methoxy-8-(4-methoxy-4-oxobutoxy)-5-oxo-2,3,11,11a-tetrahydro-1H-benzo[e]pyrrolo[1,2-a][1,4]diazepine-10(5H)-carboxylate (65)

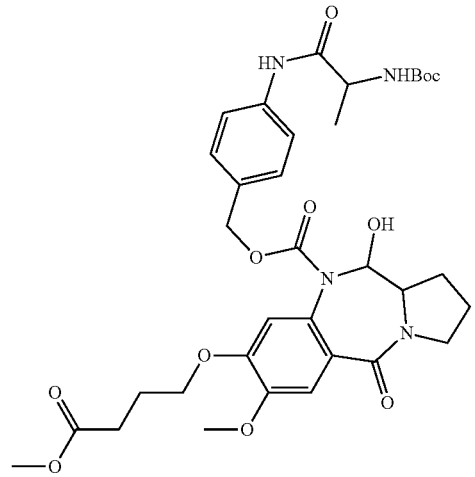

Obtained 140 mg (35%) as a yellow oil. $^1$H NMR (400 MHz, CHLOROFORM-d) δ 8.69 (br. s., 1H), 7.45 (d, J=8.06 Hz, 2H), 7.07-7.24 (m, 3H), 6.48 (s, 1H), 5.62 (d, J=13.09 Hz, 1H), 5.25-5.42 (m, 2H), 5.02-5.25 (m, 1H), 4.77 (d, J=13.09 Hz, 1H), 4.35 (br. s., 1H), 4.08 (br. s., 2H), 3.73-3.92 (m, 4H), 3.59-3.72 (m, 5H), 3.52-3.59 (m, 1H), 3.47 (td, J=5.00, 9.88 Hz, 1H), 2.48 (t, J=7.30 Hz, 2H), 2.08-2.15 (m, 2H), 1.91-2.01 (m, 2H), 1.81 (s, 2H), 1.32-1.49 (m, 12H); $^{13}$C NMR (101 MHz, CHLOROFORM-d) δ 173.8, 167.0, 160.4, 157.7, 156.2, 150.0, 148.5, 131.4, 129.1, 128.3, 125.4, 119.7, 113.8, 110.6, 86.1, 67.8, 67.4, 59.9, 56.1, 51.8, 46.4, 30.5, 38.7, 28.3, 24.2, 23.0, 17.5, 14.2. m/z (+EI) calc. $C_{34}H_{44}N_4O_{11}$ for (M)$^+$ 684.3 found 685.2 ([M]+H)$^+$.

Example 95

4-(2-(((allyloxy)carbonyl)amino)propanamido)benzyl 11-hydroxy-7-methoxy-8-(4-methoxy-4-oxobutoxy)-5-oxo-2,3,11,11a-tetrahydro-1H-benzo[e]pyrrolo[1,2-a][1,4]diazepine-10(5H)-carboxylate (66)

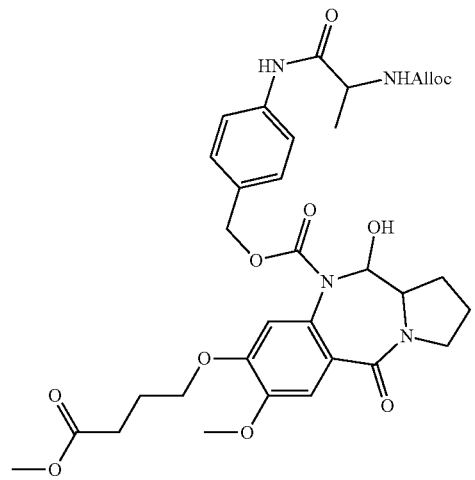

Examples 94 & 95

Oxidative Cyclization of the PBD Core (65, 66)

Impure compound 63 and 64 (0.4 g, 1 equiv.) were dissolved in DCM (5 mL) and sequentially added of TEMPO (1 equiv.) and BAIB (1.5 equiv.). The reaction was left under magnetic stirrer at r.t. overnight and in case no formation of the product was observed by LC-MS another equivalent of TEMPO and BAIB were added. The reaction mixture was the sequentially washed by saturated sodium metabisulphite aqueous solution (10 mL), saturated aqueous NaHCO$_3$ solution (10 mL) and brine (10 mL). The organic phase was dried over MgSO$_4$ and concentrated under reduced pressure using a rotary evaporation. The crude of reaction was further purified by column chromatography (mobile phase: DCM/EA, 20/80, v/v) giving pure product 65 and 66.

Obtained 120 mg (43%) as a yellow oil. $^1$H NMR (400 MHz, CHLOROFORM-d) $^1$H NMR (400 MHz, CHLOROFORM-d) δ 8.55 (br. s., 1H), 7.46 (d, J=8.31 Hz, 2H), 7.13-7.22 (m, 3H), 6.45 (s, 1H), 5.82-6.00 (m, 1H), 5.61 (d, J=8.31 Hz, 1H), 5.27-5.41 (m, 1H), 5.23 (d, J=10.32 Hz, 1H), 4.60 (d, J=5.29 Hz, 2H), 4.34-4.45 (m, 1H), 3.90-4.07 (m, 2H), 3.78-3.89 (m, 4H), 3.63-3.71 (m, 5H), 3.52-3.59 (m, 1H), 3.41-3.50 (m, 1H), 2.38-2.51 (m, 2H), 2.08-2.20 (m, 2H), 1.95-2.01 (m, 2H), 1.81 (br. s., 4H), 1.46 (d, J=6.80 Hz, 3H). $^{13}$C NMR (101 MHz, CHLOROFORM-d) δ 173.9, 167.0, 149.8, 148.5, 132.4, 129.1, 119.9, 118.1, 113.7, 110.5, 86.0, 67.8, 67.3, 66.1, 59.8, 56.0, 51.8, 51.1, 46.4, 30.4, 28.6, 24.2, 23.0, 17.9, 14.2; m/z (+EI) calc. $C_{33}H_{40}N_4O_{11}$ for (M)$^+$ 668.2 found 669.1 ([M]+H)$^+$.
Reaction Scheme—Nitroreductase Prodrugs
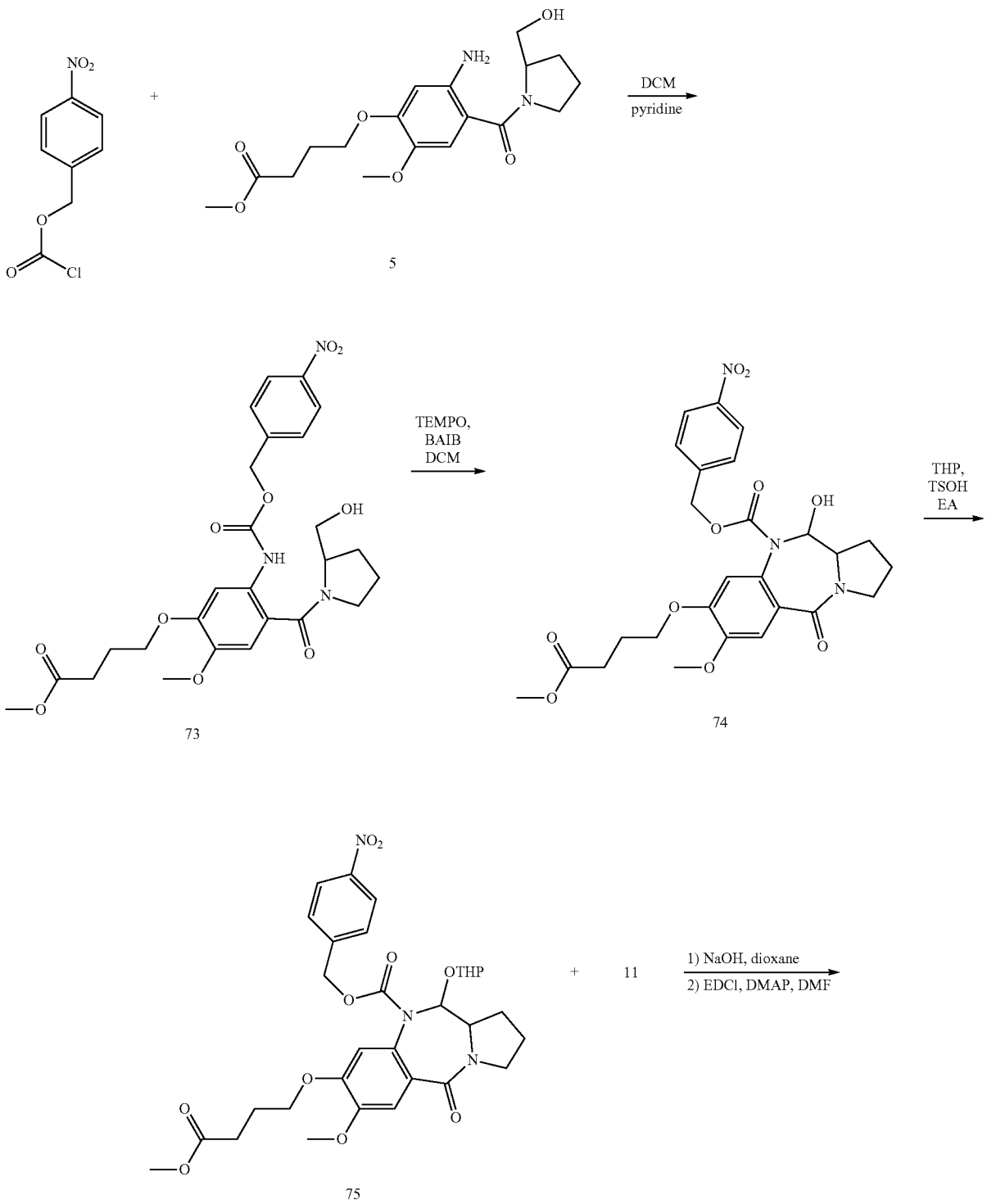

-continued

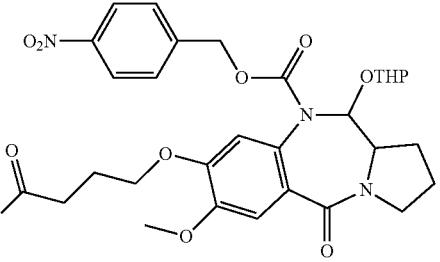

76

Example 96

Methyl 4-(4-(2-(hydroxymethyl)pyrrolidine-1-carbonyl)-2-methoxy-5-(((((4-nitrobenzyl)oxy)carbonyl)amino)phenoxy)butanoate (73)

Compound 5 (2.30 g, 1 equiv.) was dissolved in DCM (20 mL) and pyridine (1 equiv.). The reaction mixture was kept under magnetic stirrer at 0° C. during the addition of 4-nitrobenzylchloroformiate (1 equiv.). The reaction mixture was then left at r.t. under magnetic stirrer overnight until TLC showed total consumption of the starting material. The reaction mixture was then sequentially washed with saturated CuSO$_4$ solution (30 mL), saturated aqueous NaHCO$_3$ (30 mL) and brine (30 mL). The organic phase was dried over MgSO$_4$ and concentrated under reduced pressure using a rotary evaporator. The crude of reaction was subsequently purified by column chromatography (mobile phase: Diethyl ether/DCM, 50/50, v/v) giving pure 73 (2.67 g, 78%) as yellow oil. $^1$H NMR (400 MHz, CHLOROFORM-d) δ 8.99 (NH), 8.15-8.18 (2H, m), 7.68 (s, 1H), 7.48-7.51 (2H, m), 6.77 (1H, s), 5.19 (2H, d, J=4 Hz), 4.18-4.40 (2H, m), 4.03 (2H, t, J=8 Hz), 3.76 (3H, s), 3.63-3.67 (m, 1H), 3.62 (s, 3H), 3.41-3.57 (2H, m), 2.46-2.49 (2H, m), 2.07-2.14 (m, 4H), 1.50-1.71 (2H, m). m/z (+EI) calc. $C_{26}H_{31}N_3O_{10}$ for (M)$^+$ 545.2 found 546.0 ([M]+H)$^+$.

Reaction Scheme—Cephalosporine Prodrugs

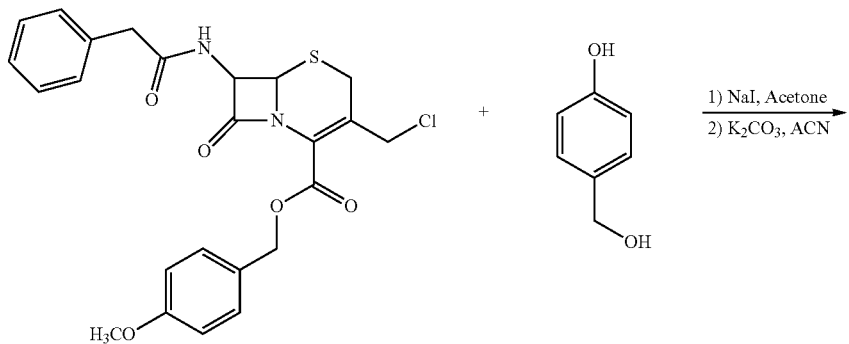

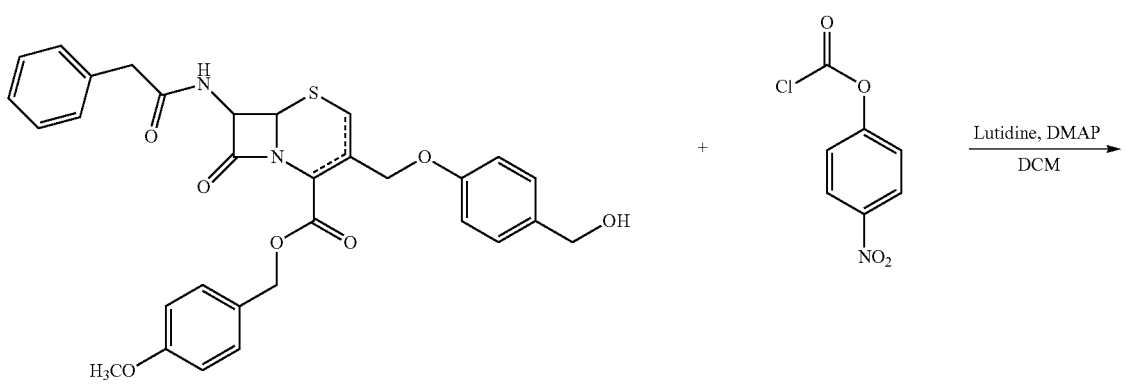

77

-continued
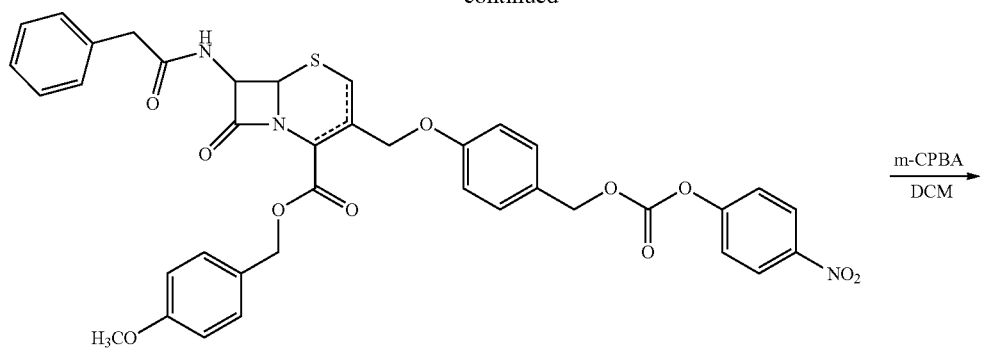
78
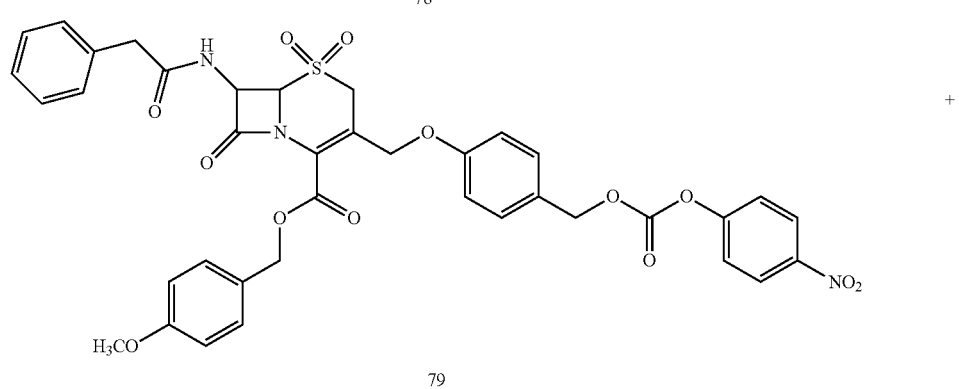
79
+
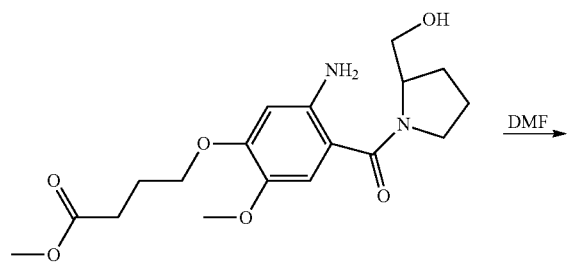
5
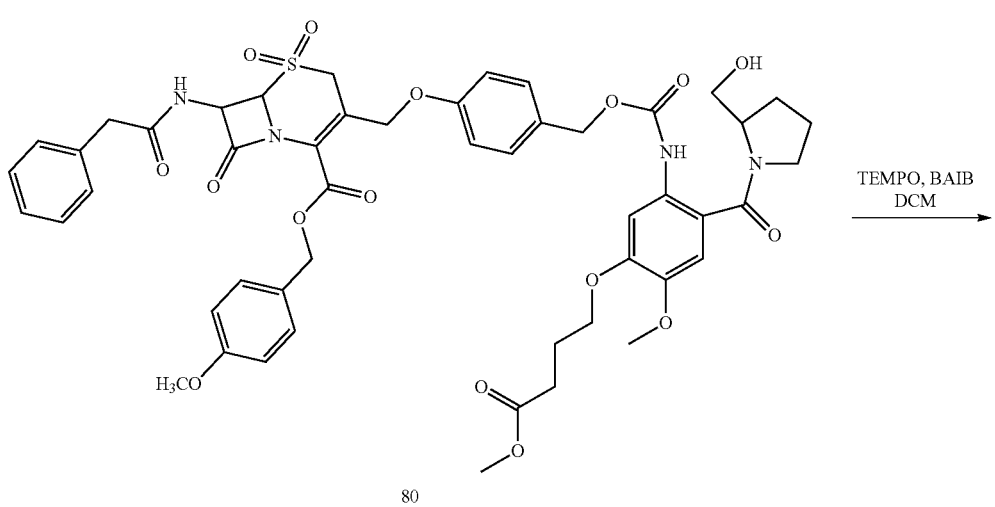
80

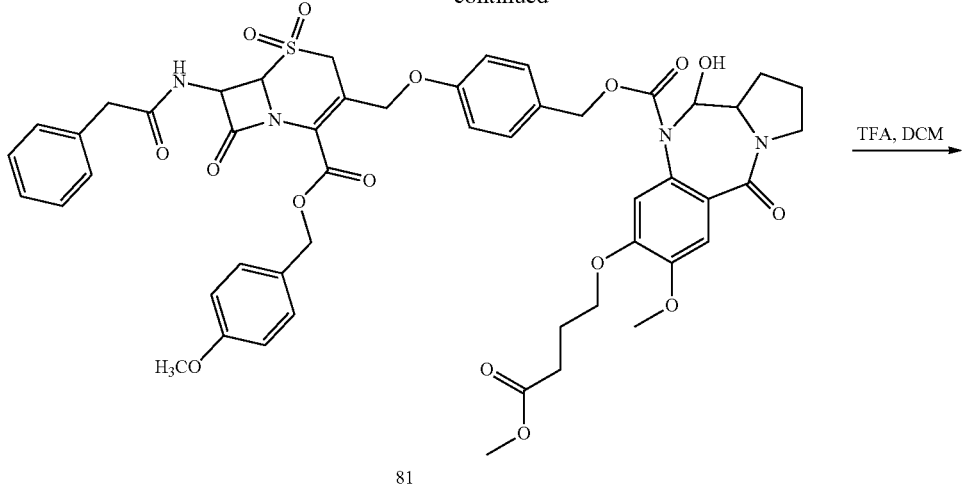

81

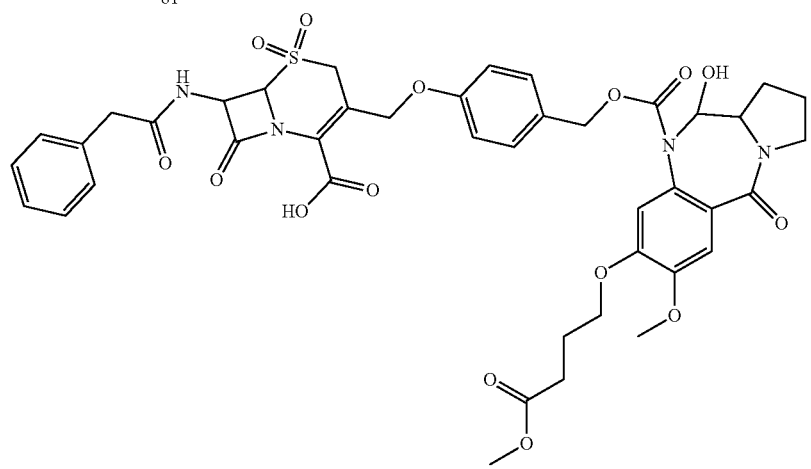

82

Example 97

4-methoxybenzyl 3-((4-(hydroxymethyl)phenoxy)methyl)-8-oxo-7-(2-phenylacetamido)-5-thia-1-azabicyclo[4.2.0]oct-2-ene-2-carboxylate (Mix of Isomers) (77)

NaI (8.4 g, 10 equiv.) was added to a solution of 4-methoxybenzyl 3-(chloromethyl)-8-oxo-7-(2-phenylacetamido)-5-thia-1-azabicyclo[4.2.0]oct-2-ene-2-carboxylate (2.72 g, 1 equiv.) in acetone (40 mL). The reaction mixture was left under magnetic stirrer at r.t. for 2 hours. At that point the solvent was evaporated under reduced pressure and the residue was dissolved in ethyl acetate (50 mL) and the organic phase washed with saturated aqueous $NaHCO_3$ solution (40 mL) and brine (40 mL). The organic phase was dried over $MgSO_4$ and concentrated under reduced pressure using a rotary evaporation. The yellow solid was dissolved in Acetonitrile (40 mL) and added of 4-(hydroxymethyl) phenol (0.818 g, 1.2 equiv.) and $K_2CO_3$ (1.52 g, 2 equiv.). The reaction was left under magnetic stirrer for 4 hours until TLC showed total consumption of the starting material. The organic phase was then sequentially washed with brine (10 mL), $NaHCO_3$ saturated aqueous solution (10 mL) and citric acid aqueous solution 0.1 M (10 mL). The collected organic phase was dried over $MgSO_4$ and subsequently evaporated using a rotary evaporator. The crude of reaction was purified by column chromatography (mobile phase: DCM/EA, 80/20, v/v) giving product 77 (0.64 g, 20%) as a yellow powder and as a mixture of isomers. Identity was confirmed by LC-MS analysis. m/z (+EI) calc. $C_{31}H_{30}N_2O_7S$ for $(M)^+$ 574.1 found 575.0 $([M]+H)^+$.

Example 98

4-methoxybenzyl 3-((4-(((((4-nitrophenoxy)carbonyl)oxy)-methyl)phenoxy)methyl)-8-oxo-7-(2-phenylacetamido)-5-thia-1-azabicyclo-[4.2.0]oct-2-ene-2-carboxylate (Mix of Isomers) (78)

Compound 77 (1.8 g, 1 equiv.) was dissolved in DCM (20 mL) and sequentially added of lutidine (0.52 mL, 1.3 equiv.), 4-nitrophenylchloroformate (0.81 g, 1.3 equiv.) and catalytic amount of DMAP. The reaction mixture was left under magnetic stirrer at r.t. overnight until TLC showed total consumption of the starting material. The reaction mixture was then evaporated under reduced pressure and the crude of reaction purified by column chromatography (mobile phase: DCM/EA, 95/5, v/v) giving product 78 (0.40 g, 17%) as yellow powder and as a mixture of isomers. Identity was confirmed by LC-MS analysis. m/z (+EI) calc. $C_{38}H_{33}N_3O_{11}S$ for $(M)^+$ 739.1 found 738.4 $([M]-H)^-$.

Example 99

4-methoxybenzyl 3-((4-((((4-nitrophenoxy)carbonyl)oxy)-methyl)phenoxy)methyl)-8-oxo-7-(2-phenylacetamido)-5-thia-1-azabicyclo-[4.2.0]oct-2-ene-2-carboxylate 5,5-dioxide (79)

Compound 78 (0.20 g, 1 equiv.) was solubilized in DCM (10 mL) and m-CPBA 77% (0.12 g, 2 equiv) was added to the reaction mixture. The reaction was left under magnetic stirrer overnight until TLC showed total consumption of the starting material. At that point the reaction mixture was sequentially washed with NaHCO$_3$ saturated aqueous solution (10 mL) and citric acid aqueous solution 0.1 M (10 mL). The collected organic phase was dried over MgSO$_4$ and subsequently evaporated using a rotary evaporator. The crude of reaction was purified by column chromatography (mobile phase: DCM/EA, 80/20, v/v) giving product 79 (0.13 g, 62%) as a white solid. $^1$H NMR (400 MHz, CHLOROFORM-d) δ 8.18 (d, J=9.32 Hz, 2H), 7.21-7.30 (m, 8H), 7.15-7.20 (m, 3H), 6.81 (d, J=8.81 Hz, 2H), 6.74 (d, J=8.81 Hz, 2H), 6.67 (d, J=10.32 Hz, 1H), 6.02 (dd, J=4.78, 10.32 Hz, 1H), 5.14-5.15 (m, 3H), 4.97 (d, J=14.35 Hz, 1H), 4.75 (d, J=14.10 Hz, 1H), 4.69 (d, J=5.04 Hz, 1H), 3.96 (d, J=19.64 Hz, 1H), 3.80 (d, J=19.14 Hz, 1H), 3.72 (s, 3H), 3.55 (d, J=3.27 Hz, 2H). $^{13}$C NMR (101 MHz, CHLOROFORM-d) δ 171.0, 163.9, 160.3, 160.2, 157.9, 155.5, 152.5, 150.0, 149.0, 145.4, 139.6, 133.1, 130.8, 129.6, 129.1, 128.2, 127.9, 127.8, 127.7, 126.2, 126.0, 125.4, 125.3, 123.3, 121.8, 120.8, 114.7, 114.1, 70.5, 68.7, 67.2, 65.7, 64.5, 58.8, 55.3, 51.3, 43.2. m/z (+EI) calc. $C_{38}H_{33}N_3O_{13}S$ for (M)$^+$ 771.1 found 770.2 ([M]–H)$^-$.

Example 100

4-methoxybenzyl 3-((4-((((2-(2-(hydroxymethyl)-pyrrolidine-1-carbonyl)-4-methoxy-5-(4-methoxy-4-oxobutoxy)phenyl)-carbamoyl)oxy)methyl)phenoxy)methyl)-8-oxo-7-(2-phenylacetamido)-5-thia-1-azabicyclo[4.2.0]oct-2-ene-2-carboxylate 5,5-dioxide (80)

Compound 79 (0.12 g, 1 equiv.) was dissolved in DMF (0.5 mL) and compound 5 (1 equiv.) was added to the solution. The reaction mixture was kept at 40° C. for 2 days and then quenched by addition of water (10 mL) that was then extracted with ethyl acetate (3×10 mL). The organic phase was then sequentially washed with brine (10 mL), NaHCO$_3$ saturated aqueous solution (10 mL) and citric acid aqueous solution 0.1 M (10 mL). The collected organic phase was dried over MgSO$_4$ and subsequently evaporated using a rotary evaporator. The crude of reaction was purified by column chromatography (mobile phase: DCM/EA, 20/80, v/v) giving product 80 (0.04 g, 20%) as a white solid. m/z (+EI) calc. $C_{50}H_{54}N_4O_{16}S$ for (M)$^+$ 998.3 found 999.2 ([M]+H)$^+$.

Reaction Scheme—Synthesis C8 Benzofused Piperazine PBD Derivative

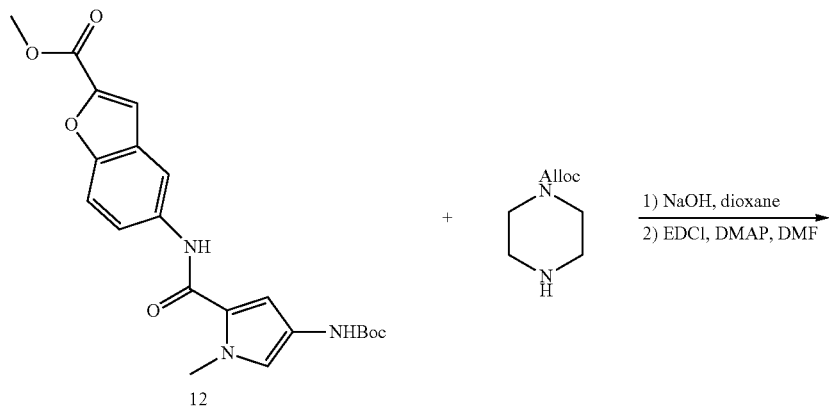

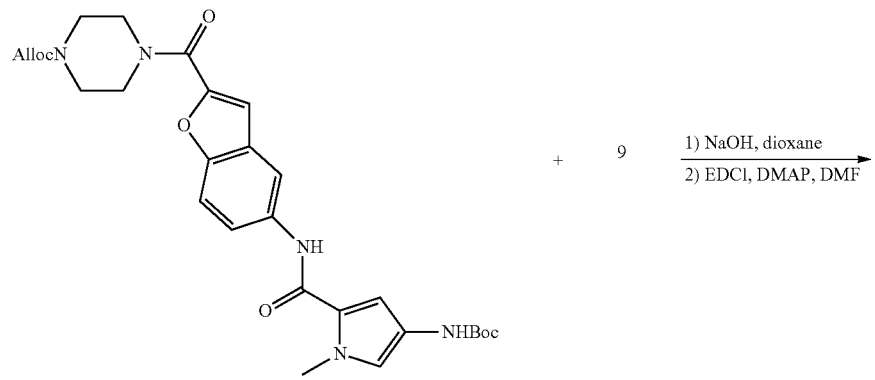

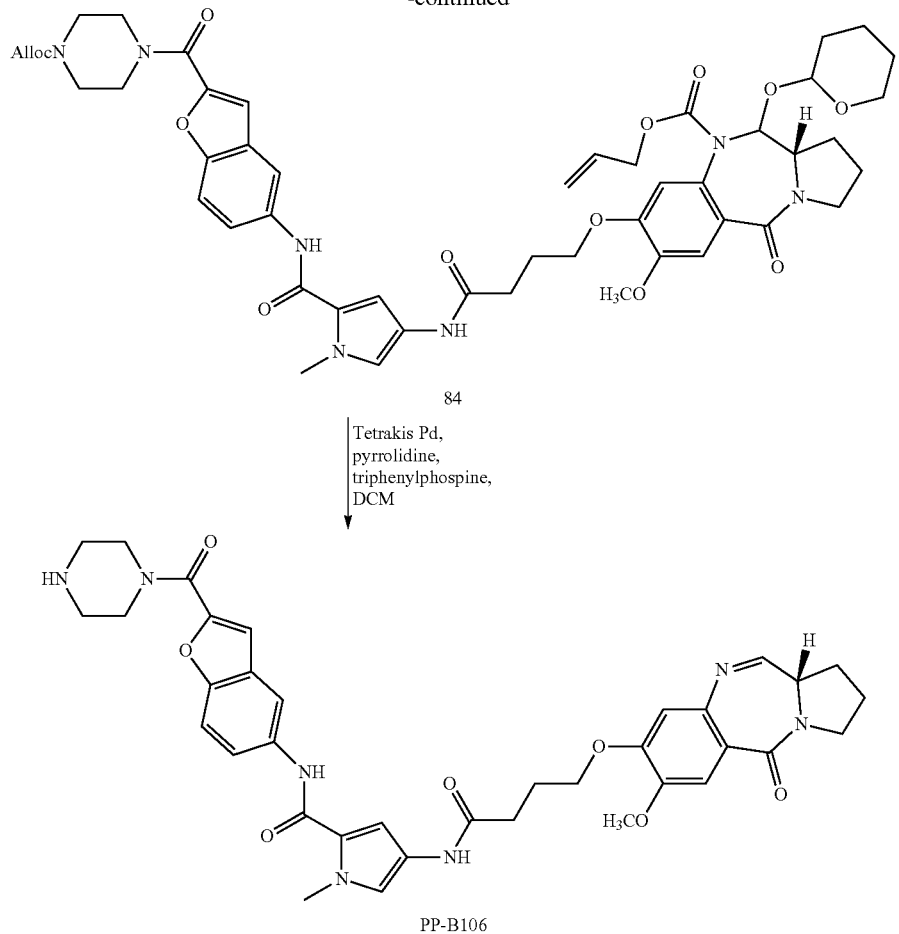

Example 101 allyl 4-(5-(4-((tert-butoxycarbonyl)amino)-1-methyl-1H-pyrrole-2-carboxamido)benzofuran-2-carbonyl)piperazine-1-carboxylate (83)

NaOH 1 M aqueous solution in excess was added to a solution of 12 (0.22 g, 1.2 equiv.) in dioxane (5 mL). The reaction mixture was left at r.t. under magnetic stirrer overnight until TLC showed completion of the reaction. Dioxane was evaporated under reduced pressure and water (20 mL) was added to the crude. Citric acid 1 M aqueous solution was added until acid pH is reached. The aqueous layer was extracted with ethyl acetate (2×10 mL). The combined organic layers were dried over MgSO₄ and concentrated under reduced pressure, giving the corresponding carboxylic acid that was immediately dissolved in DMF (5 mL). EDCI (2.4 equiv.) and DMAP (3 equiv.) were sequentially added to the solution. The reaction mixture was left for 20 minutes under magnetic stirrer in $N_2$ atmosphere. At that point Alloc-piperazine (1 equiv.) was added to the reaction mixture that was left under magnetic stirrer at r.t. overnight. The reaction was quenched by addition of water (10 mL) that was then extracted with ethyl acetate (3×10 mL). The organic phase was then sequentially washed with brine (10 mL), NaHCO₃ saturated aqueous solution (10 mL) and citric acid aqueous solution 0.1 M (10 mL). The collected organic phase was dried over MgSO4 and subsequently evaporated using a rotary evaporator. The crude of reaction was purified by column chromatography (mobile phase: DCM/Ethyl acetate, 50/50, v/v) giving the protected pure compound 8 3 (0.060 g, 23%) as a white solid. $^1$H NMR (400 MHz, CHLOROFORM-d) δ 7.92 (s, 1H), 7.75 (s, 1H), 7.32-7.40 (m, 2H), 7.18-7.25 (m, 1H), 6.79 (s, 1H), 6.62 (br. s., 1H), 6.33 (br. s., 1H), 5.81-5.97 (m, 1H), 5.25 (dd, J=1.51, 17.37 Hz, 1H), 5.17 (dd, J=1.26, 10.32 Hz, 1H), 4.57 (td, J=1.35, 5.60 Hz, 2H), 3.84 (s, 3H), 3.78 (br. s., 4H), 3.50-3.58 (m, 4H), 1.44 (s, 9H). $^{13}$C NMR (101 MHz, CHLOROFORM-d) δ: 159.8, 159.7, 155.0, 153.4, 151.4, 149.4, 134.1, 132.7, 127.2, 123.3, 121.9, 120.3, 121.9, 120.3, 118.7, 117.9, 113.5, 112.8, 112.0, 103.9, 80.3, 66.4, 43.8, 36.7, 28.3, 14.2. m/z (+EI) calc. for $C_{28}H_{33}N_5O_7$ (M)⁺ 551.2 found 552.0 ([M]+H)⁺.

Example 102

(S)-4-(4-((7-methoxy-5-oxo-2,3,5,11a-tetrahydro-1H-benzo-[e]pyrrolo[1,2-a][1,4]diazepin-8-yl)oxy)butanamido)-1-methyl-N-(2-(piperazine-1-carbonyl)benzofuran-5-yl)-1H-pyrrole-2-carboxamide (PP-106)

Compounds 83 (0.05 g, 1 equiv.) was boc-deprotected dissolving the desired derivative in MeOH (3 ml) and HCl 4M in dioxane (3 mL). The solution was left under magnetic stirrer for 2 hours until TLC showed total cleavage of protecting group. The reaction mixture was subsequently evaporated using a rotary evaporator, obtaining a solid. PBD capping unit 9 (1.2 equiv.) was dissolved in DMF (4 mL) and added of EDCI (2 equiv.) and DMAP (3 equiv.). The reaction mixture was left under magnetic stirrer in $N_2$ atmosphere for 20 minutes. At that point the deprotected compound was added to the reaction mixture and left under magnetic stirrer overnight for 15 hours until TLC and LC-MS analysis showed formation of the protected PBD-C8 derivative. The reaction was quenched by addition of water (10 mL) that was then extracted with ethyl acetate (3×10 mL). The organic phase was then sequentially washed with brine (10 mL), $NaHCO_3$ saturated aqueous solution (10 mL) and citric acid aqueous solution 0.1 M (10 mL). The collected organic phase was dried over MgSO4 and subsequently evaporated using a rotary evaporator. The crude of reaction was purified by column chromatography (mobile phase: from DCM/acetone, 50/50, v/v). The protected PBD-conjugate (0.05 g, 1 equiv.) was dissolved in DCM (4 mL) and added of Tetrakis Pd (0.5 equiv.), triphenylphospine (0.25 equiv.) and pyrrolidine (1.2 equiv). The reaction mixture was kept under magnetic stirrer for 2 hours when TLC showed completion of reaction. At that point the solvent was evaporated using a rotary evaporator and the crude of reaction was purified by column chromatography (mobile phase: from DCM/acetone, 90/10, v/v to DCM/MeOH, 90/10/, v/v) affording pure final compound PP-B106 (0.04 g, 65%) as a white solid. m/z (+EI) calc. $C_{36}H_{39}N_7O_7$ for $(M)^+$ 681.2 found 682.2 $([M]+H)^+$.

General Minimum Inhibitory Concentration (MIC) Protocol

1. Grow up cultures of bacterial strains to be tested overnight.
2. Dilute down overnight cultures to concentration of $1\times10^6$ bacteria/ml (OD0.01) in Tryptic soy broth (TSB).
3. Add 100 µl of TSB media to column 2-column 12 in 96 well plate (keeping column 1 clear).
4. Make up compound to a concentration of 64 µg/ml in water (or alternatively to twice the chosen maximum concentration to be tested).
5. Add 100 µl of antibiotic solution to the 1st and $2^{nd}$ columns.
6. Using a multichannel pipette take 100 µl from the $2^{nd}$ column wells and pipette into $3^{rd}$ column wells and repeat down the 96 well plate (remembering to include controls i.e. uninfected media and media with no antibiotic).
7. To each well (except uninfected control row H) add 100 µl of bacterially infected media at a concentration of $1\times10^6$/ml.
8. This dilutes down the concentration of the antibiotic by half (top dose is therefore 32 µg/ml in column 1) and also gives you a starting bacterial concentration of $5\times10^5$/ml.
9. Wrap plate with parafilm to prevent evaporation.
10. Leave at desired temperature (37° C. unless specified elsewhere) for 20 hours.
11. Next day check plates for growth and measure optical density (i.e. absorbance) at a wavelength of 600 nm ($OD_{600}$).

An example of such a plate is shown in FIG. 1 where column A represents wells that receive the top dose 100 µl; column B represents wells that receive the top dose 100 µl+100 µl TSB; and column C represents wells that receive 100 µl TSB. Row H which is marked by a box labelled D represents a blank where the cells receive no bacteria.

Example 103

Measuring the Activity Against Gram Positive and Gram Negative Panel

Using the MIC protocol the activity of compounds PP-A147, PP-A148, PP-A159, PP-B15, PP-B16, PP-B22, PP-B26, PP-B27 and PP-B28 was measured against a wide range of Gram positive and Gram negative bacterial strains.

In addition, comparative examples were carried out with the following compounds;

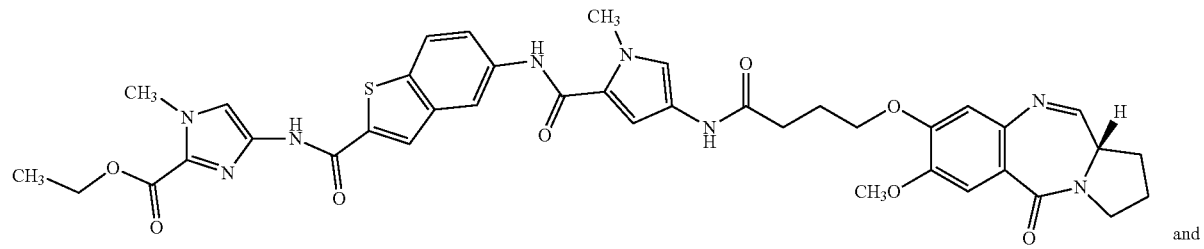

PP-B14 and

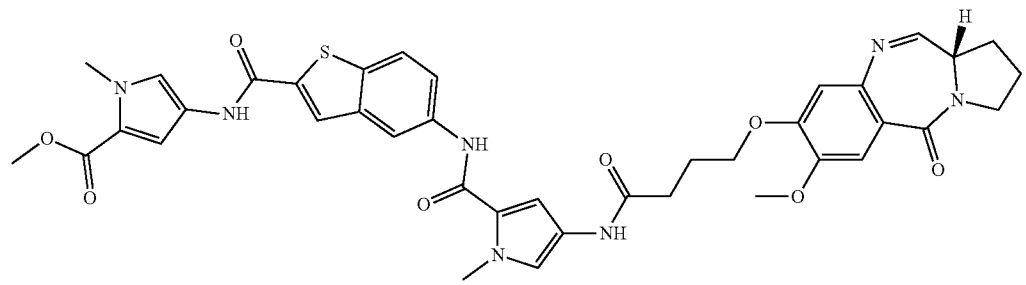

PP-B17

Table 1 below provides the results for the compounds and the comparative examples.

As can be seen from Table 1, the compounds were very effective against the panel of Gram positive bacteria. In addition, several of the compounds also provided very good results against some very resistant strains of Gram negative bacteria.

The compounds of the comparative examples were generally much less effective against Gram negative bacterial species. In addition, the compounds of the comparative examples are significantly more cytotoxic than the compounds of the present invention which make them unattractive for use as antibacterial agents.

With regard to the Gram positive bacteria in Table 1, VSE 775 is *E. faecalis* VSE NCTC 775; VRE 12204 is *E. faecium* VRE NCTC 12204; VRE 12201 is *E. faecalis* VRE NCTC 12201 and MSSA 9144 is methicillin sensitive *S. aureus* ATTC 9144 (NCTC 6571).

TABLE 1 shows the MIC values (µg/ml) that were obtained when each of a range of the prepared compounds were tested against both a Gram positive and against a Gram negative panel of bacterial species.

| | Gram positive panel | | | | | | Gram negative panel | | | | | |
|---|---|---|---|---|---|---|---|---|---|---|---|---|
| | | | | | | | KP | | | AB | | PA |
| | VSE 775 | EMRSA-15 | MSSA 9144 | VRE 12204 | VRE 12201 | EMRSA-16 | NCTC 13368 | KP-M6 | AB-AYE | NCTC 17978 | PA01 | NCTC 13437 |
| PP-A147 | <0.125 | <0.125 | <0.125 | <0.125 | <0.125 | 0.25 | 32-64 | 0.5-1 | 8 | 8 | >128 | 64 |
| PP-A148 | 1 | 2 | 0.5 | 0.01 | 0.25-0.5 | 2 | 16-32 | 0.25-0.5 | 2 | 2 | 128 | 16 |
| PP-A159 | <0.125 | <0.125 | <0.125 | <0.125 | 0.5 | <0.125 | 16 | 0.5 | 4 | 4 | 128 | 32-64 |
| KMR-14-33 | 0.03 | 0.03 | 0.03 | 0.03 | 0.03 | 0.06 | 2 | — | 1 | 0.5 | >32 | >32 |
| PP-B15 | <0.125 | <0.125 | <0.125 | <0.125 | <0.125 | <0.125 | 2 | >128 | 2 | 2 | 64 | 32 |
| PP-B16 | <0.125 | <0.125 | <0.125 | <0.125 | <0.125 | 0.5 | 8 | 64 | 8 | 8 | 64 | 32 |
| PP-B22 | 0.25 | 0.5 | <0.125 | <0.125 | <0.125 | 1 | 128 | 128 | 8 | 8 | 128 | 64 |
| PP-B26 | 0.25 | 0.25 | <0.125 | <0.125 | <0.125 | 0.5 | 64 | 8 | 2 | 2 | 128 | 32 |
| PP-B27 | 0.25 | 0.25 | <0.125 | <0.125 | <0.125 | 0.5 | 64 | 8 | 4 | 4 | 128 | 32 |
| PP-B28 | 1 | 1 | 0.5 | 1 | 0.5 | 4 | 64 | 8 | 4 | 4 | 128 | 32 |
| Comparative Example 1 PP-B14 | <0.125 | 0.5 | <0.125 | <0.125 | <0.125 | 1 | 128 | 128 | 64 | 64 | >128 | 128 |
| Comparative Example 2 PP-B17 | <0.125 | <0.125 | <0.125 | <0.125 | <0.125 | 0.25 | 128 | 128 | 32 | 8 | 128 | 64 |

Example 104

Activity Against Extended Gram-Negative Panel

The activity of the compound designated KMR-14-33 was tested against an extended panel of Gram-negative bacterial strains that have proven drug resistant difficult to treat. The MIC was measured using the general MIC protocol given above. The results against this extended panel are given in Table 2 below.

TABLE 2

Results for the MIC (µg/ml) of a selected compound KMR-14-33 against an extended panel of Gram-negative bacterial strains

| Species | Strain | KMR-14-33 MIC (µg/ml) |
|---|---|---|
| K. pneumonia | M6 | 1 |
| | NCTC 13368 | 2 |
| | NCTC 13438 | 0.5 |
| | NCTC 13439 | 2 |
| | NCTC 13443 | 2 |
| | KP16 | 0.25 |
| A. baumannii | NCTC 46704 | 1 |
| | NCTC 51851 | 2 |
| | MGH 78578 | 1 |
| | NCTC 17978 | 0.5 |
| | AYE | 1 |
| | NCTC 13424 | 0.5 |
| | ADP1 | 0.125 |
| | NCTC 13302 | 0.25 |
| | UKA2 | 0.5 |
| | UKA7 | 0.5 |
| | W1 | 1 |
| P. aeruginosa | PA01 | >32 |
| | NCTC 13437 | >32 |
| B. multivorans | C1576 (LMG 16660) | 1 |
| | C1962 (LMG 16665) | 2 |
| B. cenocepa | K56-2 | 2 |
| B. cepacia | CEP509 (LMG 18821) | 2 |
| | ATCC 17765 | 0.125 |
| | LMG 17997 | 0.125 |
| | NCTC 10743 | 1-2 |

Further details regarding the drug resistance Gram-negative bacterial strains used in this extended panel are provided below in Table 3.

TABLE 3

Details regarding the drug resistance of the extended panel of Gram-negative bacteria

| Strain | Drug resistance profile | Detection of resistance genes | | | | |
| --- | --- | --- | --- | --- | --- | --- |
| | | Carbapenemase | ESBL | Other B-lactam | QRD | ARD |

*Klebsiella*

| Strain | Drug resistance profile | Carbapenemase | ESBL | Other B-lactam | QRD | ARD |
| --- | --- | --- | --- | --- | --- | --- |
| NCTC 13438 | AMP, PIP, AMK, TOB, CTX, CAZ, IMP, MEM, ATM, CIP, LVX, CHL, TMP, SXT | $bla_{KPC-3}$ | — | $bla_{SHV-11}$ | ? | AAC-6 |
| M6 | AMP, PIP, | — | — | $bla_{SHV-11}$ | — | |
| NCTC 13443 | AMP, PIP, AMK, GEN, TOB, TZP, CTX, CAZ, IMP, MEM, ATM, CIP, LVX, CHL, TMP, SXT | $bla_{NDM-1}$ | $bla_{CTX-M-15}$ | $bla_{SHV-11}$, $bla_{TEM-1}$ | no qnr genes detected | AAC-6, armA, aadA |
| NCTC 13368 | AMP, PIP, GEN, TOB, CTX, CAZ, ATM, CHL | — | $bla_{SHV-18}$ | — | — | |
| 16 | AMP, PIP, AMK, GEN, TOB, CTX, CAZ, IMP, MEM, ATM, CIP, LVX, TMP, SXT | $bla_{OXA-48}$ | $bla_{CTX-M-15}$ | $bla_{SHV-1}$, $bla_{TEM-1}$ | ? | AAC-6, aphA |
| MGH 78578 (ATCC 7007121) | AMP, PIP, AMK, GEN, TOB, CTX, CAZ, ATM, TMP, SXT | — | $bla_{SHV-12}$ | $bla_{SHV-11}$, $bla_{TEM-1}$ | — | AAC-6, aadA, aphA |
| NCTC 13439 | AMP, PIP, GEN, TOB, TZP, CTX, CAZ, IMP, MEM, ATM, CIP, LVX, CHL, TMP, SXT | $bla_{VIM-1}$ | $bla_{SHV-12}$ | — | qnrS1 | AAC-6 |
| NCTC 51851 | AMP, PIP, AMK, GEN, TOB, CTX, CAZ, IMP, MEM, ATM, CIP, LVX, CHL, CST, TMP, SXT | ? | ? | $bla_{SHV-11}$, $bla_{TEM-1}$ | ? | AAC-6, aadA, aphA |
| NCTC 46704 | AMP, PIP, AMK, GEN, TOB, CTX, CAZ, IMP, MEM, ATM, CIP, LVX, CHL, TMP, SXT | ? | ? | $bla_{SHV-11}$, $bla_{TEM-1}$ | ? | AAC-6, aadA, aphA |

*Pseudomonas*

| Strain | Drug resistance profile | Carbapenemase | ESBL | Other B-lactam | QRD | ARD |
| --- | --- | --- | --- | --- | --- | --- |
| PA01 (ATCC 15692) | AMP, PIP, ATM, CHL | — | | ampC | — | — |
| NCTC 13437 | AMK, GEN, TOB, AMP, PIP, TZP, CAZ, ATM, IMP MEM, CIP, LVX, CHL | $bla_{VIM-10}$ | $bla_{VEB-1}$ | | no qnr genes detected | aadA |

*Acinetobacter*

| Strain | Drug resistance profile |
| --- | --- |
| ATCC 17978 | — |
| AYE (ATCC BAA-1710) | AMK, GEN, CIP, TZP, LEVO, AMI |
| NCTC 13424 | GEN, CIP, TZP, IMP, LEVO, AMI, MEM |
| NCTC 13302 | GEN, CIP, TZP, IMP, LEVO, AMI, MEM |
| UKA2 | GEN, CIP, TZP, LEVO, MEM |

TABLE 3-continued

Details regarding the drug resistance of the extended panel of Gram-negative bacteria

| Strain | Drug resistance profile | Detection of resistance genes | | | | |
|---|---|---|---|---|---|---|
| | | Carbapenemase | ESBL | Other B-lactam | QRD | ARD |
| UKA7 | GEN, CIP, TZP, IMP, LEVO, AMI, MEM | | | | | |
| W1 | GEN, CIP, LEVO, AMI | | | | | |
| ADP-1 | — | | | | | | amikacin (AMK)
gentamicin (GEN)
tobramycin (TOB)
ampicillin (AMP)
piperacillin (PIP)
piperacillin/tazobactam (TZP)
penicillin (PEN)
amoxicillin (AMX)
amoxicillin/clavulanate (AMC)
cefotaxime (CTX)
ceftazidime (CAZ)
imipenem (IMP)
meropenem (MERO/MEM)
aztreonam (ATM)
ciprofloxacin (CIP)
levofloxacin (LEVO/LVX)
colistin (CST)
chloramphenicol (CHL)
trimethoprim (TMP),
Trimethoprim/sulfamethoxazole (SXT),
chloramphenicol (CHL)

As can be seen from Table 2, KMR-14-33 provided excellent results against these drug resistant Gram-negative bacterial strains.

Example 105

Time Kill Kinetics of Compounds

Protocol:
1. Grow bacteria overnight.
2. Subculture into an autoclaved conical flask containing 10 ml of TSB to an OD of 0.01 (~1×10$^7$ Cfu/ml for KP-M6).
3. Add drug at 4×MIC.
4. Take aliquots (100 μl) at timepoints (0, 1, 2, 4, 6, 24 hours) and carry out a serial dilution in PBS (to remove drug and to dilute bacteria to countable numbers).
5. Use the serial dilution to perform a Miles Misra—i.e. Add 3×10 μl spots of each dilution onto an agar plate. Incubate overnight and count colonies on spots in the morning.
6. Control: Subculture bacteria alongside samples but with no antibiotic added. Take aliquots from this at every time point (0, 1, 2, 4, 6, 24 hours) and perform Miles Misra on these too (as detailed in points 4 and 5 above).
7. After the first experiment, if the counts seen on Miles-Misra were zero, total viable counts were determined by spreading 200 μl in a streak down the centre of a TSB agar plate, waiting for the liquid to be absorbed and then spreading over the plate and checking for growth inhibition at the sight of the original streak. This technique was used to control for the carryover of antimicrobial agent and to lower the limit of detection to 50 CFU.
8. The compound is considered bactericidal if the inoculum was reduced >3 log$_{10}$ CFU/ml and bacteriostatic if inoculum was reduced by 0-3 log$_{10}$ CFU/ml.

The time kill data for compound KMR-14-33 against a range of bacterial species was obtained using the above protocol. In addition, measurements were made for a control containing no antibiotic and also for the known antibiotic ciprofloxacin (CIP). The measurements for the known antibiotic CIP provide a further comparison for the test compounds.

Three measurements were taken for each compound at each time point. These measurements were averaged and the standard deviation was also calculated. The data is presented below in Tables 4-9.

TABLE 4

Results for bacterial strain: K. pneumonia - M6

| Time-point (hours) | Compound | n = 1 (Log CFU/ml) | n = 2 (Log CFU/ml) | n = 3 (Log CFU/ml) | Average (Log CFU/ml) | Standard Deviation |
|---|---|---|---|---|---|---|
| 0 | Control | 8500000 | 9000000 | 15000000 | 10833333.3 | 3617089.07 |
| 1 | Control | 10000000 | 14000000 | 22000000 | 15333333.3 | 6110100.93 |
| | KMR-14-33 | 3000 | 3000 | 2000 | 2666.66667 | 577.350269 |
| | CIP | 900000 | 130000 | 1100000 | 710000 | 512152.321 |

TABLE 4-continued

| | Results for bacterial strain: *K. pneumonia* - M6 | | | | | |
|---|---|---|---|---|---|---|
| Time-point (hours) | Compound | n = 1 (Log CFU/ml) | n = 2 (Log CFU/ml) | n = 3 (Log CFU/ml) | Average (Log CFU/ml) | Standard Deviation |
| 2 | Control | 85000000 | 120000000 | 90000000 | 98333333.3 | 18929694.5 |
|  | KMR-14-33 | 0 | 0 | 0 | 0 | 0 |
|  | CIP | 4700 | 2800 | 9600 | 5700 | 3508.56096 |
| 4 | Control | 1350000000 | 1450000000 | 2000000000 | 1600000000 | 350000000 |
|  | KMR-14-33 | 0 | 0 | 0 | 0 | 0 |
|  | CIP | 0 | 70 | 50 | 40.3333333 | 35.5011737 |
| 6 | Control | 8000000000 | 9000000000 | 5000000000 | 7333333333 | 2081665999 |
|  | KMR-14-33 | 0 | 0 | 0 | 0 | 0 |
|  | CIP | 0 | 85 | 25 | 37 | 43.2666153 |
| 24 | Control | 5500000000 | 7000000000 | 7500000000 | 6666666667 | 1040833000 |
|  | KMR-14-33 | 0 | 0 | 0 | 0 | 0 |
|  | CIP | 0 | 2500000000 | 1800000000 | 1433333334 | 1289702808 |

Figure 2:
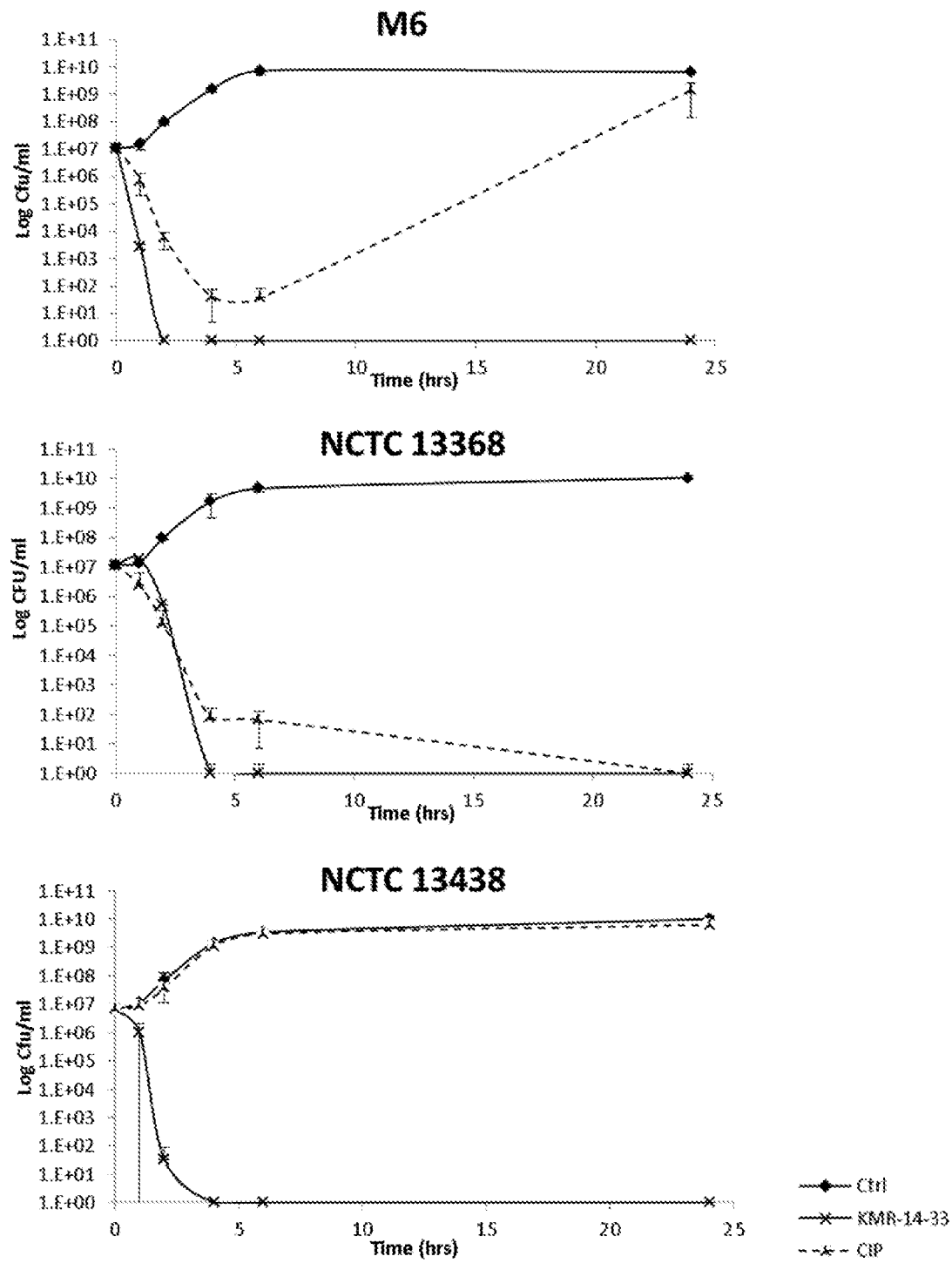
FIG. 2 shows time kill data against three *K. pneumoniae* species for a control (Ctrl), for a compound (KMR-14-33) and for the known antibiotic ciprofloxacin (CIP).

The results for the Control, KMR-14-33 and for CIP are shown in FIG. 2.

TABLE 5

| | Results for bacterial strain: *K. pneumonia* - NCTC 13368 | | | | | |
|---|---|---|---|---|---|---|
| Time-point (hours) | Compound | n = 1 (Log CFU/ml) | n = 2 (Log CFU/ml) | n = 3 (Log CFU/ml) | Average (Log CFU/ml) | Standard Deviation |
| 0 | Control | 10000000 | 13000000 | 13000000 | 12000000 | 1732051 |
| 1 | Control | 18000000 | 11500000 | 13000000 | 14166667 | 3403430 |
|  | KMR-14-33 | 1700000 | 36000000 |  | 18850000 | 24253763 |
|  | CIP | 7000000 | 110000 | 28000 | 2379333 | 4001825 |
| 2 | Control | 90000000 | 90000000 | 120000000 | 1E+08 | 17320508 |
|  | KMR-14-33 | 110000 | 900000 |  | 505000 | 558614.4 |
|  | CIP | 350000 | 650 | 2500 | 117716.7 | 201165.4 |
| 4 | Control | 2400000000 | 270000000 | 2400000000 | 1.69E+09 | 1.23E+09 |
|  | KMR-14-33 | 0 | 0 |  | 0 | 0 |
|  | CIP | 0 | 55 | 170 | 75.33333 | 86.31531 |
| 6 | Control | 5000000000 | 5500000000 | 3300000000 | 4.6E+09 | 1.15E+09 |
|  | KMR-14-33 | 0 | 0 |  | 0 | 0 |
|  | CIP | 0 | 80 | 115 | 65.33333 | 58.39806 |
| 24 | Control | 10000000000 | 12000000000 | 10000000000 | 1.07E+10 | 1.15E+09 |
|  | KMR-14-33 | 0 | 0 |  | 0 | 0 |
|  | CIP | 0 | 0 | 0 | 0 | 0 |

The results for the Control, KMR-14-33 and for CIP are shown in FIG. 2.

TABLE 6

| | Results for bacterial strain: *K. pneumonia* - NCTC 13438 | | | | | |
|---|---|---|---|---|---|---|
| Time-point (hours) | Compound | n = 1 (Log CFU/ml) | n = 2 (Log CFU/ml) | n = 3 (Log CFU/ml) | Average (Log CFU/ml) | Standard Deviation |
| 0 | Control | 6000000 | 5500000 | 9000000 | 6833333 | 1892969 |
| 1 | Control | 10000000 | 11500000 | 12000000 | 11166667 | 1040833 |
|  | KMR-14-33 | 1000000 | 2000000 | 1 | 1000000 | 999999.5 |
|  | CIP | 10000000 | 9000000 | 7000000 | 8666667 | 1527525 |
| 2 | Control | 80000000 | 6500000 | 120000000 | 68833333 | 57568076 |
|  | KMR-14-33 | 0 | 100 | 0 | 34 | 57.15768 |
|  | CIP | 38000000 | 37000000 | 33000000 | 36000000 | 2645751 |
| 4 | Control | 1900000000 | 1400000000 | 1000000000 | 1.43E+09 | 4.51E+08 |
|  | KMR-14-33 | 0 | 0 | 0 | 0 | 0 |
|  | CIP | 1500000000 | 1000000000 | 1000000000 | 1.17E+09 | 2.89E+08 |
| 6 | Control | 3600000000 | 3400000000 | 3300000000 | 3.43E+09 | 1.53E+08 |
|  | KMR-14-33 | 0 | 0 | 0 | 0 | 0 |
|  | CIP | 3900000000 | 2500000000 | 2800000000 | 3.07E+09 | 7.37E+08 |
| 24 | Control | 13000000000 | 8000000000 | 9000000000 | 1E+10 | 2.65E+09 |
|  | KMR-14-33 | 0 | 0 | 0 | 0 | 0 |
|  | CIP | 6000000000 | 6700000000 | 6000000000 | 6.23E+09 | 4.04E+08 |

The results for the Control, KMR-14-33 and for CIP are shown in FIG. 2.

TABLE 7

Results for bacterial strain: A. baumannii - NCTC 17978

| Time-point (hours) | Compound | n = 1 (Log CFU/ml) | n = 2 (Log CFU/ml) | n = 3 (Log CFU/ml) | Average (Log CFU/ml) | Standard Deviation |
|---|---|---|---|---|---|---|
| 0 | Control | 13000000 | 5000000 | 5200000 | 7733333 | 4562163 |
| 1 | Control | 13500000 | 13500000 | 17000000 | 14666667 | 2020726 |
|   | KMR-14-33 | 0 | 0 | 0 | 0 | 0 |
|   | CIP | 19000 | 0 | 2000 | 7000.333 | 10439.97 |
| 2 | Control | 160000000 | 70000000 | 50000000 | 93333333 | 58594653 |
|   | KMR-14-33 | 0 | 0 | 0 | 0 | 0 |
|   | CIP | 1500 | 0 | 250 | 583.6667 | 803.2748 |
| 4 | Control | 1800000000 | 2300000000 | 1750000000 | 1.95E+09 | 3.04E+08 |
|   | KMR-14-33 | 0 | 0 | 0 | 0 | 0 |
|   | CIP | 0 | 30 | 0 | 10.66667 | 16.74316 |
| 6 | Control | 3450000000 | 4200000000 | 3200000000 | 3.62E+09 | 5.2E+08 |
|   | KMR-14-33 | 0 | 0 | 0 | 0 | 0 |
|   | CIP | 0 | 0 | 0 | 0 | 0 |
| 24 | Control | 8500000000 | 10000000000 | 1000000000 | 6.5E+09 | 4.82E+09 |
|   | KMR-14-33 | 0 | 0 | 0 | 0 | 0 |
|   | CIP | 10 | 0 | 0 | 4 | 5.196152 |

Figure 3:
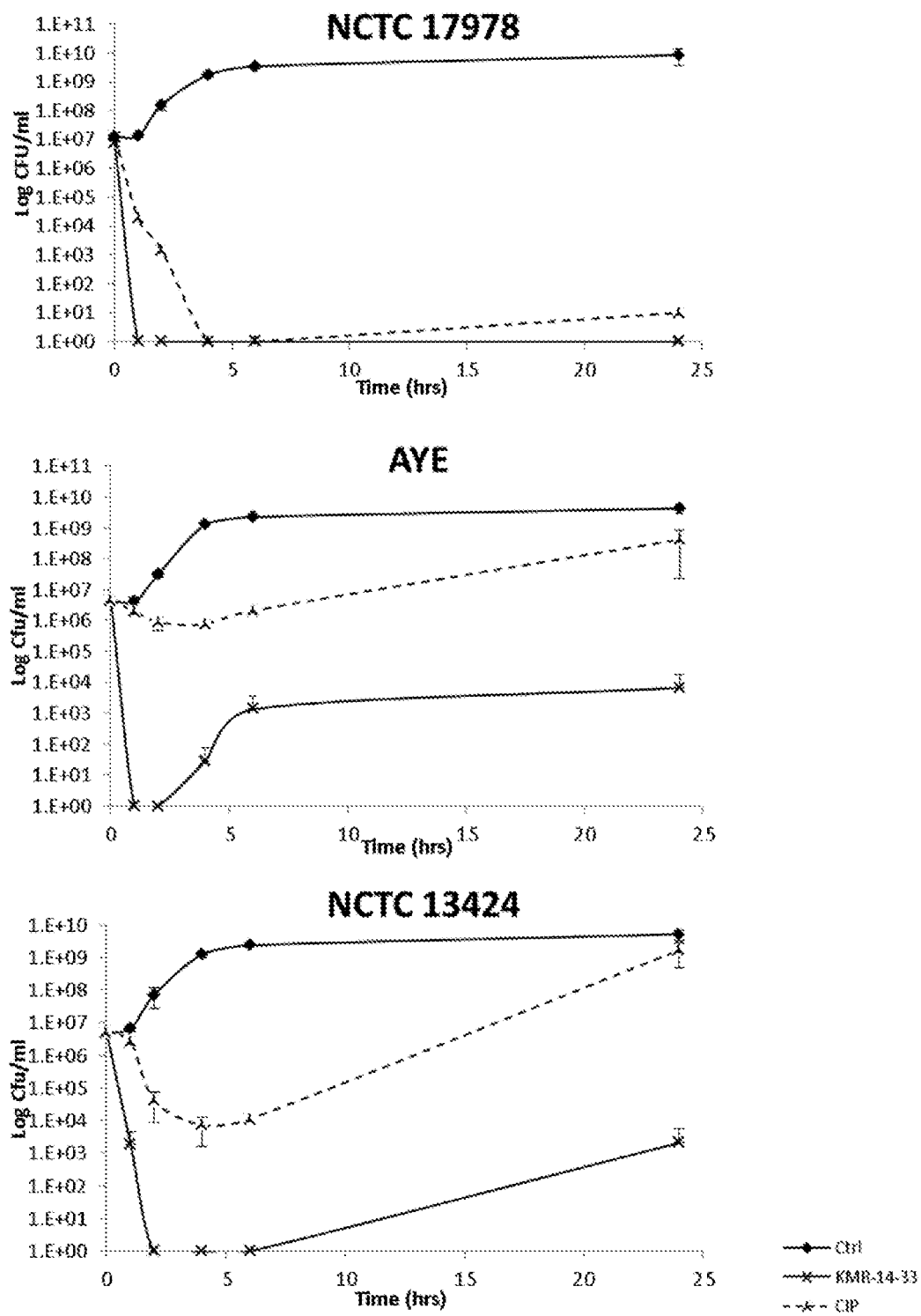
FIG. 3 shows time kill data against three *A. baumannii* species for a control (Ctrl), for a compound (KMR-14-33) and for the known antibiotic ciprofloxacin (CIP).

The results for the Control, KMR-14-33 and for CIP are shown in FIG. 3.

TABLE 8

Results for bacterial strain: A. baumannii - AYE

| Time-point (hours) | Compound | n = 1 (Log CFU/ml) | n = 2 (Log CFU/ml) | n = 3 (Log CFU/ml) | Average (Log CFU/ml) | Standard Deviation |
|---|---|---|---|---|---|---|
| 0 | Control | 3800000 | 4000000 | 6000000 | 4600000 | 1216553 |
| 1 | Control | 3400000 | 3000000 | 6000000 | 4133333 | 1628906 |
|   | KMR-14-33 | 0 | 0 | 0 | 0 | 0 |
|   | CIP | 2100000 | 1900000 |   | 2000000 | 141421.4 |
| 2 | Control | 34000000 | 25000000 | 34000000 | 31000000 | 5196152 |
|   | KMR-14-33 | 0 | 0 | 0 | 0 | 0 |
|   | CIP | 1200000 | 600000 |   | 900000 | 424264.1 |
| 4 | Control | 1100000000 | 1600000000 | 1200000000 | 1.3E+09 | 2.65E+08 |
|   | KMR-14-33 | 0 | 0 | 85 | 29 | 48.49742 |
|   | CIP | 800000 | 700000 |   | 750000 | 70710.68 |
| 6 | Control | 2400000000 | 1900000000 | 2400000000 | 2.23E+09 | 2.89E+08 |
|   | KMR-14-33 | 0 | 0 | 4000 | 1334 | 2308.824 |
|   | CIP | 2000000 | 2200000 |   | 2100000 | 141421.4 |
| 24 | Control | 3200000000 | 3700000000 | 6000000000 | 4.3E+09 | 1.49E+09 |
|   | KMR-14-33 | 0 | 20000 | 0 | 6667.333 | 11546.43 |
|   | CIP | 700000000 | 140000000 |   | 4.2E+08 | 3.96E+08 |

The results for the Control, KMR-14-33 and for CIP are shown in FIG. 3.

TABLE 9

Results for bacterial strain: A. baumannii - NCTC13424

| Time-point (hours) | Compound | n = 1 (Log CFU/ml) | n = 2 (Log CFU/ml) | n = 3 (Log CFU/ml) | Average (Log CFU/ml) | Standard Deviation |
|---|---|---|---|---|---|---|
| 0 | Control | 5000000 | 6000000 | 4000000 | 5000000 | 1000000 |
| 1 | Control | 8000000 | 7000000 | 5000000 | 6666667 | 1527525 |
|   | KMR-14-33 | 0 | 940 | 4830 | 1923.667 | 2560.373 |
|   | CIP | 2500000 | 2200000 | 3000000 | 2566667 | 404145.2 |
| 2 | Control | 110000000 | 23000000 | 80000000 | 71000000 | 44192760 |
|   | KMR-14-33 | 0 | 0 | 0 | 0 | 0 |
|   | CIP | 80000 | 21000 | 25000 | 42000 | 32969.68 |
| 4 | Control | 1100000000 | 1100000000 | 1500000000 | 1.23E+09 | 2.31E+08 |
|   | KMR-14-33 | 0 | 0 | 0 | 0 | 0 |
|   | CIP | 12000 | 1000 | 9000 | 7333.333 | 5686.241 |

TABLE 9-continued

Results for bacterial strain: A. baumannii - NCTC13424

| Time-point (hours) | Compound | n = 1 (Log CFU/ml) | n = 2 (Log CFU/ml) | n = 3 (Log CFU/ml) | Average (Log CFU/ml) | Standard Deviation |
|---|---|---|---|---|---|---|
| 6 | Control | 2500000000 | 2500000000 | 2000000000 | 2.33E+09 | 2.89E+08 |
|   | KMR-14-33 | 0 | 0 | 0 | 0 | 0 |
|   | CIP | 10000 | 14300 | 9200 | 11166.67 | 2742.87 |
| 24 | Control | 7000000000 | 5000000000 | 3300000000 | 5.1E+09 | 1.85E+09 |
|   | KMR-14-33 | 6250 | 0 | 0 | 2084 | 3607.862 |
|   | CIP | 360000000 | 1900000000 | 2750000000 | 1.67E+09 | 1.21E+09 |

The results for the Control, KMR-14-33 and for CIP are shown in FIG. 3.

Figure 4:
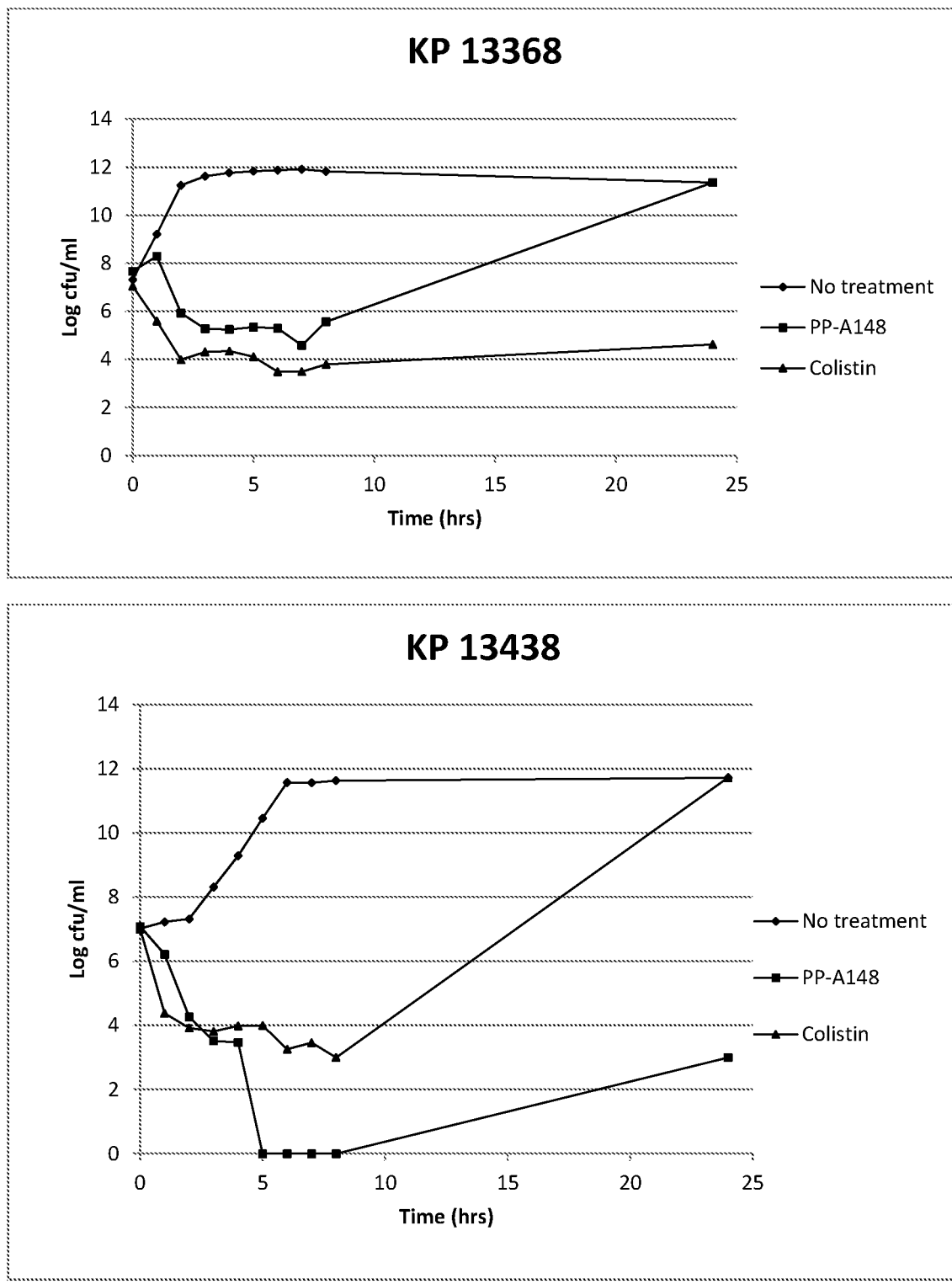
FIG. 4 shows time kill data against three *Klebsiella* species for a control (Ctrl), for a compound (PP-A148) and for the known antibiotic colistin.
Figure 4:
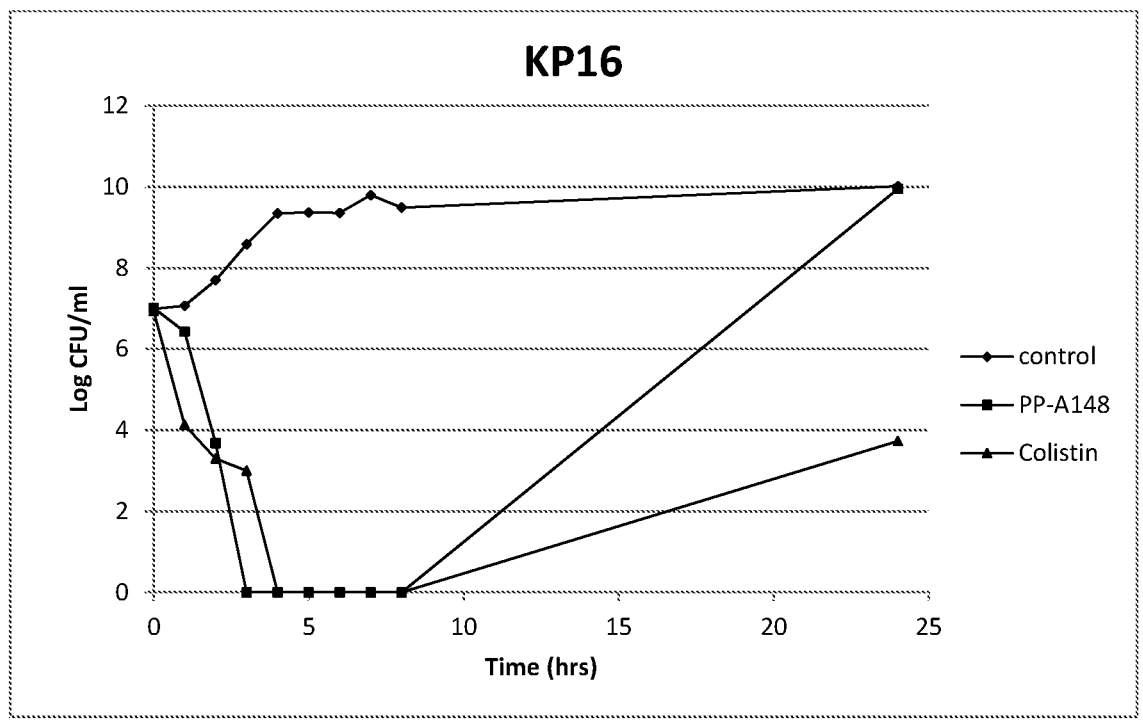

Using the same protocol as above, time kill data was obtain for compound PP-A148 against each of the *Klebisella* bacterial species KP 13368, KP 13438 and KP 16. In addition, measurements were made for a control containing no antibiotic and, for comparison, also for the known antibiotic collistin (available from Actavis plc) against each bacterial species. The results are shown in FIG. 4.

Compounds mediate rapid bactericidal kill with occasional breakthrough resistance in some drug-strain combinations.

Example 106

Effect of Efflux Pump Inhibitors (EPIs)

1. Grow up cultures of bacterial strains to be tested overnight.
2. Dilute down overnight cultures to concentration of $1 \times 10^6$ bacteria/ml (OD0.01) in Tryptic soy broth (TSB).
3. Add 100 µl of TSB media to column 2-column 12 in 96 well plate (keeping column 1 clear).
4. Make up compound to a concentration of 64 µg/ml in water.
5. Add 100 µl of antibiotic solution to the 1st and $2^{nd}$ columns.
6. Using a multichannel pipette take 100 µl from the $2^{nd}$ column wells and pipette into $3^{rd}$ column wells and repeat down the 96 well plate (remember to include controls i.e. uninfected media and media with no antibiotic).
7. To each well (except uninfected control row H) add 50 µl/well of EPI at 4× final concentration in TSB.
8. Add 50 µl/well bacteria at OD600=0.02.
9. In wells used to test the effect of the EPI carbonyl cyanide 3-chlorophenylhydrazone (CCCP) the CCCP is added at 10 µg/ml final concentration.
10. In wells used to test the effect of the EPI phenylalanine-arginine β-naphthylamide (PABN) the PABN is added at 25 µg/ml final concentration.
11. In wells used to test the effect of the PABN+Mg, the PABN is added at 25 µg/ml final concentration, with 1 mM $MgSO_4$ in TSB.
12. Wrap plate with parafilm to prevent evaporation.
13. Leave at desired temperature (37° C. unless specified elsewhere) for 20 hours.
14. Next day check plates for growth and measure optical density (i.e. absorbance) at a wavelength of 600 nm ($OD_{600}$).

Compound KMR-14-33 was tested against a range of bacterial species using the above protocol. Compound PP-A148 was also tested against a more limited range of bacterial species using the above protocol. For KMR-14-33 measurements were carried out for the compound alone, for the compound plus CCCP, for the compound plus PABN and for the compound plus PABN and plus Mg. For PP-A148 measurements were carried out for the compound alone and for the compound plus PABN. The MIC values obtained from these measurements are provided in Table 10 below.

TABLE 10

Results showing the Effect of Efflux Pump Inhibitors

| Bacterial Strain | Compound | Control with no EPI MIC (µg/ml) | +CCCP MIC (µg/ml) | +PABN MIC (µg/ml) | +PABN + Mg MIC (µg/ml) |
|---|---|---|---|---|---|
| M6 | PP-A148 | 0.25-0.5 | ND | 0.125 | ND |
|  | KMR-14-33 | 1 | 0.125 | 0.125 | 0.25 |
| NCTC 13368 | PP-A148 | 16-32 | ND | 2-8 | ND |
|  | KMR-14-33 | 2 | 2 | 1 | 0.5 |
| NCTC 13438 | KMR-14-33 | 0.5 | 0.5 | 0.125 | 0.25 |
| NCTC 17978 | PP-A148 | 2 | ND | 0.125-0.5 | ND |
|  | KMR-14-33 | 0.5 | 0.25 | 0.06 | 0.25 |
| AYE | PP-A148 | 2 | ND | 0.125-0.5 | ND |
|  | KMR-14-33 | 1 | 0.125 | 0.125 | 0.25 |
| NCTC 13424 | KMR-14-33 | 0.5 | 0.25 | 0.125 | 0.25 |
| PA01 | PP-A148 | 128 | ND | 4-8 | ND |
|  | KMR-14-33 | >32 | >32 | 4 | 2 |
| NCTC 13437 | PP-A148 | 16 | ND | 0.25-2 | ND |
|  | KMR-14-33 | >32 | >32 | 16 | 16 |

ND = not determined

Efflux pump inhibitors reduce the MIC for selected compounds in strains of *K. pneumoniae*, *A. bauamnnii* and *P. aeruginosa*. Hence, these results indicate that the compounds are being kept in the cell longer.

Example 107

Calculation of c Log P Values for PBD Derivatives

The values of c Log P were calculated for the compounds using Chembiodraw Ultra 14.0, CambridgeSoft. It was found that the addition of a third moiety (the $R_7$ substituent) bearing a nitrogen connected to, for example, a benzofused ring that is ultimately attached by the C8 position to the PBD results in molecules characterized by lower c Log P in comparison to the PBD monomers and dimers previously reported as active only against Gram positive strains. Literature sources (33, 34) indicate that antibacterial drugs, especially the ones active against Gram-negative bacteria, are characterized by higher polarity compared to the set of other classes of drugs.

The most active molecules in the new series are characterized by calculated log P<1. The only exception to this trend is given by KMR-14-33 that despite having a c Log P value of 1.8 is still one of the best molecule of the series. Considering the compounds with the third moiety being an aliphatic closed ring (morpholine, thiomorpholine and piperidine) the benzofuran series is more active than the benzothiophene one as benzofuran analogues have a lower c Log P values.

TABLE 11

| | cLogP for the Compounds | |
|---|---|---|
| Name | Structure | cLogP |
| PP-A147 | | 0.04 |
| PP-A148 | | 0.76 |
| PP-A159 | | 0.44 |
| PP-B15 | | 2.12 |
| PP-B16 | | 1.4 |

TABLE 11-continued cLogP for the Compounds

| Name | Structure | cLogP |
|---|---|---|
| KMR14-33 | 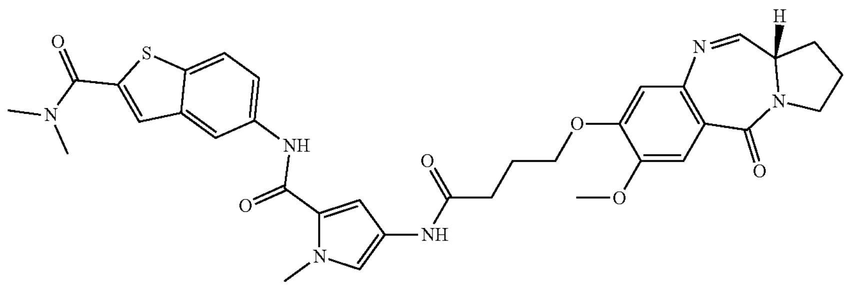 | 1.8 |
| PP-B22 | 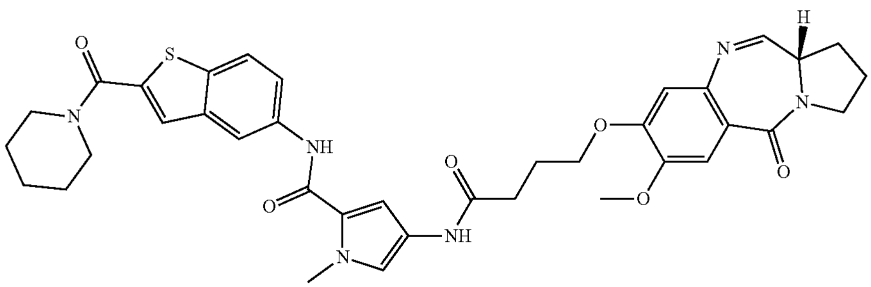 | 2.53 |
| PP-B26 | 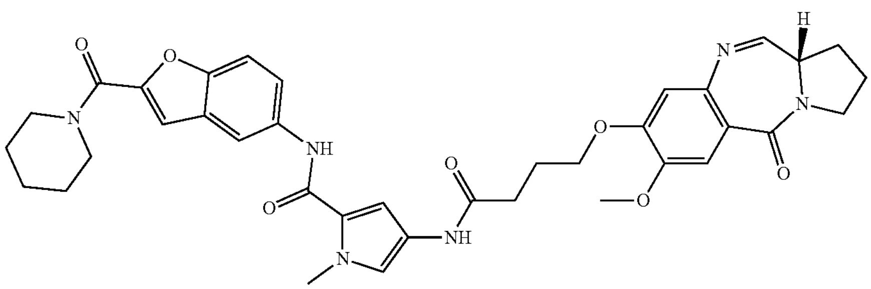 [SMILES: COc1cc2c(cc1OCCCC(=O)Nc1cc(C(=O)Nc3ccc4sc(C(=O)N5CCSCC5)cc4c3)n(C)c1)N=C[C@@H]1CCCN1C2=O] | 1.17 |
| PP-B27 | 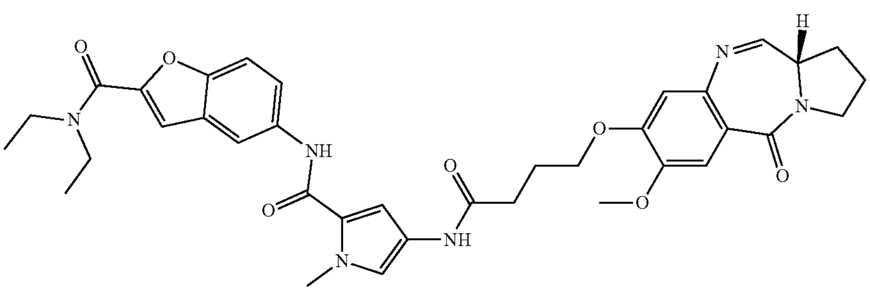 | 1.11 |
| PP-B28 | 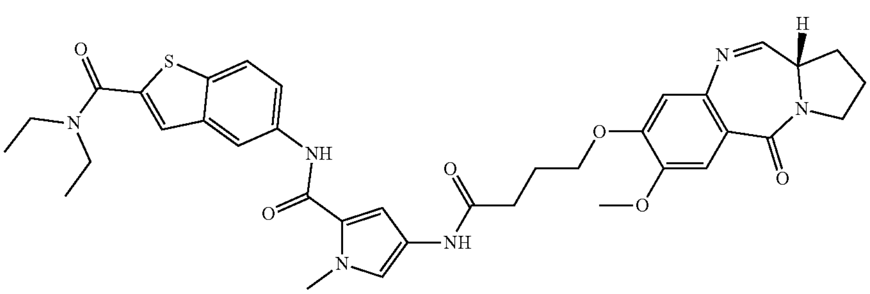 [SMILES: CCN(CC)C(=O)c1cc2cc(NC(=O)c3cc(NC(=O)CCCOc4cc5c(cc4OC)C(=O)N4CCC[C@H]4C=N5)cn3C)ccc2o1] | 2.48 |

Example 108

Cytotoxic Tests

Cell Culture

Two immortalised human cell lines, HeLa and WI38 were used for cytotoxicity screening of the compounds. HeLa is a human cervical cancer cell line and WI38 is a normal healthy cell line. The cell lines were obtained from the American Type Culture Collection. The cell-lines were maintained in monolayer culture in 75 cm2 flasks (TPP, Switzerland) under a humidified 5% CO2 atmosphere at 37° C. The HeLa cell line was maintained in Dulbecco's Modified Eagles Media (DMEM; Invitrogen) supplemented with foetal bovine serum (10% v/v; Invitrogen), L-glutamine (2 mM; Invitrogen), non-essential amino acids (1×; Invitrogen) and Penicillin-Streptomycin (1% v/v, Invitrogen). For WI38, Eagle's Minimum Essential Medium, and Penicillin-Streptomycin (1% v/v, Invitrogen) and foetal bovine serum (10%, nvitrogen) was used. For passaging, cells were washed with phosphate buffered saline [PBS] (GIBCO 14040, Invitrogen, UK), incubated with trypsine (GIBCO 25300, Invitrogen, UK), and re-seeded into fresh medium. For seeding, cells were counted using a Neubauer haemocytometer (Assistant, Germany) by microscopy (Nikon, USA) on a non-adherent suspension of cells that were washed in PBS, trypsinised, centrifuged at 8° C. at 8000 rpm for 5 min and re-suspended in fresh medium.

MTT Assay

The cells were grown in normal cell culture conditions at 37° C. under a 5% $CO_2$ humidified atmosphere using appropriate medium. The cell count was adjusted to $10^5$ cells/ml/ and 20,000 cells were added per well. The cells were incubated for 24 hours and 1 μl of the appropriate inhibitor concentrations were to the wells in triplicates. After 24 h of continuous exposure to each compound, the cytotoxicity was determined using the MIT (3-(4,5-Dimethylthiazol-2-yl)-2,5-diphenyltetrazolium bromide) (Lancaster Synthesis Ltd, UK) colorimetric assay. Absorbance was quantified by spectrophotometry at λ=570 nm (Envision Plate Reader, PerkinElmer, USA). IC50 values were calculated by a dose-response analysis using the Prism Graphpad Prism® software. The cytotoxicity results are shown below in Table 12.

TABLE 12

Cytotoxicity of C8-PBD compounds against eukaryotic cell lines $IC_{50}$ (μM)

| Compound | HeLa (Cervical cancer cell line) | WI38 (Healthy cell line)* |
|---|---|---|
| PP-A147 | >20 | >20 |
| PP-A148 | >20 | >20 |
| PP-A159 | 18.5 | >20 |
| KMR-14-33 | 15.6 | >20 |
| PP-B15 | >20 | >20 |
| PP-B16 | >20 | >20 |
| PP-B22 | >20 | >20 |
| PP-B26 | >20 | >20 |
| PP-B27 | >20 | >20 |
| PP-B28 | >20 | >20 |
| PP-A147 | >20 | >20 |

All compounds tested did not kill enough cells at the highest concentration tested (20 μM) to obtain a measurable $IC_{50}$.

Example 109

Activity Against Gram-Negative Panel Compared with Known Antibacterial Compounds The activity of the compound designated PP-A148 was tested against an extended panel of *Klebsiella* and *Pseudomonas* Gram-negative bacterial strains that have proven drug resistant difficult to treat. The effects were compared with those for three commercially available antibacterial compounds ciprofloxacin (available from Bayer plc), levofloxacin (available from Actavis plc) and collistin (available from Actavis plc). The minimum inhibitory concentration (MIC) was measured using the general MIC protocol given above. The results against this extended panel are given in Table 13 below.

TABLE 13

Results for the MIC of a selected compound PP-A418 compared with commercially available antibacterial agents against *Klebsiella* and *Pseudomonas* Gram-negative bacterial strains

| | | MIC (μg/ml) | | | |
|---|---|---|---|---|---|
| | | PP-A148 | Cipro-floxacin | Levo-floxacin | Collistin |
| *Psueudomonas* | GH12 | >128 | 16 | >16 | ND |
| | PA01 | >128 | 1 | 4 | ND |
| *Klebsiella* | NCTC 13443 | 16 | >16 | >16 | 2 |
| | NCTC 13439 | 4-8 | 8-16 | 16 | 4 |
| | NCTC 13438 | 4-8 | >16 | >16 | 2 |
| | KP 16 | 0.25-0.5 | >16 | 8-16 | 1 |
| | KP 342 | 4-8 | 0.125-0.25 | 0.5-1 | 4 |
| | KP 51851 | 4 | >16 | >16 | 64 |
| | MGH 78578 | 4-8 | 1 | 1 | 8 |

ND = Not Determined

Example 110

Activity Against Gram-Negative Strains Following Resistance Development

The MIC of PP-A418 and colistin against the strains used in the time kill analysis of Example 31 following resistance development were measured. The MIC was measured using the general MIC protocol given above. The results are given in Table 14 below where the MIC values of resistant mutants are shown in the brackets.

TABLE 14

Results for the MIC of PP-A148 and colistin following resistance

| | MIC (μg/ml) | |
|---|---|---|
| | PP-A148 | Colistin |
| KP 16 | 0.25-0.5 (4-8) | 2-4 (64-128) |
| KP 13368 | 16-32 (>128) | 4 (32-64) |
| KP 13438 | 4-8 (64) | 2 (64-128) |

Example 40

Gyrase Activity and DNA Topoisomerase Assays

The effect of the antimicrobial agents on gyrase was assessed using *E. coli* gyrase microplate assay kit (# TRG01)

and with *S. aureus* gyrase microplate assay kit (# SATRG01). The effect of topoisomerase IV using was assessed using *E. coli* Topo IV microplate assay kit (# TRIV01) and with the *S. aureus* Topo IV microplate assay kit (# SATRIV01). All of these assay kits were obtained from Inspiralis (Norwich, UK). These assay kits are supplied with the relevant enzyme, substrate and buffers.

Gyrase Protocol

1. Rehydrate wells with 3×200 µl Wash buffer (diluted from 20× stock with ultra-pure water).
2. Immobilise 100 µl of 500 nM TF01 oligo in each well (5 µl of 10 µM TF01 oligo in 95 µl wash buffer).
3. Incubate 5 minutes at room temperature.
4. Wash off excess oligo with 3×200 µl Wash buffer.
5. Incubate 2U (0.4 µl stock) of gyrase with 0.75 µg of relaxed pN01 in a reaction volume of 30 µl at 37° C. for 30 minutes in assay buffer—This is the part agent is added therefore the reaction volume is adjusted to account for this.
6. Add 100 µl TF buffer (diluted from 20× stock) to well and incubate for a further 30 minutes at room temperature to allow triplex formation.
7. Remove liquid from well and wash with 3×200 µl TF buffer to wash away unbound plasmid.
8. Stain with DNA detection dye (diluted to ix with T10 buffer). Add 200 µl per well and incubate for 10-20 minutes at room temperature.
9. Mix well and read in fluorescence plate reader Excitation wavelength: 495 nm; Emission wavelength: 537 nm. Use 485/520 filters in plate reader in 231.
10. If required 10 µl of sample can be used to run on 1% agarose gel.

Amount of agent to add:

As the reaction volume is 30 µl make concentrations at 30× greater than required so 1 µl of the appropriate concentration can be added to the reaction. For each agent concentrations from a range of 10-75 µM.

The procedure for assessing effect of the agents on topoisomerase IV was the same as for the gyrase apart from the following changes; 1.5 U of topoisomerase IV was used in place of gyrase and supercoiled pN01 instead of relaxed pN01 was used in step 5. Results obtained were normalised using the following equation:

$$Xi_{O-1} = \frac{Xi - Xmin}{X_{max} - X_{min}}$$

Xi—each data point
$X_{min}$—minima among all data points
$X_{max}$—maxima among all data points
$Xi_{0-1}$—data point normalised between 0-1

Figure 5:
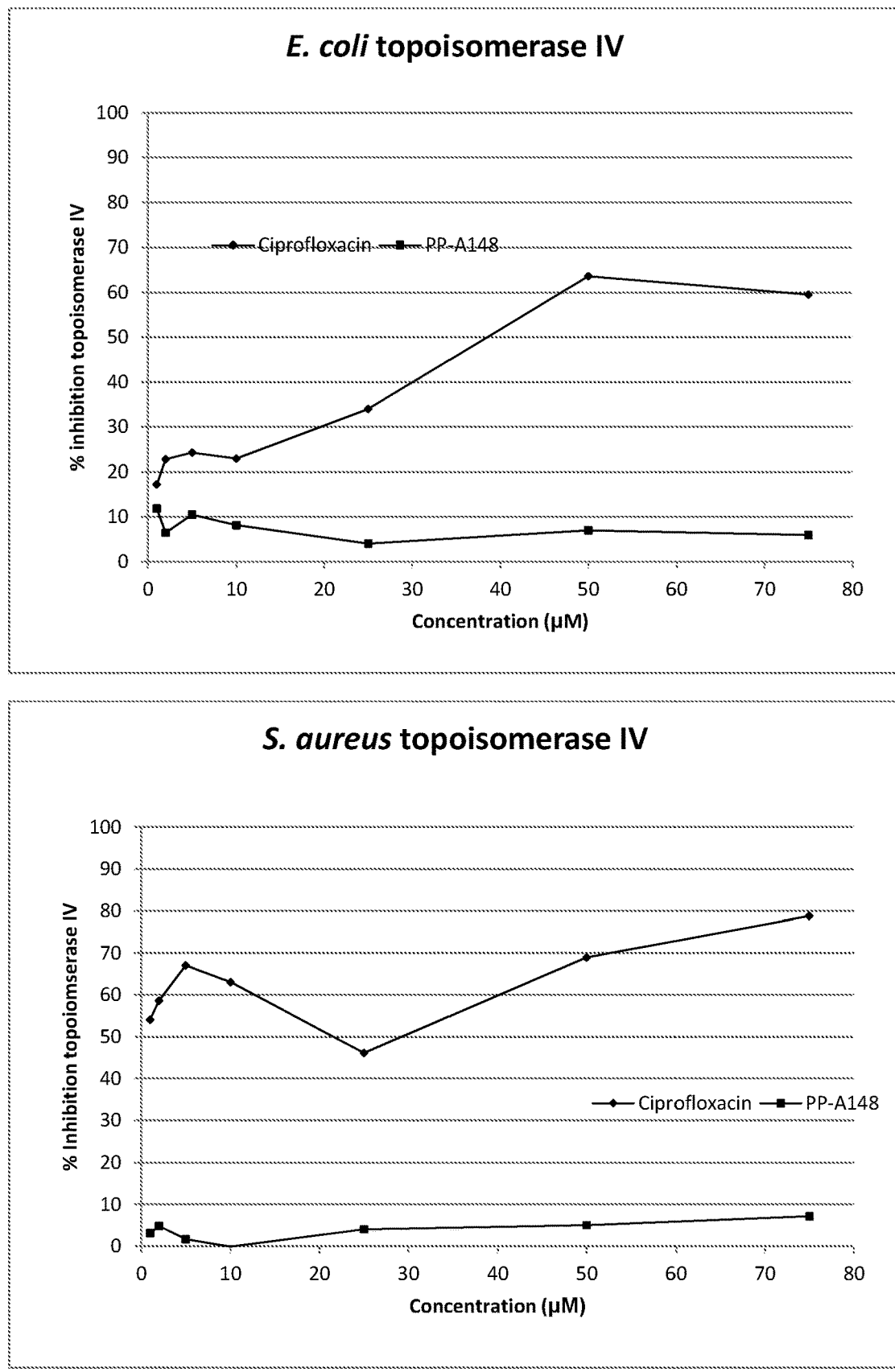
FIG. 5 shows the interaction of PP-A148 and CIP with topoisomerase IV from *E. coli*, and *S. aureus* a) and b) respectively.
Figure 6:
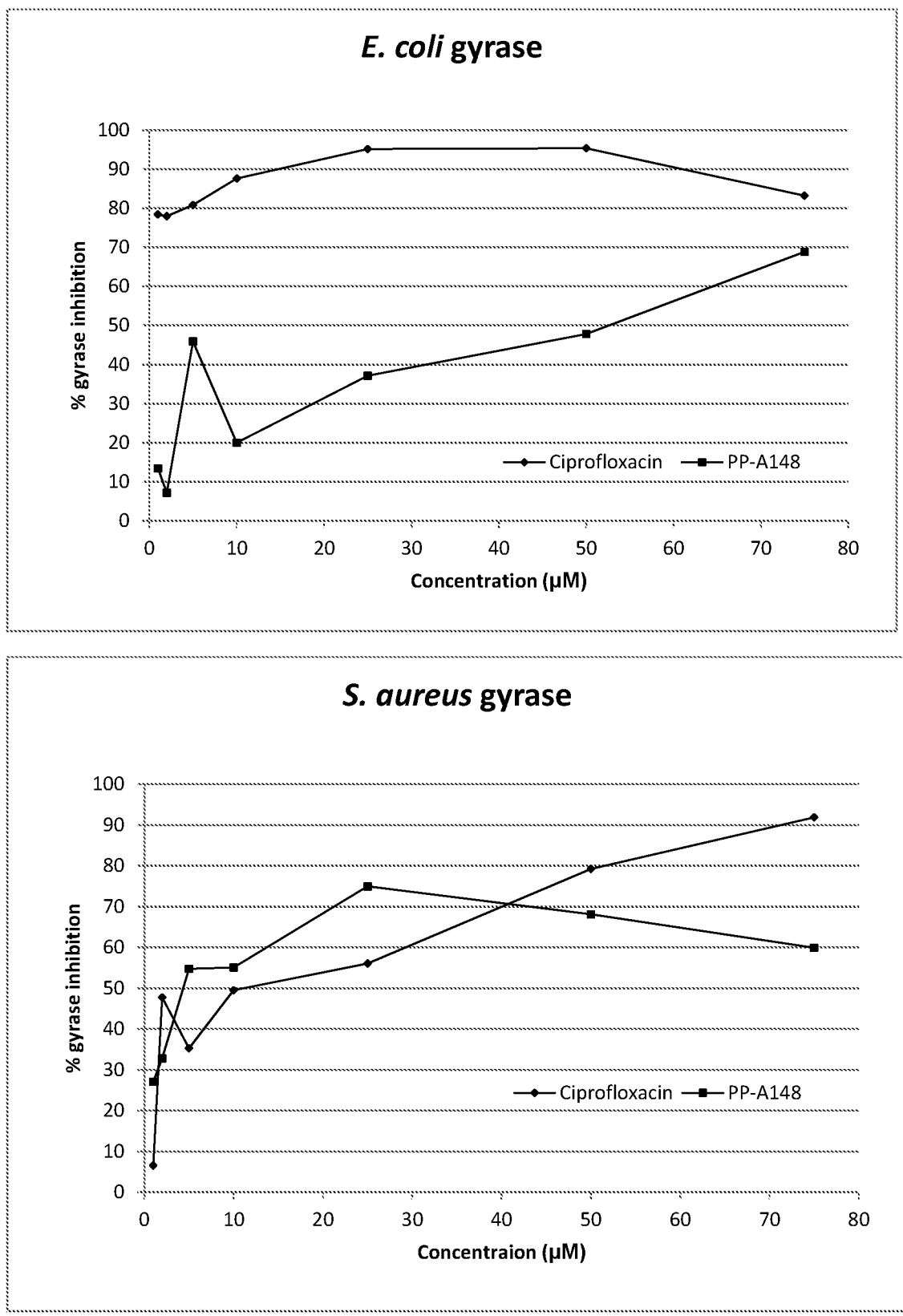
FIG. 6 shows the interaction of PP-A148 and CIP with gyrase from *E. coli*, and *S. aureus*.

The results for the effect of PP-A148 and for the known antibacterial agent ciprofloxacin on topoisomerase IV are shown in FIG. 5 and those for the effect on gyrase are shown in FIG. 6.

As can be seen, the test compound PP-A148 inhibits DNA gyrase but does not inhibit topoisomerase IV. This contrast with ciprofloxacin which inhibits DNA gyrase and both topoisomerase IV. This difference in behaviour indicates that PP-A148 has a novel mechanism of action.

Example 111

Activity Against *Pseudomonas* Strains

The activity of compound KMR-14-33 alone and in the presence of polymyxin B nonapeptide (PMBN) at 30 µg/ml against two *Pseudomonas* strains (PA01 and NCTC 13437) was measured. The MIC was measured using the general MIC protocol given above. The results are given in Table 15 below.

TABLE 15

Results for the MIC of KMR-14-33 alone and with PMBN against two *Pseudomonas* strains

|  | PA01 | NCTC 13437 |
| --- | --- | --- |
| KMR-14-33 | >32 | 32 |
| KMR-14-33 + PMBN | 2-16 | <0.03-1 |

These results show that a compound of the invention can be highly active against two *Pseudomonas* bacterial species that against which it is routine to test, provided that the compound can access the cell interior.

All publications mentioned in the above specification are herein incorporated by reference. Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

REFERENCES

1. Antonow, D., and Thurston, D. E. (2011) *Chem Rev* 111, 2815-2864.
2. Cipolla, L., Araujo, A. C., Airoldi, C., and Bini, D. (2009) *Anticancer Agents Med Chem* 9, 1-31.
3. Gerratana, B. (2012) *Med Res Rev* 32, 254-293.
4. Hartley, J. A. (2011) *Expert Opin Investig Drugs* 20, 733-744.
5. Kamal, A., Reddy, K. L., Devaiah, V., Shankaraiah, N., and Reddy, D. R. (2006) *Mini Rev Med Chem* 6, 53-69.
6. Hurley, L. H., Reck, T., Thurston, D. E., Langley, D. R., Holden, K. G., Hertzberg, R. P., Hoover, J. R., Gallagher, G., Jr., Faucette, L. F., Mong, S. M., (1988) *Chem Res Toxicol* 1, 258-268.
7. Wells, G., Martin, C. R., Howard, P. W., Sands, Z. A., Laughton, C. A., Tiberghien, A., Woo, C. K., Masterson, L. A., Stephenson, M. J., Hartley, J. A., Jenkins, T. C., Shnyder, S. D., Loadman, P. M., Waring, M. J., and Thurston, D. E. (2006) *J Med Chem* 49, 5442-5461.
8. Brucoli, F., Hawkins, R. M., James, C. H., Jackson, P. J., Wells, G., Jenkins, T. C., Ellis, T., Kotecha, M., Hochhauser, D., Hartley, J. A., Howard, P. W., and Thurston, D. E. (2013) *J Med Chem* 56, 6339-6351.
9. Kotecha, M., Kluza, J., Wells, G., O'Hare, C. C., Forni, C., Mantovani, R., Howard, P. W., Morris, P., Thurston, D. E., Hartley, J. A., and Hochhauser, D. (2008) *Mol Cancer Ther* 7, 1319-1328.
10. Puvvada, M. S., Hartley, J. A., Jenkins, T. C., and Thurston, D. E. (1993) *Nucleic Acids Res* 21, 3671-3675.
11. Clingen, P. H., De Silva, I. U., McHugh, P. J., Ghadessy, F. J., Tilby, M. J., Thurston, D. E., and Hartley, J. A. (2005) *Nucleic Acids Res* 33, 3283-3291.
12. Puvvada, M. S., Forrow, S. A., Hartley, J. A., Stephenson, P., Gibson, I., Jenkins, T. C., and Thurston, D. E. (1997) *Biochemistry* 36, 2478-2484.
13. Barkley, M. D., Cheatham, S., Thurston, D. E., and Hurley, L. H. (1986) *Biochemistry* 25, 3021-3031.

14. Seifert, J., Pezeshki, S., Kamal, A., and Weisz, K. (2012) *Organic & Biomolecular Chemistry* 10, 6850-6860.
15. Smellie, M., Bose, D. S., Thompson, A. S., Jenkins, T. C., Hartley, J. A., and Thurston, D. E. (2003) *Biochemistry* 42, 8232-8239.
16. Kopka, M. L., et al., (1994) *Biochemistry* 33, 13593-13610.
17. Kizu, R., Draves, P. H., and Hurley, L. H. (1993) *Biochemistry* 32, 8712-8722.
18. Leimgruber, W., Stefanovic, V., Schenker, F., Karr, A., and Berger, J. (1965) *J Am Chem Soc* 87, 5791-5793.
19. Arima, K., et al., (1972) *J Antibiot (Tokyo)* 25, 437-444.
20. Sato, S., Iwata, F., Yamada, S., Kawahara, H., and Katayama, M. (2011) *Bioorg Med Chem Lett* 21, 7099-7101.
21. Thurston D. E. and Bose D. S., *Chem Rev* (1994); 94:433-465.
22. Damayanthi, Y., et al.; *Journal of Organic Chemistry* (1999), 64, 290-292;
23. Kumar, et al., *Heterocyclic Communications* (2002) 8, 19-26.
24. Kumar, R, Lown, J. W.; *Oncology Research*, (2003) 13, 221-233.
25. Baraldi, P. G. et al., *Journal of Medicinal Chemistry* (1999) 42, 5131-5141.
26. Wells, G., et al., *Proc. Am. Assoc. Canc. Res.* (2003) 44, 452.
27. Thurston, D. E.; Howard, P. W. WO 2004/043963.
28. Levy S B, Marshall B., *Nature Medicine* (2004) 10, S122-S129.
29. Davies J, Davies D., *Microbiology and Molecular Biology Reviews* (2010) 74, 417-433.
31. Hadjivassileva, T., Thurston, D. E.; Taylor, P. W., *Journal of Antimicrobial Chemotherapy* (2005) 56, 513-518.
32. Rahman K M, et al., *Journal of Medicinal Chemistry* (2013) 56, 2911-2935.
33. O'Shea, R. et al. *J. Med. Chem.*, (2008) 51, 2871-2878.
34. Brown, D G. et al. *J. Med. Chem.*, (2014) 57, 10144-10161.
35. Turton, J F. et al. *J. Clin Microbiol*, (2005) 43, 3074-3082.
36. Turton, J F. et al. *Clin Microbiol Infect*, (2007) 13, 807-815.
37. Smith, K. et al. *Antimicrob Agents Chemother*, (2010) 54, 380-387.
38. Masschelein, J, et al. *Appl. Environ. Microbiol.* (2015) 81, 1139-1146.
39. Loessner, M. J., *Curr. Opin. Microbiol.* (2005) 8, 480-487.
40. Borysowski J, et al. *Exp Biol Med (Maywood)*, (2006) 231, 366-77.
41. Schmelcher M, et al. *Future Microbiol.* (2012) 7, 1147-1171
42. Nakonieczna, A., et al., *Journal of Applied Microbiology* (2015) 119, 620-631.
43. Melton, R. G., et al., *J. of the National Cancer Institute*, (1996) 88, 153-165.
44. Rooseboom, M., et al., *Pharmacological Reviews*, (2004) 56, 53-102.
45. Huttunen, K. M., et al., *Pharmacological Reviews*, (2011) 63, 750-771.
46. Stella V J, et al., *Prodrugs: Challenges and Rewards Part* 1 & 2, (2007) Springer Science BusinessMedia, New York.
47. Alouane, A., et al., *Angewandte Reviews*, (2015) 54, 7492-7509.

What is claimed:
1. A compound of formula (I):

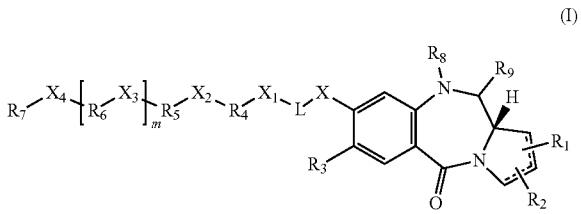

and salts and solvates thereof;
wherein:
the dotted lines indicates the optional presence of a double bond between C1 and C2, or C2 and C3;
X is $(CR_{15}R_{16})_nO$, $O(CR_{15}R_{16})_n$, S, $NR_{15}$, $CR_{15}R_{16}$, C(O), $C(O)NR_{15}$, $NR_{15}C(O)$, O—C(O) or C(O)—O;
$X_1$ is $(CH_2)_pO$, $O(CH_2)_p$, C(O), NHC(O), C(O)NH or is absent;
$X_2$ is $(CH_2)_qO$, $O(CH_2)_q$, C(O), NHC(O), C(O)NH or is absent;
$X_3$ is $(CH_2)_sO$, $O(CH_2)_s$, C(O), NHC(O), C(O)NH or is absent;
$X_4$ is $(CH_2)_tO$, $O(CH_2)_t$, C(O), NHC(O), or C(O)NH;
L is $C_{1-12}$ alkylene;
$R_1$ is H, $C_{1-6}$ alkyl, $OC_{1-6}$ alkyl, OH, CN, =$CHR_{17}$, halogen, $CO_2H$ or $CO_2(C_{1-6}$ alkyl);
$R_2$ is H, $C_{1-6}$ alkyl, $OC_{1-6}$ alkyl, OH, CN, =$CHR_{18}$, halogen, $CO_2H$ or $CO_2(C_{1-6}$ alkyl);
$R_3$ is H, F, OH, $OC_{1-6}$ alkyl, $OCH_2Ph$, a monosaccharide moiety or an amino monosaccharide moiety, wherein the monosaccharide and amino monosaccharide moieties may be optionally acetyl substituted;
$R_4$, $R_5$ and $R_6$ are independently phenylene, cyclopentanylene, cyclohexanylene, 5- to 9-membered heteroarylene or 5- to 6-membered hetereocyclylene groups, and these groups are optionally substituted with up to three optional substituent groups each independently selected from the group consisting of: OH, $C_{1-6}$ alkyl, $OC_{1-6}$ alkyl, halogen, $(CH_2)_j$—$CO_2R_{10}$ and $(CH_2)_j$—$NR_{10}R_{11}$;
$R_7$ is $N(C_{1-6}$ alkyl)($C_{1-6}$ alkyl), 5- to 6-membered nitrogen-containing hetereocyclyl groups, a monosaccharide moiety or an amino monosaccharide moiety, wherein these nitrogen-containing hetereocyclyl groups are optionally substituted with up to three optional substituent groups each independently selected from the group consisting of: OH, $C_{1-6}$ alkyl, $OC_{1-6}$ alkyl, halogen, $(CH_2)_k$—$CO_2R_{12}$, $(CH_2)_k$—$NR_{12}R_{13}$ and a prodrug moiety, and wherein the monosaccharide and amino monosaccharide moieties may be optionally acetyl substituted;
$R_8$ and $R_9$ either together form a double bond, or are H or $OR_{14}$, or $R_8$ is a prodrug moiety and $R_9$ is $OR_{14}$;
m is 0 or 1;
j, k, n, p, q, s and t are each independently an integer from 0 to 6;
v is an integer from 1 to 6; and
each $R_{10}$, $R_{11}$, $R_{12}$, $R_{13}$, $R_{15}$, $R_{16}$, $R_{17}$ and $R_{18}$ are independently H or $C_{1-6}$ alkyl;
$R_{14}$ is H, $C_{1-6}$ alkyl or tetrahydro-2H-pyran-2-yl;
with the proviso that when $X_4$ is C(O)NH then the up to three optional substituents of $R_7$ are not $(CH_2)_k$—$CO_2R_{12}$;

with the proviso that when $X_4$ is $(CH_2)_tO$ then $R_4$ is not phenylene, m is 1 and $R_6$ is not a 5- to 9-membered heteroarylene; and with the proviso that when $X_4$ is C(O)NH or NHC(O) that $R_4$, $R_6$, or both $R_4$ and $R_6$ are not 5- to 9-membered heteroarylene.

2. A compound of formula (I) and salts and solvates thereof according to claim 1, wherein:
- $R_3$ is H, OH, $OC_{1-6}$ alkyl or $OCH_2Ph$;
- $R_7$ is $N(C_{1-6}$ alkyl)$(C_{1-6}$ alkyl) or 5- to 6-membered nitrogen-containing hetereocyclyl groups, and these hetereocyclyl groups are optionally substituted with up to three optional substituent groups each independently selected from the group consisting of: OH, $C_{1-6}$ alkyl, $OC_{1-6}$ alkyl, halogen, $(CH_2)_k$—$CO_2R_{12}$ and $(CH_2)_k$—$NR_{12}R_{13}$;
- $R_8$ and $R_9$ either together form a double bond, or are H or $OR_{14}$; and
- $R_{14}$ is H or $C_{1-6}$ alkyl.

3. A compound of formula (I) and salts and solvates thereof according to claim 1, wherein $R_1$ is H.

4. A compound of formula (I) and salts and solvates thereof according to claim 1, wherein $R_2$ is H.

5. A compound of formula (I) and salts and solvates thereof according to claim 1, wherein $R_3$ is $OCH_3$ or $OCH_2CH_3$.

6. A compound of formula (I) and salts and solvates thereof according to claim 1, wherein $R_4$ is phenylene, cyclopentanylene, cyclohexanylene, pyrrolylene, N-methylpyrrolylene, furanylene, thiophenyenel, N-methylimidazolylene, imidazolylene, triazolylene, oxazolylene, oxadiazolylene, thiazolylene, pyridinylene, indolylene, N-methylindolylene, benzofuranylene, benzothiophenylene, benzimidazolylene, N-methylbenzoimidazolylene, benzoxazolylene, benzothiazolylene, pyrrolidinylene, tetrahydrofuranylene, tetrahydrothiphenylene, imidazolidinylene, pyrazolidinylene, oxazol idinylene, isoxazolidinylene, thiazolidinylene, isothiazolidinylene, piperidinylene, oxanylene, thianylene, pipazinylene, morpholinylene or thiomorpholinylene groups, and these groups are optionally substituted with up to three optional substituent groups each independently selected from the group consisting of: OH, $C_{1-6}$ alkyl, $OC_{1-6}$ alkyl, halogen, $(CH_2)_j$—$CO_2R_{10}$ and $(CH_2)_j$—$NR_{10}R_{11}$.

7. A compound of formula (I) and salts and solvates thereof according to claim 1, wherein $R_5$ is phenylene, cyclopentanylene, cyclohexanylene, pyrrolylene, N-methylpyrrolylene, furanylene, thiophenyenel, N-methylimidazolylene, imidazolylene, triazolylene, oxazolylene, oxadiazolylene, thiazolylene, pyridinylene, indolylene, N-methylindolylene, benzofuranylene, benzothiophenylene, benzimidazolylene, N-methylbenzoimidazolylene, benzoxazol ylene, benzothiazolylene, pyrrolidinylene, tetrahydrofuranylene, tetrahydrothiphenylene, imidazolidinylene, pyrazolidinylene, oxazolidinylene, isoxazolidinylene, thiazolidinylene, isothiazolidinylene, piperidinylene, oxanylene, thianylene, pipazinylene, morpholinylene or thiomorpholinylene groups, and these groups are optionally substituted with up to three optional substituent groups independently selected from the group consisting of: OH, $C_{1-6}$ alkyl, $OC_{1-6}$ alkyl, halogen, $(CH_2)_j$—$CO_2R_{10}$ and $(CH_2)_j$—$NR_{10}R_{11}$.

8. A compound of formula (I) and salts and solvates thereof according to claim 1, wherein $R_7$ is $N(C_{1-6}$ alkyl)$(C_{1-6}$ alkyl) and 5- to 6-membered nitrogen-containing hetereocyclyl groups selected from pyrrolidinyl, imidazolidinyl, pyrazolidinyl, oxazolidinyl, isoxazolidinyl, thiazolidinyl, isothiazolidinyl, piperidinyl, pipazinyl, morpholinyl or thiomorpholinyl, and these hetereocyclyl groups are optionally substituted with up to three optional substituent groups each independently selected from the group consisting of: OH, $C_{1-6}$ alkyl, $OC_{1-6}$ alkyl halogen, $(CH_2)_k$—$CO_2R_{12}$ and $(CH_2)_k$—$NR_{12}R_{13}$.

9. A compound of formula (I) and salts and solvates thereof according to claim 1, wherein X is O, C(O), C(O)NH or NHC(O).

10. A compound of formula (I) and salts and solvates thereof according to claim 1, wherein $X_1$ is NHC(O).

11. A compound of formula (I) and salts and solvates thereof according to claim 1, wherein $X_2$ is NHC(O).

12. A compound of formula (I) and salts and solvates thereof according to a claim 1, wherein $X_4$ is $(CH_2)_tO$ or C(O).

13. A compound of formula (I) and salts and solvates thereof according claim 1, wherein the compound is a compound of formula (IX):

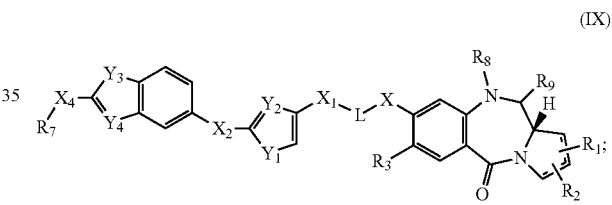

wherein:
- $Y_1$ is NH, N($C_{1-6}$ alkyl), S or O;
- $Y_2$ is CH, N, S or O;
- $Y_3$ is NH, N($C_{1-6}$ S or O; and
- $Y_4$ is CH, N, S or O.

14. A compound of formula (I) and salts and solvates thereof according to claim 1, wherein the compound is:
(aa) (S)—N-(2-(dimethylcarbamoyl)benzo[b]thiophen-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

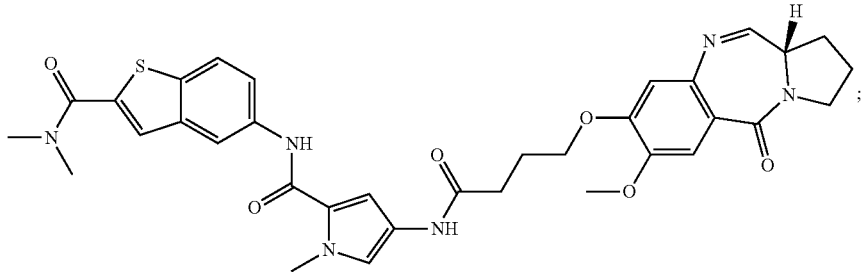

(KMR-14-33)

(ab) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(thiomorpholine-4-carbonyl)benzo-furan-5-yl)-1H-pyrrole-2-carboxamide

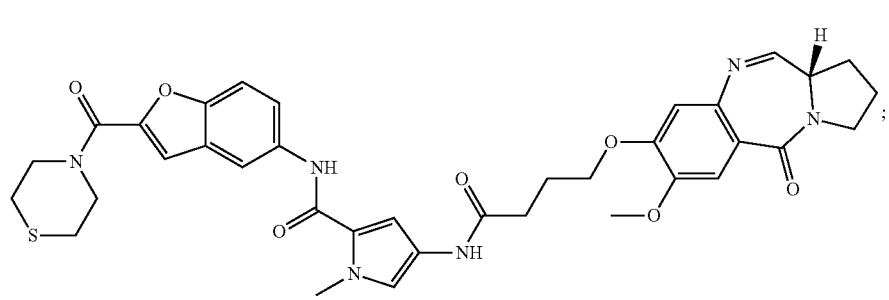

(PP-A148)

(ac) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(2-(morpholine-4-carbonyl)benzofuran-5-yl)-1H-pyrrole-2-carboxamide

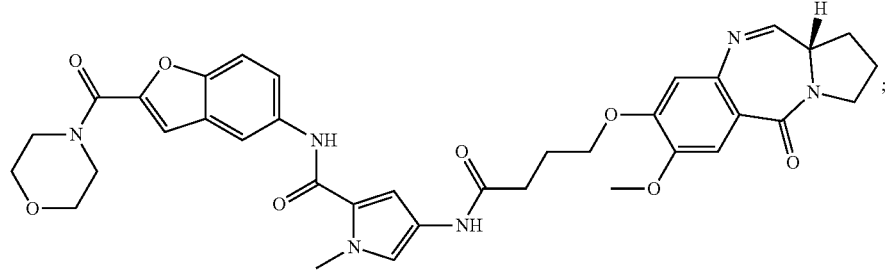

(PP-A147)

(ad) (S)—N-(2-(dimethylcarbamoyl)benzofuran-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

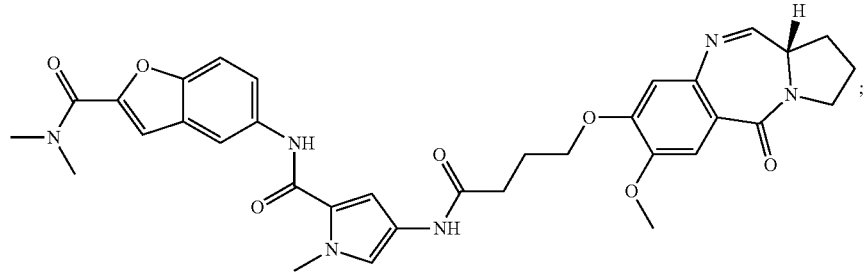

(PP-A159)

(ae) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(thiomorpholine-4-carbonyl)benzo-[b]thiophen-5-yl)-1H-pyrrole-2-carboxamide

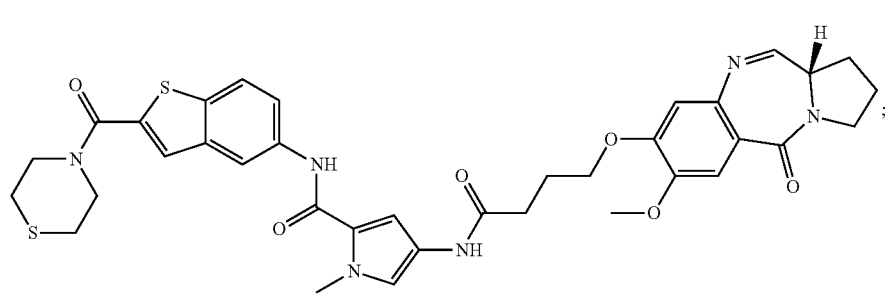
(PP-B15)

(af) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(2-(morpholine-4-carbonyl)benzo[b]-thiophen-5-yl)-1H-pyrrole-2-carboxamide

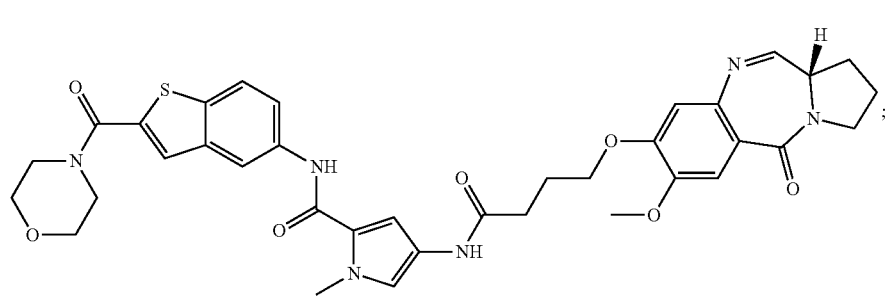
(PP-B16)

(ag) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(piperidine-1-carbonyl)benzo[b]-thiophen-5-yl)-1H-pyrrole-2-carboxamide

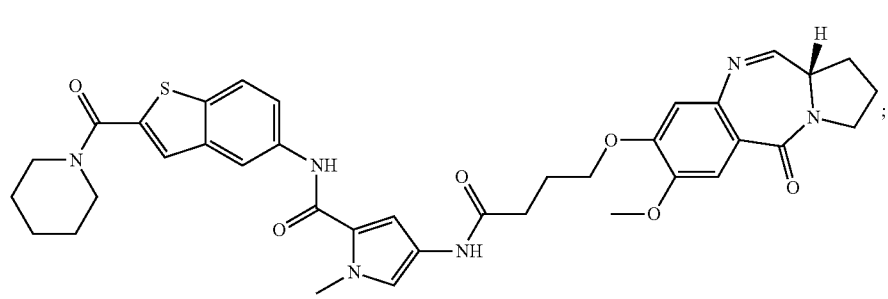
(PP-B22)

(ah) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(2-(piperidine-1-carbonyl)benzofuran-5-yl)-1H-pyrrole-2-carboxamide

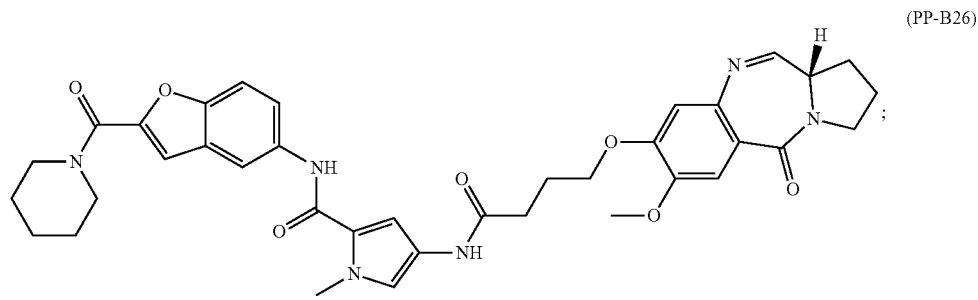 [SMILES: COc1cc2c(cc1OCCCC(=O)Nc1cc(C(=O)Nc3ccc4sc(C(=O)N5CCOCC5)cc4c3)n(C)c1)N=C[C@@H]1CCCN1C2=O]
(PP-B26)

(ai) (S)—N-(2-(diethylcarbamoyl)benzofuran-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

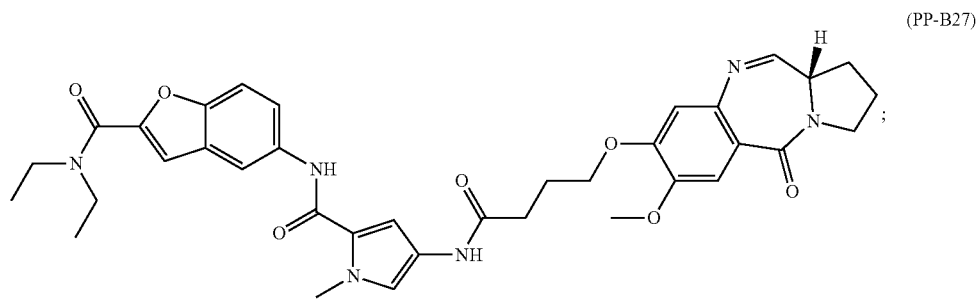 [SMILES: CCN(CC)C(=O)c1cc2cc(NC(=O)c3cc(NC(=O)CCCOc4cc5c(cc4OC)C(=O)N4CCC[C@H]4C=N5)cn3C)ccc2o1]
(PP-B27)

(aj) (S)—N-(2-(diethylcarbamoyl)benzo[b]thiophen-5-yl)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide

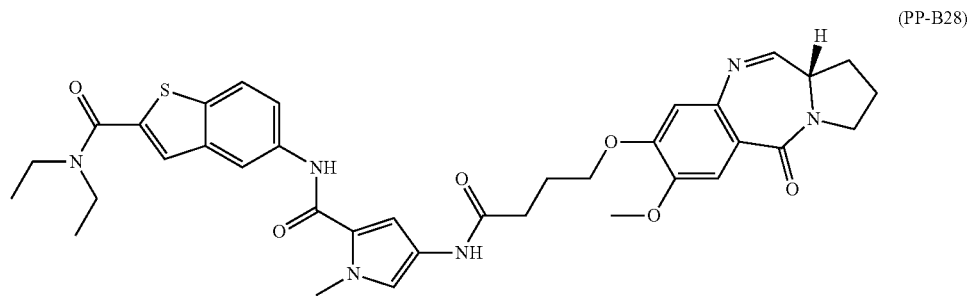 [SMILES: CCN(CC)C(=O)c1cc2cc(NC(=O)c3cc(NC(=O)CCCOc4cc5c(cc4OC)C(=O)N4CCC[C@H]4C=N5)cn3C)ccc2s1]
(PP-B28)

(ak) (S)-4-(4-47-methoxy-5-oxo-2,3,5,11a-tetrahydro-1H-benzo-[e]pyrrolo[1,2-a][1,4]-diazepin-8-yl)oxy)butanamido)-1-methyl-N-(2-(thio-morpholine-4-carbonyl)benzo-furan-5-yl)-1H-imidazole-2-carboxamide

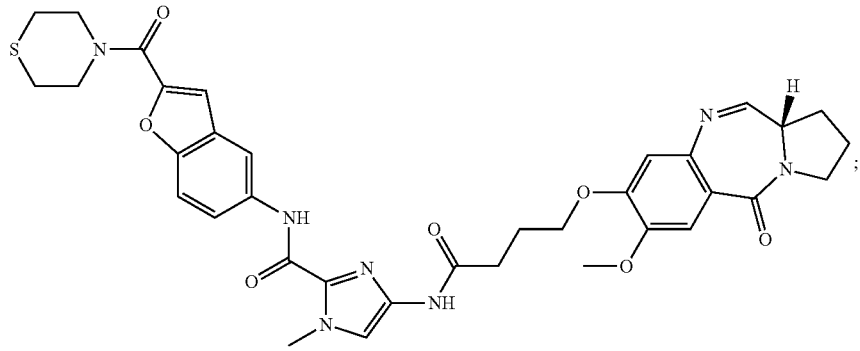

(PP-B52)

(al) (1S,4R)-4-(4-(((S)-7-methoxy-5-oxo-2,3,5,11a-tetrahydro-1H-benzo[e]pyrrolo[1,2-a][1,4]diazepin-8-yl)oxy)butanamido)-N-(2-(thio-morpholine-4-carbonyl)benzofuran-6-yl)cyclohexane-1-carboxamide

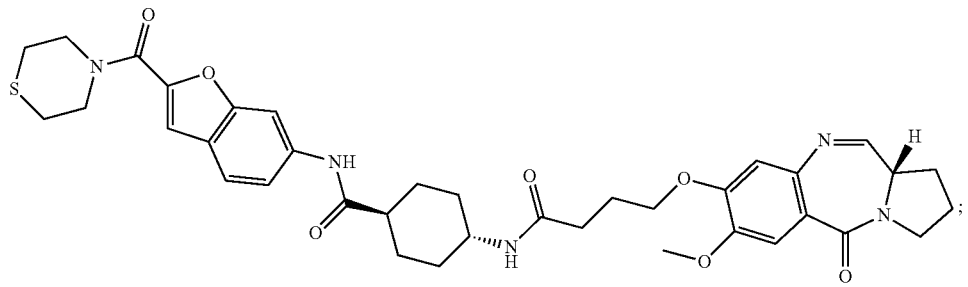

(PP-B53)

(am) (1R,4S)-4-(4-(((S)-7-methoxy-5-oxo-2,3,5,11a-tetrahydro-1H-benzo[e]pyrrolo[1,2-a][1,4]diazepin-8-yl)oxy)butanamido)-N-(2-(thio-morpholine-4-carbonyl)benzofuran-6-yl)cyclohexane-1-carboxamide

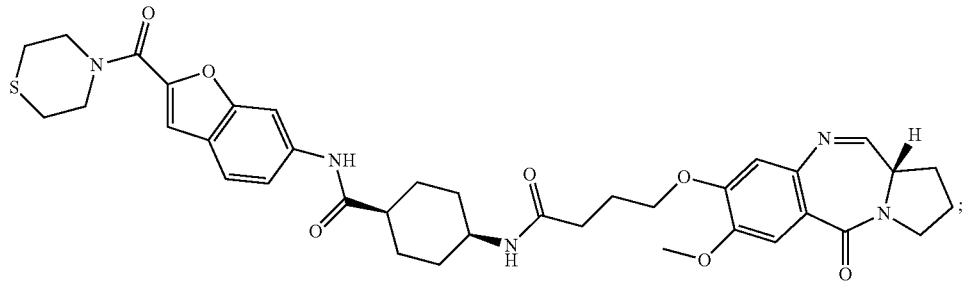

(PP-B54)

(an) (S)-4-(4-47-methoxy-5-oxo-2,3,5,11a-tetrahydro-1H-benzo[e]pyrrolo[1,2-a][1,4]-diazepin-8-yl)oxy)butanamido)-N-(2-(thiomorpholine-4-carbonyl)benzofuran-6-yl)-benzamide (PP-B57)

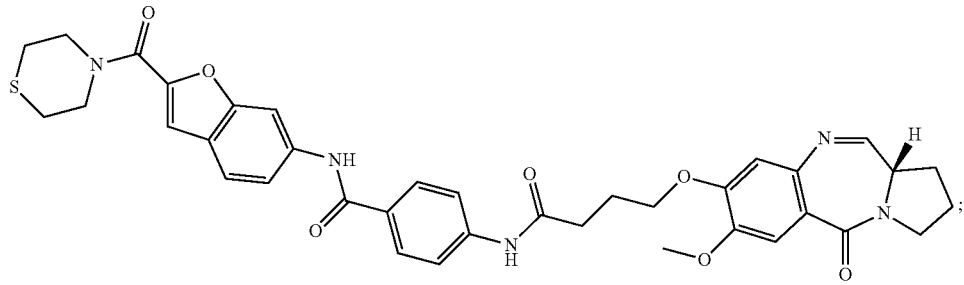

(ao) (S)—N-(2-(dimethylcarbamoyl)benzo[b]-thiophen-5-yl)-4-(4-4-((7-methoxy-5-oxo-2,3,5,11a-tetrahydro-1H-benzo[e]-imidazole[1,2-a][1,4]diazepin-8-yl)oxy)butan-amido)-1-methyl-1H-pyrrole-2-carboxamide (PP-B73)

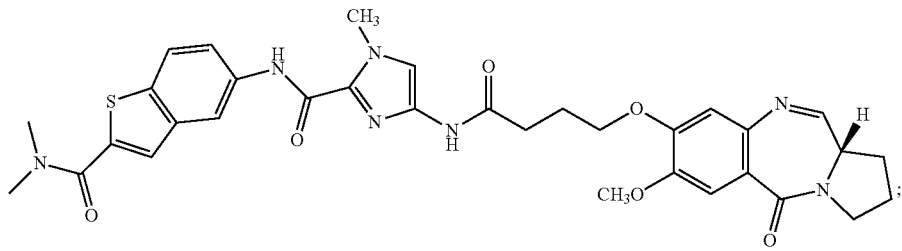

(ap) (S)-4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)-N,N,1-trimethyl-1H-pyrrole-2-carboxamide (LDM-46)

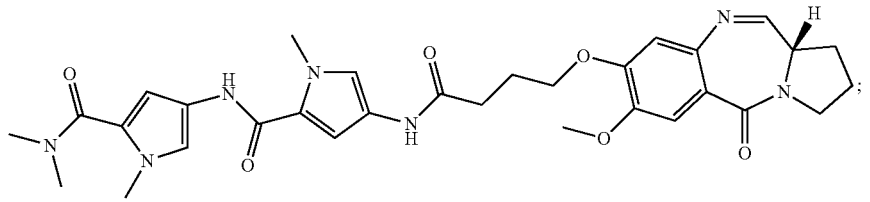

(aq) (S)—N,N-diethyl-4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carbox-amido)-1-methyl-1H-pyrrole-2-carboxamide

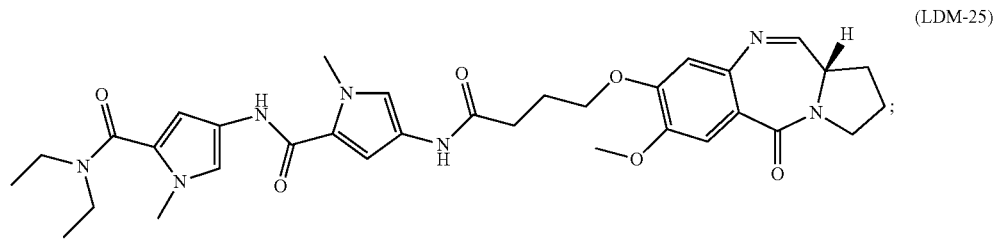 [SMILES: CCN(CC)C(=O)c1cc(NC(=O)c2cc(NC(=O)CCCOc3cc4c(cc3OC)C(=O)N3CCC[C@H]3C=N4)cn2C)cn1C]
(LDM-25)

(ar) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(pyrrolidine-1-carbonyl)-1H-pyrrol-3-yl)-1H-pyrrole-2-carboxamide

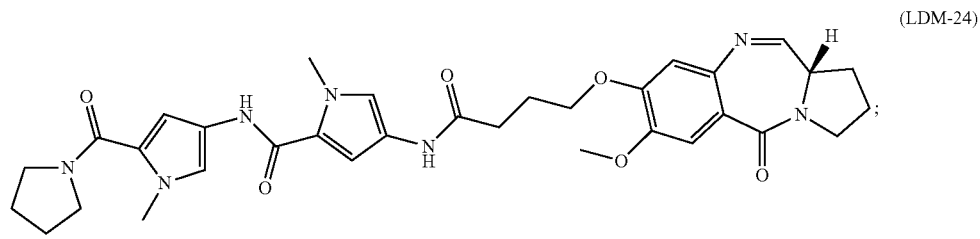 [SMILES: COc1cc2c(cc1OCCCC(=O)Nc1cc(C(=O)Nc3cc(C(=O)N4CCCC4)n(C)c3)n(C)c1)N=C[C@@H]1CCCN1C2=O]
(LDM-24)

(as) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(piperidine-1-carbonyl)-1H-pyrrol-3-yl)-1H-pyrrole-2-carboxamide

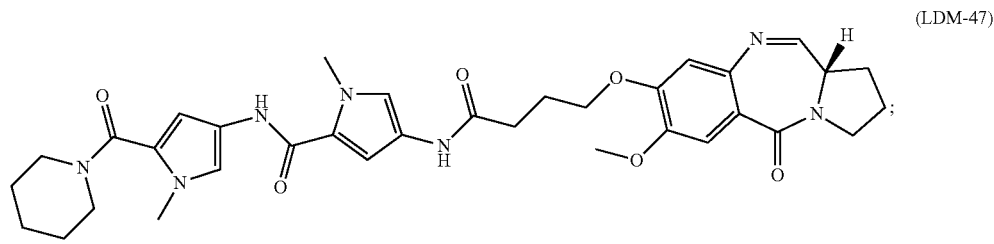 [SMILES: COc1cc2c(cc1OCCCC(=O)Nc1cc(C(=O)Nc3cc(C(=O)N4CCCCC4)n(C)c3)n(C)c1)N=C[C@@H]1CCCN1C2=O]
(LDM-47)

(at) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(1-methyl-5-(morpholine-4-carbonyl)-1H-pyrrol-3-yl)-1H-pyrrole-2-carboxamide

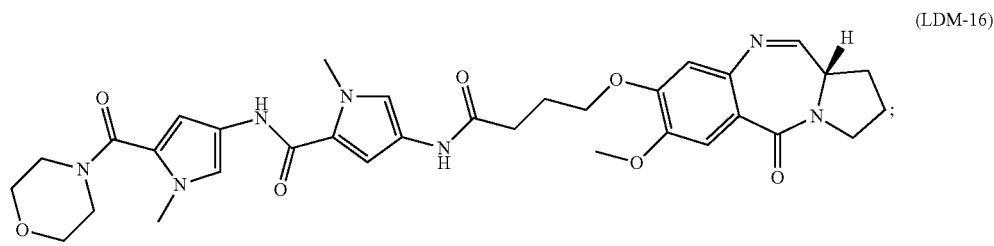 [SMILES: COc1cc2c(cc1OCCCC(=O)Nc1cc(C(=O)Nc3cc(C(=O)N4CCOCC4)n(C)c3)n(C)c1)N=C[C@@H]1CCCN1C2=O]
(LDM-16)

(au) (S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(1-methyl-5-(thiomorpholine-4-carbonyl)-1H-pyrrol-3-yl)-1H-pyrrole-2-carboxamide

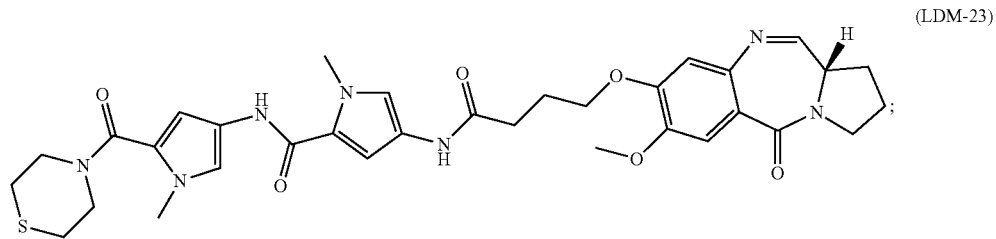 [SMILES: COc1cc2c(cc1OCCCC(=O)Nc1cc(C(=O)Nc3cc(C(=O)N4CCSCC4)n(C)c3)n(C)c1)N=C[C@@H]1CCCN1C2=O]

(LDM-23)

(av) (S)-4-(4-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)phenyl)-N,N,1-trimethyl-1H-pyrrole-2-carboxamide

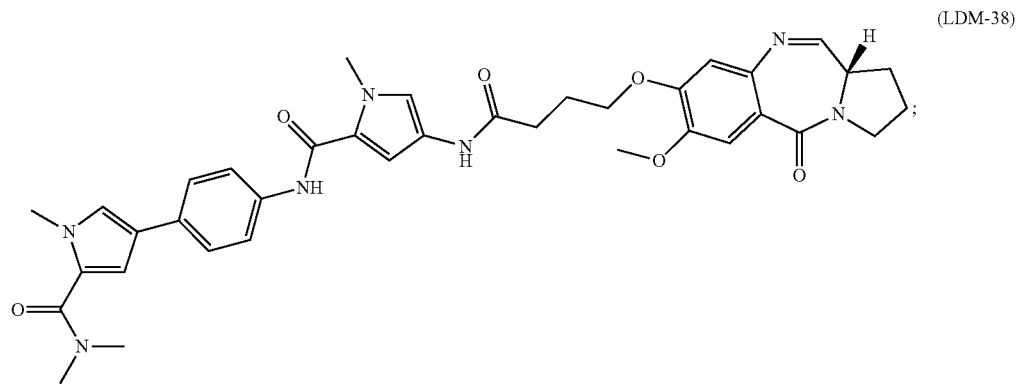 [SMILES: COc1cc2c(cc1OCCCC(=O)Nc1cc(C(=O)Nc3ccc(-c4cc(C(=O)N(C)C)n(C)c4)cc3)n(C)c1)N=C[C@@H]1CCCN1C2=O]

(LDM-38)

(aw) (S)—N,N-diethyl-4-(4-(4-(4-((7-methoxy-5-oxo-2,3,5,11a-tetrahydro-1H-benzo[e]-pyrrolo[1,2-a][1,4]diazepin-8-yl)oxy)butanamido)-1-methyl-1H-pyrrole-2-carbox-amido)phenyl)-1-methyl-1H-pyrrole-2-carboxamide

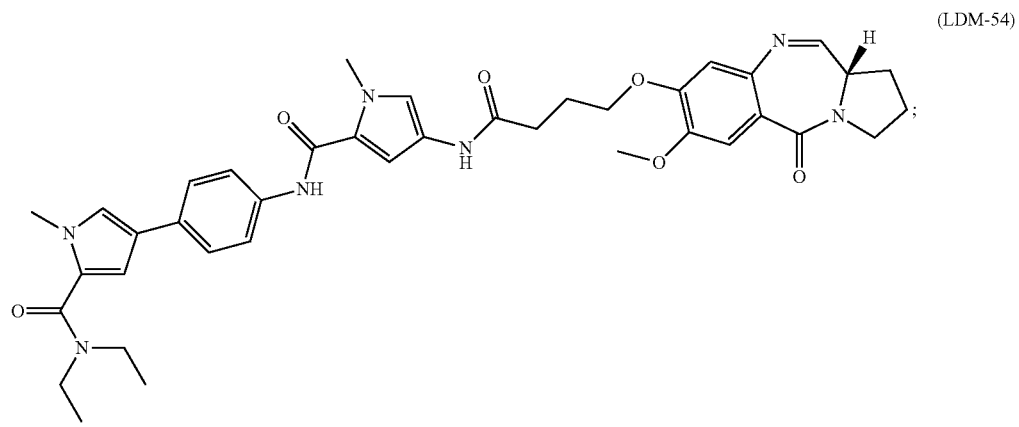 [SMILES: CCN(CC)C(=O)c1cc(-c2ccc(NC(=O)c3cc(NC(=O)CCCOc4cc5c(cc4OC)C(=O)N4CCC[C@H]4C=N5)cn3C)cc2)cn1C]

(LDM-54)

(ax) (S)-4-(4-((7-methoxy-5-oxo-2,3,5,11a-tetrahydro-1H-benzo-[e]pyrrolo[1,2-a][1,4]-diazepin-8-yl)oxy)butanamido)-1-methyl-N-(4-(1-methyl-5-(pyrrolidine-1-carbonyl)-1H-pyrrol-3-yl)phenyl)-1H-pyrrole-2-carboxamide
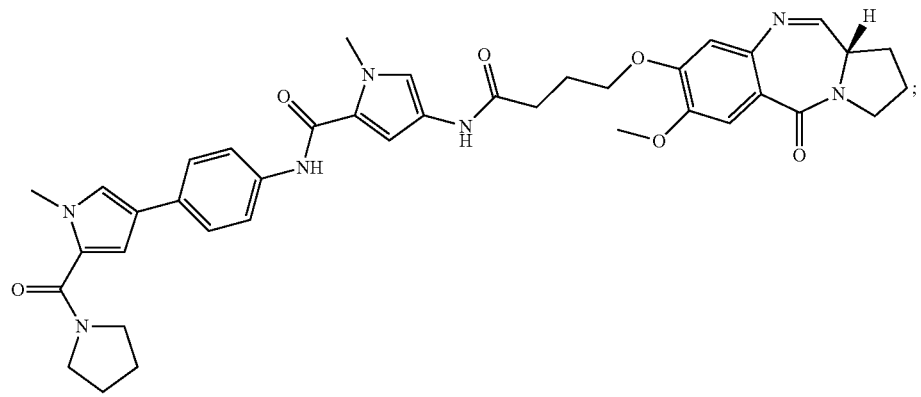
(LDM-53)
(ay) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(4-(1-methyl-5-(piperidine-1-carbonyl)-1H-pyrrol-3-yl)phenyl)-1H-pyrrole-2-carboxamide
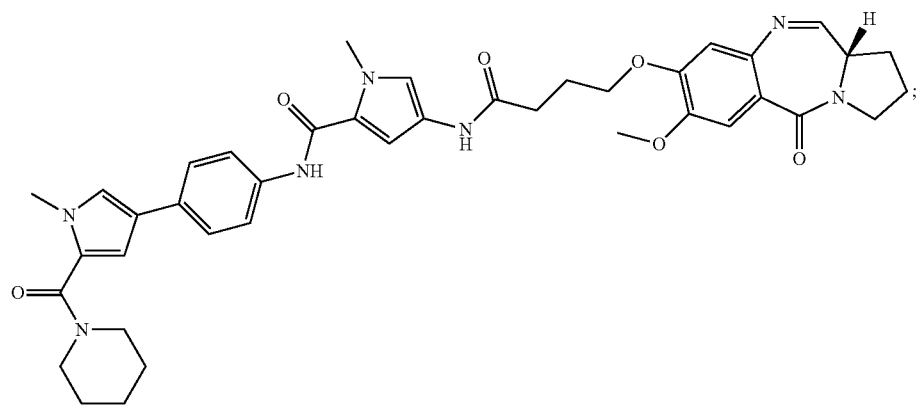
(LDM-50)

(az) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(4-(1-methyl-5-(morpholine-4-carbonyl)-1H-pyrrol-3-yl)phenyl)-1H-pyrrole-2-carboxamide
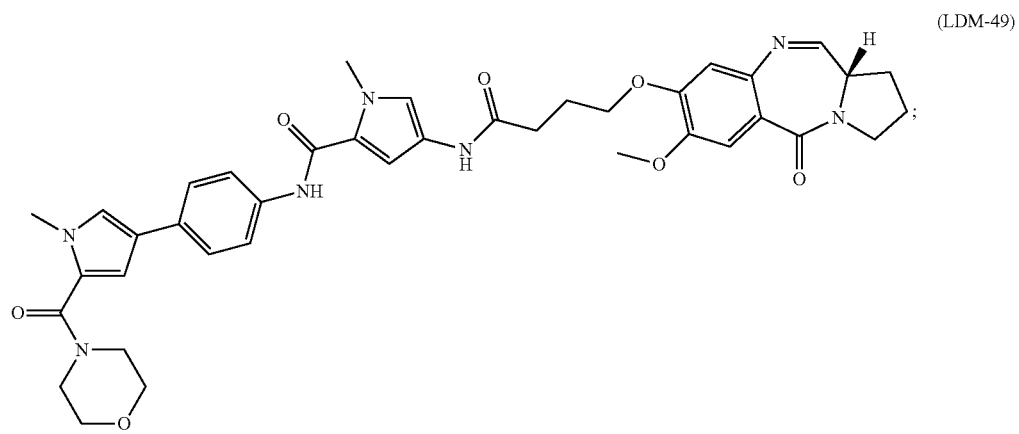 [SMILES: COc1cc2c(cc1OCCCC(=O)Nc1cc(C(=O)Nc3ccc(-c4cc(C(=O)N5CCOCC5)n(C)c4)cc3)n(C)c1)N=C[C@@H]1CCCN1C2=O]
(LDM-49)
(ba) (S)-4-(4-((7-methoxy-5-oxo-2,3,5,11a-tetrahydro-1H-benzo[e]pyrrolo[1,2-a][1,4]-diazepin-8-yl)oxy)butanamido)-1-methyl-N-(4-(1-methyl-5-(thiomorpholine-4-carbonyl)-1H-pyrrol-3-yl)phenyl)-1H-pyrrole-2-carboxamide
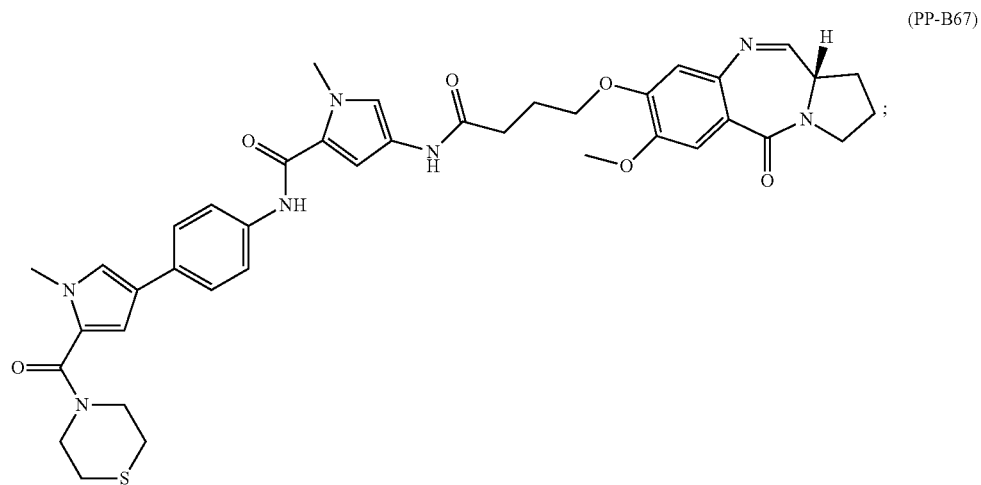 [SMILES: COc1cc2c(cc1OCCCC(=O)Nc1cc(C(=O)Nc3ccc(-c4cc(C(=O)N5CCSCC5)n(C)c4)cc3)n(C)c1)N=C[C@@H]1CCCN1C2=O]
(PP-B67)

(bb) (S)—N-(2-(dimethylcarbamoyl)benzo[b]thiophen-5-yl)-4-(4-47-fluoro-5-oxo-2,3,5,11a-tetrahydro-1H-benzo[e]pyrrolo[1,2-a][1,4]-diazepin-8-yl)oxy)butanamido)-1-methyl-1H-pyrrole-2-carboxamide (PP-B82)

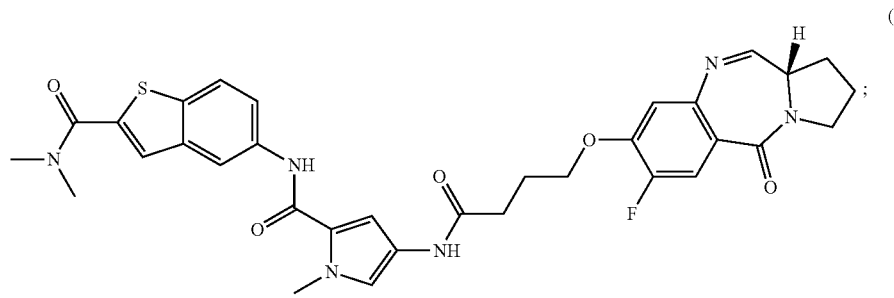

(bc) (S)-4-(4-((7-fluoro-5-oxo-2,3,5,11a-tetrahydro-1H-benzo[e]pyrrolo[1,2-a][1,4]-diazepin-8-yl)oxy)butanamido)-1-methyl-N-(2-(thiomorpholine-4-carbonyl)-benzofuran-5-yl)-1H-pyrrole-2-carboxamide (PP-B68)

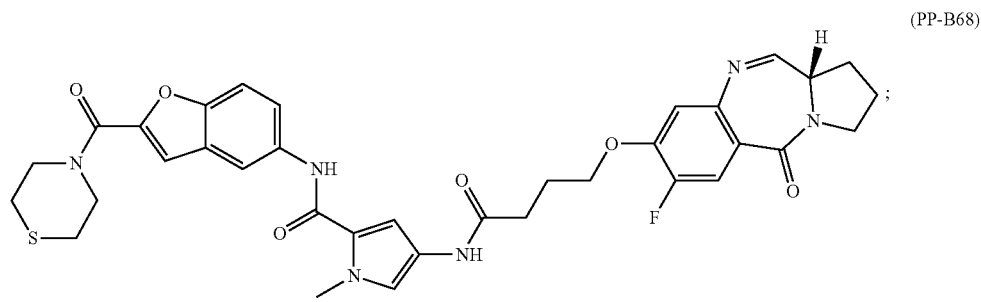 [SMILES: Cn1cc(NC(=O)CCCOc2cc3c(cc2F)C(=O)N2CCC[C@H]2C=N3)cc1C(=O)Nc1ccc2oc(C(=O)N3CCSCC3)cc2c1]

(bd) 4-(4-(((S)-7-methoxy-5-oxo-2,3,5,11a-tetrahydro-1H-benzo[e]pyrrolo[1,2-a][1,4]-diazepin-8-yl)oxy)butanamido)-1-methyl-N-(2-((2,4,5-trihydroxy-6-(hydroxymethyl)-tetrahydro-2H-pyran-3-yl)carbamoyl)benzofuran-5-yl)-1H-pyrrole-2-carboxamide PP-B102 deprotected

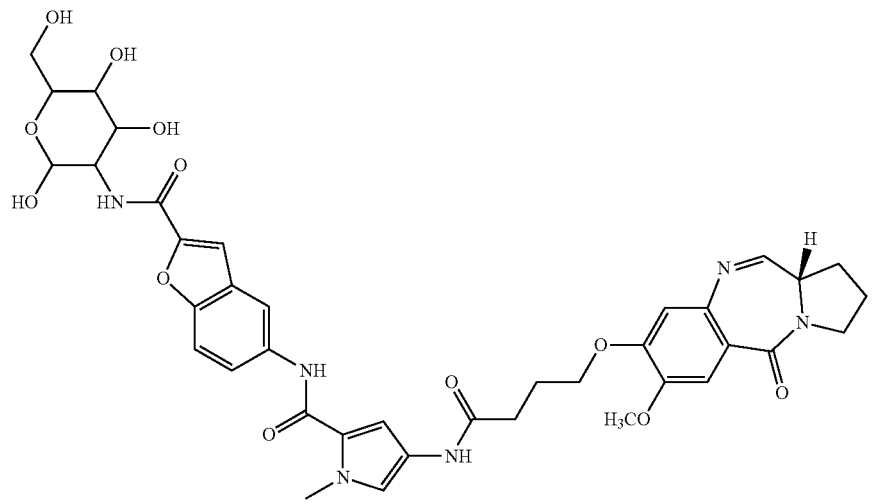

(be) 4-(2-aminopropanamido)benzyl 8-(4-((4-((2-(dimethylcarbamoyl)benzo[b]-thiophen-5-yl)carbamoyl)-1-methyl-1H-pyrrol-2-yl)amino)-4-oxobutoxy)-11-hydroxy-7-methoxy-5-oxo-2,3,11,11a-tetrahydro-1H-benzo[e]pyrrolo[1,2-a][1,4]diazepine-10(5H)-carboxylate (71)

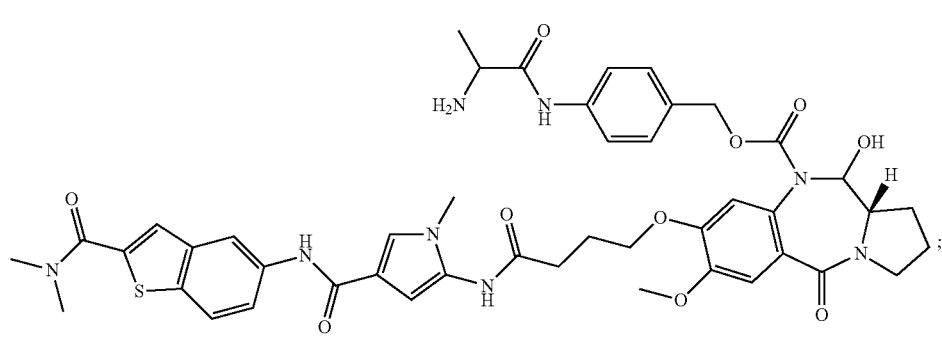

(bf) 4-nitrobenzyl 8-(4-((4-((2-(dimethylcarbamoyl)benzo[b]thiophen-5-yl)-carbamoyl)-1-methyl-1H-pyrrol-2-yl)amino)-4-oxobutoxy)-7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (76)

76

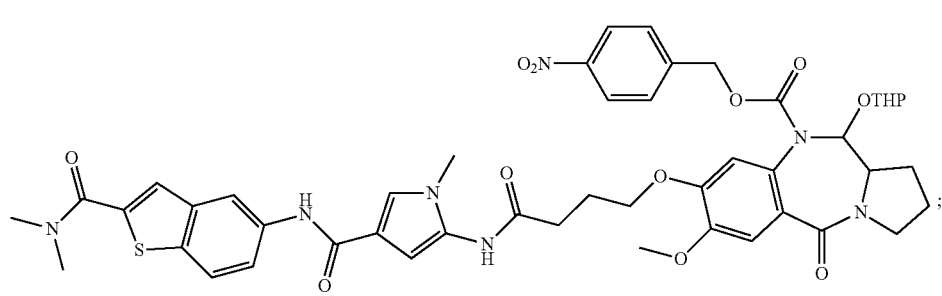

or
(bg) 4-nitrobenzyl 8-(4-((4-((2-(dimethylcarbamoyl)benzo[b]thiophen-5-yl)-carbamoyl)-1-methyl-1H-pyrrol-2-yl)amino)-4-oxobutoxy)-11-hydroxy-7-methoxy-5-oxo-2,3,11,11a-tetrahydro-1H-benzo[e]pyrrolo[1,2-a][1,4]diazepine-10(5H)-carboxylate 15. A pharmaceutical composition comprising a compound of formula (I) and salts and solvates thereof according to claim 1 and a pharmaceutically acceptable carrier or diluent.

16. A pharmaceutical composition according to claim 15, further comprising an efflux pump inhibitor.

17. A pharmaceutical composition according to claim 15, further comprising an agent for increasing the permeability of bacterial membranes.

18. A kit comprising:
(i) a compound of formula (I) and salts and solvates thereof according to claim 1;
(ii) an agent for increasing the permeability of bacterial membranes; and/or
(ii) an efflux pump inhibitor.

19. A method of treating a condition in a subject, the method comprising administering a therapeutically effective amount of a compound of formula (I) and salts and solvates

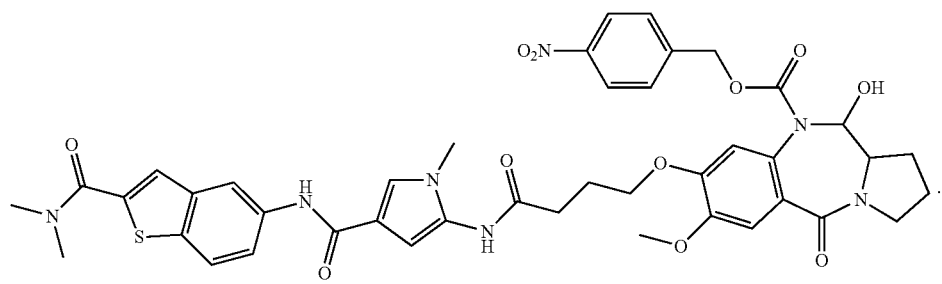 [SMILES: COc1cc2c(cc1OCCCC(=O)Nc1cc(C(=O)Nc3ccc4sc(C(=O)N(C)C)cc4c3)cn1C)N(C(=O)OCc1ccc([N+](=O)[O-])cc1)C(O)C1CCCN1C2=O]

thereof according to claim 1 or a pharmaceutical composition according to claim 15 to the subject, wherein the condition is the group consisting of: a bacterial infection, a skin infection, pneumonia, a urinary tract infection, a soft tissue injury, sepsis and bacteremia.

20. A method according to claim 19, wherein the condition is a bacterial infection caused by at least one bacterium of selected from the genera *Enterococcus, Staphylococcus, Streptococcus, Bacillus, Acinetobacter, Burkholderia, Coxiella, Francisella, Yersina, Klebsiella, Escherichia, Enterobacter* or *Pseudomonas*.

21. A method according to claim 20, wherein the bacterial infection is caused by at least one bacterium of the species *Enterococcus faeculis, Enterococcus faecium, Staphylococcus aureus, Streptococcus pyogenes, Streptococcus pneumoniae, Streptococcus agalactiae, Bacillus anthracis, Bacillus cereus, Bacillus subtilis, Haemophilus influenzae, Acinetobacter baumannii, Burkholderia multivorans, Burkholderia cenocepacia, Burkholderia cepacia, Burkholderia mallei, Burkholderia pseudomallei, Coxiella burnetii, Citrobacter freundii, Escherichia coli, Enterobacter cloacae, Enterobacter aerogenes, Francisella tularensis, Yersina pestis, Klebsiella pneumoniae, Serratia marcesens, Salmonella typhi, Salmonella typhimurum, Stenotrophomonas maltophilia, Pseudomonas aeruginosa* or *Neisseria gonorrhoeae*.

22. A compound of formula (I) and salts and solvates thereof according to claim 1, wherein, wherein the monosaccharide and amino monosaccharide moiety is

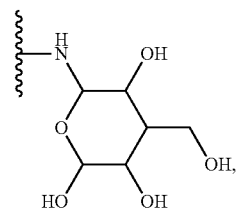 (MS1)

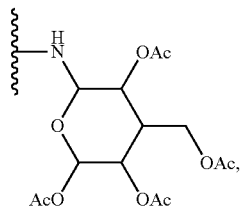 (MS2)

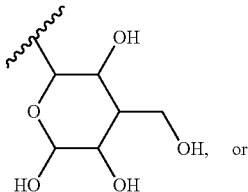 (MS3)

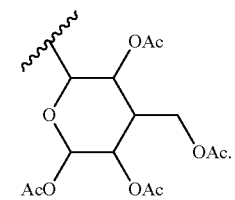 (MS4)

* * * * *